US012528804B2

(12) United States Patent
Jankowska et al.

(10) Patent No.: US 12,528,804 B2

(45) **Date of Patent: *Jan. 20, 2026**

(54) LACTIVICIN COMPOUNDS, THEIR PREPARATION AND USE AS ANTIBACTERIAL AGENTS

(71) Applicant: FEDORA PHARMACEUTICALS INC., Edmonton (CA)

(72) Inventors: Renata Jankowska, Edmonton (CA); Sameeh M. Salama, Edmonton (CA); Samarendra N. Maiti, Edmonton (CA)

(73) Assignee: FEDORA PHARMACEUTICALS INC., Edmonton (CA)

( * ) Notice: Subject to any disclaimer, the term of this patent is extended or adjusted under 35 U.S.C. 154(b) by 420 days.

This patent is subject to a terminal disclaimer.

(21) Appl. No.: 18/225,859

(22) Filed: Jul. 25, 2023

(65) Prior Publication Data

US 2023/0374005 A1 Nov. 23, 2023

Related U.S. Application Data

(63) Continuation-in-part of application No. 17/707,297, filed on Mar. 29, 2022, now Pat. No. 11,780,832.

(60) Provisional application No. 63/168,406, filed on Mar. 31, 2021.

(51) Int. Cl.

| | |
|---|---|
| ***C07D 471/04*** | (2006.01) |
| ***A61K 45/06*** | (2006.01) |
| ***C07D 417/14*** | (2006.01) |
| ***C07D 471/08*** | (2006.01) |
| ***C07D 487/04*** | (2006.01) |
| ***C07D 493/08*** | (2006.01) |
| ***C07D 513/04*** | (2006.01) |
| ***C07D 519/00*** | (2006.01) |

(52) U.S. Cl.

CPC ............ *C07D 471/04* (2013.01); *A61K 45/06* (2013.01); *C07D 417/14* (2013.01); *C07D 471/08* (2013.01); *C07D 487/04* (2013.01); *C07D 493/08* (2013.01); *C07D 513/04* (2013.01); *C07D 519/00* (2013.01)

(58) Field of Classification Search

CPC ................ C07D 471/04; C07D 417/14; C07D 471/08; C07D 487/04; C07D 493/08; C07D 513/04; C07D 519/00; A61K 45/06; A61K 31/422; A61K 31/427; A61K 31/428; A61K 31/437

See application file for complete search history.

(56) References Cited

U.S. PATENT DOCUMENTS

2015/0148326 A1 5/2015 Brown et al.

FOREIGN PATENT DOCUMENTS

| | | |
|---|---|---|
| CN | 86 1 02923 | 11/1986 |
| WO | 86/06380 | 11/1986 |
| WO | 87/00527 | 1/1987 |

OTHER PUBLICATIONS

Calvopina, Karina et al., “Sideromimic Modification of Lactivicin Dramatically Increases Potency against Extensively Drug-Resistant Stenotrophomonas maltophilia Clinical Isolates”, Antimicrobial Agents and Chemotherapy, 2016, vol. 60, No. 7, pp. 4170-4175 (Year: 2016).*

International Search Report and Written Opinion of the International Searching Authority issued Jun. 13, 2022 in International (PCT) Application No. PCT/IB2022/052900.

Starr, Jeremy et al., “Siderophore Receptor-Mediated Uptake of Lactivicin Analogs in Gram-Negative Bacteria”, J. Med. Chem., 2014, vol. 57, No. 9, pp. 3845-3855.

Calvopiña, Karina et al., “Sideromimic Modification of Lactivicin Dramatically Increases Potency against Extensively Drug-Resistant *Stenotrophomonas maltophilia* Clinical Isolates”, Antimicrobial Agents and Chemotherapy, 2016, vol. 60, No. 7, pp. 4170-4175.

Tamura, Norikazu et al., “Synthesis and Antibacterial Activity of Lactivicin Derivatives”, Chemical and Pharmaceutical Bulletin, 1990, vol. 38, No. 1, pp. 116-122.

Nozaki, Yukimasa et al., “Lactivicin, A Naturally Occurring Non-ß-Lactam Antibiotic Having ß-Lactam-Like Action: Biological Activities and Mode of Action”, The Journal of Antibiotics, 1989, vol. 42, No. 1, pp. 84-93.

Tamura, Norikazu et al., “Synthesis of Lactivicin Analogues”, Tetrahedron, 1988, vol. 44, No. 11, pp. 3231-3240.

Extended European Search Report dated Jun. 17, 2024 in European Application No. 22779276.9.

Goldberg, Joel A. et al., “A γ-Lactam Siderophore Antibiotic Effective against Multidrug-Resistant Gram-Negative Bacilli”, Journal of Medicinal Chemistry, 2020, vol. 63, pp. 5990-6002.

* cited by examiner

*Primary Examiner* — Joseph K McKane

*Assistant Examiner* — David M Shim

(74) *Attorney, Agent, or Firm* — Wenderoth, Lind & Ponack, L.L.P.

(57) ABSTRACT

Lactivicin compounds of formula (I) and pharmaceutically acceptable salts of the compounds of formula (I) are provided, wherein the compounds comprise antibiotics suitable for use either alone or in combination with β-lactamase inhibitors and/or additional antibiotics (including β-lactam and non-β-lactam antibiotics) in the treatment or prevention of bacterial infections.

15 Claims, No Drawings

LACTIVICIN COMPOUNDS, THEIR PREPARATION AND USE AS ANTIBACTERIAL AGENTS

TECHNICAL FIELD

This invention relates to novel lactivicin compounds bearing the unique structure of a dicyclic dipeptide, which is 2-[(4S)-4-acetamido-3-oxo-1,2-oxazolidin-2-yl]-5-oxooxolane-2-carboxylic acid, and to their pharmaceutically acceptable salts, their use, and to methods for preparation of these compounds. More particularly, new lactivicin compounds having improved antibacterial activity and combinations of these compounds with β-lactamase inhibitors that are active against a number of resistant pathogenic microorganisms are provided.

BACKGROUND ART

Public health experts and officials consider the emergence and spread of antibiotic resistant bacteria as one of the major public health problems of the 21$^{st}$ century. While the most resistant isolates continue to emerge in the hospital setting, physicians and epidemiologists are encountering increasing numbers of resistant bacteria in the community among people without previous healthcare contact. Therapeutic agents are especially limited for infections due to the multi-drug resistant Gram-negative pathogens including the bacteria that constitute the ESKAPE organisms, generally encompassed by the following six pathogens: *Enterococcus faecium, Staphylococcus aureus, Klebsiella pneumoniae, Acinetobacter baumannli, Pseudomonas aeruginosa*, and *Enterobacter* species.

The highly successful and well-tolerated class of β-lactam antibiotics has historically been one mainstay for the treatment of infections caused by Gram-negative pathogens. However, a vast array of more than 1000 different β-lactamases produced by bacteria and further bacterial resistance mechanisms severely endanger the mid-term usability of the current β-lactam antibiotics. Extended-spectrum β-lactamases (ESBLs) and carbapenemases are especially important drivers of resistance, inactivating β-lactam antibiotics and rendering them ineffective in the treatment of infections. As a result, the morbidity and mortality caused by bacterial infections in both hospital and community settings continue to rise and bacterial resistance has become a significant public health concern.

New agents with resistance breaking properties are urgently needed to fill up the gap. Thus, there is a demand for the development of new classes of antibiotics which exhibit more potent antimicrobial activity and that are particularly more effective against a variety of β-lactamase producing Gram-negative bacteria.

Lactivicin is the first non-β-lactam antibiotic having a dicyclic dipeptide skeleton described in the literature. It was isolated by the Takeda group from soil samples collected in Japan. Lactivicin possesses a unique dicyclic dipeptide structure, and it has been shown to have an affinity for bacterial penicillin-binding proteins (PBPs) similar to β-lactam antibiotics. However, it is less susceptible to beta-lactamase enzymes. [Nature, 1987, Vol. 325, pp. 179-180; J. Chem. Soc. Chem. Commun., 1987, (2), pp. 62-63; Tetrahedron Lett., 1986, Vol. 27, No. 51, pp. 6229-6232; Tetrahedron, 1988, Vol. 44, No. 11, pp. 3231-3240; Tetrahedron, 1988, Vol. 44, No. 21, pp. 6589-6606; J. Antibiot., 1989, Vol. 42, No. 1, pp. 84-93; Chem. Pharm. Bull., 1990, Vol. 38. No. 1, pp. 116-122; U.S. Pat. No. 4,851,422 (1989); EP 0191989 A1; WO 87/00527; EP 0219923 A1].

As particular examples of lactivicins, U.S. Pat. No. 4,851,422 and EP 0219923 B1 disclose 2-(3-oxo-2-isoxazolidinyl)-5-oxo-2-tetrahydrofuran carboxylates of the formula shown below, which is an exemplary structure of lactivicins:

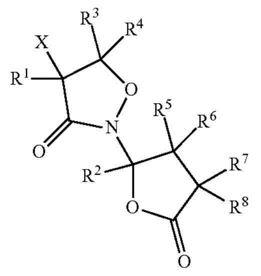

whereby $R^5$, $R^6$, $R^7$ and $R^8$ are independently hydrogen, $C_{1-6}$ alkyl, phenyl or benzyl which may be substituted with $C_{1-6}$ acylamino or $C_{1-6}$ alkoxy and which may be bonded through an oxygen or a sulfur atom, or $R^5$ and/or $R^6$ forms with $R^7$ or $R^8$ a chemical bond to form a double bond, or $R^5$ or $R^6$ with $R^7$ or $R^8$ form a phenyl ring.

In search for a different class of antibiotics with a new nucleus, the Takeda group made several derivatives of lactivicin having various acylamino moieties at the C-4 position [J. Chem. Soc. Chem. Commun., 1987, (2), pp. 62-63]. The compound having a 2-aminothiazol-4-yl-(Z)-2-methoxy-iminoacetyl side chain showed improved and enhanced antibacterial activity when compared with natural lactivicin. Furthermore, some of the compounds showed protective effects in experimentally infected mice [Chem. Pharm. Bull., 1990, Vol. 38, No. 1, pp. 116-122; Tetrahedron, 1988, Vol. 44, No. 21, pp. 6589-6606].

The attempt to enhance the cellular uptake of the β-lactams by using iron-siderophore uptake systems in microorganisms is a concept that has been explored in the monobactam field by Basilea (WO 2007/065288), NAEJA Pharmaceutical (WO 2002/022613) and Squibb & Sons (U.S. Pat. No. 5,290,929, EP 531976, EP 484881). Furthermore, BMS-180680 is a catechol-containing monobactam which appears to use the Cir and Fiu iron-regulated outer membrane receptor proteins and the TonB-dependent iron transport system for enhanced uptake across the bacterial outer membrane. As a result, BMS-180680 has excellent activity against many Gram-negative bacteria [Antimicrob. Agents & Chemother., 1997, Vol. 41, No. 5, pp. 1010-1016]. Additionally, Shionogi & Co. Ltd. discovered a new catechol-containing cephalosporin [Antimicrob. Agents & Chemother., 2016, Vol. 60, No. 12, pp. 7396-7401] and introduced it into the clinic as Cefiderocol. Recently, Pfizer re-investigated lactivicins that carry a catechol group for siderophore receptor-mediated uptake in Gram-negative bacteria [J. Med. Chem. 2014, 57, 3845-3855]. Another group [Antimicrob. Agents & Chemother., 2016, Vol. 60, No. 7, pp. 4170-4175] showed sideromimic modification of lactivicin dramatically increases potency against extensively drug-resistant *Stenotrophomonas maltophilia* clinical isolates. Overall, the lactivicin-sideromimic conjugates are clearly an under-explored class with a novel dicyclic dipeptide nucleus that merits further investigation through preparation of additional novel analogs in the quest to find new effective antibacterial agents. The present invention is directed to these and other important goals.

SUMMARY OF THE INVENTION

In view of the increasing development of resistance in pathogenic bacteria to known classes of antibacterial agents, including bacteria exhibiting multiple resistances, there is an ongoing need to find novel antibacterial substances, in particular compounds that have structural motifs that differ from traditional antimicrobial molecules.

While studies on lactivicins have shown promising results, there remains a need for new lactivicin compounds having increased antibiotic efficacy, particularly in highly resistant Gram-negative bacteria, with such compounds having structural features that are significantly different from the compounds described in the patents and publications cited above.

To this end, the present invention relates to and encompasses compounds of formula (I)

(I)

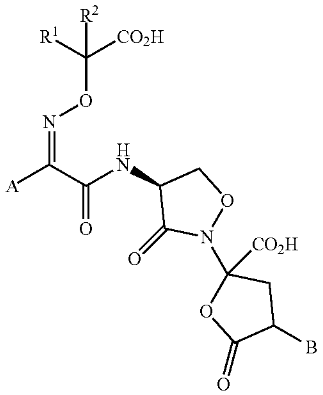

where A is defined by formula (Ia)

(Ia)

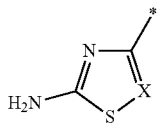

and wherein X is N or $CR^3$, and $R^3$ represents hydrogen or halogen. Suitable halogens include chlorine and fluorine.

In formula (I), $R^1$ and $R^2$ together with the carbon atom to which they are bonded may form a ($C_3$-$C_8$) cycloalkyl, wherein (i) the cycloalkyl may contain one heteroatom selected from O, N and S; and/or (ii) the cycloalkyl may be substituted with one, two, three or four substituents selected independently of one another from the group consisting of ($C_1$-$C_3$) alkyl and halogen. Suitable halogens include chlorine and fluorine.

Alternatively, in formula (I), $R^1$ and $R^2$ may, independently of one another, represent hydrogen or ($C_1$-$C_3$) alkyl, whereby ($C_1$-$C_3$) alkyl may be substituted with a substituent selected from hydroxy and chlorine.

In formula (I), B is a bicyclic catechol or hydroxypyridone moiety bearing fragment set forth in formula (Ia') that has the ability to enhance intracellular uptake of the compounds of formula (I) via utilization of the bacterial iron uptake process in Gram-negative bacteria.

(Ia')

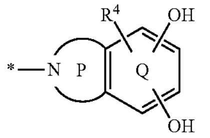

In formula (Ia'), the P ring is an unsaturated 5-membered or 6-membered ring, which optionally may contain one carbonyl (CO) group, or two carbonyl (CO) groups, or one sulfone ($SO_2$) group, or a combination of one carbonyl (CO) and one sulfone ($SO_2$) group, and may further contain up to two additional N atoms. In a particular embodiment, the P ring is an unsaturated 5-membered ring.

In formula (Ia'), the Q ring may contain up to two N atoms, wherein the substituent $R^4$ is selected from the group consisting of hydrogen, ($C_1$-$C_3$) alkyl, carbonyl, trifluoromethyl, cyano and a halogen. Particular examples of Q rings are benzene, pyridine and pyridazine. Suitable halogens include fluorine and chlorine.

The present invention also includes salts of the compounds of formula (I), solvates of the compounds of formula (I), and solvates of the salts of the compounds of formula (I).

The compounds of the invention may, depending on their structure, exist in stereoisomeric forms (e.g., enantiomers, diastereomers). The invention therefore also encompasses the enantiomers and diastereomers of the compounds of formula (I) as defined herein and respective mixtures thereof. The stereoisomerically uniform constituents can be isolated in a known manner from such mixtures of enantiomers and/or diastereomers, and such constituents are also considered compounds of the present invention.

Regarding the compounds of formula (I), it is to be understood that these compounds include Z-isomers, E-isomers, and mixtures thereof. As used herein, the term “isomers” refers to different compounds that have the same molecular formula but differ in arrangement and configuration of the atoms, such as geometrical isomers and optical isomers.

If the compounds of the invention may occur in tautomeric forms, the present invention encompasses all tautomeric forms of the compounds of formula (I).

Salts preferred for the purposes of the present invention are “pharmaceutically acceptable salts” of the compounds of the invention, i.e. the compounds of formula (I). Also encompassed however are salts which are themselves not suitable for pharmaceutical applications (“non-pharmaceutically acceptable salts”) but can be used, for example, for the isolation or purification of the compounds of the invention.

Examples of pharmaceutically acceptable salts of the compounds of formula (I) include salts of inorganic bases like ammonium salts, alkali metal salts, in particular sodium or potassium salts, alkaline earth metal salts, in particular magnesium or calcium salts; salts of organic bases derived from n-propylamine, n-butylamine, cyclohexylamine, benzylamine, octylamine, ethanolamine, diethanolamine, diethylamine, triethylamine, dicyclohexylamine, procaine, choline, picoline, N,N-dibenzylethylenediamine, N-methylglucamine, morpholine, pyrrolidine, pyridine, piperidine, N-ethylpiperidine and N-methylmorpholine. Basic amino acids that can form basic amino acid salts include lysine, arginine, ornithine and histidine. As will be appreciated by one skilled in the art, the compounds of formula (I) containing a basic nitrogen atom are capable of forming acid addition salts. Such salts with pharmaceutically acceptable acids are Included herein. Examples of such acids are hydrochloric, hydrobromic, phosphoric, sulfuric, citric, oxalic, maleic, fumaric, glycolic, mandelic, tartaric, aspartic, succinic, malic, formic, acetic, trifluoroacetic, methanesulfonic, ethanesulfonic, trifluoromethanesulfonic, benzenesulfonic, p-toluenesulfonic and the like.

Moreover, some compounds of formula (I), when they contain a basic group such as NH, $NH_2$ or pyridine, piperazine and the like, may form an inner zwitterionic salt with a COOH group. Such inner salts are also contemplated and included herein.

Solvates for the purposes of the invention refer to those forms of the compounds of the invention which in the solid or liquid state form a complex by coordination with solvent molecules. Hydrates are a specific form of solvates in which the coordination takes place with water. A molecular complex of a compound or moiety of a compound and a solvent can be stabilized by non-covalent intra-molecular forces such as, for example, electrostatic forces, Van der Waals forces or hydrogen bonds. A molecular complex of a compound of the present invention can be formed with one or more solvent molecules in a stoichiometric or non-stoichiometric amount.

In the context of this invention, the substituents defined for formula (I) have the following definitions unless specified otherwise.

The term "cycloalkyl" refers to aliphatic $C_3$-$C_8$, preferably $C_3$-$C_6$, rings such as in particular cyclopropyl, cyclobutyl, cyclopentyl and cyclohexyl, but also including $C_3$-$C_4$ rings, $C_3$-$C_5$ rings, and $C_3$-$C_7$ rings. The term "cycloalkyl" includes aliphatic $C_3$ rings, $C_4$ rings, $C_5$ rings, $C_6$ rings, $C_7$ rings, and $C_8$ rings.

The term "halogen" refers to fluorine and chlorine.

The term "alkyl" refers to straight-chain or branched ($C_1$-$C_6$) alkyl, preferably ($C_1$-$C_4$) alkyl, such as in particular methyl, ethyl, propyl, butyl, isopropyl, isobutyl and tert-butyl, but also including ($C_1$-$C_2$) alkyl, ($C_1$-$C_3$) alkyl, ($C_1$-$C_5$) alkyl and ($C_1$-$C_6$) alkyl. The term alkyl Includes straight-chain or branched $C_3$ alkyls, straight-chain or branched $C_4$ alkyls, straight-chain or branched $C_5$ alkyls, and straight-chain or branched $C_6$ alkyls.

The term "5-membered ring" refers to 5-membered heterocyclic ring containing at least one to up to three N atoms and optionally one S atom.

The term "6-membered ring" refers to 6-membered heterocyclic ring containing at least one N atom.

Accordingly, in some embodiments of the invention, lactivicin compounds and pharmaceutically acceptable salts thereof, i.e. compounds of formula (I) and pharmaceutically acceptable salts thereof, are provided. In some aspects, these compounds may exhibit activity against pathogenic microorganisms, therefore useful in the treatment and/or prevention of bacterial infections in humans or animals, either alone or in combination with one or more additional antibiotics, such as β-lactam antibiotics and non-β-lactam antibiotics, and β-lactamase inhibitors.

In other embodiments of the invention, pharmaceutical compositions comprising one or more compounds of formula (I), or pharmaceutically acceptable salts thereof, and a pharmaceutically acceptable carrier or diluent are provided. In some aspects, these compositions may exhibit activity against pathogenic microorganisms.

In other embodiments of the invention, processes for the preparation of new lactivicin compounds and salts thereof, i.e. the compounds of formula (I) and pharmaceutically acceptable salts thereof, are provided.

In other embodiments of the invention, pharmaceutical compositions comprising (i) one or more compounds of formula (I) or pharmaceutically acceptable salts thereof, (ii) one or more β-lactamase inhibitors, and (iii) a pharmaceutically acceptable carrier or diluent are provided. In some aspects, these compositions may exhibit activity against pathogenic microorganisms.

In other embodiments of the invention, pharmaceutical compositions comprising (i) one or more compounds of formula (I) or pharmaceutically acceptable salts thereof, (ii) one or more additional antibiotics, and (iii) a pharmaceutically acceptable carrier or diluent are provided. The additional antibiotics may be β-lactam antibiotics, or non-β-lactam antibiotics, or both. In some aspects, these compositions may exhibit activity against pathogenic microorganisms.

In other embodiments of the invention, pharmaceutical compositions comprising (i) one or more compounds of formula (I) or pharmaceutically acceptable salts thereof, (ii) one or more β-lactamase inhibitors, (iii) one or more additional antibiotics and (iv) a pharmaceutically acceptable carrier or diluent are provided. The additional antibiotics may be β-lactam antibiotics, or non-β-lactam antibiotics, or both. In some aspects, these compositions may exhibit activity against pathogenic microorganisms.

In other embodiments of the invention, provided herein are methods for treating or preventing bacterial infections in a subject, comprising administering to a subject in need thereof:

(i) a therapeutically effective amount of one or more compounds of formula (I) or pharmaceutically acceptable salts thereof;

(ii) a therapeutically effective amount of a pharmaceutical composition comprising one or more compounds of formula (I) or pharmaceutically acceptable salts thereof, and a pharmaceutically acceptable carrier or diluent;

(iii) a therapeutically effective amount of a combination comprising (a) one or more compounds of formula (I) or pharmaceutically acceptable salts thereof, and (b) one or more β-lactamase inhibitors; administered in any order or timing;

(iv) a therapeutically effective amount of a combination comprising (a) one or more compounds of formula (I) or pharmaceutically acceptable salts thereof, and (b) one or more additional antibiotics (e.g. β-lactam antibiotics and non-β-lactam antibiotics); administered in any order or timing;

(v) a therapeutically effective amount of a combination comprising (a) one or more compounds of formula (I) or pharmaceutically acceptable salts thereof, (b) one or more β-lactamase inhibitors, and (c) one or more additional antibiotics (e.g. β-lactam antibiotics and non-β-lactam antibiotics); administered in any order or timing;

(vi) a therapeutically effective amount of a pharmaceutical composition comprising (a) one or more compounds of formula (I) or pharmaceutically acceptable salts thereof, (b) one or more β-lactamase inhibitors, and (c) a pharmaceutically acceptable carrier or diluent;

(vii) a therapeutically effective amount of a pharmaceutical composition comprising (a) one or more compounds of formula (I) or pharmaceutically acceptable salts thereof, (b) one or more additional antibiotics (e.g. β-lactam antibiotics and non-β-lactam antibiotics), and (c) a pharmaceutically acceptable carrier or diluent;

(viii) a therapeutically effective amount of a pharmaceutical composition comprising (a) one or more compounds of formula (I) or pharmaceutically acceptable salts thereof, (b) one or more β-lactamase inhibitors, (c) one or more additional antibiotics (e.g. β-lactam antibiotics and non-β-lactam antibiotics), and (d) a pharmaceutically acceptable carrier or diluent.

In other embodiments of the invention, the use of a compound of formula (I) for the treatment or prevention of bacterial infections in a subject is provided. In some aspects, the compound is included in a composition that may further comprise a β-lactamase inhibitor and/or additional antibiotics such as β-lactam antibiotics, non-β-lactam antibiotics, or both, and may involve the preparation of a therapeutically effective medicament.

According to embodiments of the invention herein, the subject may be a human being or an animal in which the present compounds and compositions may provide a beneficial antibacterial effect.

DETAIL DESCRIPTION OF THE INVENTION

According to embodiments herein, lactivicin compounds of formula (I) and pharmaceutically acceptable salts of the compounds of formula (I) are provided, wherein the compounds comprise antibiotics suitable for use either alone or in combination with β-lactamase Inhibitors and/or additional antibiotics (including β-lactam and non-β-lactam antibiotics) in the treatment or prevention of bacterial infections. The term "antibiotic" refers to a compound or composition which decreases the viability of a microorganism, or which inhibits the growth or proliferation of a microorganism, and is further intended to include an antimicrobial, bacteriostatic or bactericidal agent.

Compounds of the Invention

In particular, the present invention relates to compounds of formula (I)

(I)

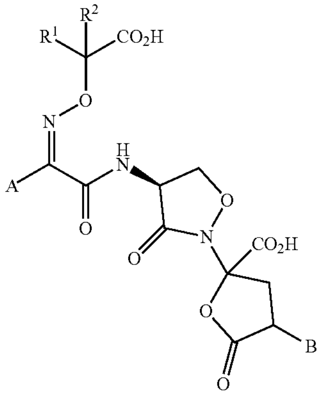

where A is defined by formula (Ia)

(Ia)

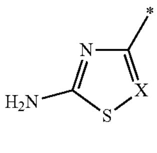

and wherein X is N or $CR^3$, and $R^3$ represents hydrogen or halogen;

$R^1$ and $R^2$, together with the carbon atom to which they are bonded, may form a $(C_3\text{-}C_8)$ cycloalkyl, wherein
(i) the cycloalkyl may contain one heteroatom selected from O, N and S, and/or
(ii) the cycloalkyl may be substituted with one, two, three or four substituents selected independently of one another from the group consisting of $(C_1\text{-}C_3)$ alkyl and halogen; or $R^1$ and $R^2$ may, independently of one another, represent hydrogen or $(C_1\text{-}C_3)$ alkyl, wherein $(C_1\text{-}C_3)$ alkyl may be substituted with a substituent selected from hydroxy and chlorine;

B is a bicyclic catechol or hydroxypyridone moiety bearing fragment defined by formula (Ia')

(Ia')

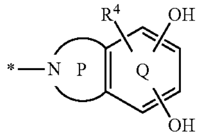

wherein P is an unsaturated 5-membered or 6-membered ring, which optionally may contain one carbonyl (CO) group, or two carbonyl (CO) groups, or one sulfone ($SO_2$) group, or a combination of one carbonyl (CO) and one sulfone ($SO_2$) group, and may further contain up to two additional N atoms; and wherein Q may contain up to two N atoms, and wherein $R^4$ is selected from the group consisting of hydrogen, $(C_1\text{-}C_3)$ alkyl, carbonyl, trifluoromethyl, cyano and a halogen; and salts thereof, solvates thereof, and solvates of the salts thereof.

In formula (I), particular examples of halogens include fluorine and chlorine.

In formula (Ia'), a particular example of the P ring is an unsaturated 5-membered ring.

In formula (Ia'), particular examples of Q ring are benzene, pyridine and pyridazine.

In formula (Ia'), particular bicyclic catechol or hydroxypyridone moiety bearing fragments are those that have the ability to enhance Intracellular uptake of the compounds of formula (I) via utilization of the bacterial iron uptake process in Gram-negative bacteria.

In the formula (I), examples of

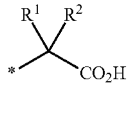

include, but are not limited to, the fragments:

(i)

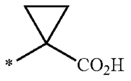

(ii)

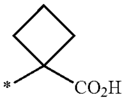

-continued
(iii)
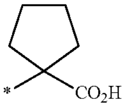
(iv)
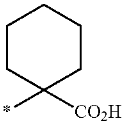
(v)
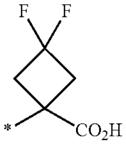
(vi)
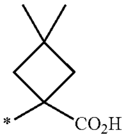
(vii)
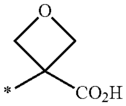
(viii)
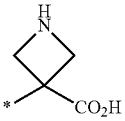
(ix)
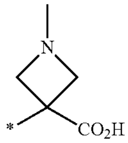
(x)
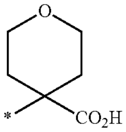
(xi)
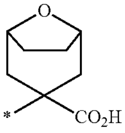
(xii)
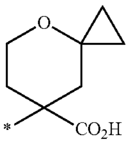
(xiii)
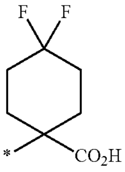
-continued
(xiv)
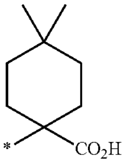
(xv)
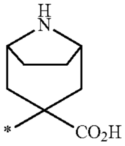
(xvi)
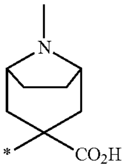
(xvii)
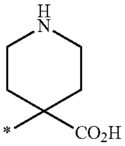
(xviii)
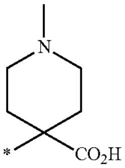
(xix)
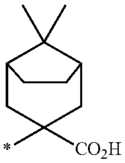
(xx)
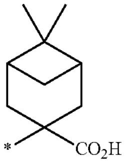
(xxi)
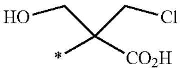
(xxii)
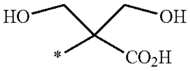
(xxiii)
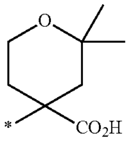

-continued
(xxiv)
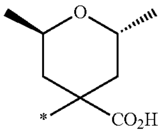
(xxv)
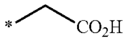
In the formula (I), examples of "A" include, but are not limited to, the following:
(a)
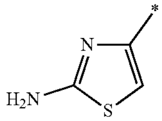
(b)
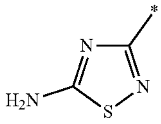
(c)
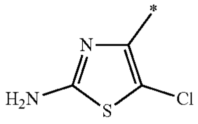
In the formula (I), examples of "B3" include, but are not limited to, the following:
(d)
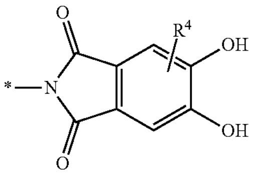
(e)
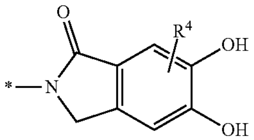
(f)
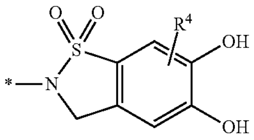
(g)
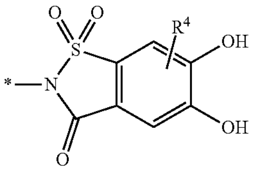
-continued
(h)
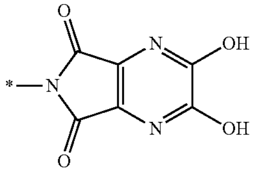
(i)
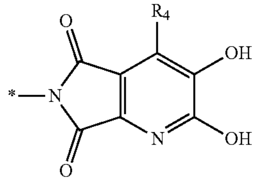
(j)
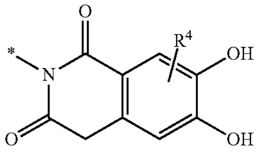
(k)
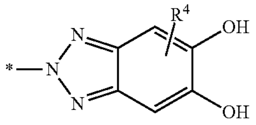
(l)
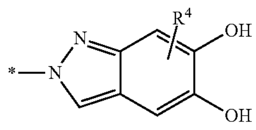
(m)
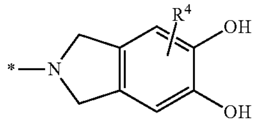
(n)
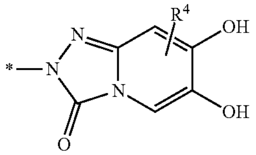
(o)
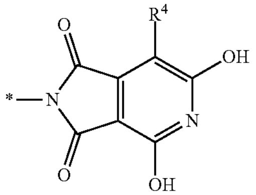
(p)
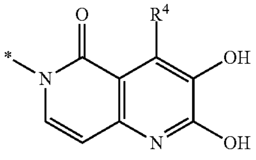

-continued (q)

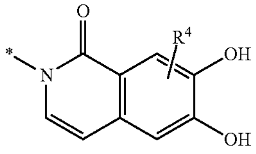

(r)

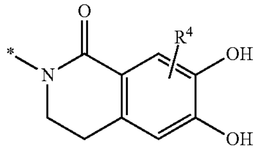

(s)

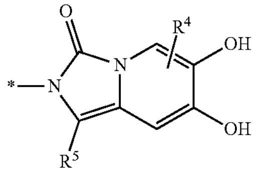

-continued (t)

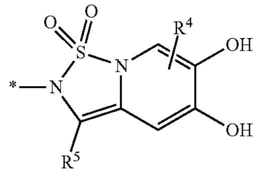

(u)

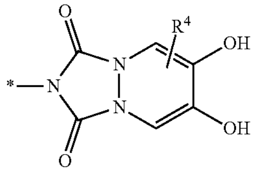

$R^4$ is selected from hydrogen, $(C_1-C_3)$ alkyl, trifluoromethyl, cyano or halogen, wherein the halogen is preferably chlorine or fluorine, and $R^5$ is hydrogen or $CH_3$.

Examples of compounds of the formula (I) encompassed by the invention, without being limiting to the specified compounds, are provided in the following Table 1.

TABLE 1

| Cmpd No. | | Chemical Name |
|---|---|---|
| 1 | 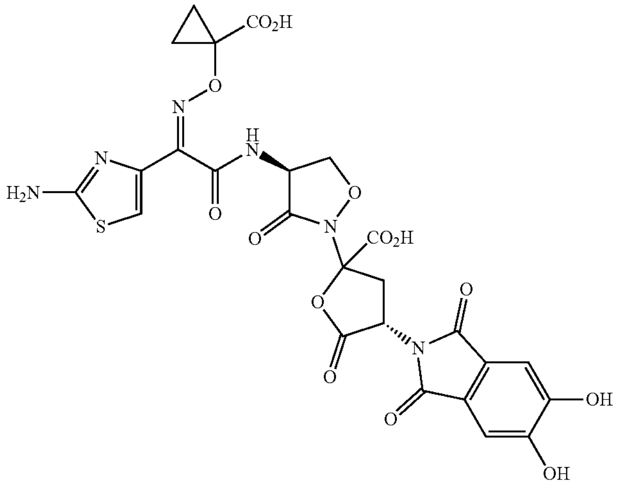 [SMILES: Nc1nc(/C(=N/OC2(C(=O)O)CC2)C(=O)N[C@H]2CON(C3(C(=O)O)C[C@H](N4C(=O)c5cc(O)c(O)cc5C4=O)C(=O)O3)C2=O)cs1] | (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 2 | 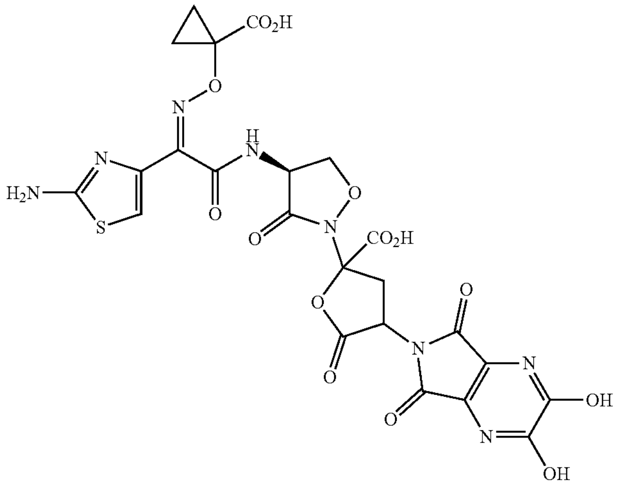 [SMILES: Nc1nc(/C(=N/OC2(C(=O)O)CC2)C(=O)N[C@H]2CON(C3(C(=O)O)CC(N4C(=O)c5nc(O)c(O)nc5C4=O)C(=O)O3)C2=O)cs1] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyrazin-6-yl)-5-oxooxolane-2-carboxylic acid |

TABLE 1-continued

| Cmpd No. | | Chemical Name |
|---|---|---|
| 3 | 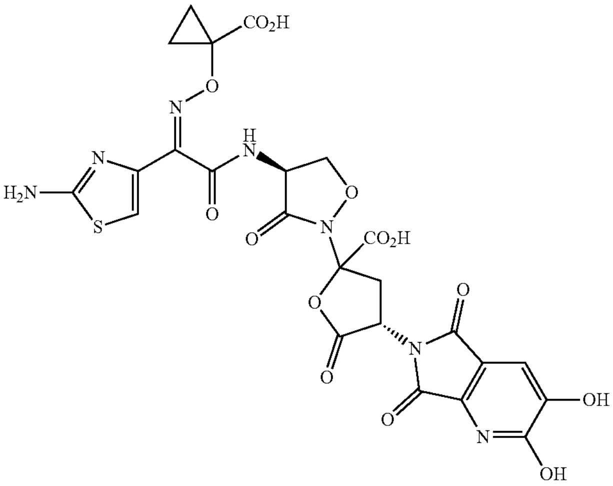 [SMILES: Nc1nc(/C(=N/OC2(C(=O)O)CC2)C(=O)N[C@H]2CON(C3(C(=O)O)C[C@H](N4C(=O)c5cc(O)c(O)nc5C4=O)C(=O)O3)C2=O)cs1] | (4S)-2-((S)-4-((Z)-2-(2-aminothiazol-4-yl)-2-((1-carboxycyclopropoxy)imino)acetamido)-3-oxoisoxazolidin-2-yl)-4-(2,3-dihydroxy-5,7-dioxo-5,7-dihydro-6H-pyrrolo[3,4-b]pyridin-6-yl)-5-oxotetrahydrofuran-2-carboxylic acid |
| 4 | 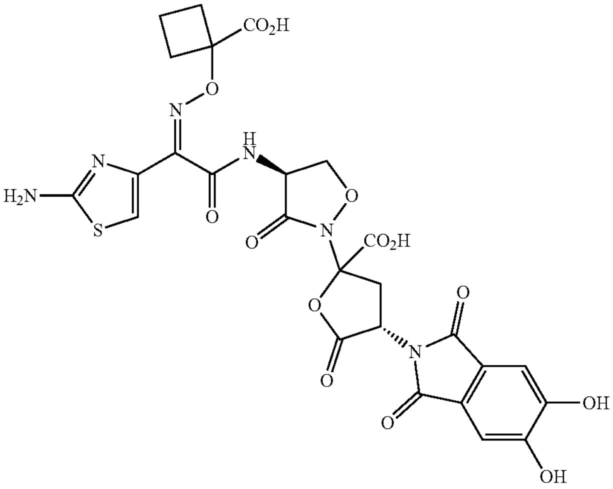 [SMILES: Nc1nc(/C(=N/OC2(C(=O)O)CCC2)C(=O)N[C@H]2CON(C3(C(=O)O)C[C@H](N4C(=O)c5cc(O)c(O)cc5C4=O)C(=O)O3)C2=O)cs1] | (4S)-2-[(4S)-4-{[(2Z)-2-(2-amino-1,3-thiazol-4-yl)-2-{[(1-carboxycyclobutyl)oxy]imino]acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 5 | 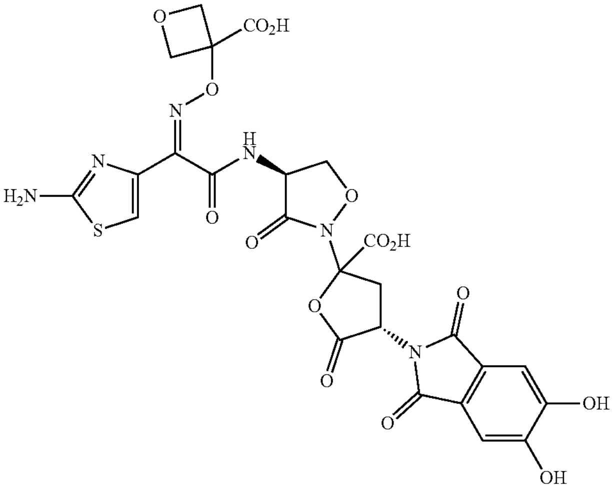 [SMILES: Nc1nc(/C(=N/OC2(C(=O)O)COC2)C(=O)N[C@H]2CON(C3(C(=O)O)C[C@H](N4C(=O)c5cc(O)c(O)cc5C4=O)C(=O)O3)C2=O)cs1] | (4S)-2-[(4S)-4-{[(2Z)-2-(2-amino-1,3-thiazol-4-yl)-2-{[(3-carboxyoxetan-3-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |

TABLE 1-continued

| Cmpd No. | | Chemical Name |
|---|---|---|
| 6 | 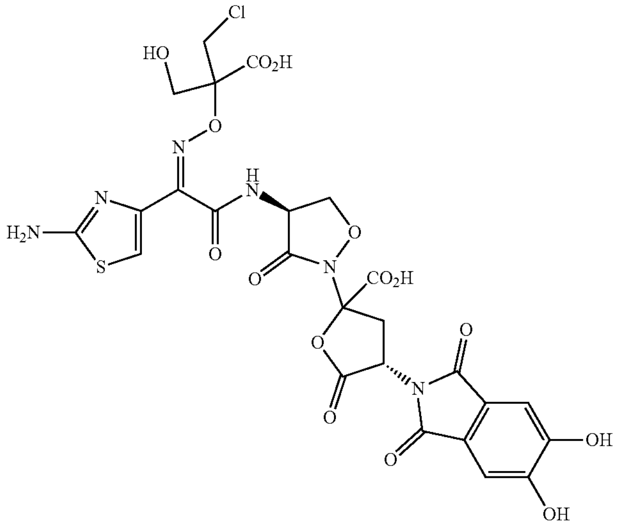 [SMILES: Nc1nc(/C(=N/OC(CO)(CCl)C(=O)O)C(=O)N[C@H]2CON(C3(C(=O)O)C[C@H](N4C(=O)c5cc(O)c(O)cc5C4=O)C(=O)O3)C2=O)cs1] | (4S)-2-[(4S)-4-{[(2Z)-2-(2-amino-1,3-thiazol-4-yl)-2-{[(2-carboxy-1-chloro-3-hydroxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 7 | 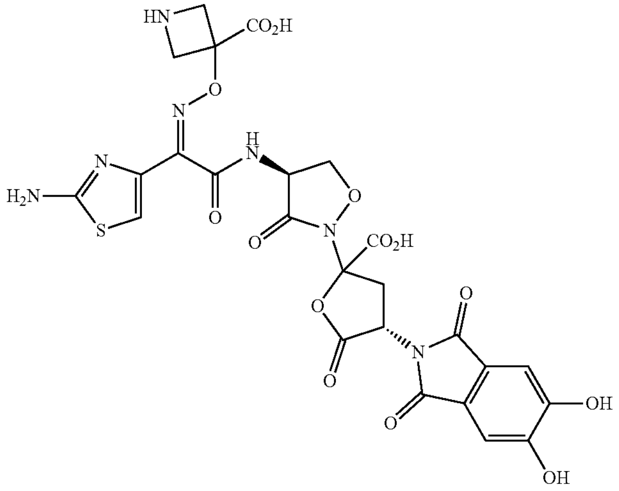 [SMILES: Nc1nc(/C(=N/OC2(C(=O)O)CNC2)C(=O)N[C@H]2CON(C3(C(=O)O)C[C@H](N4C(=O)c5cc(O)c(O)cc5C4=O)C(=O)O3)C2=O)cs1] | 3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)azetidine-3-carboxylic acid |
| 8 | 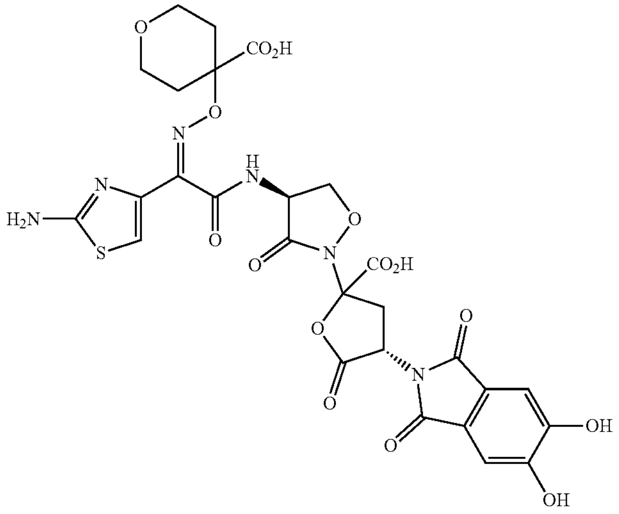 | 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
|---|---|---|
| 9 | 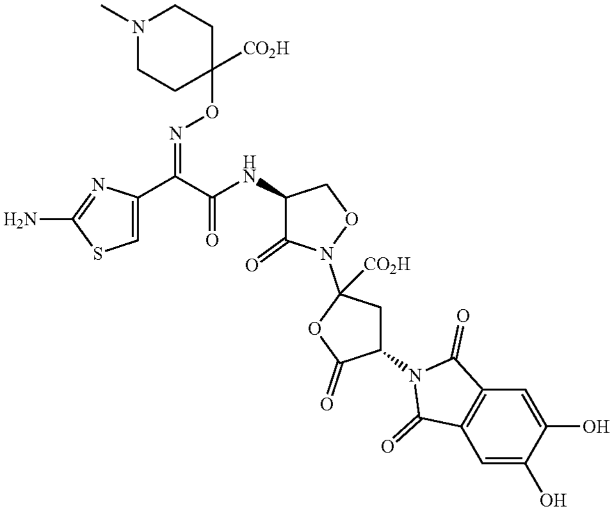 [SMILES: CN1CCC(O/N=C(\C(=O)N[C@H]2CON(C3(C(=O)O)C[C@H](N4C(=O)c5cc(O)c(O)cc5C4=O)C(=O)O3)C2=O)c2csc(N)n2)(C(=O)O)CC1] | 4-((((Z)-1-(2-aminothiazol-4-yl)-2-(((4S)-2-((4S)-2-carboxy-4-(5,6-dihydroxy-1,3-dioxoisoindolin-2-yl)-5-oxotetrahydrofuran-2-yl)-3-oxoisoxazolidin-4-yl)amino)-2-oxoethylidene)amino)oxy)-1-methylpiperidine-4-carboxylic acid |
| 10 | 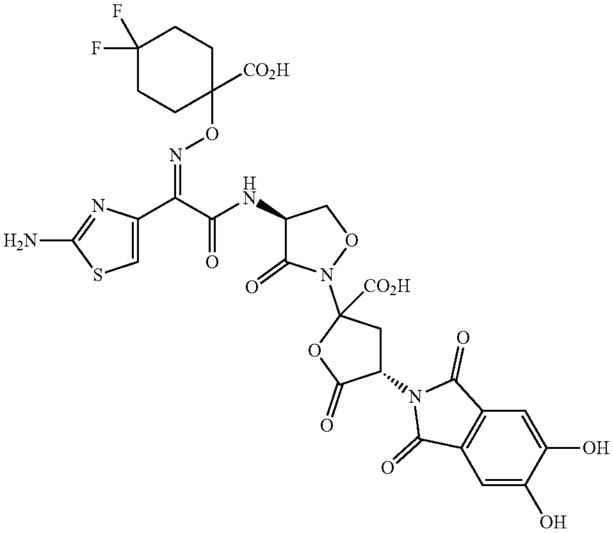 [SMILES: Nc1nc(/C(=N/OC2(C(=O)O)CCC(F)(Cl)CC2)C(=O)N[C@H]2CON(C3(C(=O)O)C[C@H](N4C(=O)c5cc(O)c(O)cc5C4=O)C(=O)O3)C2=O)cs1] | (4S)-2-((S)-4-((Z)-2-(2-aminothiazol-4-yl)-2-(((1-carboxy-4,4-difluorocyclohexyl)oxy)imino)acetamido)-3-oxoisoxazolidin-2-yl)-4-(5,6-dihydroxy-1,3-dioxoisoindolin-2-yl)-5-oxotetrahydrofuran-2-carboxylic acid |
| 11 | 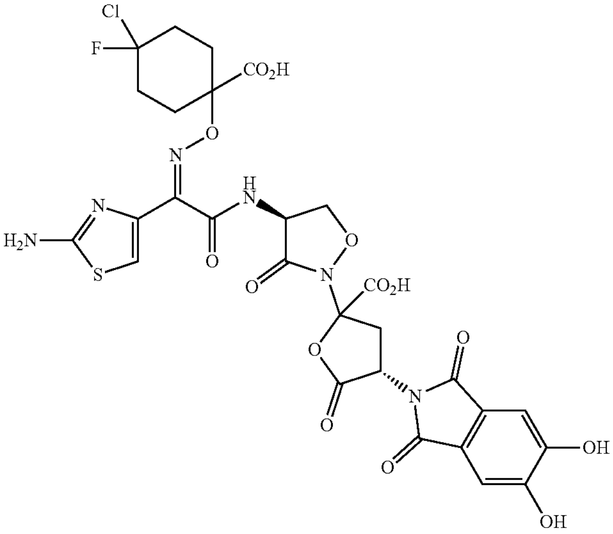 | (4S)-2-((S)-4-((Z)-2-(2-aminothiazol-4-yl)-2-(((1-carboxy-4-chloro-4-fluorocyclohexyl)oxy)imino)acetamido)-3-oxoisoxazolidin-2-yl)-4-(5,6-dihydroxy-1,3-dioxoisoindolin-2-yl)-5-oxotetrahydrofuran-2-carboxylic acid |

TABLE 1-continued

| Cmpd No. | | Chemical Name |
|---|---|---|
| 12 | 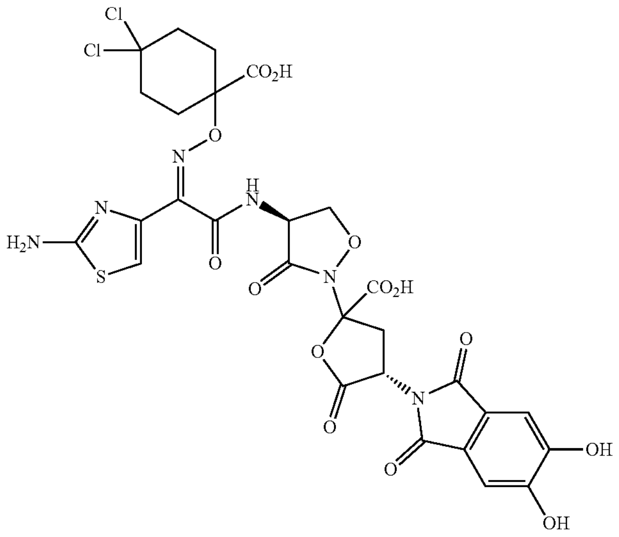 [SMILES: Nc1nc(/C(=N/OC2(C(=O)O)CCC(Cl)(Cl)CC2)C(=O)N[C@H]2CON(C3(C(=O)O)C[C@H](N4C(=O)c5cc(O)c(O)cc5C4=O)C(=O)O3)C2=O)cs1] | (4S)-2-((S)-4-((Z)-2-(2-aminothiazol-4-yl)-2-(((1-carboxy-4,4-dichlorocyclohexyl)oxy)imino)acetamido)-3-oxoisoxazolidin-2-yl)-4-(5,6-dihydroxy-1,3-dioxoisoindolin-2-yl)-5-oxotetrahydrofuran-2-carboxylic acid |
| 13 | 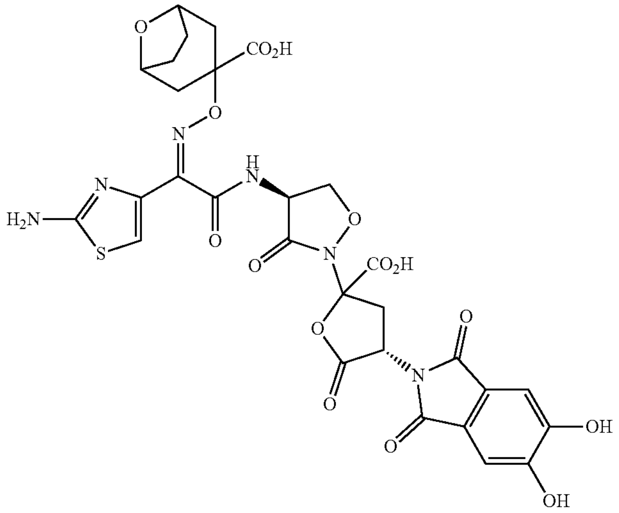 | 3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid |
| 14 | 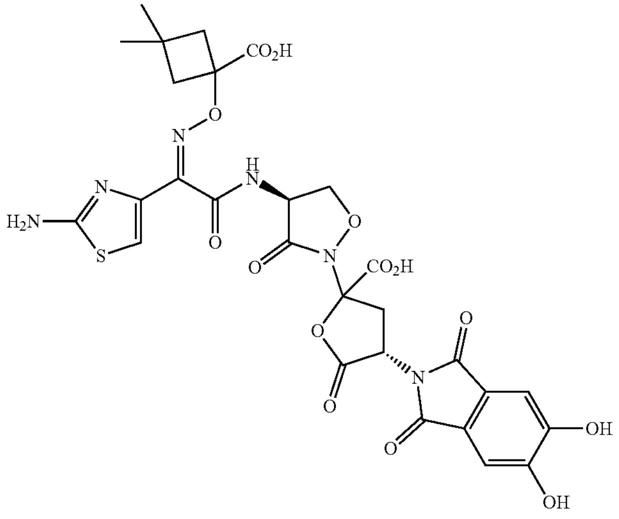 [SMILES: CC1(C)CC(O/N=C(\C(=O)N[C@H]2CON(C3(C(=O)O)C[C@H](N4C(=O)c5cc(O)c(O)cc5C4=O)C(=O)O3)C2=O)c2csc(N)n2)(C(=O)O)C1] | (4S)-2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |

TABLE 1-continued

| Cmpd No. | | Chemical Name |
|---|---|---|
| 15 | 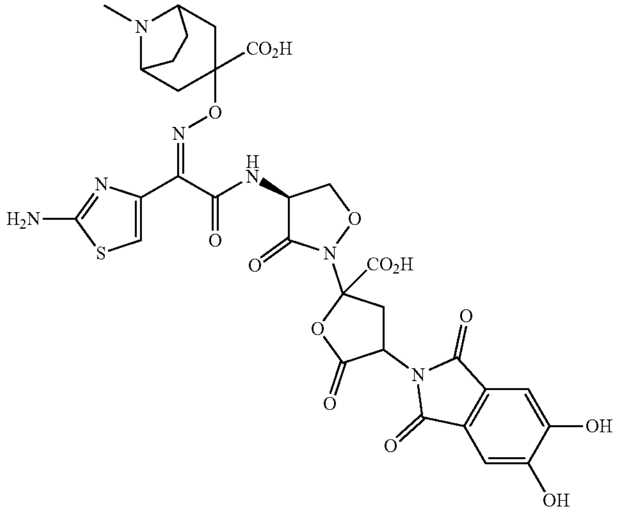 [SMILES: CN1C2CCC1CC(O/N=C(\C(=O)N[C@H]1CON(C3(C(=O)O)CC(N4C(=O)c5cc(O)c(O)cc5C4=O)C(=O)O3)C1=O)c1csc(N)n1)(C(=O)O)C2] | 3-({(Z)-[1-(2-amino-1,3-thiazol-4-yl)-2-({(4S)-2-[2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-8-methyl-8-azabicyclo[3.2.1]octane-3-carboxylic acid |
| 16 | 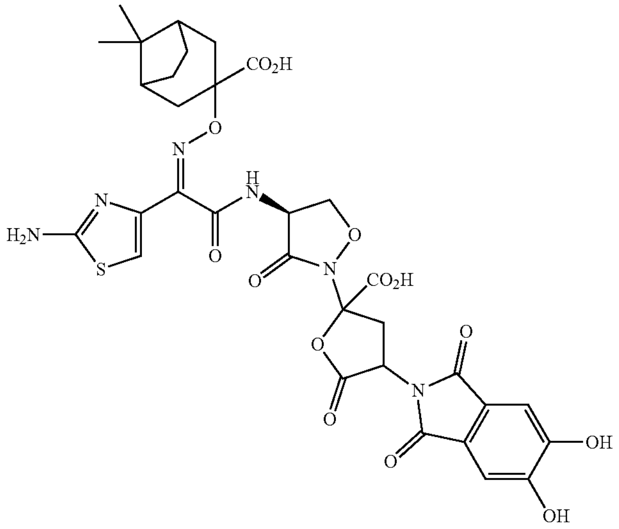 [SMILES: CC1(C)C2CCC1CC(O/N=C(\C(=O)N[C@H]1CON(C3(C(=O)O)CC(N4C(=O)c5cc(O)c(O)cc5C4=O)C(=O)O3)C1=O)c1csc(N)n1)(C(=O)O)C2] | 2-[(4S)-4-{[(2Z)-2-(2-amino-1,3-thiazol-4-yl)-2-{[(3-carboxy-8,8-dimethylbicyclo[3.2.1]octan-3-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 17 | 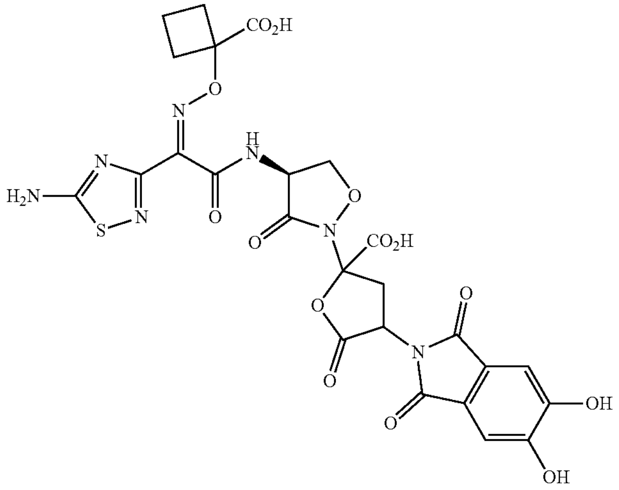 [SMILES: Nc1nc(/C(=N/OC2(C(=O)O)CCC2)C(=O)N[C@H]2CON(C3(C(=O)O)CC(N4C(=O)c5cc(O)c(O)cc5C4=O)C(=O)O3)C2=O)ns1] | 2-[(4S)-4-{[(2Z)-2-(5-amino-1,2,4-thiadiazol-3-yl)-2-{[(1-carboxycyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |

TABLE 1-continued

| Cmpd No. | | Chemical Name |
|---|---|---|
| 18 | 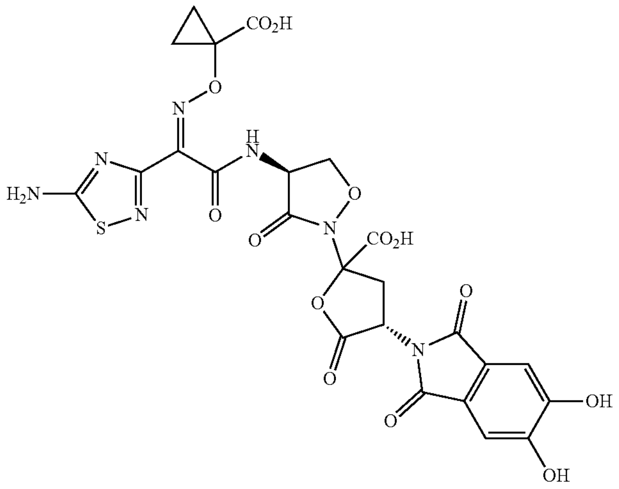 | (4S)-2-[(4S)-4-{[(2Z)-2-(5-amino-1,2,4-thiadiazol-3-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 19 | 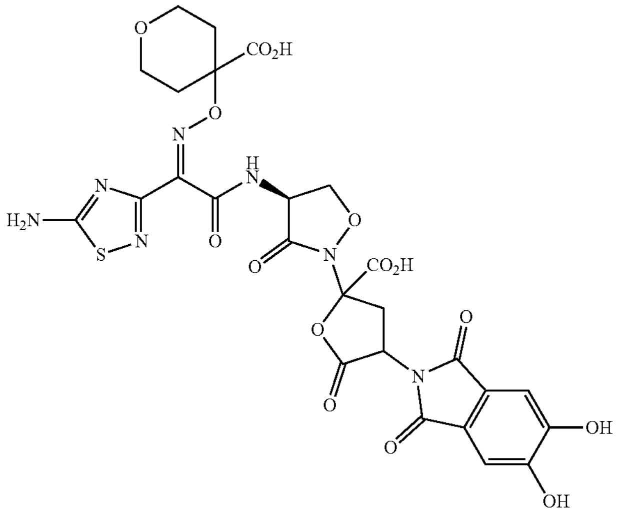 [SMILES: Nc1nc(/C(=N/OC2(C(=O)O)CCOCC2)C(=O)N[C@H]2CON(C3(C(=O)O)CC(N4C(=O)c5cc(O)c(O)cc5C4=O)C(=O)O3)C2=O)ns1] | 4-({(Z)-[1-(5-amino-1,2,4-thiadiazol-3-yl)-2-({(4S)-2-[2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid |
| 20 | 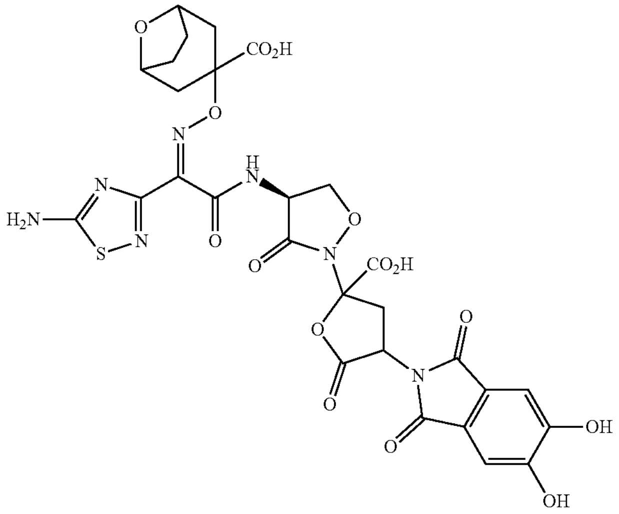 [SMILES: Nc1nc(/C(=N/OC2(C(=O)O)CC3CCC(C2)O3)C(=O)N[C@H]2CON(C3(C(=O)O)CC(N4C(=O)c5cc(O)c(O)cc5C4=O)C(=O)O3)C2=O)ns1] | 3-({(Z)-[1-(5-amino-1,2,4-thiadiazol-3-yl)-2-({(4S)-2-[2-carboxy-4-(5,6-dihydroxy-1,3-dioxo-1,3-dihydro-2H-isoindol-2-yl)-5-oxooxolan-2-yl]-3-oxo-1,2-oxazolidin-4-yl)amino)-2-oxoethylidene]amino}oxy)-8-oxabicyclo[3.2.1]octane-3-carboxylic acid |

TABLE 1-continued

| Cmpd No. | | Chemical Name |
|---|---|---|
| 21 | 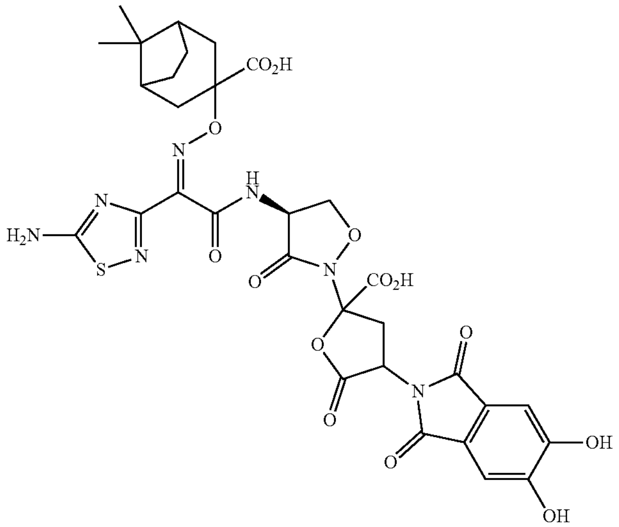 | 2-[(4S)-4-{[(2Z)-2-(5-amino-1,2,4-thiadiazol-3-yl)-2-{[(3-carboxy-8,8-dimethylbicyclo[3.2.1]octan-3-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 22 | 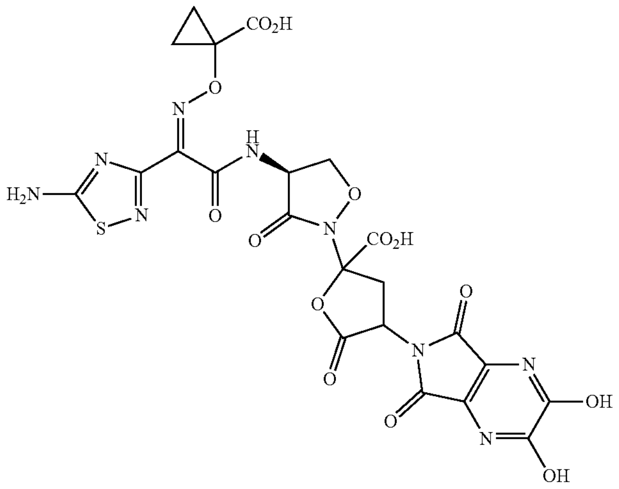 | 2-[(4S)-4-{[(2Z)-2-(5-amino-1,2,4-thiadiazol-3-yl)-2-{[(1-carboxycyclopropyl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyrazin-6-yl)-5-oxooxolane-2-carboxylic acid |
| 23 | 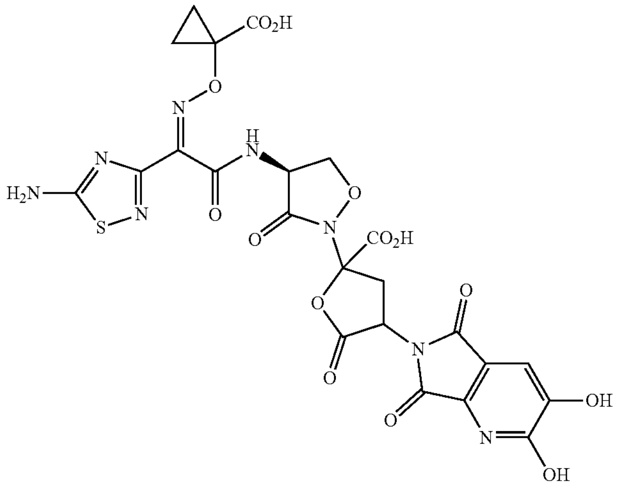 | 2-[(4S)-4-{[(2Z)-2-(5-amino-1,2,4-thiadiazol-3-yl)-2-{[(1-carboxycyclopropyl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid |

TABLE 1-continued

| Cmpd No. | | Chemical Name |
|---|---|---|
| 24 | 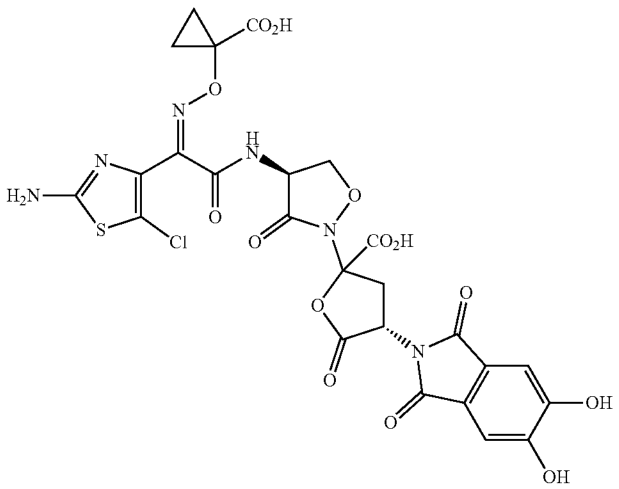 [SMILES: Nc1nc(/C(=N/OC2(C(=O)O)CC2)C(=O)N[C@H]2CON(C3(C(=O)O)C[C@H](N4C(=O)c5cc(O)c(O)cc5C4=O)C(=O)O3)C2=O)c(Cl)s1] | (4S)-2-[(4S)-4-{[(2Z)-2-(2-amino-5-chloro-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 25 | 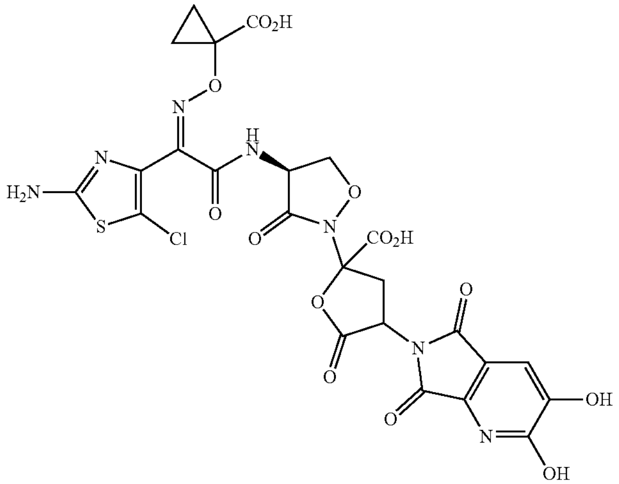 [SMILES: Nc1nc(/C(=N/OC2(C(=O)O)CC2)C(=O)N[C@H]2CON(C3(C(=O)O)CC(N4C(=O)c5cc(O)c(O)nc5C4=O)C(=O)O3)C2=O)c(Cl)s1] | 2-[(4S)-4-{[(2Z)-2-(2-amino-5-chloro-1,3-thiazol-4-yl)-2-{[(1-carboxycyclopropyl)oxy]imino)acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid |
| 26 | 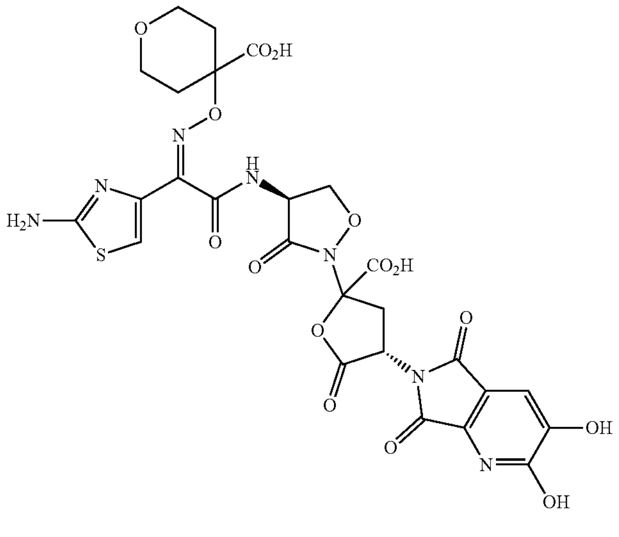 [SMILES: Nc1nc(/C(=N/OC2(C(=O)O)CCOCC2)C(=O)N[C@H]2CON(C3(C(=O)O)C[C@H](N4C(=O)c5cc(O)c(O)nc5C4=O)C(=O)O3)C2=O)cs1] | 4-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
|---|---|---|
| 27 | 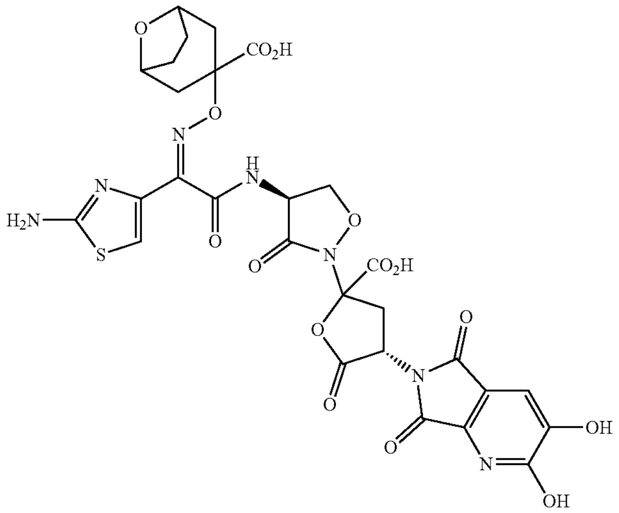 [SMILES: Nc1nc(/C(=N/OC2(C(=O)O)CC3CCC(C2)O3)C(=O)N[C@H]2CON(C3(C(=O)O)C[C@H](N4C(=O)c5cc(O)c(O)nc5C4=O)C(=O)O3)C2=O)cs1] | 3-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl]amino)-2-oxoethylidene]amino}oxy)-8-oxabicyclo[3.2.1]octane-3-carboxylic acid |
| 28 | 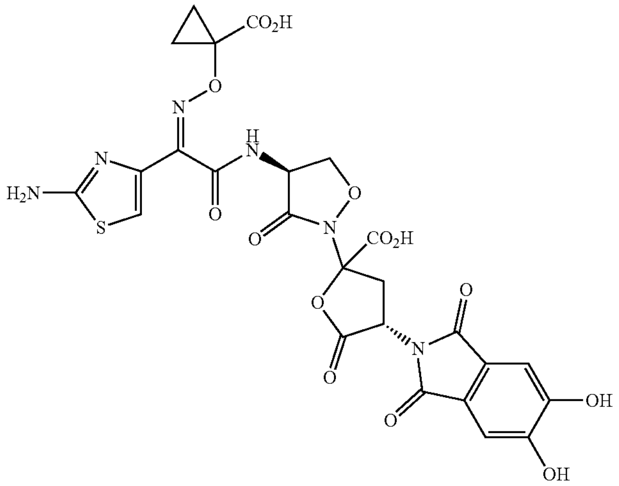 | (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid |
| 29 | 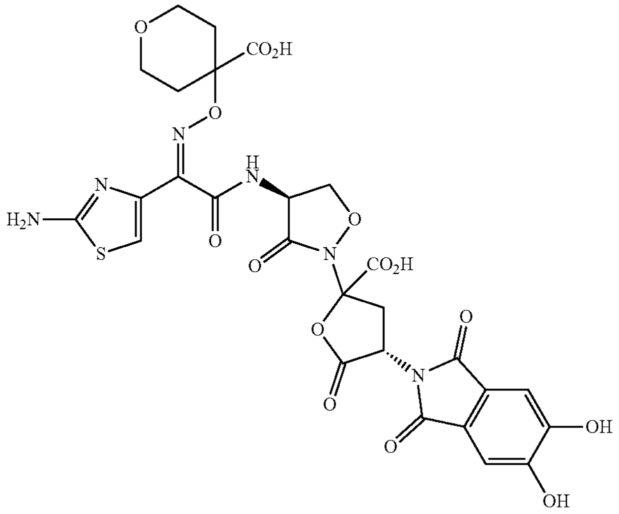 [SMILES: Nc1nc(/C(=N/OC2(C(=O)O)CCOCC2)C(=O)N[C@H]2CON(C3(C(=O)O)C[C@H](N4C(=O)c5cc(O)c(O)cc5C4=O)C(=O)O3)C2=O)cs1] | 4({(Z)-[1-(2-amino-1,3-thiazol-4yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
|---|---|---|
| 30 | 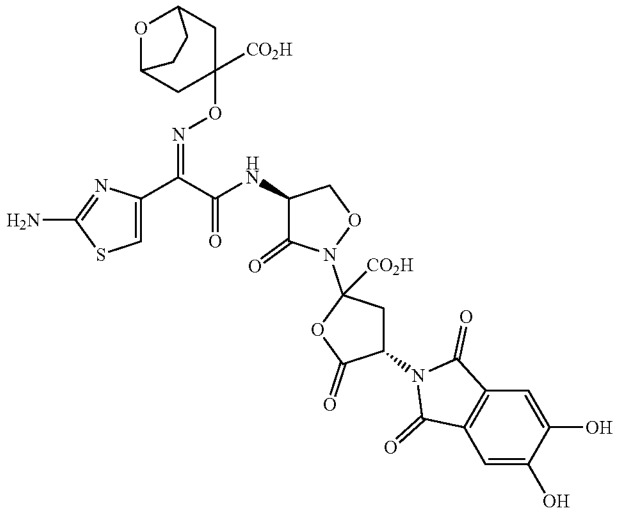 [SMILES: Nc1nc(/C(=N/OC2(C(=O)O)CC3CCC(C2)O3)C(=O)N[C@H]2CON(C3(C(=O)O)C[C@H](N4C(=O)c5cc(O)c(O)cc5C4=O)C(=O)O3)C2=O)cs1] | 3-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid |
| 31 | 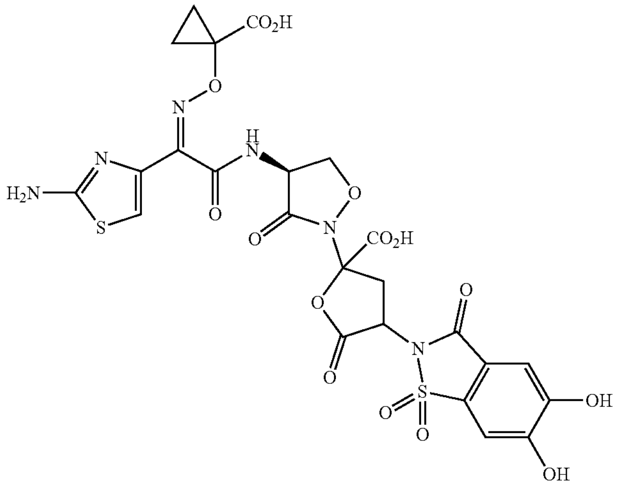 [SMILES: Nc1nc(/C(=N/OC2(C(=O)O)CC2)C(=O)N[C@H]2CON(C3(C(=O)O)CC(N4C(=O)c5cc(O)c(O)cc5S4(=O)=O)C(=O)O3)C2=O)cs1] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid |
| 32 | 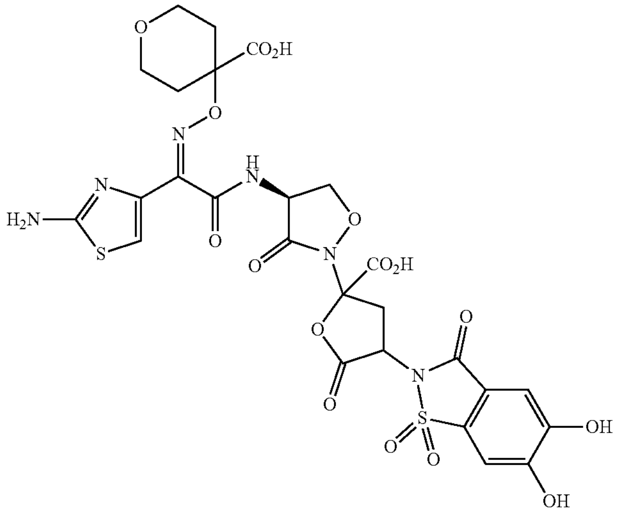 [SMILES: Nc1nc(/C(=N/OC2(C(=O)O)CCOCC2)C(=O)N[C@H]2CON(C3(C(=O)O)CC(N4C(=O)c5cc(O)c(O)cc5S4(=O)=O)C(=O)O3)C2=O)cs1] | 4-({(Z)-[1-(2-amino-1,3-thiazol-4-yl)-2-({(4S)-2-[2-carboxy-4-(5,6-dihydroxy-1,1,3-trioxo-1,3-dihydro-2H-1λ$^6$,2-benzothiazol-2-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
| --- | --- | --- |
| 33 | 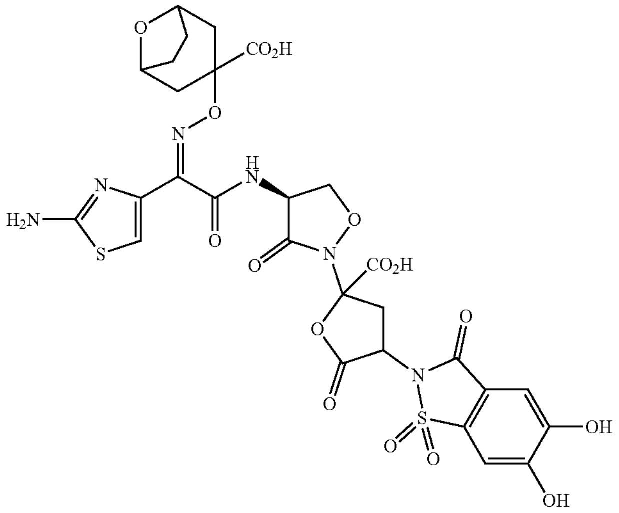 [SMILES: Nc1nc(/C(=N/OC2(C(=O)O)CC3CCC(C2)O3)C(=O)N[C@H]2CON(C3(C(=O)O)CC(N4C(=O)c5cc(O)c(O)cc5S4(=O)=O)C(=O)O3)C2=O)cs1] | 3-({(Z)-[1-(2-amino-1,3-thiazol-4-yl)-2-({(4S)-2-[2-carboxy-4-(5,6-dihydroxy-1,1,3-trioxo-1,3-dihydro-2H-1)5,2-benzothiazol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid |
| 34 | 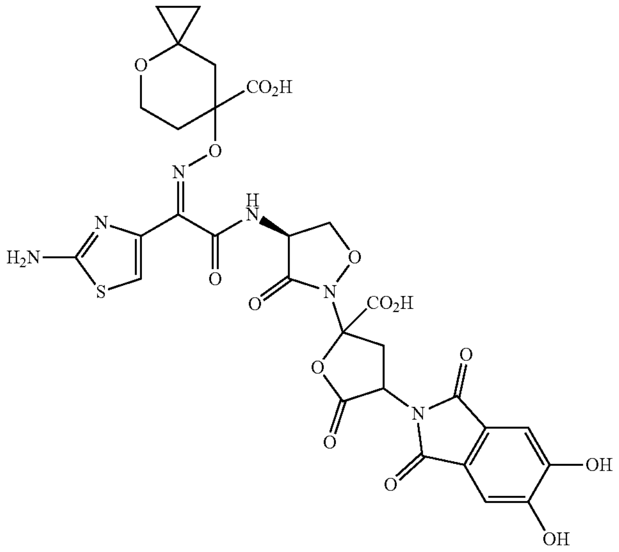 [SMILES: Nc1nc(/C(=N/OC2(C(=O)O)CCOC3(CC3)C2)C(=O)N[C@H]2CON(C3(C(=O)O)CC(N4C(=O)c5cc(O)c(O)cc5C4=O)C(=O)O3)C2=O)cs1] | 7-({(Z)-[1-(2-amino-1,3-thiazol-4-yl)-2-({(4S)-2-[2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-4-oxaspiro[2.5]octane-7-carboxylic acid |
| 35 | 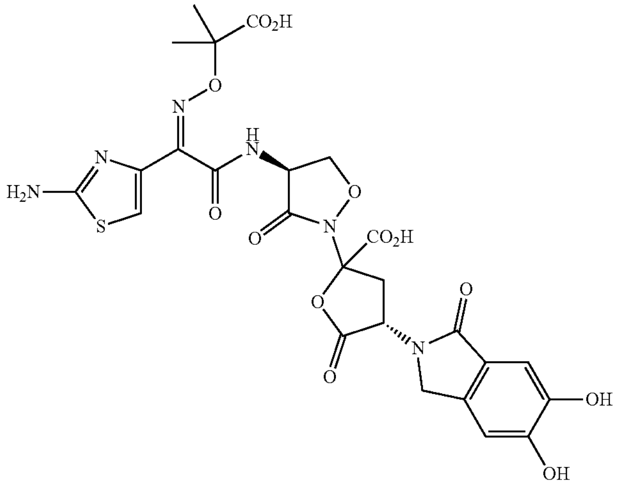 [SMILES: CC(C)(O/N=C(\C(=O)N[C@H]1CON(C2(C(=O)O)C[C@H](N3Cc4cc(O)c(O)cc4C3=O)C(=O)O2)C1=O)c1csc(N)n1)C(=O)O] | (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid |

TABLE 1-continued

| Cmpd No. | | Chemical Name |
|---|---|---|
| 36 | 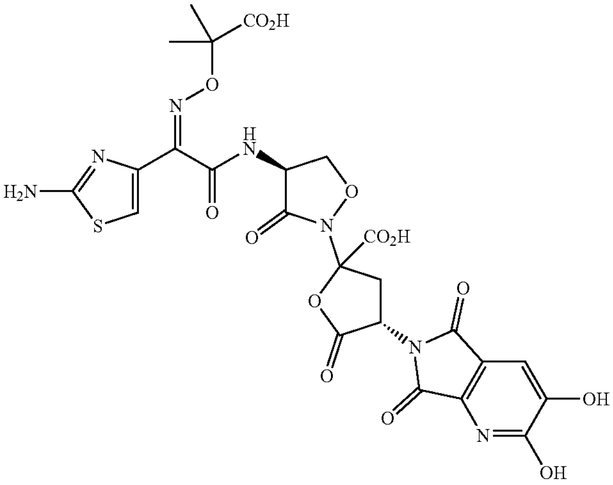 [SMILES: CC(C)(O/N=C(\C(=O)N[C@H]1CON(C2(C(=O)O)C[C@H](N3C(=O)c4cc(O)c(O)nc4C3=O)C(=O)O2)C1=O)c1csc(N)n1)C(=O)O] | (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid |
| 37 | 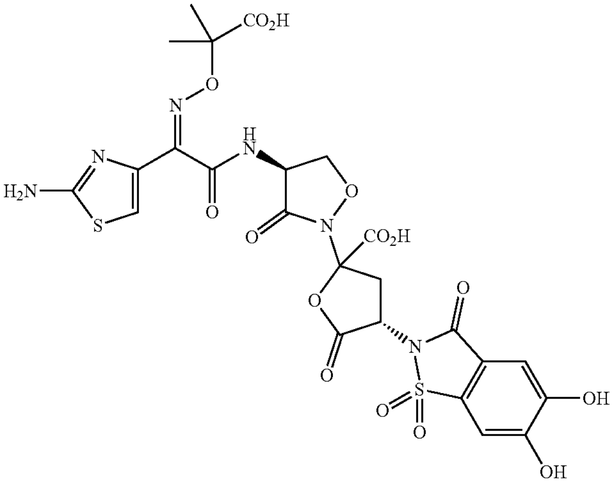 [SMILES: CC(C)(O/N=C(\C(=O)N[C@H]1CON(C2(C(=O)O)C[C@H](N3C(=O)c4cc(O)c(O)cc4S3(=O)=O)C(=O)O2)C1=O)c1csc(N)n1)C(=O)O] | (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$, 2-benzothiazol-2-yl)-5-oxooxolane-2-carboxylic acid |
| 38 | 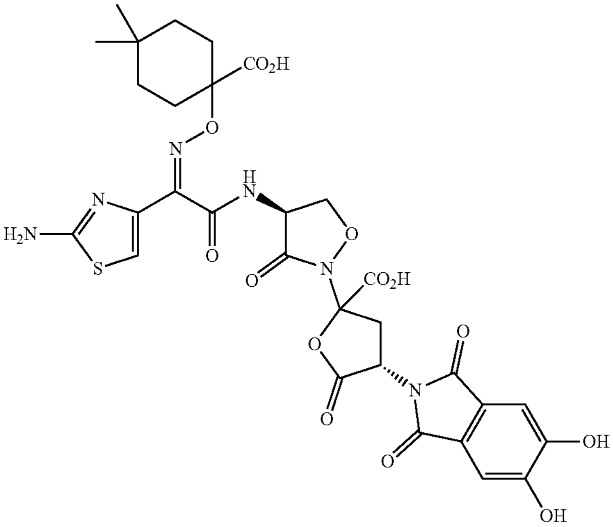 [SMILES: CC1(C)CCC(O/N=C(\C(=O)N[C@H]2CON(C3(C(=O)O)C[C@H](N4C(=O)c5cc(O)c(O)cc5C4=O)C(=O)O3)C2=O)c2csc(N)n2)(C(=O)O)CC1] | (4S)-2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |

TABLE 1-continued

| Cmpd No. | | Chemical Name |
|---|---|---|
| 39 | 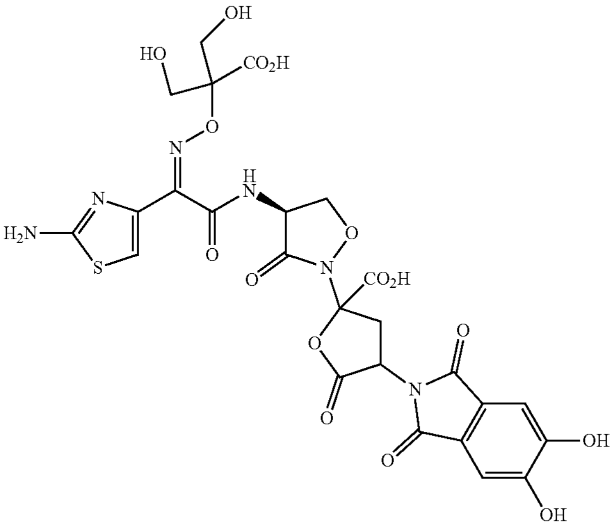 [SMILES: Nc1nc(/C(=N/OC(CO)(CO)C(=O)O)C(=O)N[C@H]2CON(C3(C(=O)O)CC(N4C(=O)c5cc(O)c(O)cc5C4=O)C(=O)O3)C2=O)cs1] | 2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 40 | 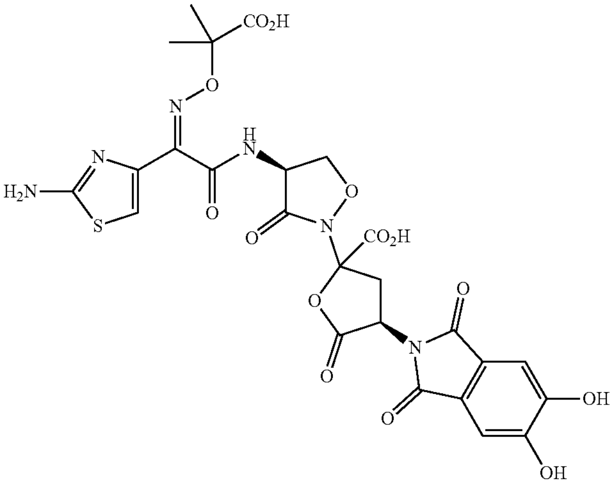 [SMILES: CC(C)(O/N=C(\C(=O)N[C@H]1CON(C2(C(=O)O)C[C@@H](N3C(=O)c4cc(O)c(O)cc4C3=O)C(=O)O2)C1=O)c1csc(N)n1)C(=O)O] | (4R)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid |
| 41 | 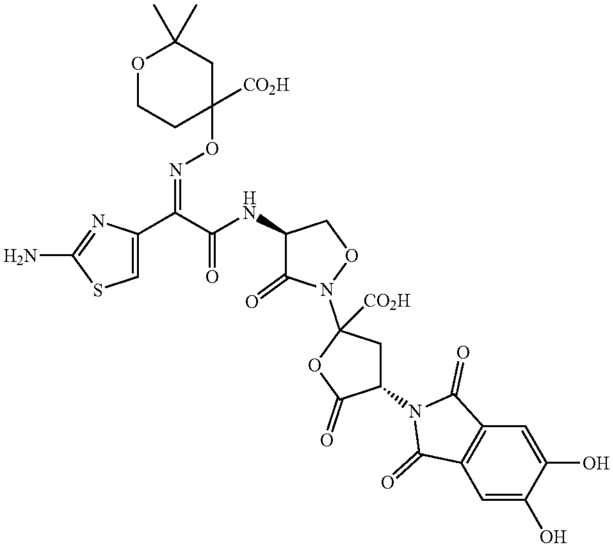 [SMILES: CC1(C)CC(O/N=C(\C(=O)N[C@H]2CON(C3(C(=O)O)C[C@H](N4C(=O)c5cc(O)c(O)cc5C4=O)C(=O)O3)C2=O)c2csc(N)n2)(C(=O)O)CCO1] | 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,2-dimethyloxane-4-carboxylic acid |

TABLE 1-continued

| Cmpd No. | | Chemical Name |
|---|---|---|
| 42 | 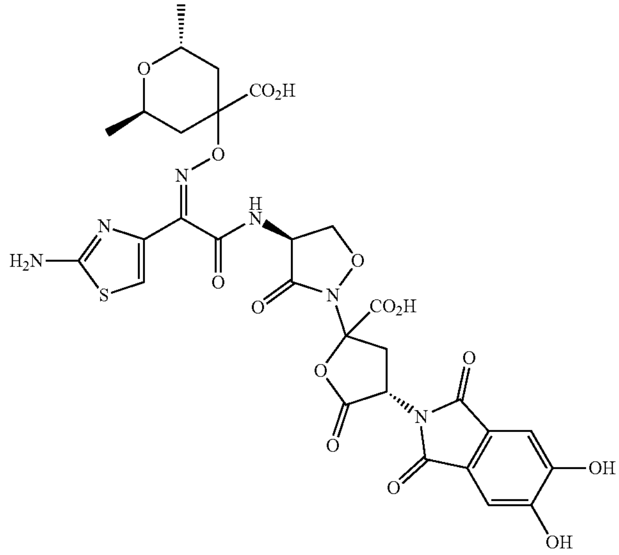 [SMILES: C[C@@H]1CC(O/N=C(\C(=O)N[C@H]2CON(C3(C(=O)O)C[C@H](N4C(=O)c5cc(O)c(O)cc5C4=O)C(=O)O3)C2=O)c2csc(N)n2)(C(=O)O)C[C@@H](C)O1] | (2R,6R)-4-({(Z)-[1-(2-amino-1,3-thiazol-4-yl)2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,6-dimethyloxane-4-carboxylic acid |
| 43 | 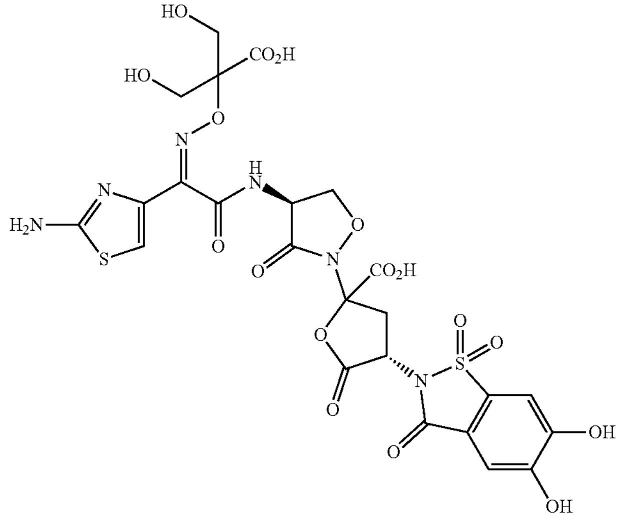 [SMILES: Nc1nc(/C(=N/OC(CO)(CO)C(=O)O)C(=O)N[C@H]2CON(C3(C(=O)O)C[C@H](N4C(=O)c5cc(O)c(O)cc5S4(=O)=O)C(=O)O3)C2=O)cs1] | (4S)-2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid |
| 44 | 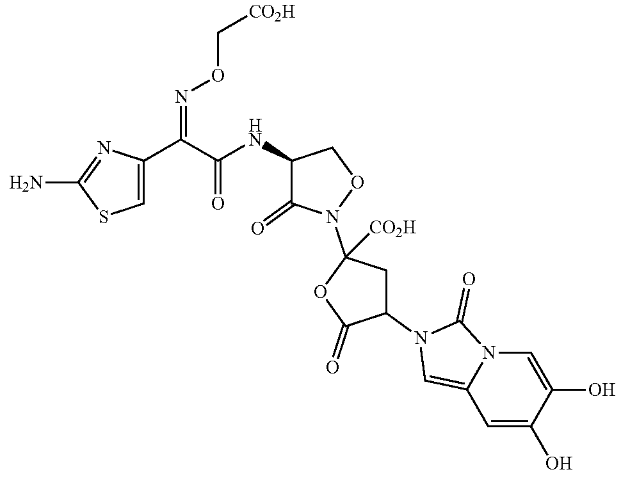 [SMILES: Nc1nc(/C(=N/OCC(=O)O)C(=O)N[C@H]2CON(C3(C(=O)O)CC(n4cc5cc(O)c(O)cn5c4=O)C(=O)O3)C2=O)cs1] | 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(6,7-dihydroxy-3-oxoimidazo(1,5-a]pyridin-2(3H)-yl)-5-oxooxolane-2-carboxylic acid |

TABLE 1-continued

| Cmpd No. | | Chemical Name |
|---|---|---|
| 45 | 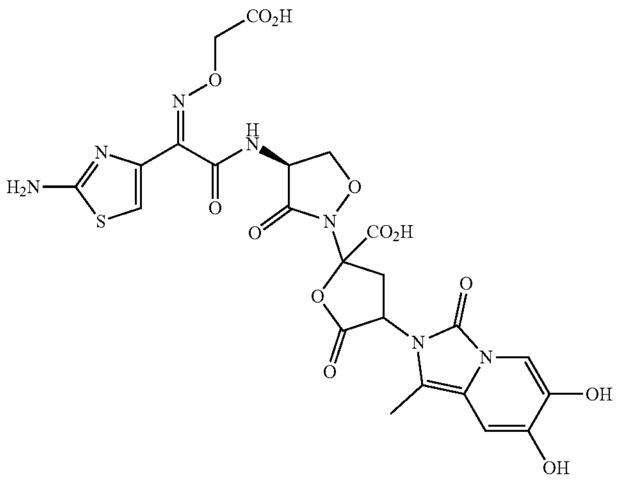 [SMILES: Cc1c2cc(O)c(O)cn2c(=O)n1C1CC(C(=O)O)(N2OC[C@H](NC(=O)/C(=N\OCC(=O)O)c3csc(N)n3)C2=O)OC1=O] | 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(6,7-dihydroxy-1-methyl-3-oxoimidazo[1,5-a]pyridin-2(3H)-yl)-5-oxooxolane-2-carboxylic acid |
| 46 | 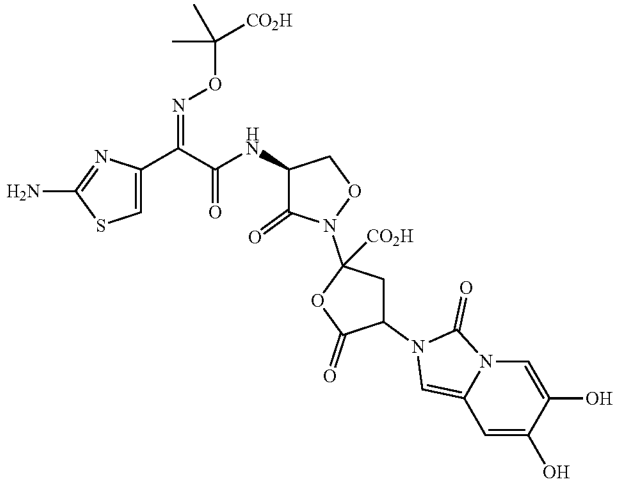 [SMILES: CC(C)(O/N=C(\C(=O)N[C@H]1CON(C2(C(=O)O)CC(n3cc4cc(O)c(O)cn4c3=O)C(=O)O2)C1=O)c1csc(N)n1)C(=O)O] | 2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 47 | 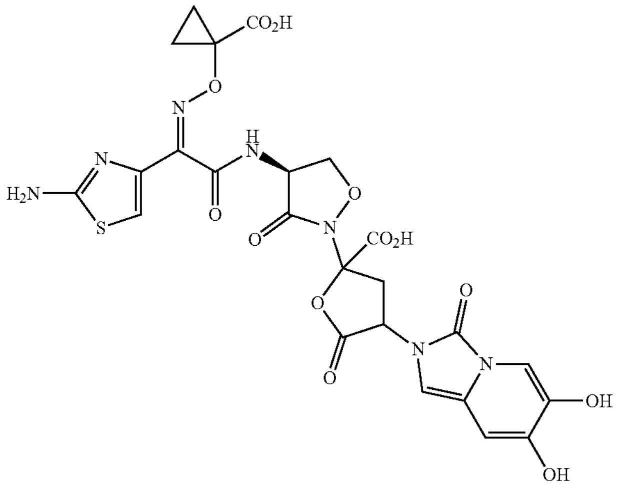 [SMILES: Nc1nc(/C(=N/OC2(C(=O)O)CC2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |

TABLE 1-continued

| Cmpd No. | | Chemical Name |
|---|---|---|
| 48 | 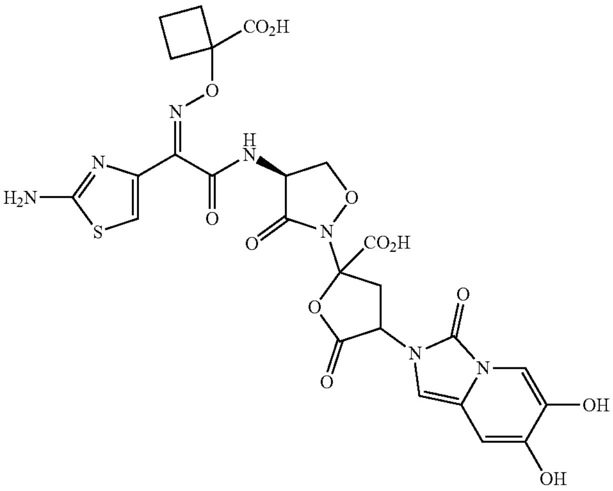 [SMILES: Nc1nc(/C(=N/OC2(C(=O)O)CCC2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(1-carboxycyclobutyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 49 | 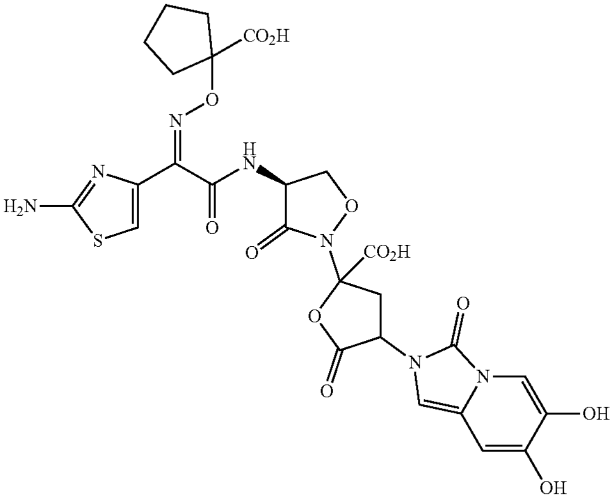 [SMILES: Nc1nc(/C(=N/OC2(C(=O)O)CCCC2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(1-carboxycyclopentyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 50 | 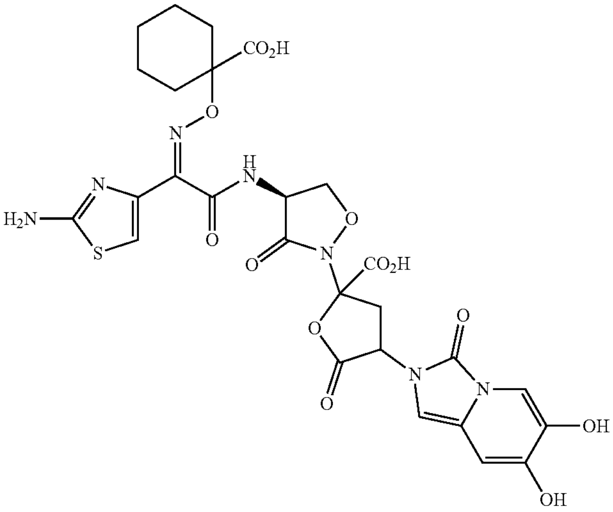 [SMILES: Nc1nc(/C(=N/OC2(C(=O)O)CCCCC2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(1-carboxycyclohexyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |

TABLE 1-continued

| Cmpd No. | | Chemical Name |
|---|---|---|
| 51 | 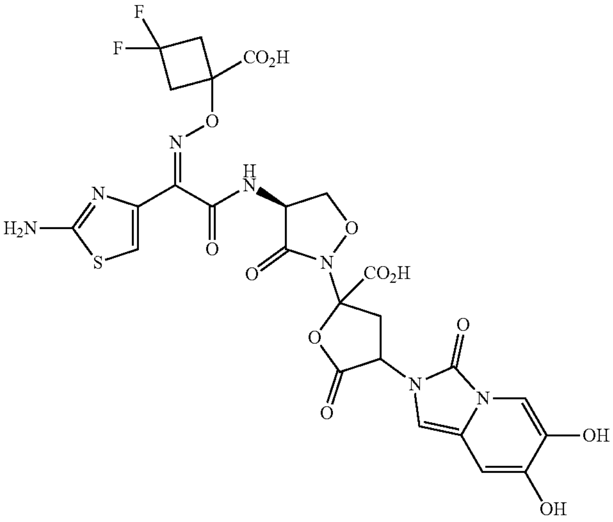 [SMILES: Nc1nc(/C(=N/OC2(C(=O)O)CC(F)(F)C2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(1-carboxy-3,3-difluorocyclobutyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 52 | 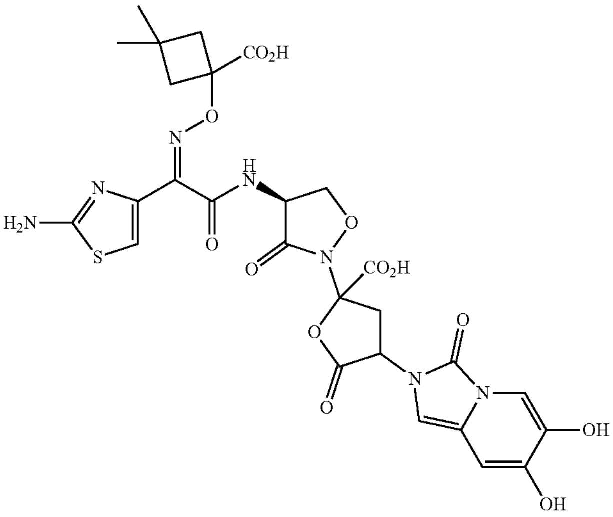 [SMILES: CC1(C)CC(O/N=C(\C(=O)N[C@H]2CON(C3(C(=O)O)CC(n4cc5cc(O)c(O)cn5c4=O)C(=O)O3)C2=O)c2csc(N)n2)(C(=O)O)C1] | 2-[4S)-4-{[(2Z)-2-(2-amino-1,3-thiazol-4-y)-2-{[(1-carboxy-3,3-dimethylcyclobutyl)oxy]imino]acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 53 | 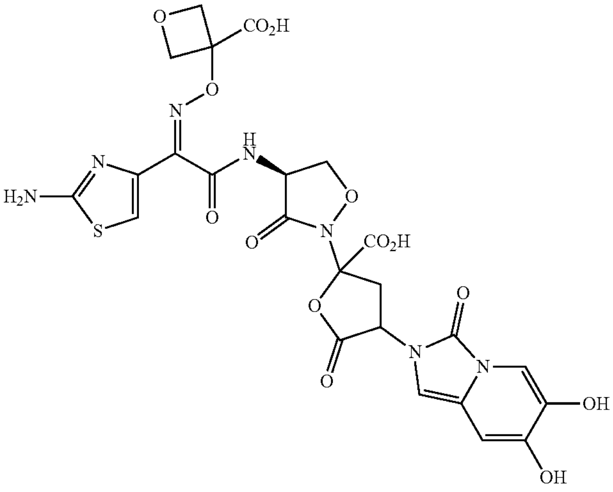 [SMILES: Nc1nc(/C(=N/OC2(C(=O)O)COC2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-(((3-carboxyoxetan-3-yl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |

TABLE 1-continued

| Cmpd No. | | Chemical Name |
|---|---|---|
| 54 | 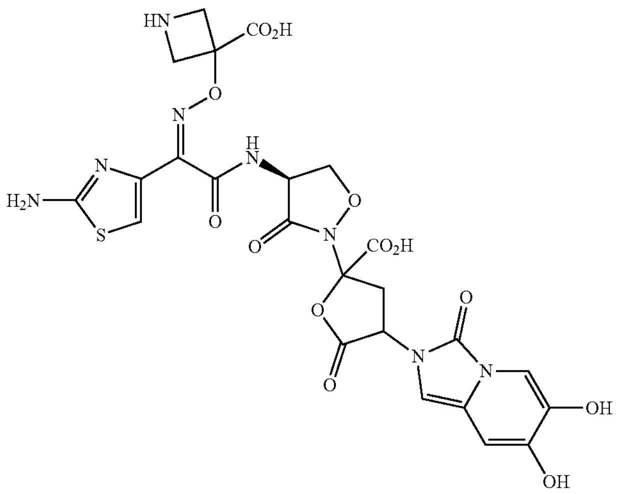 [SMILES: Nc1nc(/C(=N/OC2(C(=O)O)CNC2)C(=O)N[C@H]2CON(C3(C(=O)O)CC(n4cc5cc(O)c(O)cn5c4=O)C(=O)O3)C2=O)cs1] | 3-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl)amino)-2-oxoethylidene]amino}oxy)azetidine-3-carboxylic acid |
| 55 | 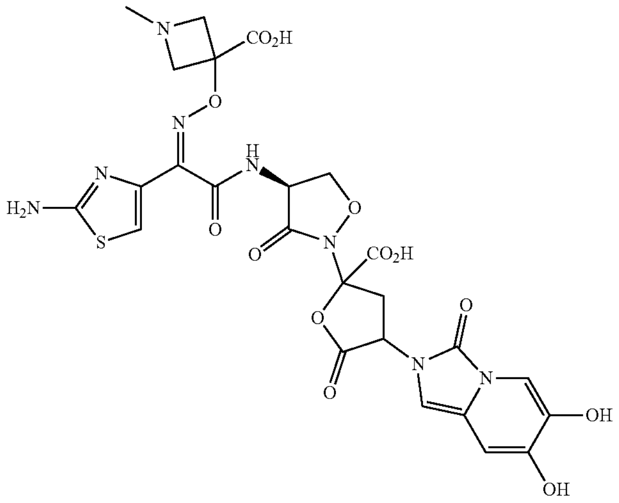 [SMILES: CN1CC(O/N=C(\C(=O)N[C@H]2CON(C3(C(=O)O)CC(n4cc5cc(O)c(O)cn5c4=O)C(=O)O3)C2=O)c2csc(N)n2)(C(=O)O)C1] | 3-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl)amino)-2-oxoethylidene]amino}oxy)-1-methylazetidine-3-carboxylic acid |
| 56 | 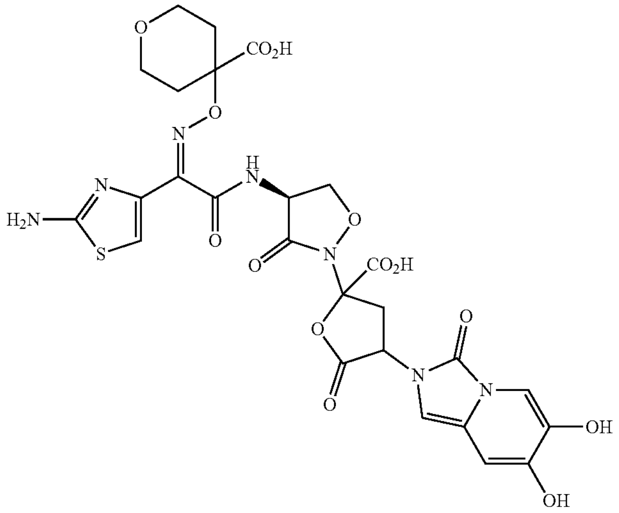 [SMILES: Nc1nc(/C(=N/OC2(C(=O)O)CCOCC2)C(=O)N[C@H]2CON(C3(C(=O)O)CC(n4cc5cc(O)c(O)cn5c4=O)C(=O)O3)C2=O)cs1] | 4-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
|---|---|---|
| 57 | 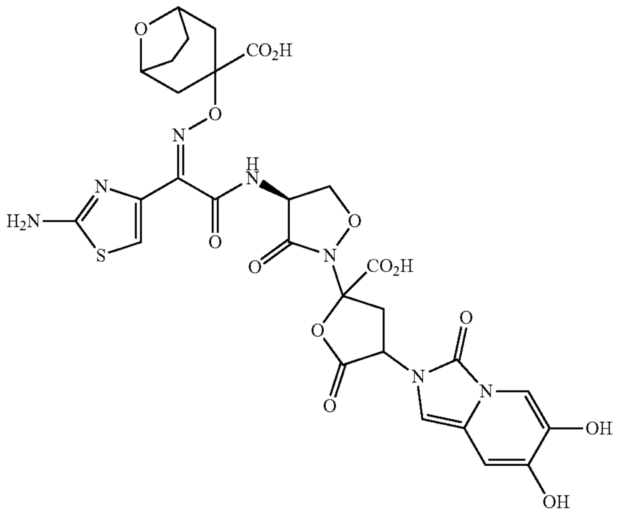 [SMILES: Nc1nc(/C(=N/OC2(C(=O)O)CC3CCC(C2)O3)C(=O)N[C@H]2CON(C3(C(=O)O)CC(n4cc5cc(O)c(O)cn5c4=O)C(=O)O3)C2=O)cs1] | 3-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl)amino)-2-oxoethylidene]amino}oxy)-8-oxabicyclo[3.2.1]octane-3-carboxylic acid |
| 58 | 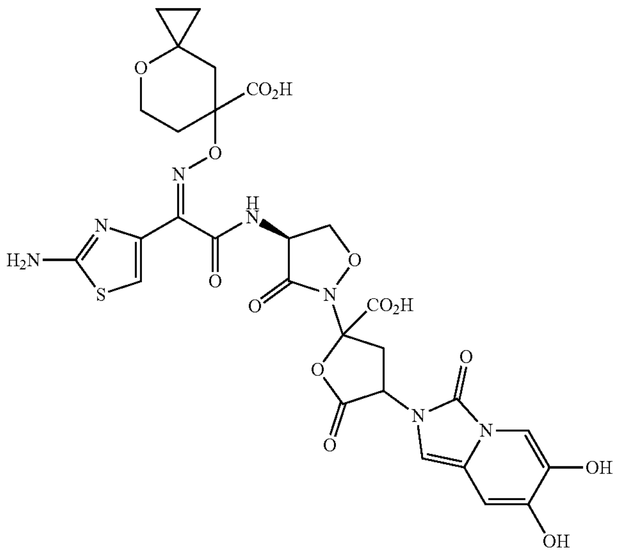 [SMILES: Nc1nc(/C(=N/OC2(C(=O)O)CCOC3(CC3)C2)C(=O)N[C@H]2CON(C3(C(=O)O)CC(n4cc5cc(O)c(O)cn5c4=O)C(=O)O3)C2=O)cs1] | 7-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl}amino)-2-oxoethylidene]amino}oxy)-4-oxaspiro[2.5]octane-7-carboxylic acid |
| 59 | 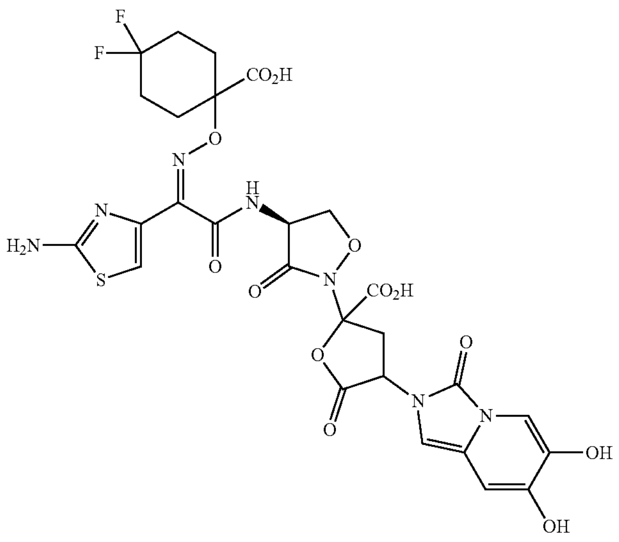 [SMILES: Nc1nc(/C(=N/OC2(C(=O)O)CCC(F)(F)CC2)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |

TABLE 1-continued

| Cmpd No. | | Chemical Name |
|---|---|---|
| 60 | 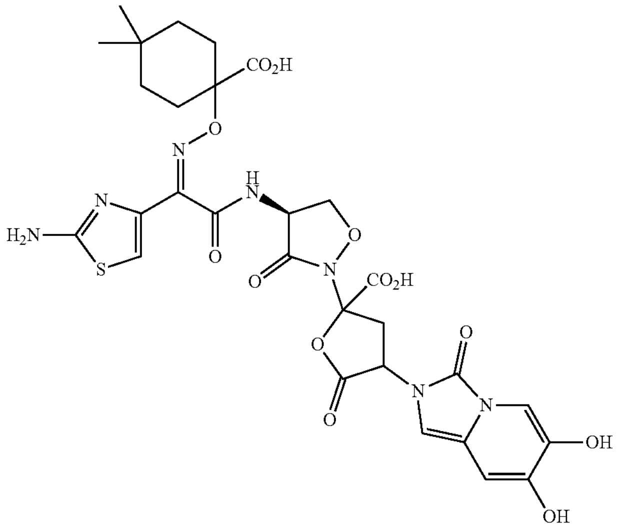 [SMILES: CC1(C)CCC(O/N=C(\C(=O)N[C@H]2CON(C3(C(=O)O)CC(n4cc5cc(O)c(O)cn5c4=O)C(=O)O3)C2=O)c2csc(N)n2)(C(=O)O)CC1] | 2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 61 | 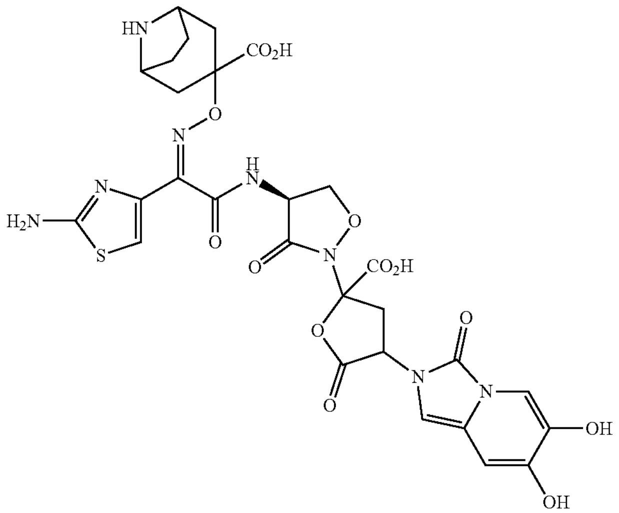 [SMILES: Nc1nc(/C(=N/OC2(C(=O)O)CC3CCC(C2)N3)C(=O)N[C@H]2CON(C3(C(=O)O)CC(n4cc5cc(O)c(O)cn5c4=O)C(=O)O3)C2=O)cs1] | 3-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl)amino)-2-oxoethylidene]amino}oxy)-8-azabicyclo[3.2.1]octane-3-carboxylic acid |
| 62 | 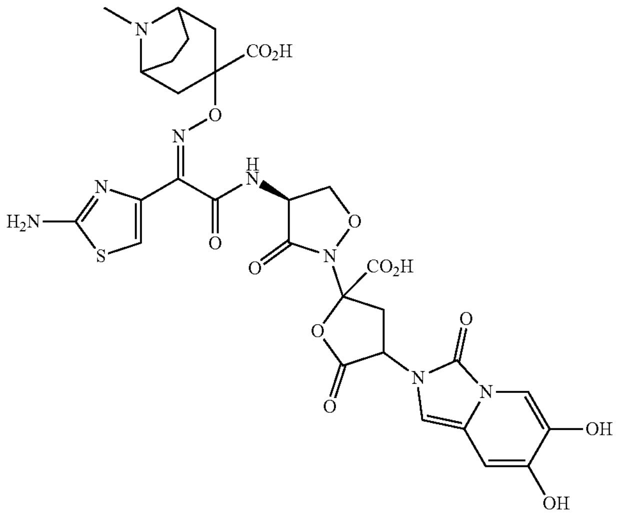 [SMILES: CN1C2CCC1CC(O/N=C(\C(=O)N[C@H]1CON(C3(C(=O)O)CC(n4cc5cc(O)c(O)cn5c4=O)C(=O)O3)C1=O)c1csc(N)n1)(C(=O)O)C2] | 3-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl}amino)-2-oxoethylidene]amino}oxy)-8-methyl-8-azabicyclo[3.2.1]octane-3-carboxylic acid |

TABLE 1-continued

| Cmpd No. | | Chemical Name |
|---|---|---|
| 63 | 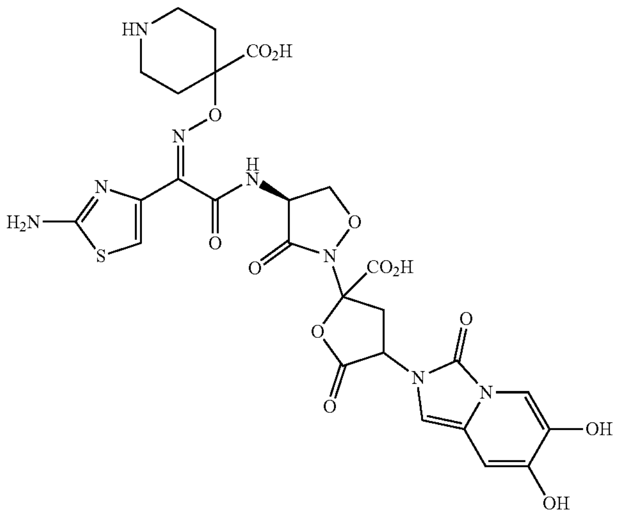 [SMILES: Nc1nc(/C(=N/OC2(C(=O)O)CCNCC2)C(=O)N[C@H]2CON(C3(C(=O)O)CC(n4cc5cc(O)c(O)cn5c4=O)C(=O)O3)C2=O)cs1] | 4-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl)amino)-2-oxoethylidene]amino}oxy)piperidine-4-carboxylic acid |
| 64 | 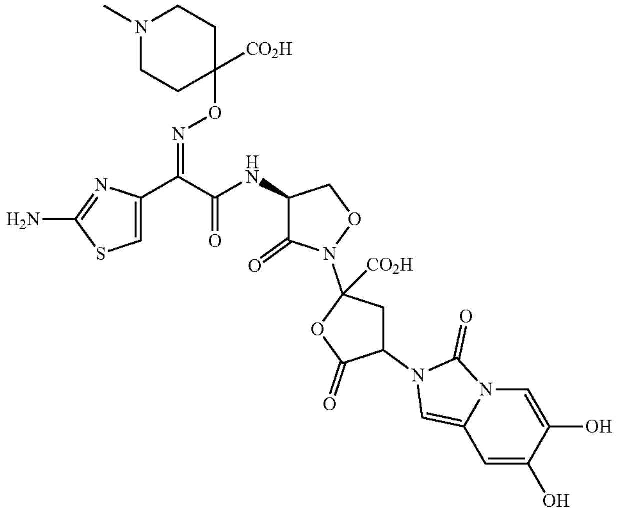 [SMILES: CN1CCC(O/N=C(\C(=O)N[C@H]2CON(C3(C(=O)O)CC(n4cc5cc(O)c(O)cn5c4=O)C(=O)O3)C2=O)c2csc(N)n2)(C(=O)O)CC1] | 4-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl}amino)-2-oxoethylidene]amino}oxy)-1-methylpiperidine-4-carboxylic acid |
| 65 | 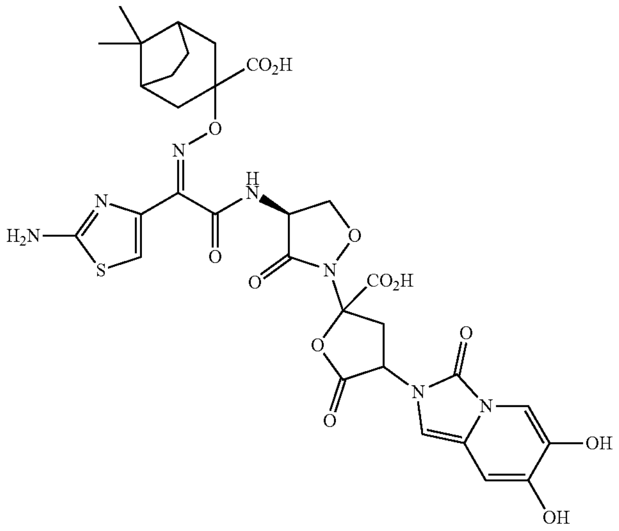 [SMILES: CC1(C)C2CCC1CC(O/N=C(\C(=O)N[C@H]1CON(C3(C(=O)O)CC(n4cc5cc(O)c(O)cn5c4=O)C(=O)O3)C1=O)c1csc(N)n1)(C(=O)O)C2] | 2-[(4S)-4-{[(2Z)-2-(2-amino-1,3-thiazol-4-yl)-2-{[(3-carboxy-8,8-dimethylbicyclo[3.2.1]octan-3-yl)oxy]imino}acetyl]amino}-3-oxo-1,2-oxazolidin-2-yl]-4-(6,7-dihydroxy-3-oxoimidazo(1,5-a]pyridin-2(3H)-yl)-5-oxooxolane-2-carboxylic acid |

TABLE 1-continued

| Cmpd No. | | Chemical Name |
|---|---|---|
| 66 | 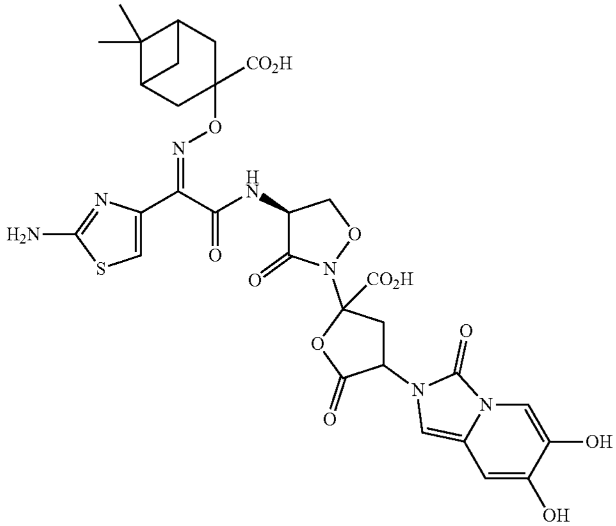 [SMILES: CC1(C)C2CC1CC(O/N=C(\C(=O)N[C@H]1CON(C3(C(=O)O)CC(n4cc5cc(O)c(O)cn5c4=O)C(=O)O3)C1=O)c1csc(N)n1)(C(=O)O)C2] | 2-[(4S)-4-{[(2Z)-2-(2-amino-1,3-thiazol-4-yl)-2-{[(3-carboxy-6,6-dimethylbicyclo[3.1.1]heptan-3-yl)oxy]imino}acetyl]amino)-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 67 | 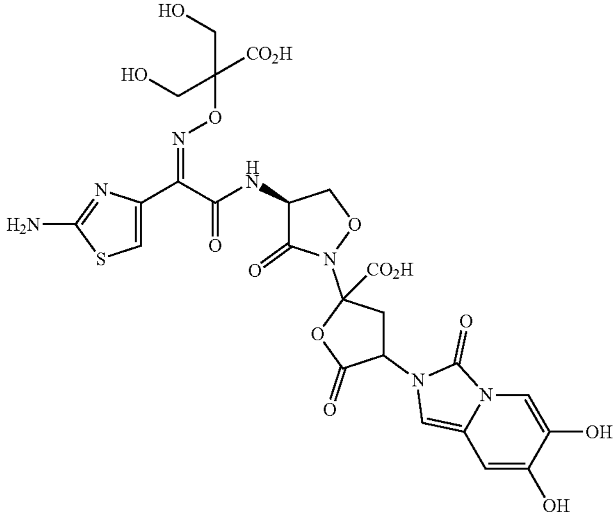 [SMILES: Nc1nc(/C(=N/OC(CO)(CO)C(=O)O)C(=O)N[C@H]2CON(C3(C(=O)O)CC(n4cc5cc(O)c(O)cn5c4=O)C(=O)O3)C2=O)cs1] | 2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(6,7-dihydroxy-3-oxoimidazo[1,5-a]pyridin-2(3H)-yl)-5-oxooxolane-2-carboxylic acid |
| 68 | 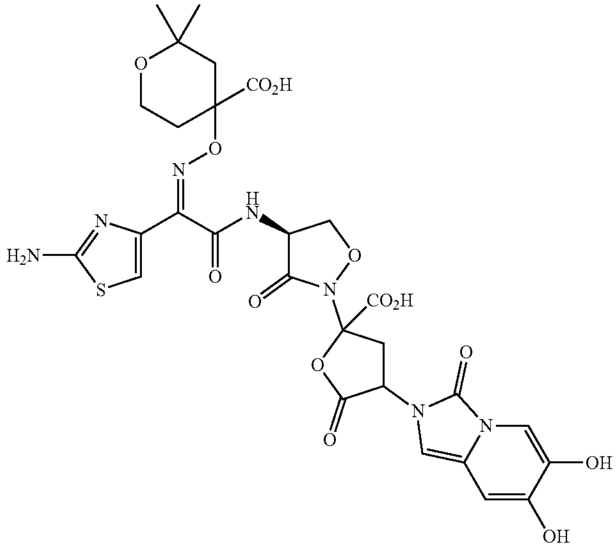 [SMILES: CC1(C)CC(O/N=C(\C(=O)N[C@H]2CON(C3(C(=O)O)CC(n4cc5cc(O)c(O)cn5c4=O)C(=O)O3)C2=O)c2csc(N)n2)(C(=O)O)CCO1] | 4-({(Z)-[1-(2-amino-1,3-thiazol-4-yl)-2-({(4S)-2-[2-carboxy-4-(6,7-dihydroxy-3-oxoimidazo[1,5-a]pyridin-2(3H)-yl)-5-oxooxolan-2-yl]-3-oxo-1,2-oxazolidin-4-yl}amino)-2-oxoethylidene]amino}oxy)-2,2-dimethyloxane-4-carboxylic acid |

TABLE 1-continued

| Cmpd No. | | Chemical Name |
|---|---|---|
| 69 | 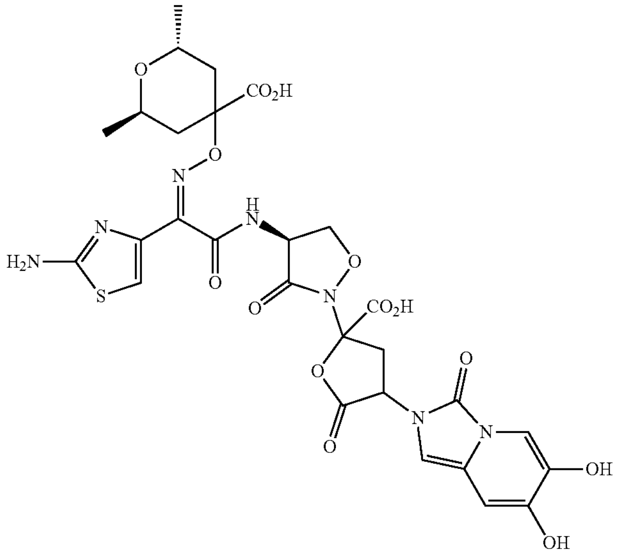 [SMILES: C[C@@H]1CC(O/N=C(\C(=O)N[C@H]2CON(C3(C(=O)O)CC(n4cc5cc(O)c(O)cn5c4=O)C(=O)O3)C2=O)c2csc(N)n2)(C(=O)O)C[C@@H](C)O1] | (2R,6R)-4-({(Z)-[1-(2-amino-1,3-thiazol-4-yl)-2-({(4S)-2-[2-carboxy-4-(6,7-dihydroxy-3-oxoimidazo(1,5-a]pyridin-2(3H)-yl)-5-oxooxolan-2-yl]-3-oxo-1,2-oxazolidin-4-yl)amino)-2-oxoethylidene]amino}oxy)-2,6-imethyloxane-4-carboxylic acid |
| 70 | 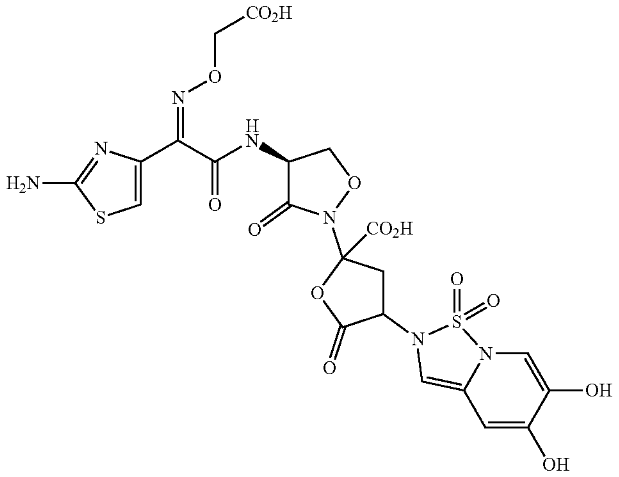 [SMILES: Nc1nc(/C(=N/OCC(=O)O)C(=O)N[C@H]2CON(C3(C(=O)O)CC(N4C=C5C=C(O)C(O)=CN5S4(=O)=O)C(=O)O3)C2=O)cs1] | 2-[(4S)-4-({(2Z)-2-(2-amino-1,3-thiazol-4-yl)-2-[(carboxymethoxy)imino]acetyl)amino)-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 71 | 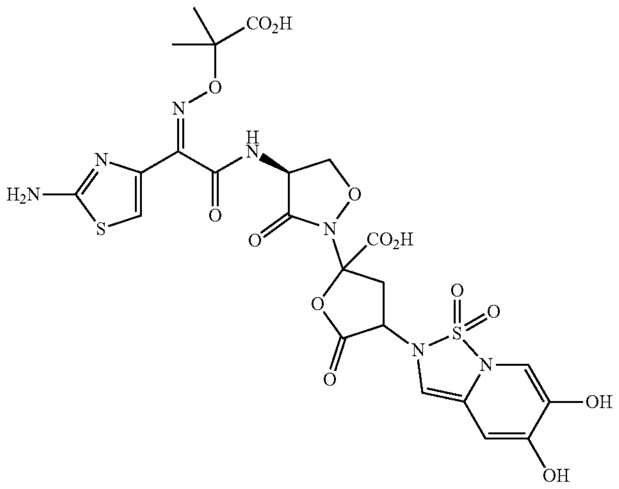 [SMILES: CC(C)(O/N=C(\C(=O)N[C@H]1CON(C2(C(=O)O)CC(N3C=C4C=C(O)C(O)=CN4S3(=O)=O)C(=O)O2)C1=O)c1csc(N)n1)C(=O)O] | 2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-o]pyridin-2(1H)-yl)-5-oxooxolane-2-carboxylic acid |

TABLE 1-continued

| Cmpd No. | | Chemical Name |
|---|---|---|
| 72 | 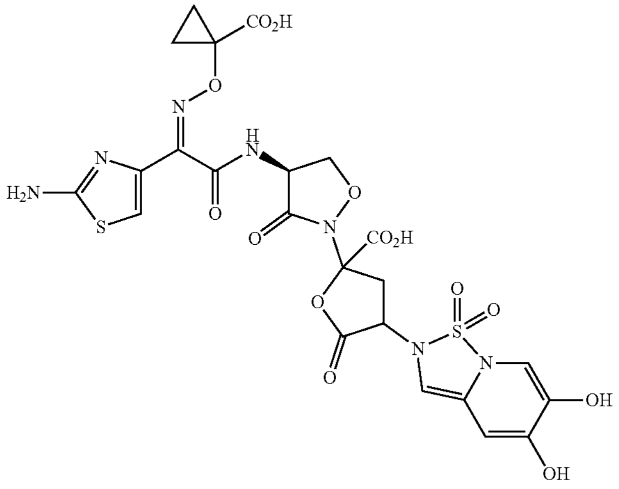 [SMILES: Nc1nc(/C(=N/OC2(C(=O)O)CC2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 73 | 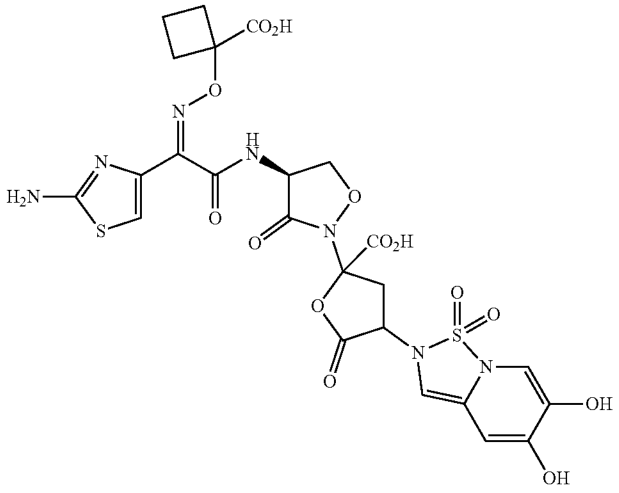 [SMILES: Nc1nc(/C(=N/OC2(C(=O)O)CCC2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-(((1-carboxycyclobutyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 74 | 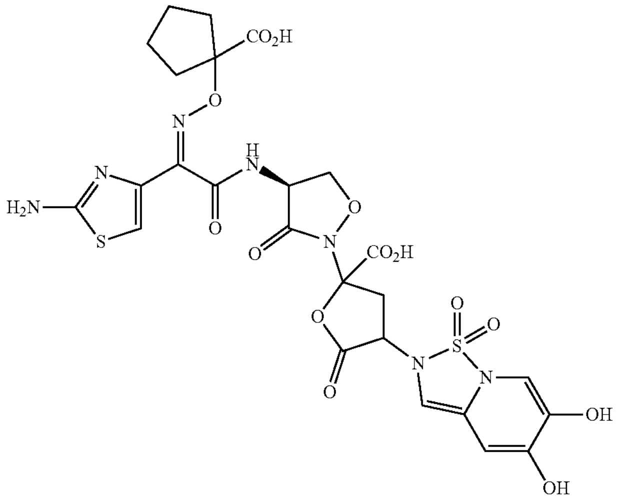 [SMILES: Nc1nc(/C(=N/OC2(C(=O)O)CCCC2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-y)-2-{[(1-carboxycyclopentyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |

TABLE 1-continued

| Cmpd No. | | Chemical Name |
|---|---|---|
| 75 | 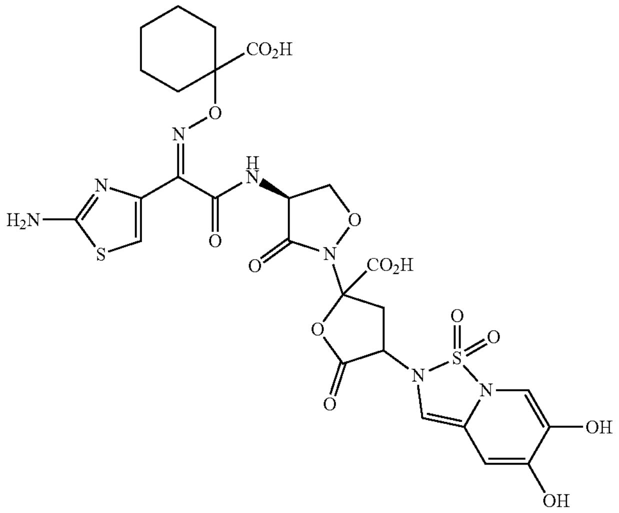 [SMILES: Nc1nc(/C(=N/OC2(C(=O)O)CCCCC2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-{1(1-carboxycyclohexyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 76 | 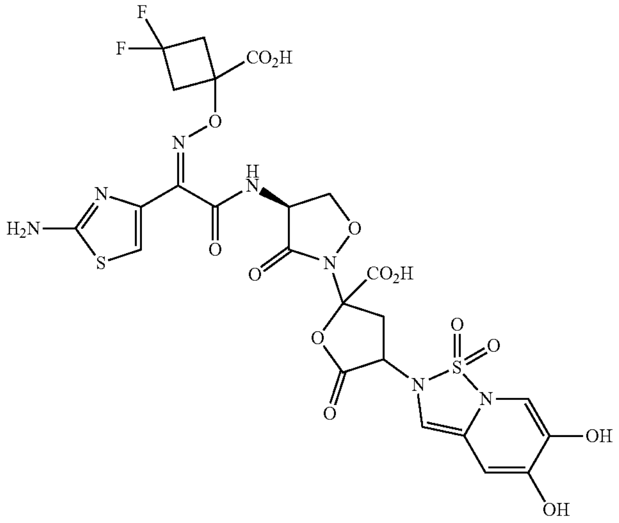 [SMILES: Nc1nc(/C(=N/OC2(C(=O)O)CC(F)(F)C2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-{[(1-carboxy-3,3-difluorocyclobutyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 77 | 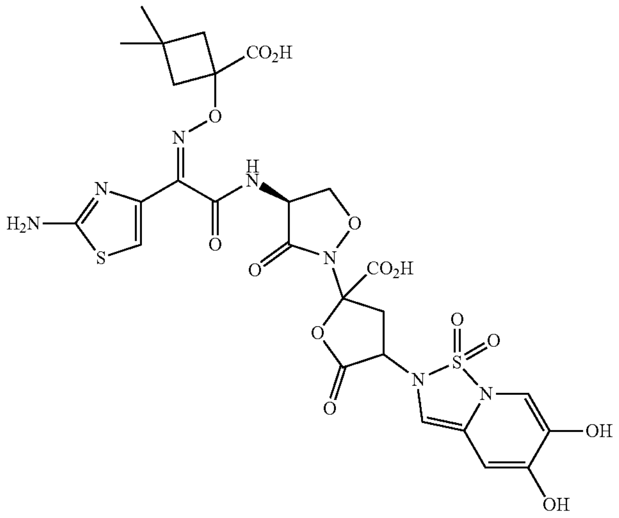 [SMILES: CC1(C)CC(O/N=C(\C(=O)N[C@H]2CON(C3(C(=O)O)CC(N4C=C5C=C(O)C(O)=CN5S4(=O)=O)C(=O)O3)C2=O)c2csc(N)n2)(C(=O)O)C1] | 2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |

TABLE 1-continued

| Cmpd No. | | Chemical Name |
|---|---|---|
| 78 | 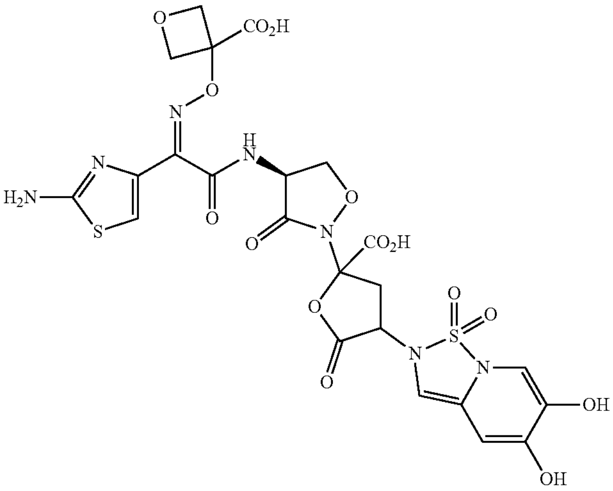 [SMILES: Nc1nc(/C(=N/OC2(C(=O)O)COC2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-{[(3-carboxyoxetan-3-yl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 79 | 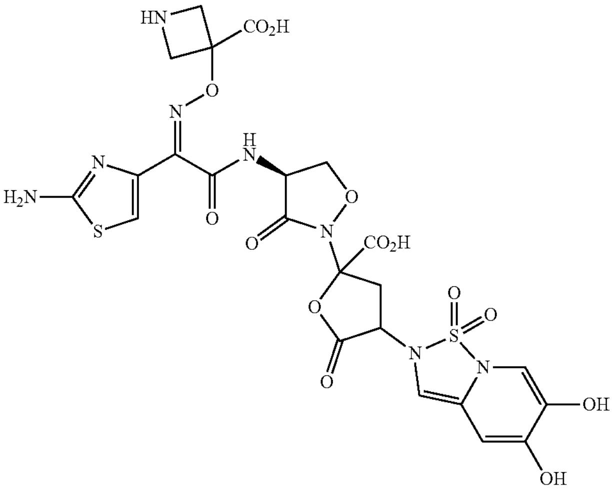 [SMILES: Nc1nc(/C(=N/OC2(C(=O)O)CNC2)C(=O)N[C@H]2CON(C3(C(=O)O)CC(N4C=C5C=C(O)C(O)=CN5S4(=O)=O)C(=O)O3)C2=O)cs1] | 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)azetidine-3-carboxylic acid |
| 80 | 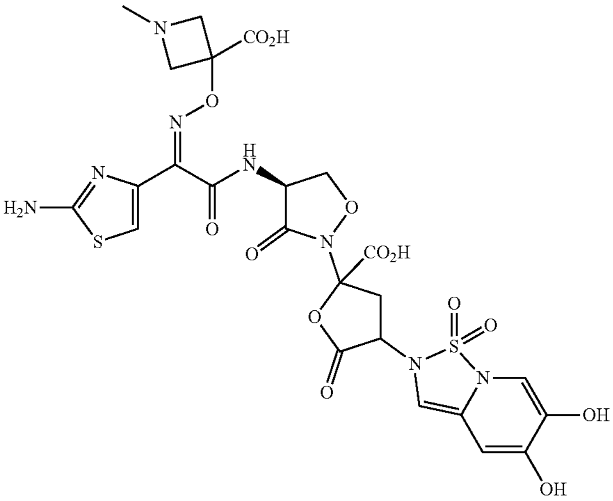 [SMILES: CN1CC(O/N=C(\C(=O)N[C@H]2CON(C3(C(=O)O)CC(N4C=C5C=C(O)C(O)=CN5S4(=O)=O)C(=O)O3)C2=O)c2csc(N)n2)(C(=O)O)C1] | 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)-1-methylazetidine-3-carboxylic acid |

TABLE 1-continued

| Cmpd No. | | Chemical Name |
|---|---|---|
| 81 | 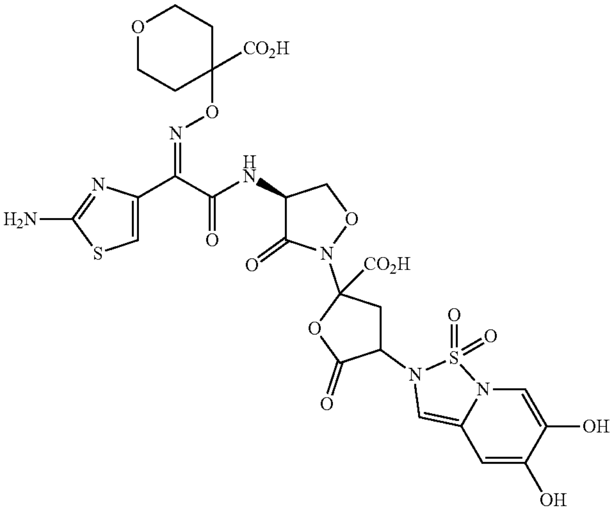 [SMILES: Nc1nc(/C(=N/OC2(C(=O)O)CCOCC2)C(=O)N[C@H]2CON(C3(C(=O)O)CC(N4C=C5C=C(O)C(O)=CN5S4(=O)=O)C(=O)O3)C2=O)cs1] | 4-({(Z)-[1-(2-amino-1,3-thiazol-4-yl)-2-({(4S)-2-[2-carboxy-4-(5,6-dihydroxy-1,1-dioxo-1λ[6]-[1,2,5]thiadiazolo[2,3-a]pyridin-2(1H)-y)-5-oxooxolan-2-yl]-3-oxo-1,2-oxazolidin-4-yl}amino)-2-oxoethylidene]amino}oxy)oxane-4-carboxylic acid |
| 82 | 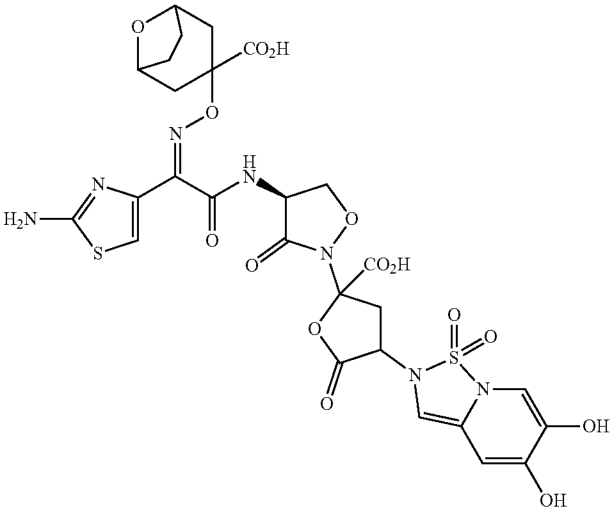 [SMILES: Nc1nc(/C(=N/OC2(C(=O)O)CC3CCC(C2)O3)C(=O)N[C@H]2CON(C3(C(=O)O)CC(N4C=C5C=C(O)C(O)=CN5S4(=O)=O)C(=O)O3)C2=O)cs1] | 3-({(Z)-[1-(2-amino-1,3-thiazol-4-yl)-2-({(4S)-2-[2-carboxy-4-(5,6-dihydroxy-1,1-dioxo-1λ[6]-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid |
| 83 | 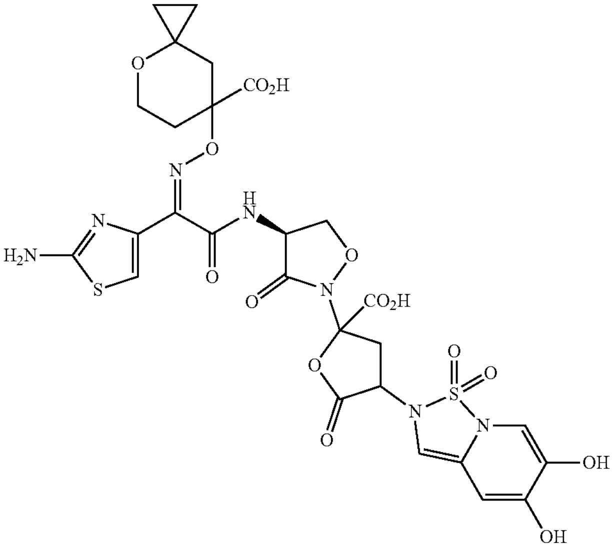 [SMILES: Nc1nc(/C(=N/OC2(C(=O)O)CCOC3(CC3)C2)C(=O)N[C@H]2CON(C3(C(=O)O)CC(N4C=C5C=C(O)C(O)=CN5S4(=O)=O)C(=O)O3)C2=O)cs1] | 7-({(Z)-[1-(2-amino-1,3-thiazol-4-yl)-2-({(4S)-2-[2-carboxy-4-(5,6-dihydroxy-1,1-dioxo-1λ[6]-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)-4-oxaspiro[2.5]octane-7-carboxylic acid |

TABLE 1-continued

| Cmpd No. | | Chemical Name |
|---|---|---|
| 84 | 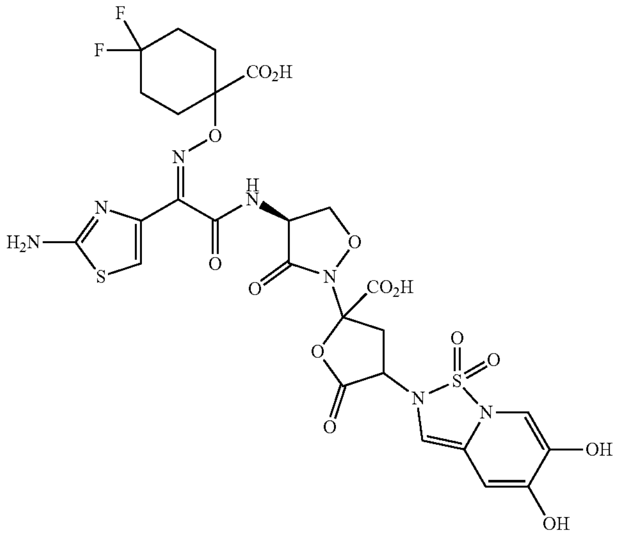 [SMILES: Nc1nc(/C(=N/OC2(C(=O)O)CCC(F)(F)CC2)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 85 | 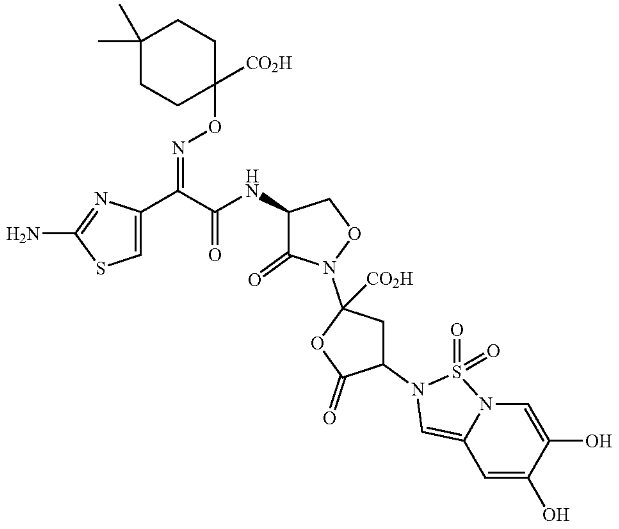 [SMILES: CC1(C)CCC(O/N=C(\C(=O)N[C@H]2CON(C3(C(=O)O)CC(N4C=C5C=C(O)C(O)=CN5S4(=O)=O)C(=O)O3)C2=O)c2csc(N)n2)(C(=O)O)CC1] | 2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 86 | 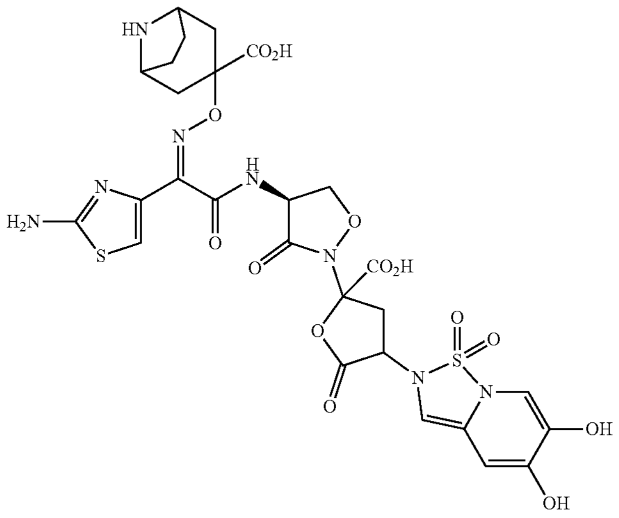 [SMILES: Nc1nc(/C(=N/OC2(C(=O)O)CC3CCC(C2)N3)C(=O)N[C@H]2CON(C3(C(=O)O)CC(N4C=C5C=C(O)C(O)=CN5S4(=O)=O)C(=O)O3)C2=O)cs1] | 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)-8-azabicyclo[3.2.1]octane-3-carboxylic acid |

TABLE 1-continued

| Cmpd No. | | Chemical Name |
|---|---|---|
| 87 | 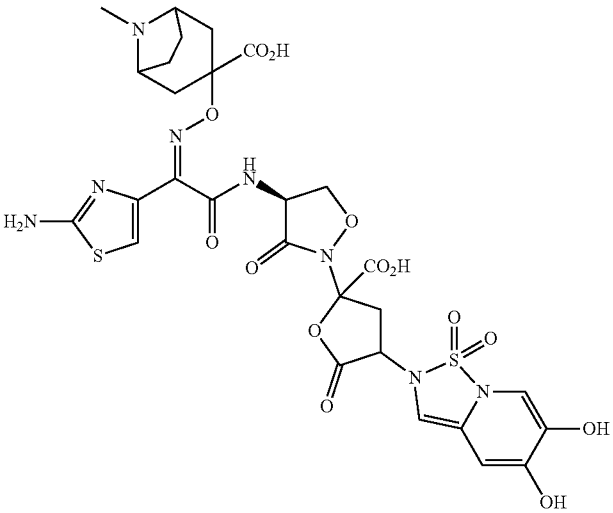 [SMILES: CN1C2CCC1CC(O/N=C(\C(=O)N[C@H]1CON(C3(C(=O)O)CC(N4C=C5C=C(O)C(O)=CN5S4(=O)=O)C(=O)O3)C1=O)c1csc(N)n1)(C(=O)O)C2] | 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl)amino)-2-oxoethylidene]amino}oxy)-8-methyl-8-azabicyclo[3.2.1]octane-3-carboxylic acid |
| 88 | 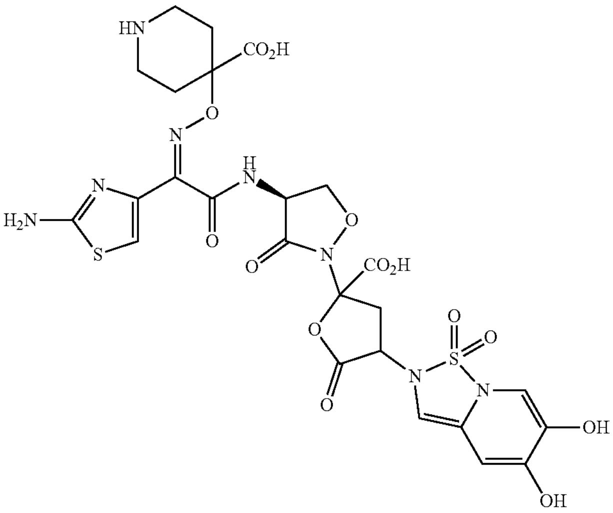 [SMILES: Nc1nc(/C(=N/OC2(C(=O)O)CCNCC2)C(=O)N[C@H]2CON(C3(C(=O)O)CC(N4C=C5C=C(O)C(O)=CN5S4(=O)=O)C(=O)O3)C2=O)cs1] | 4-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-o]pyridin-2(1H)-yl)-5-oxooxolan-2-yl]-3-oxo-1,2-oxazolidin-4-yl}amino)-2-oxoethylidene]amino}oxy)piperidine-4-carboxylic acid |
| 89 | 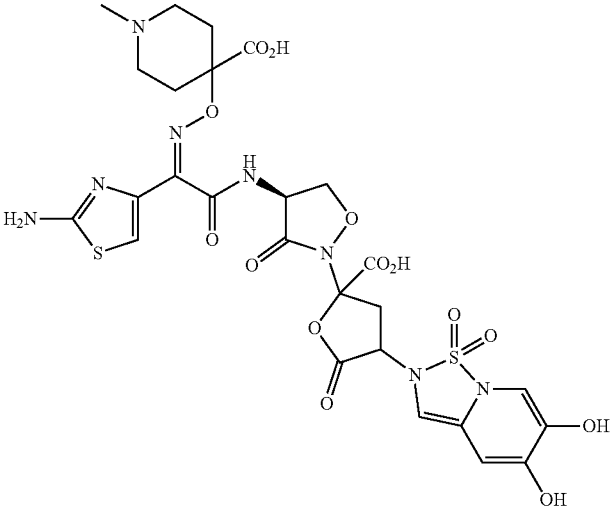 [SMILES: CN1CCC(O/N=C(\C(=O)N[C@H]2CON(C3(C(=O)O)CC(N4C=C5C=C(O)C(O)=CN5S4(=O)=O)C(=O)O3)C2=O)c2csc(N)n2)(C(=O)O)CC1] | 4-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)-1-methylpiperidine-4-carboxylic acid |

TABLE 1-continued

| Cmpd No. | | Chemical Name |
|---|---|---|
| 90 | 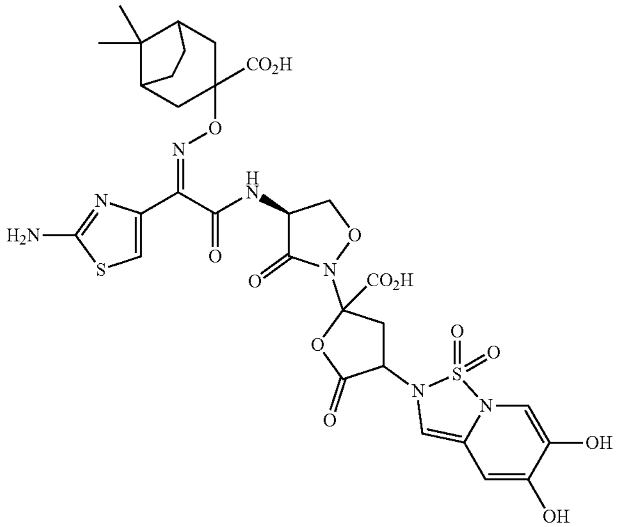 [SMILES: CC1(C)C2CCC1CC(O/N=C(\C(=O)N[C@H]1CON(C3(C(=O)O)CC(N4C=C5C=C(O)C(O)=CN5S4(=O)=O)C(=O)O3)C1=O)c1csc(N)n1)(C(=O)O)C2] | 2-[(4S)-4-{[(2Z)-2-(2-amino-1,3-thiazol-4-yl)-2-{[(3-carboxy-8,8-dimethylbicyclo[3.2.1]octan-3-yl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 91 | 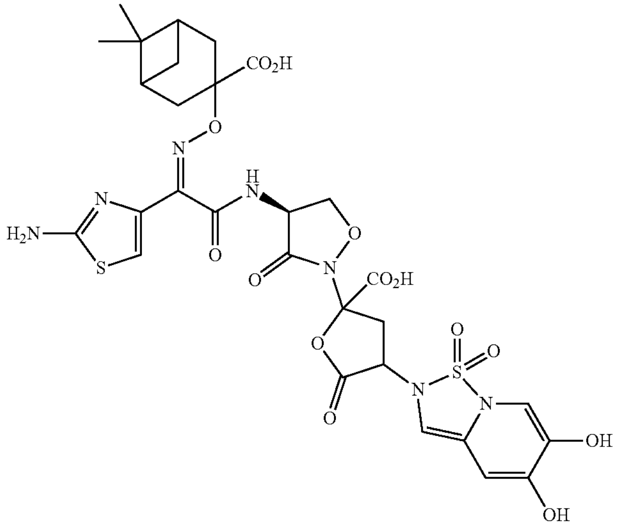 [SMILES: CC1(C)C2CC1CC(O/N=C(\C(=O)N[C@H]1CON(C3(C(=O)O)CC(N4C=C5C=C(O)C(O)=CN5S4(=O)=O)C(=O)O3)C1=O)c1csc(N)n1)(C(=O)O)C2] | 2-[(4S)-4-{[(2Z)-2-(2-amino-1,3-thiazol-4-yl)-2-{[(3-carboxy-6,6-dimethylbicyclo[3.1.1]heptan-3-yl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |
| 92 | 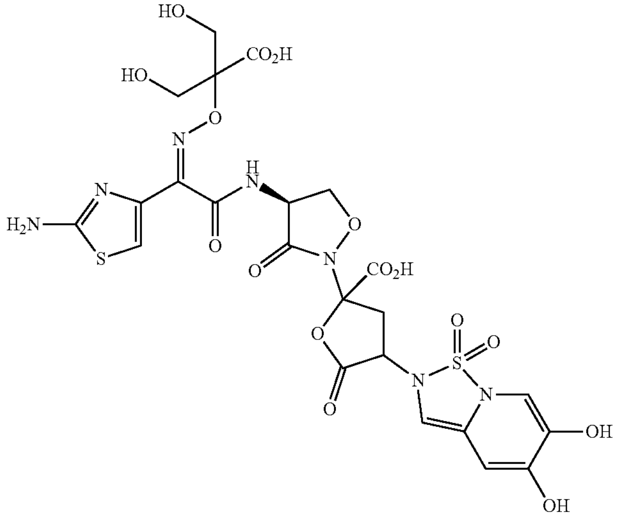 [SMILES: Nc1nc(/C(=N/OC(CO)(CO)C(=O)O)C(=O)N[C@H]2CON(C3(C(=O)O)CC(N4C=C5C=C(O)C(O)=CN5S4(=O)=O)C(=O)O3)C2=O)cs1] | 2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2(1H)-yl)-5-oxooxolane-2-carboxylic acid |

TABLE 1-continued

| Cmpd No. | | Chemical Name |
|---|---|---|
| 93 | 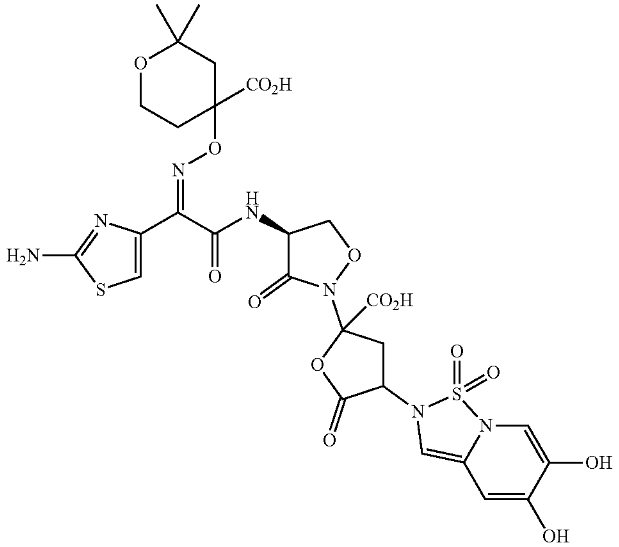 [SMILES: CC1(C)CC(O/N=C(\C(=O)N[C@H]2CON(C3(C(=O)O)CC(N4C=C5C=C(O)C(O)=CN5S4(=O)=O)C(=O)O3)C2=O)c2csc(N)n2)(C(=O)O)CCO1] | 4-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl)amino)-2-oxoethylidene]amino}oxy)-2,2-dimethyloxane-4-carboxylic acid |
| 94 | 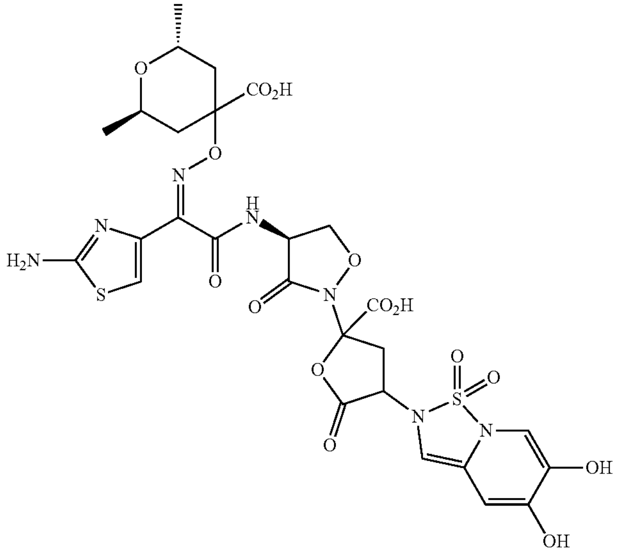 [SMILES: C[C@@H]1CC(O/N=C(\C(=O)N[C@H]2CON(C3(C(=O)O)CC(N4C=C5C=C(O)C(O)=CN5S4(=O)=O)C(=O)O3)C2=O)c2csc(N)n2)(C(=O)O)C[C@@H](C)O1] | (2R,6R)-4-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)-2,6-dimethyloxane-4-carboxylic acid |
| 95 | 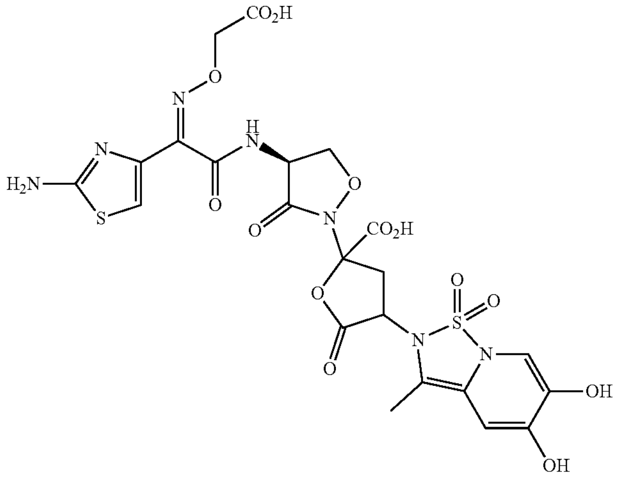 [SMILES: CC1=C2C=C(O)C(O)=CN2S(=O)(=O)N1C1CC(C(=O)O)(N2OC[C@H](NC(=O)/C(=N\OCC(=O)O)c3csc(N)n3)C2=O)OC1=O] | 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(5,6-dihydroxy-3-methyl-1,1-dioxo-1λ$^6$-[1,2,5]thiadiazolo[2,3-a]pyridin-2(1H)-yl)-5-oxooxolane-2-carboxylic acid |

TABLE 1-continued

| Cmpd No. | | Chemical Name |
|---|---|---|
| 96 | 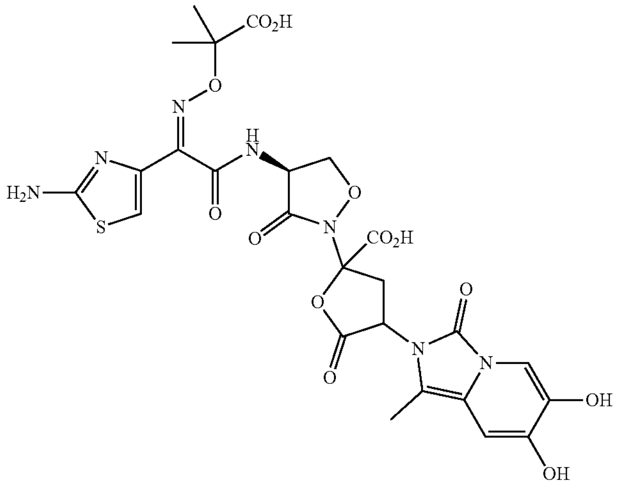 [SMILES: Cc1c2cc(O)c(O)cn2c(=O)n1C1CC(C(=O)O)(N2OC[C@H](NC(=O)/C(=N\OC(C)(C)C(=O)O)c3csc(N)n3)C2=O)OC1=O] | 2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(6,7-dihydroxy-1-methyl-3-oxoimidazo[1,5-a]pyridin-2(3H)-yl)-5-oxooxolane-2-carboxylic acid |
| 97 | 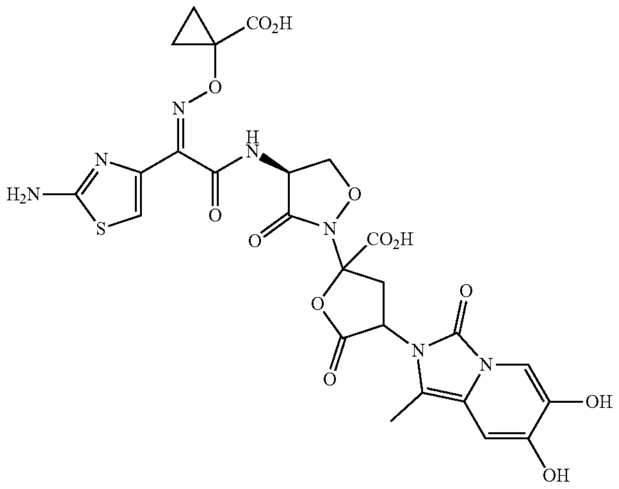 [SMILES: Cc1c2cc(O)c(O)cn2c(=O)n1C1CC(C(=O)O)(N2OC[C@H](NC(=O)/C(=N\OC3(C(=O)O)CC3)c3csc(N)n3)C2=O)OC1=O] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(6,7-dihydroxy-1-methyl-3-oxoimidazo[1,5-a]pyridin-2(3H)-yl)-5-oxooxolane-2-carboxylic acid |
| 98 | 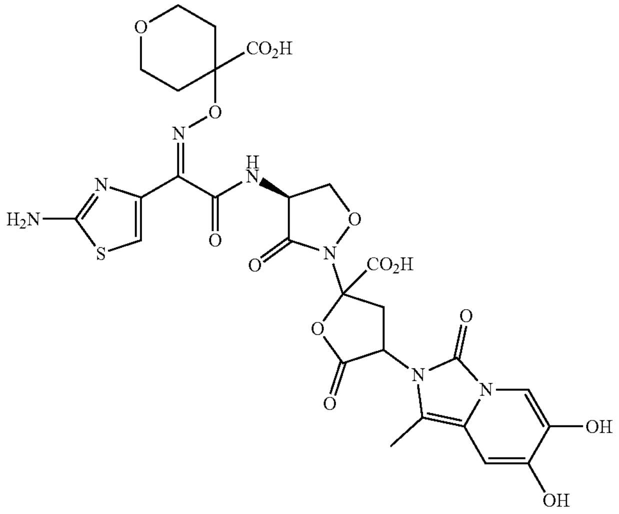 [SMILES: Cc1c2cc(O)c(O)cn2c(=O)n1C1CC(C(=O)O)(N2OC[C@H](NC(=O)/C(=N\OC3(C(=O)O)CCOCC3)c3csc(N)n3)C2=O)OC1=O] | 4-({(Z)-[1-(2-amino-1,3-thiazol-4-yl)-2-({(4S)-2-[2-carboxy-4-(6,7-dihydroxy-1-methyl-3-oxoimidazo[1,5-a]pyridin-2(3H)-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
|---|---|---|
| 99 | 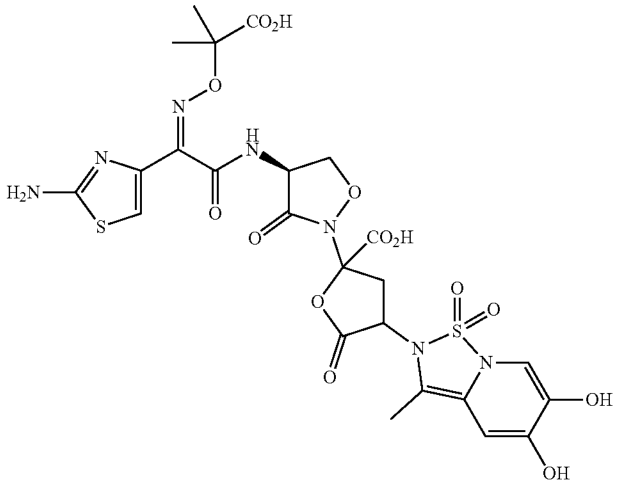 [SMILES: CC1=C2C=C(O)C(O)=CN2S(=O)(=O)N1C1CC(C(=O)O)(N2OC[C@H](NC(=O)/C(=N\OC(C)(C)C(=O)O)c3csc(N)n3)C2=O)OC1=O] | 2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-3-methyl-1,1-dioxo-1λ$^6$-[1,2,5]thiadiazolo[2,3-a]pyridin-2(1H)-yl)-5-oxooxolane-2-carboxylic acid |
| 100 | 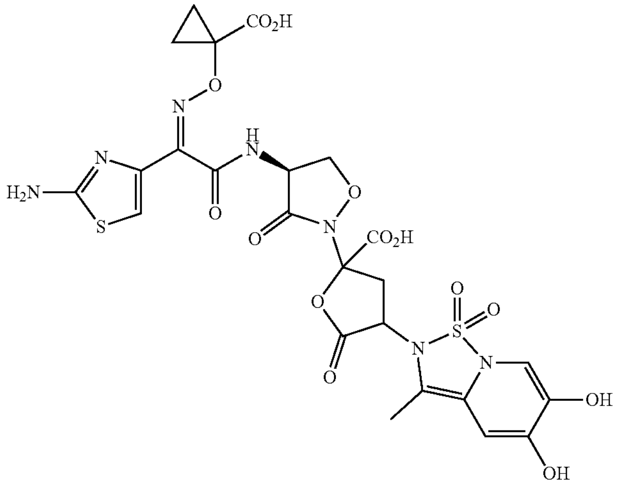 [SMILES: CC1=C2C=C(O)C(O)=CN2S(=O)(=O)N1C1CC(C(=O)O)(N2OC[C@H](NC(=O)/C(=N\OC3(C(=O)O)CC3)c3csc(N)n3)C2=O)OC1=O] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl)-4-(5,6-dihydroxy-3-methyl-1,1-dioxo-1λ$^6$-[1,2,5]thiadiazolo[2,3-a]pyridin-2(1H)-yl)-5-oxooxolane-2-carboxylic acid |
| 101 | 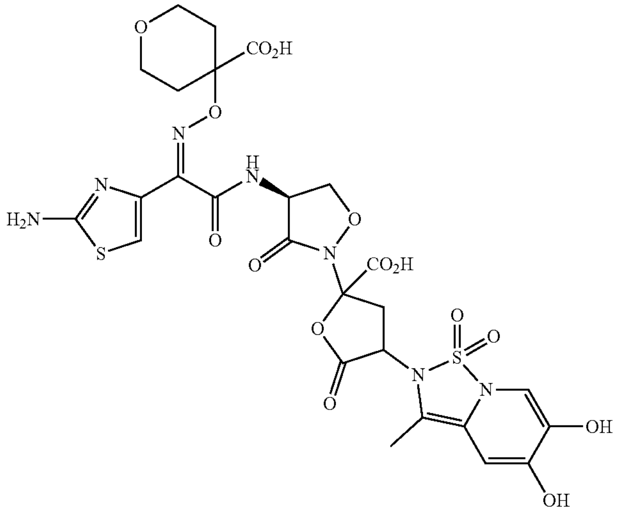 [SMILES: CC1=C2C=C(O)C(O)=CN2S(=O)(=O)N1C1CC(C(=O)O)(N2OC[C@H](NC(=O)/C(=N\OC3(C(=O)O)CCOCC3)c3csc(N)n3)C2=O)OC1=O] | 4-({(Z)-[1-(2-amino-1,3-thiazol-4-yl)-2-({(4S)-2-[2-carboxy-4-(5,6-dihydroxy-3-methyl-1,1-dioxo-1λ$^6$-[1,2,5]thiadiazolo[2,3-a]pyridin-2(1H)-yl)-5-oxooxolan-2-yl]-3-oxo-1,2-oxazolidin-4-yl}amino)-2-oxoethylidene]amino}oxy)oxane-4-carboxylic acid |

TABLE 1-continued

| Cmpd No. | | Chemical Name |
|---|---|---|
| 102 | 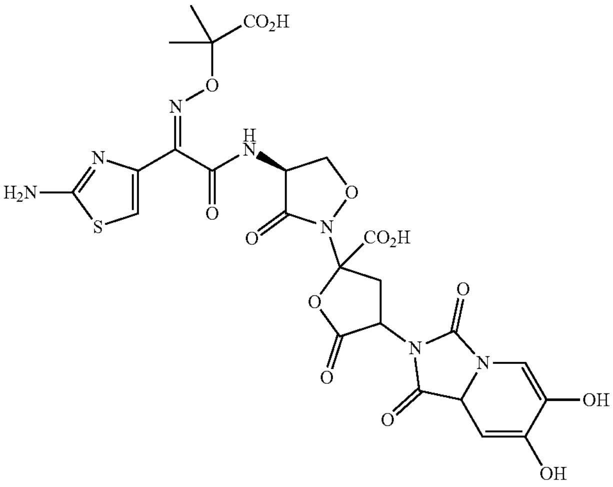 [SMILES: CC(C)(O/N=C(\C(=O)N[C@H]1CON(C2(C(=O)O)CC(N3C(=O)C4C=C(O)C(O)=CN4C3=O)C(=O)O2)C1=O)c1csc(N)n1)C(=O)O] | 2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(6,7-dihydroxy-1,3-dioxo-1H-[1,2,4]triazolo[1,2-a]pyridazin-2(3H)-yl)-5-oxooxolane-2-carboxylic acid |
| 103 | 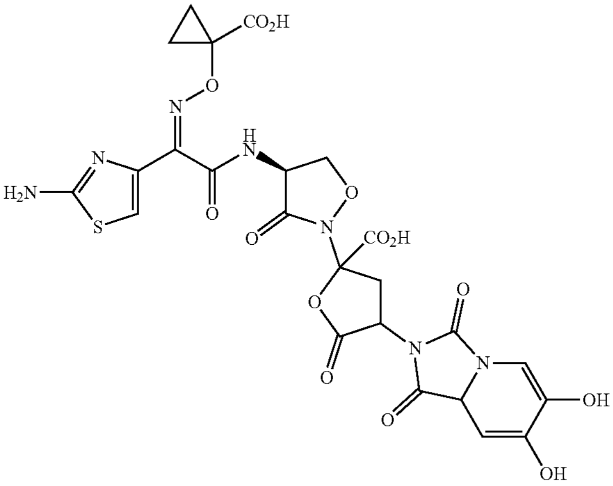 [SMILES: Nc1nc(/C(=N/OC2(C(=O)O)CC2)C(=O)N[C@H]2CON(C3(C(=O)O)CC(N4C(=O)C5C=C(O)C(O)=CN5C4=O)C(=O)O3)C2=O)cs1] | 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(6,7-dihydroxy-1,3-dioxo-1H-[1,2,4]triazolo[1,2-a]pyridazin-2(3H)-yl)-5-oxooxolane-2-carboxylic acid |

As used herein, reference to the compounds of formula (I) specifically excludes the following compounds I', I" and I'".

I'

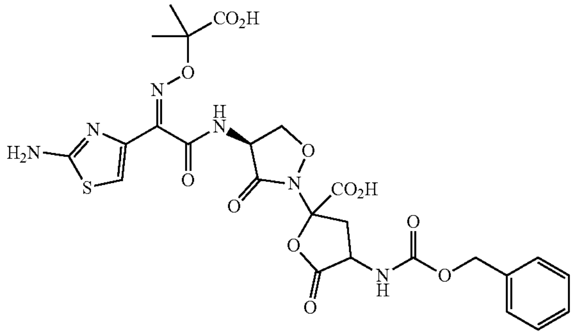

-continued

I"

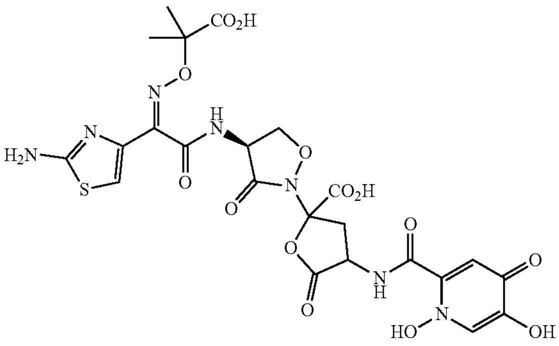

-continued

I'''

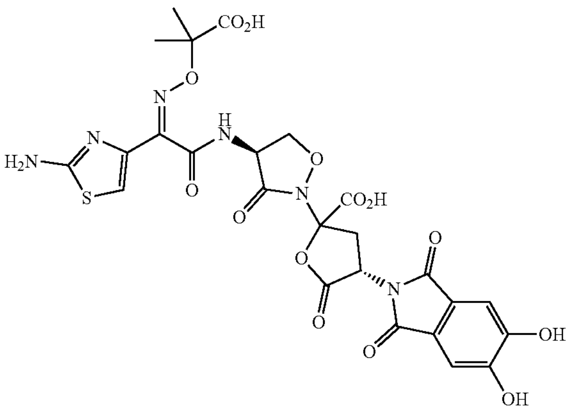

The compounds of the invention are thus the compounds of formula (I), and salts, solvates, and solvates of the salts thereof, and include the compounds of Table 1, but excludes compounds I', I" and I'".

The compounds of the invention of formula (I) and Table 1 include enantiomers or diastereomers and respective mixtures thereof.

The compounds of the invention of formula (I) and Table 1 include Z-isomers, E-isomers and mixtures thereof.

The compounds of the invention of formula (I) and Table 1 may occur in tautomeric forms, and the present invention encompasses all tautomeric forms.

The salts of the compounds of the present invention may be "pharmaceutically acceptable salts", examples for which are defined before.

The compounds of the present invention may be inner salts such as a zwitterionic salt formed with a COOH group and a basic group, such as NH, $NH_2$, pyridine or piperazine present in the formula (I).

Compositions of the Invention

The compounds of the invention show a broad range of antibacterial effects. In some aspects, the compounds may exhibit activity against pathogenic microorganisms, and therefore may be useful in the treatment and/or prevention of bacterial infections in humans or animals, either alone or in combination with one or more of β-lactam antibiotics, other non-β-lactam antibiotics, and β-lactamase inhibitors. The compounds of the invention are therefore suitable for use in pharmaceutical compositions and as medicaments for the treatment, prevention and/or prophylaxis of diseases in humans and animals.

Accordingly, the present invention also relates to pharmaceutical compositions comprising (i) one or more compounds of formula (I), or pharmaceutically acceptable salts thereof, and (ii) a pharmaceutically acceptable carrier or diluent. In some aspects, these compositions may exhibit activity against pathogenic organisms. As used herein, the terms "pharmaceutical composition" and "medicament" are synonymous.

In other embodiments, the invention relates to pharmaceutical compositions comprising (I) one or more compounds of formula (I) or pharmaceutically acceptable salts thereof, (ii) one or more β-lactamase inhibitors, and (ill) a pharmaceutically acceptable carrier or diluent. In some aspects, these compositions may exhibit activity against pathogenic microorganisms. Such combinations may exhibit a synergistic effect when used in the treatment or prevention of bacterial infections.

The present invention further relates to pharmaceutical compositions comprising (I) one or more compounds of formula (I), or pharmaceutically acceptable salts thereof, (ii) one or more β-lactamase inhibitors, where the β-lactamase inhibitors may be selected from formula ($1^a$) to ($1^{z'}$), for example, and (iii) a pharmaceutically acceptable carrier or diluent. It should be understood that the compounds of formula (I) may be used in combination with other (β-lactamase inhibitors as well. Such combinations may exhibit a synergistic effect when used in the treatment or prevention of bacterial Infections.

$1^a$

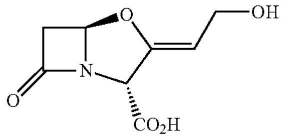

(clavulanic acid)

$1^b$

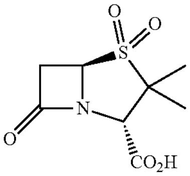

(sulbactam)

$1^c$

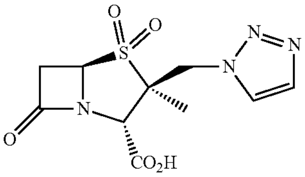

(tazobactam)

$1^d$

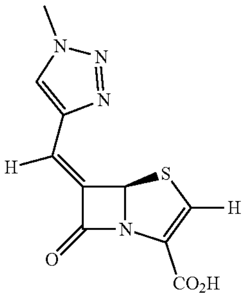

(BRL-42715)

$1^e$

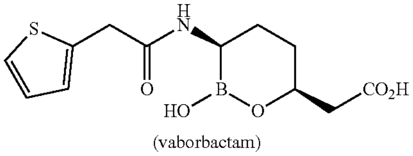

(vaborbactam)

-continued
$1^{f}$
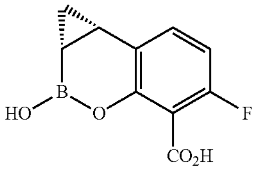
(QPX-7728)
$1^{g}$
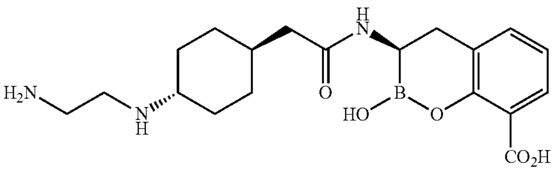
(taniborbactam, VNRX-5133)
$1^{h}$
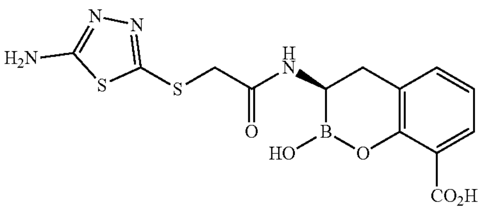
(RPX-7262)
$1^{i}$
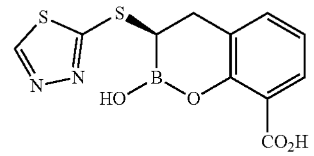
(RPX-7282)
$1^{j}$
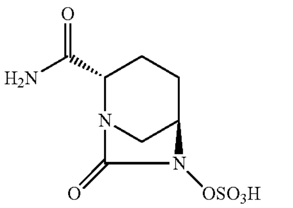
(NXL-104)
$1^{k}$
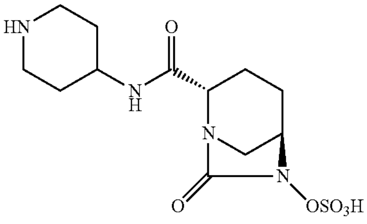
(relebactam)
-continued
$1^{l}$
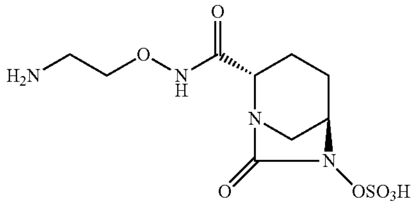
(nacubactam)
$1^{m}$
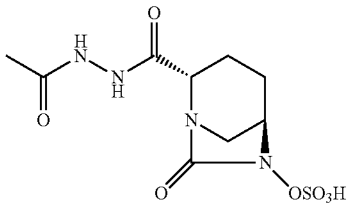
(FPI-1523)
$1^{n}$
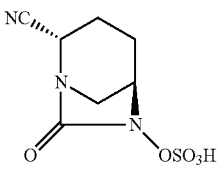
(WCK 4234)
$1^{o}$
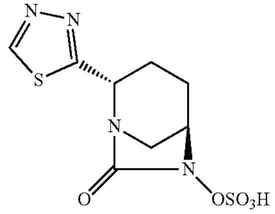
$1^{p}$
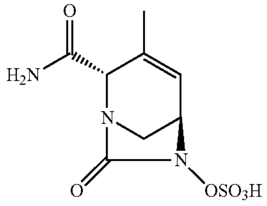
(durlobactam)
$1^{q}$
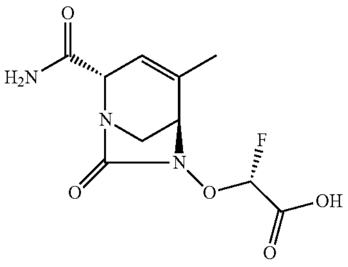
(ETX-1317)

-continued $1^r$

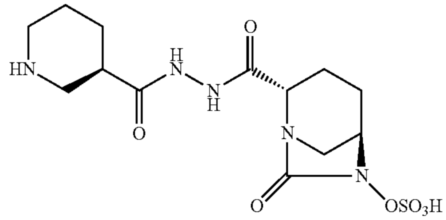

(zidebactam)

$1^s$

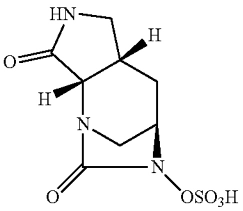

$1^t$

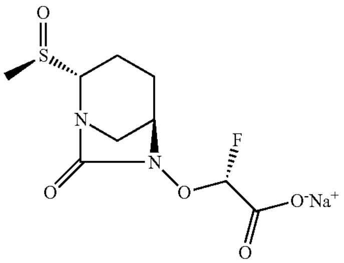

$1^u$

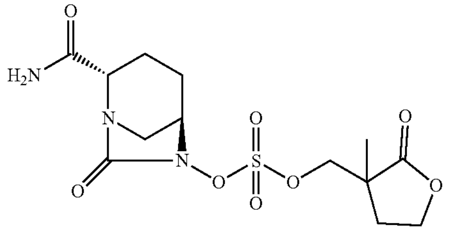

$1^v$

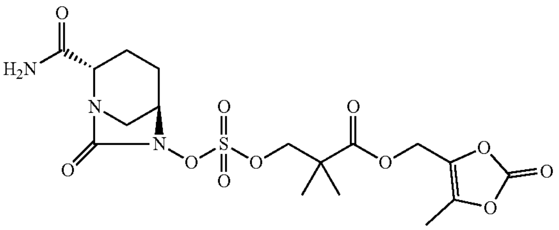

$1^w$

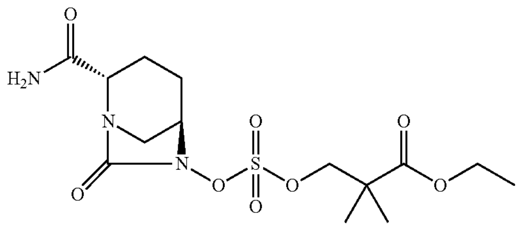

(ARX-1796)

-continued $1^x$

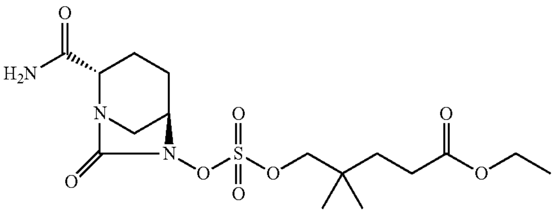

$1^y$

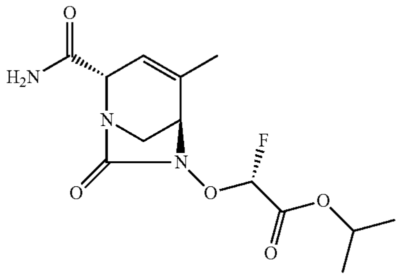

(ETX-0282)

$1^z$

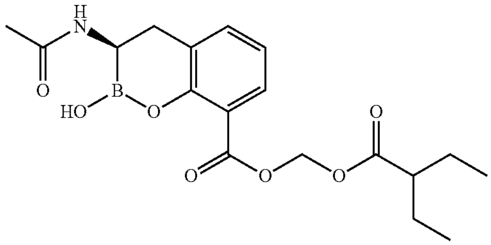

(VNRX-7145)

$1^{z'}$

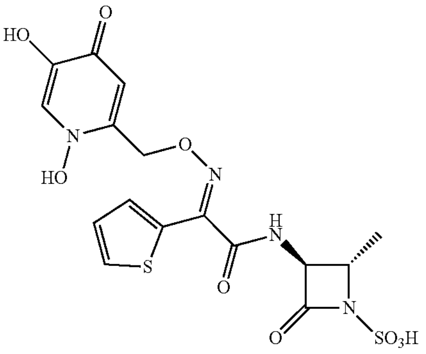

(Syn2190)

The term "β-lactamase inhibitor" refers to a compound which is capable of inhibiting β-lactamase activity, such as the compounds of formula ($1^a$) to ($1^{z'}$), for example, where inhibiting β-lactamase activity means inhibiting the activity of a class A, B, C and/or D β-lactamase. The term "β-lactamase" denotes an enzyme capable of inactivating a β-lactam antibiotic.

In the present invention it has been found that the efficacy of lactivicin compounds of formula (I) herein against Gram-negative bacteria can be potentiated by co-using a β-lactamase inhibitor selected from any of the formula ($1^a$) to ($1^{z'}$) mentioned above, but the invention should not be construed to be limited to use of only the aforementioned β-lactamase inhibitors.

In other embodiments, the invention relates to pharmaceutical compositions comprising (i) one or more compounds of formula (I) or pharmaceutically acceptable salts thereof, (ii) one or more additional antibiotic agents, and (iii) a pharmaceutically acceptable carrier or diluent. The additional antibiotics may be β-lactam antibiotics, or non-β-lactam antibiotics, or both. Such combinations may exhibit a synergistic effect when used in the treatment or prevention of bacterial infections.

In other embodiments, the invention relates to pharmaceutical compositions comprising (i) one or more compounds of formula (I) or pharmaceutically acceptable salts thereof, (ii) one or more additional antibiotic agents, (iii) one or more β-lactamase inhibitors, and (iv) a pharmaceutically acceptable carrier or diluent. The additional antibiotics may be β-lactam antibiotics, or non-β-lactam antibiotics, or both. Such combinations may exhibit a synergistic effect when used in the treatment or prevention of bacterial infections.

As used herein, the term "additional antibiotics" means compounds or compositions, other than the compounds of formula (I) or pharmaceutically acceptable salts thereof. As defined above, "antibiotics" are compounds and compositions which decrease the viability of a microorganism, or which inhibit the growth or proliferation of a microorganism, and is further intended to include antimicrobials, bacteriostatics and bactericidal agents.

Suitable additional antibiotics include both β-lactam and non-β-lactam antibiotics including, but not limited to, (i) antibiotics of the following classes of antibiotics: aminoglycosides, macrolides, ketolides, streptogramins, oxazolidinones, tetracyclines, fluoroquinolones, glycopeptides, and lipoglycopeptides; (ii) antibiotics of the following groups of antibiotics: penicillin group, cephalosporin group, monobactam group, and carbapenem group; and (iii) the following specific antibiotics: fosfomycin, tobramycin, linezolid, daptomycin, vancomycin. The additional antibiotic may also be in the form of a parent compound or a prodrug.

The compounds and compositions of the Invention may act systemically and/or locally. They can for this purpose be administered in a suitable way such as, for example, parenterally, pulmonarily, nasally, sublingually, lingually, buccally, rectally, dermally, transdermally, conjunctivally, otically or as an implant or stent.

For these administration routes the pharmaceutical compositions comprising the compounds of the present invention can be administered in suitable administration forms.

Parenteral administration can take place with avoidance of an absorption step (e.g. Intravenous, intraarterial, intracardiac, intraspinal or intralumbar) or with inclusion of an absorption step (e.g. Intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions, sprays, tablets, films/wafers or capsules, for lingual, sublingual or buccal administration, suppositories, preparations for ears or eyes, aqueous suspensions (lotions, shaking mixtures), lipophilic suspensions, ointments, creams, transdermal therapeutic systems (such as for example patches), pastes, foams, dusting powders, implants or stents.

The compounds of the invention can be converted into the stated administration forms, i.e. the pharmaceutical compositions of the invention. This can take place in a manner known per se by mixing with inert, non-toxic, pharmaceutically acceptable carriers or diluents such as starch, glucose, lactose, sucrose, gelatin, gum Arabic, malt, rice, flour, chalk, silica gel, sodium stearate, glycerol monostearate, talc, sodium chloride, dried skim milk, glycerol, propylene glycol, water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium.

Pharmaceutical compositions of the present invention, if desired, can also contain minor amounts of wetting agents (for example sodium dodecyl sulfate, polyoxyethylene sorbitan oleate), dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen.

In pharmaceutical compositions comprising the compounds of formula (I), the weight ratio of active Ingredient to carrier will normally be in the range of 1:20 to 20:1.

When co-administered with a β-lactamase inhibitor, the present compounds and the 3-lactamase inhibitor may, in combination, provide a synergistic effect. The term "synergistic effect" refers to the effect produced when two or more agents are co-administered that is greater than the additive effect produced when the agents are administered individually. Alternatively, the compound of formula (I) or a salt thereof can be administered as a separate agent during a course of treatment with the β-lactamase Inhibitor.

"Therapeutically effective amount" refers to the amount of a compound that, when administered to a subject for treating a disease or condition, is sufficient to affect such treatment of the disease or condition, or ameliorating a symptom of the disease or condition. The therapeutically effective amount can vary depending, for example, on the compound, the disease, condition, and/or symptoms of the disease, severity of the disease or condition, and the age, weight, and/or health of the patient to be treated.

Typically, the therapeutically effective amount of a compound of the invention for adult humans is about 50 mg to about 3000 mg of a compound of formula (I). In another embodiment, the therapeutically effective amount is about 100 mg to about 2000 mg. In another embodiment, the therapeutically effective amount is about 500 mg to about 1200 mg. Typically, the dosages (noted amounts) are given 1 to 4 times per day. In one embodiment, the dosages are given 3 times per day. In some cases, it may be necessary to use dosages outside these limits.

The terms "dose", "unit dose", "unit dosage" or "effective dose" refers to physically discrete units that contain a predetermined quantity of active ingredient calculated to produce a desired therapeutic effect.

The present invention further relates to medicaments which comprise at least one compound of the invention, usually together with one or more inert, non-toxic, pharmaceutically acceptable carrier or diluent, as well as to their use for the aforementioned purposes. The compositions can take the form of injectable preparations, suspensions, emulsions, coated tablets, pellets, gelatin-capsules, capsules containing liquids, powders, granules, sustained release formulations, suppositories, aerosols, sprays, ointments, creams or any other form suitable for use.

Methods of Treatment

The present invention also relates to the use of the compounds of the invention for the treatment, prevention and/or prophylaxis of diseases caused by bacteria, especially Gram-negative bacteria.

The present invention further relates to the use of the compounds of the invention for the manufacture of a medicament for the treatment, prevention and/or prophylaxis of diseases, especially of bacterial infections.

Accordingly, the present invention includes methods for the treatment, prevention and/or prophylaxis of a bacterial infection via administration of the compounds of the invention to a subject in need thereof.

In one embodiment, the methods of the invention comprise administering a therapeutically effective amount of one or more compounds of formula (I), as defined herein, to a subject having a bacterial infection, or a subject at risk of developing a bacterial infection.

In another embodiment, the methods of the invention comprise administering a therapeutically effective amount of a pharmaceutical composition comprising one or more compounds of formula (I), as defined herein, and pharmaceutically acceptable carrier or diluent to a subject having a bacterial infection, or a subject at risk of developing a bacterial infection.

In a further embodiment, the methods of the invention comprise administering a therapeutically effective amount of a pharmaceutical composition comprising (I) one or more compounds of formula (I), as defined herein, (ii) a pharmaceutically acceptable carrier or diluent, and (iii) one or more β-lactamase inhibitors, to a subject having a bacterial infection, or a subject at risk of developing a bacterial infection. In this later the embodiment, the β-lactamase inhibitors may be, for example, selected from formula $(1^{a})$ to $(1^{z'})$.

In a further embodiment, the methods of the invention comprise administering a therapeutically effective amount of a pharmaceutical composition comprising (i) one or more compounds of formula (I), as defined herein, (ii) one or more additional antibiotics, and (iii) a pharmaceutically acceptable carrier or diluent, to a subject having a bacterial infection, or a subject at risk of developing a bacterial infection. The additional antibiotics may be β-lactam antibiotics, or non-β-lactam antibiotics, or both.

In a further embodiment, the methods of the invention comprise administering a therapeutically effective amount of a pharmaceutical composition comprising (i) one or more compounds of formula (I), as defined herein, (ii) one or more additional antibiotics, (iii) one or more A-lactamase inhibitors, and (iv) a pharmaceutically acceptable carrier or diluent, to a subject having a bacterial infection, or a subject at risk of developing a bacterial infection. The additional antibiotics may be β-lactam antibiotics, or non-β-lactam antibiotics, or both.

The compounds of the invention exhibit excellent antibacterial spectrum against Gram-negative bacteria. Compounds of this invention are particularly useful in the treatment of humans and in veterinary medicine for the prophylaxis, prevention and/or treatment of local and systemic infections. Thus, in each of the embodiments and aspects of the invention, the subject is a human, a non-human primate, bird, horse, cow, goat, sheep, a companion animal, such as a dog, cat or rodent, or other mammal.

Examples of bacteria against which the compounds of the invention will have antibacterial activity include, but are not limited to *Enterobacterales, Escherichia coli, Enterabacter* spp., *Klebsiella* spp., *Serratia* spp., *Pseudomonas* spp., *Stenotrophomanas* spp., *Citrobacter* spp., *Acinetobacter* spp., *Campylobacter* spp., *Helicobacter* spp., *Vibrio* spp., *Bordetella* spp., *Salmonella* spp., *Shigella* spp., *Francisella* spp., *Burkholderia* spp., *Clostridia* spp., *Alcaligenes* spp., *Moraxella* spp., *Proteus* spp., *Neisseria* spp., *Haemophilus* spp., *Achromobacter* spp. and *Erwinia* spp.

Methods of Making

The present invention also relates to methods for preparation of compounds of formula (I). The following Scheme 1 illustrates the general method of preparation, and it is not intended to be limiting to any specific compound described herein.

Scheme 1

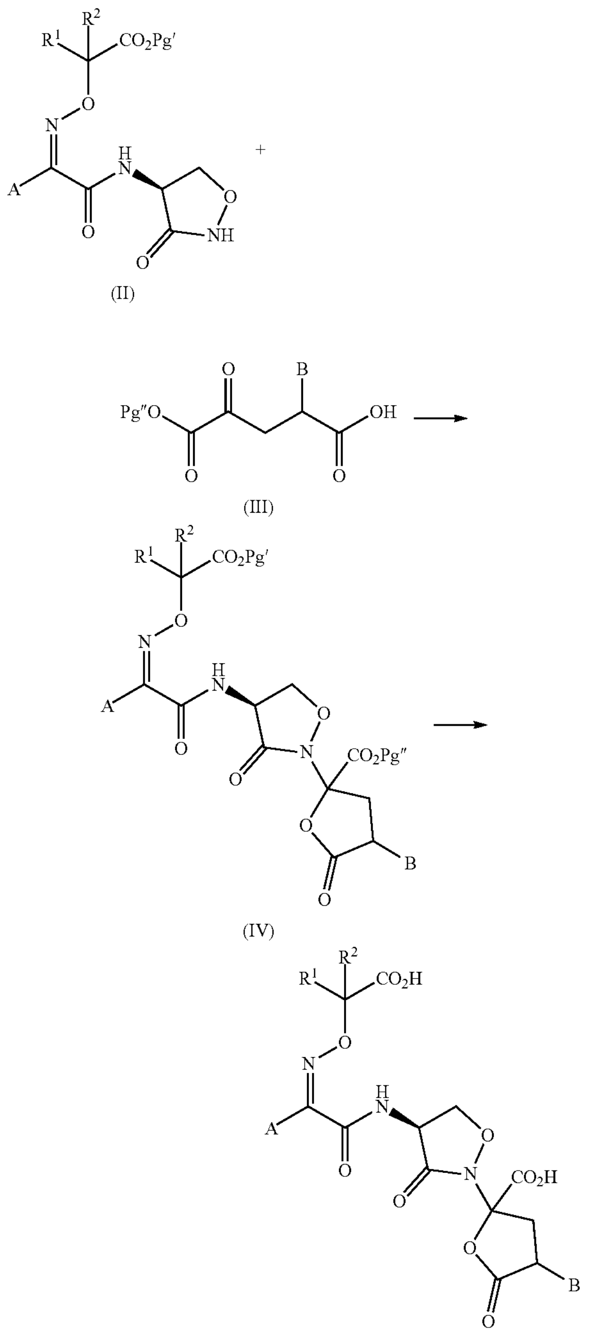

(II)

(III)

(IV)

(I)

Pg' and Pg" in formula (II), (III) and (IV) represent carboxyl protecting groups frequently used in the β-lactam chemistry to protect carboxyl groups.

Carboxyl protecting groups Pg' and Pg" may be the residue of an ester-forming aliphatic or araliphatic alcohol.

Examples of carboxyl protecting groups include iso-propyl, tert-butyl, methoxymethyl, ethoxymethyl, iso-butoxymethyl, acetoxymethyl, propionyloxymethyl, butyryloxymethyl, pivaloyloxymethyl, 1-methoxycarbonyloxyethyl, 1-ethoxycarbonyloxyethyl, p-methoxybenzyl, benzyl, o-nitrobenzyl, p-nitrobenzyl, 2,4-dinitrobenzyl, benzhydryl, phthalidyl and allyl.

In any of the intermediates to prepare formula (I), when an amino group is present in the molecule, it is to be understood that it has to be protected with a suitable amino protecting group commonly used in the β-lactam chemistry.

Examples of amino protecting groups include trityl, p-nitrobenzyloxycarbonyl (PNZ) and tert-butoxycarbonyl (Boc) and the like.

Similarly, it is to be understood that the hydroxy groups of catechol or hydroxypyridone moiety present in formula (II) and (IV) have to be protected with suitable hydroxy protecting groups.

Examples of suitable hydroxy protecting groups include, but are not limited to benzyl ether, diphenylmethyl ether and diphenylmethylene ketal.

Protecting groups may be removed by any convenient method as described in the literature or known to the skilled chemist as appropriate for the removal of the protecting group in question, such as methods being chosen so as to effect removal of the protecting group with minimum disturbance of groups elsewhere in the molecule.

The removal of the carboxyl protecting groups, the amino protecting groups and the hydroxy protecting groups of catechol or hydroxypyridone moiety of intermediate (IV) may be effected by a per se conventional procedure such as treatment with an acid or a reducing agent. As the acid, exemplary acids include trifluoracetic acid, formic acid, acetic acid, and hydrochloric acid. The Lewis acid to be employed is exemplified by boron trifluoride etherate, zinc chloride, tin tetrachloride, aluminum chloride, titanium tetrachloride or boron trichloride.

When the removal is conducted through catalytic hydrogenolysis, there may be adopted any procedure using palladium or platinum catalysts.

The removal of carboxyl protecting groups, hydroxy protecting groups of catechol and hydroxypyridone moiety, and amino protecting groups may be preferably conducted simultaneously or by stepwise approach.

Also included in the present invention are methods of preparation of specific fragments, such as compounds (IIIa') and (IIIa") of formula (III) in the Scheme 1, as described in the following Schemes 2 and 3, respectively, which illustrate the general method of preparation only and are not intended to be limiting to any specific compound described herein.

Scheme 2

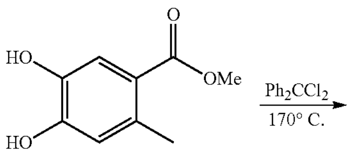

-continued

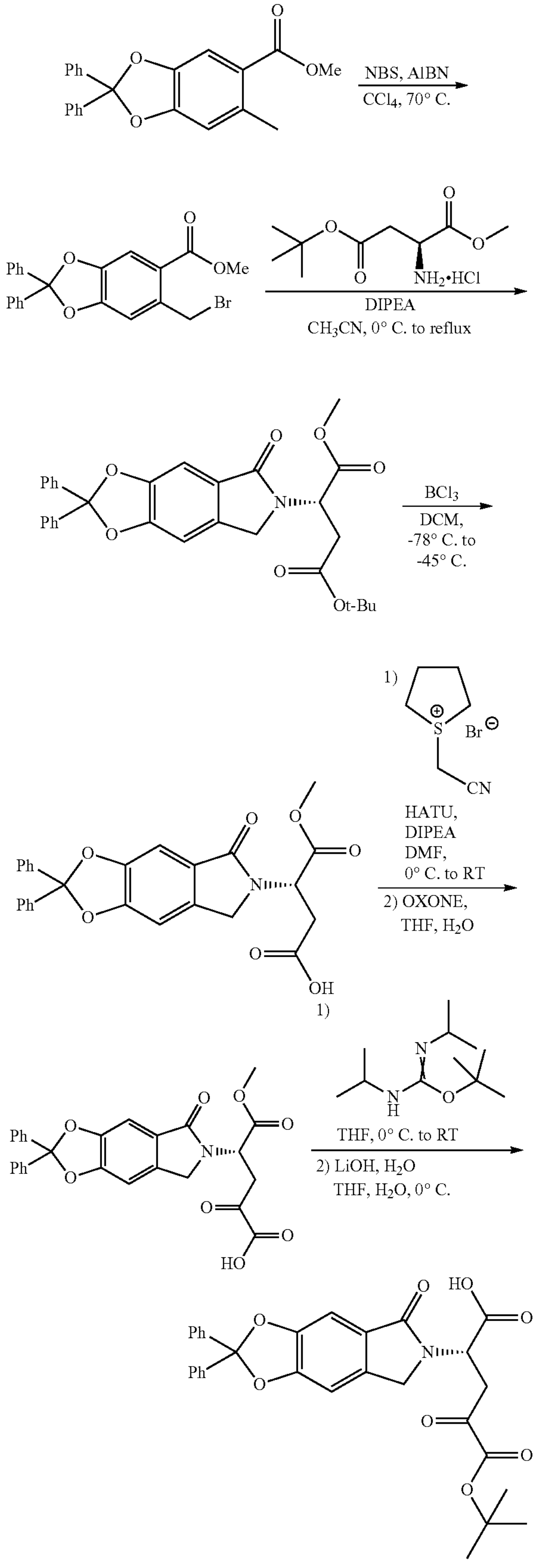

(IIIa')

Scheme 3

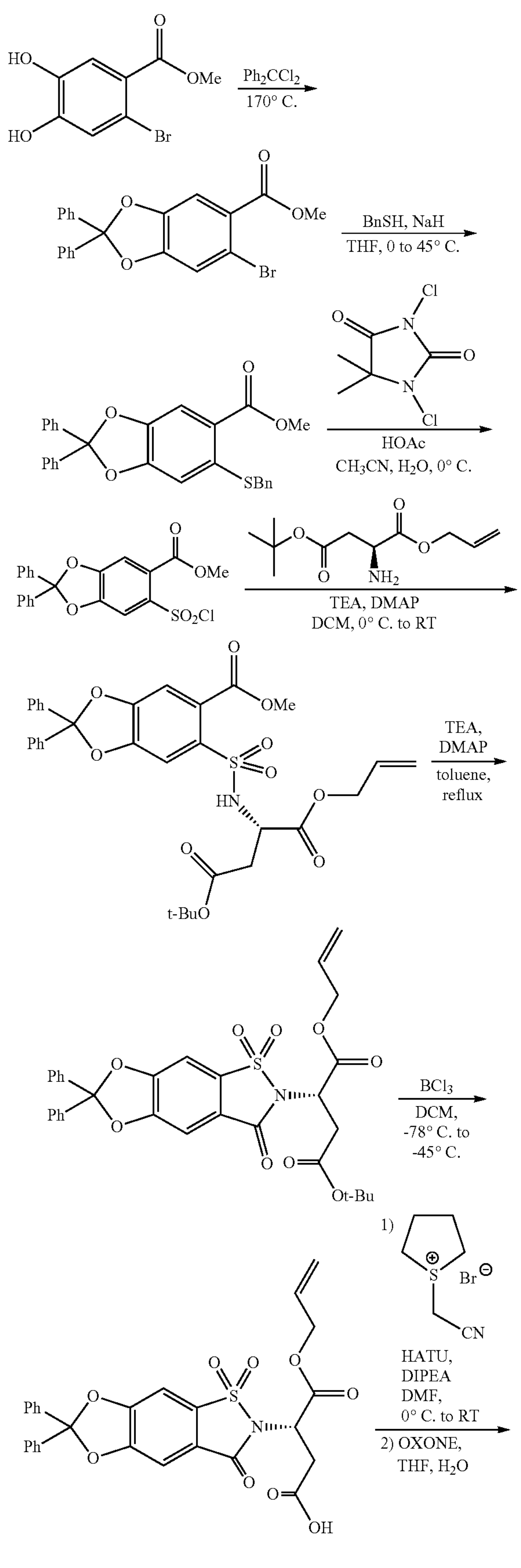

-continued

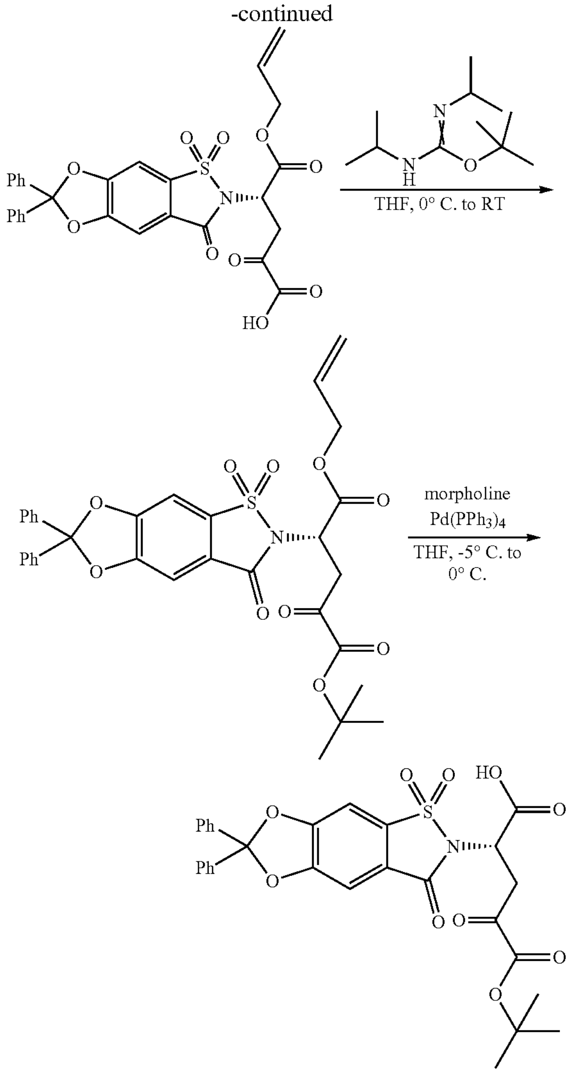

(IIIa")

The compounds of the present invention may be prepared by removing the protecting groups from compounds of formula (IV) under acidic conditions and catalytic hydrogenolysis. Acidic conditions may involve treating the compounds of formula (IV) with boron trichloride, formic acid, acetic acid, trifluoroacetic acid or hydrochloric acid at temperatures ranging from −78° C. to 100° C. for a time ranging from 10 min to 16 hours. Boron trichloride is preferably used at temperatures ranging from −78° C. to −20° C. for 1-3 hours.

Compounds of formula (II) can be synthesized according to the following literature references, which are incorporated herein by reference in their entireties: Chem. Pharm. Bull., 1990, Vol. 38, No. 11, pp. 116-122; J. Chem. Soc., Chem. Commun., 1987, (2), pp. 62-63; 1. Med. Chem., 2014, Vol. 57, pp. 3845-3855 or by adapting the referenced procedures in a way known to a person skilled in the art.

Substituted 2-oxoglutaric aid esters of formula (III) can be synthesized according to the following literature reference: J. Med. Chem., 2014, Vol. 57, pp. 3845-3855 or by adapting the referenced procedures in a way known to a person skilled in the art. Preparation of specific fragments like (IIIa') and (IIIa") is shown according to Scheme 2 and Scheme 3, respectively.

Coupling reaction of an Intermediate of formula (II) with an intermediate of formula (III) generally takes place in inert solvents in the presence of a coupling reagent and, where applicable, with addition of a base at a temperature ranging from −20° C. to 80° C. for 1-24 hours preferably at a temperature of 20-30° C. overnight. Inert solvents are for example dichloromethane (DCM), toluene, tetrahydrofuran (THF), 1,4-dioxane, N,N-dimethylformamide (DMF), N,N-dimethylacetamide (DMA), N-methylpyrrolidin-2-one (NMP) and acetonitrile as well as mixtures of the aforementioned solvents. A preferred solvent is tetrahydrofuran.

Suitable coupling reagents are, for example, carbodiimides such as N,N'-diethyl-, N,N'-dipropyl-, N,N'-diisopropyl-, N,N'-dicyclohexylcarbodiimide, N-ethyl-N'-(3-dimethylaminopropyl)carbodiimide hydrochloride (EDC), carbonyldiimidazole (CDI), 0-(benzotriazol-1-yl)-N,N,N',N'-tetramethyluroniumhexafluorophosphate (HBTU), or O-(7-azabenzotriazol-1-yl)-N,N,N',N'-tetramethyluroniumhexafluorophosphate (HATU) or 1-hydroxybenzotriazole (HOBt) or (benzotriazol-1-yloxy)tris(dimethylamino)phosphonium hexafluorophosphate (BOP), or (benzotriazol-1-yloxy)tripyrrolidinophosphonium hexafluorophosphate (PyBOP), or N-hydroxysuccinimide as well as mixtures of the aforementioned coupling reagents with or without the addition of a base. Suitable bases are for example carbonates and bicarbonates, triethylamine, diisopropylethylamine, N-methylmorpholine, N-methylpiperidine or 4-dimethylaminopyridine.

The reaction generally takes place in a single solvent or in solvent mixtures at a temperature ranging from 0° C. to 100° C. for 1-24 hours. Suitable protic solvents are, for example, methanol, ethanol, isopropanol, tert-butanol, water. Solvents suitable to form mixtures are for example dichloromethane, trichloromethane, tetrahydrofuran, 1,4-dioxane, acetonitrile and N,N-dimethylformamide.

EXAMPLES

As indicated above, the present invention also includes methods for the preparation of compounds of formula (I). The following examples provide specific methodologies for the preparation of some of the specific compounds of Table 1.

In the following description, the following symbols are used to represent the particular meanings:

Ac: acetyl
br: broad (spectral)
Boc: tert-butyloxycarbonyl
Bn: benzyl
d: doublet (spectral)
DBU: 1,8-diazabicyclo[5.4.0]undec-7-ene
DCM: dichloromethane
DCC: N,N'-dicyclohexylcarbodiimide
DI: deionized
DIC: N,N'-diisopropylcarbodiimide
DIPEA: N,N-diisopropylethylamine
DMA: N,N-dimethylacetamide
DMAP: 4-dimethylaminopyridine
DMF: N,N-dimethylformamide
DMSO: dimethyl sulfoxide
h: hour(s)
HATU: 1-[bis(dimethylamino)methylene]-1H-1,2,3-triazolo[4,5-b]pyridinium 3-oxide hexafluorophosphate
m: multiplet (spectral)
min: minute(s)
MW: microwave
NHS: N-hydroxysuccinimide
Ph: phenyl
s: singlet (spectral)
t: triplet (spectral)
t-Bu: tert-butyl
TBSCl: tert-butyldimethylsilyl chloride
TEA: triethylamine
THF: tetrahydrofuran
TMEDA: tetramethylethylenediamine
TMS: trimethylsilyl group
TMSCN: trimethylsilyl cyanide

Example 1

(4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 1, Table 1)

Compound 1

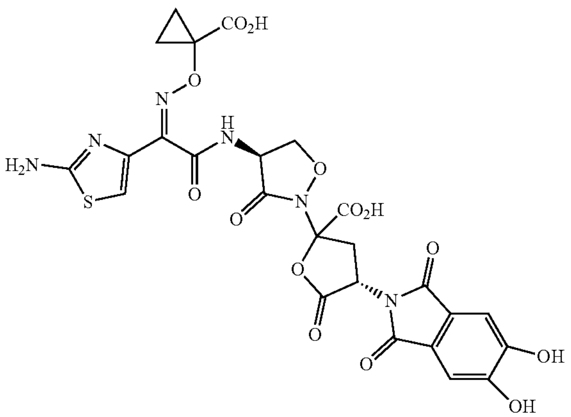

Step 1: tert-butyl 1-(aminooxy)cyclopropane-1-carboxylate (2)

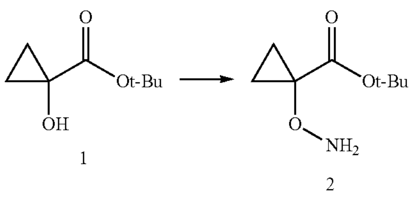 [SMILES: CC(C)(C)OC(=O)C1(O)CC1 ; CC(C)(C)OC(=O)C1(ON)CC1]

A solution of tert-butyl 1-hydroxycyclopropane-1-carboxylate 1 (4.86 g, 30.72 mmol) in anhydrous THF (120 mL) was cooled to 0-5° C. and O-diphenylphosphinylhydroxylamine (9.32 g, 39.97 mmol) was added, followed by sodium tert-butoxide (3.84 g, 39.96 mmol). The reaction mixture was stirred for 2 h at 0-10° C. and then hexanes (30 mL) and brine (75 mL) were added. The resulting suspension was stirred at 15-25° C. for 30 min. The precipitated solids were removed by filtration and washed with 10% ethyl acetate in hexanes. The organic phase of the filtrate was separated, and the aqueous layer was further extracted with ethyl acetate. The combined organic extracts were washed with brine, dried over sodium sulfate, filtered and concentrated under reduced pressure. The residue was treated with hexanes and filtered. The filtrate was concentrated under reduced pressure to afford tert-butyl 1-(aminooxy)cyclopropane-1-carboxylate 2 (5.02 g, 94%) as a yellow oil.

$^1$H NMR (400 MHz, $CDCl_3$) δ 5.78 (br s, 2H), 1.49 (s, 9H), 1.34-1.28 (m, 2H), 1.22-1.16 (m, 2H).

Step 2: (2Z)-{2-[(tert-butoxycarbonyl)amino]-1,3-thiazol-4-yl}({[1-(tert-butoxycarbonyl)cyclopropyl]oxy}imino)acetic acid (3)

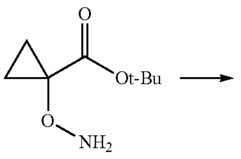

2

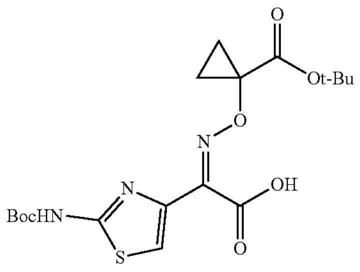

3

To a solution of tert-butyl 1-(aminooxy)cyclopropane-1-carboxylate 2 (5.92 g, 34.18 mmol) in MeOH (100 ml) was added {2-[(tert-butoxycarbonyl)amino]-1,3-thiazol-4-yl}(oxo)acetic acid (8.46 g, 31.07 mmol) and the resulting mixture was stirred for 4 h at room temperature. The reaction mixture was then concentrated to half volume and quenched by the addition of water (100 ml) and 0.5 M HCl solution (100 ml). The mixture was extracted with ethyl acetate and the combined organic extracts were washed with brine, dried over sodium sulfate, filtered and concentrated under reduced pressure. The residue was dissolved in EtOH (50 ml) and water was added slowly until no more precipitate was formed. The resulting suspension was stirred at 0-10° C. for 15 min, the precipitated solid was collected by filtration and air-dried to afford (2Z)-{2-[(tert-butoxycarbonyl)amino]-1,3-thiazol-4-yl}({[1-(tert-butoxycarbonyl)cyclopropyl]oxy}imino)acetic acid 3 (12.20 g, 92%) as an off-white solid.

$^1$H NMR (400 MHz, DMSO-$d_6$) δ 13.91 (br s, 1H), 11.78 (s, 1H), 7.42 (s, 1H), 1.45 (s, 9H), 1.41-1.31 (m, 11H), 1.27-1.19 (m, 2H).

MS (ESI) m/z: $[M+1]^+$ 428.1

Step 3: tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}cyclopropane-1-carboxylate (4)

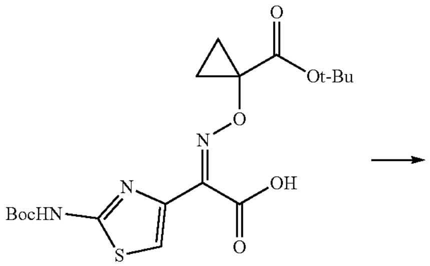

3

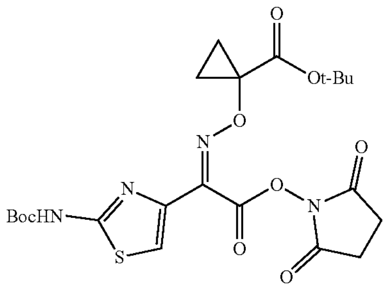

4

To a mixture of (2Z)-{2-[(tert-butoxycarbonyl)amino]-1,3-thiazol-4-yl}({[1-(tert-butoxycarbonyl)-cyclopropyl]oxy}imino)acetic acid 3 (10.93 g, 25.57 mmol) and NHS (3.53 g, 30.67 mmol) in anhydrous DCM (120 mL) was slowly added DIC (4.59 mL, 29.64 mmol) at 0° C. The reaction mixture was stirred at 0° C. for 15 min and then at room temperature for 3 h. The resulting suspension was filtered, and the solids were rinsed with DCM. The filtrate was concentrated under reduced pressure and the residue was treated with a mixture of methanol (50 ml) and heptane (40 ml). The mixture was stirred at room temperature for 30 min, then at ~10° C. for an additional 30 min and subsequently filtered to afford tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}cyclopropane-1-carboxylate 4 (13.50 g, 100%) as a white solid.

$^1$H NMR (400 MHz, $CDCl_3$) δ 8.36 (s, 1H), 7.60 (s, 1H), 2.99-2.83 (m, 4H), 1.54 (s, 9H), 1.51-1.45 (m, 4H), 1.43 (s, 9H).

MS (ESI) m/z: $[M+1]^+$ 525.0

Step 4: tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclopropane-1-carboxylate (5)

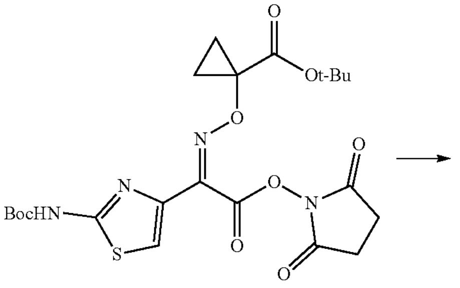

4

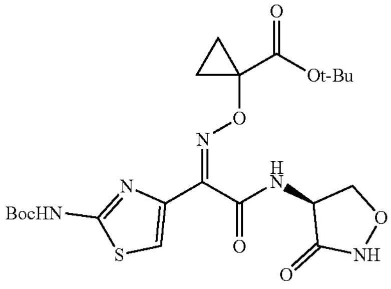

5

To a solution of tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}cyclopropane-1-carboxylate 4 (13.50 g, 25.57 mmol) and L-cycloserine (3.13 g, 30.66 mmol) in anhydrous DMF (140 ml) was added DIPEA (5.34 mL, 30.72 mmol) at room temperature. The reaction mixture was stirred at 45° C. for 18 h and then concentrated to dryness under reduced pressure. The residue was purified by silica gel column chromatography using a gradient of 0 to 2.5% methanol in DCM, followed by trituration using DCM and hexanes to afford tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclopropane-1-carboxylate 5 (5.56 g, 43%) as a white solid.

$^1$H NMR (400 MHz, DMSO-$d_6$) δ 11.81 (s, 1H), 11.59 (s, 1H), 9.00 (d, J=8.0 Hz, 1H), 7.45 (s, 1H), 4.90 (d, J=7.4 Hz, 1H), 4.58 (t, J=8.5 Hz, 1H), 4.08-3.96 (m, 1H), 1.45 (s, 9H), 1.37 (s, 9H), 1.34-1.18 (m, 4H).

MS (ESI) m/z: [M+Na]$^+$ 534.1

Step 5: tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (7)

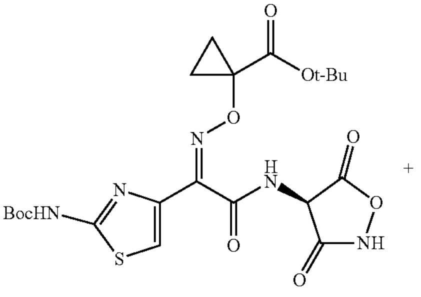

5

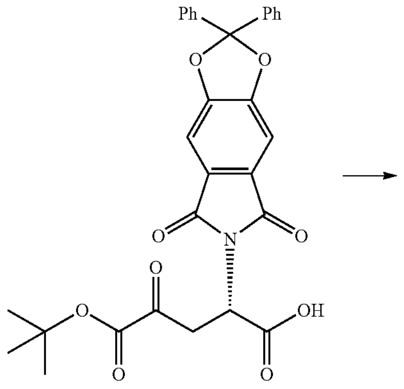

6

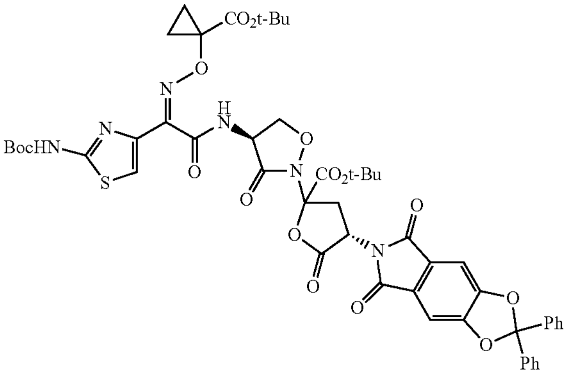

7

To a solution of tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclopropane-1-carboxylate 5 (1.04 g, 2.03 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (1.10 g, 2.02 mmol, prepared as described in J. Med. Chem., 2014, Vol. 57, pp. 3845-3855) in anhydrous THF (60 mL) was added DMAP (50 mg, 0.41 mmol), followed by DCC (585 mg, 2.84 mmol). The reaction mixture was stirred at room temperature for 18 h and then concentrated under reduced pressure. The residue was treated with 30% DCM in hexanes and the precipitated solids were removed by filtration. The filtrate was concentrated in vacuo and the residue was purified by silica gel column chromatography using a gradient of 10 to 35% ethyl acetate in hexanes to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 7 (720 mg, 34%) as a brown foam.

$^1$H NMR (400 MHz, $CDCl_3$) δ 8.68-8.56 (m, 1H), 8.56-8.26 (m, 1H), 7.58-7.49 (m, 4H), 7.46-7.35 (m, 7H), 7.30 (d, J=1.1 Hz, 2H), 5.38 (m, 1H), 5.21-4.81 (m, 2H), 4.40-4.19 (m, 1H), 3.70-3.28 (m, 1H), 2.93-2.70 (m, 1H), 1.66-1.46 (m, 21H), 1.46-1.30 (m, 10H).

MS (ESI) m/z: $[M+Na]^+$ 1059.4

Step 6: (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 1, Table 1)

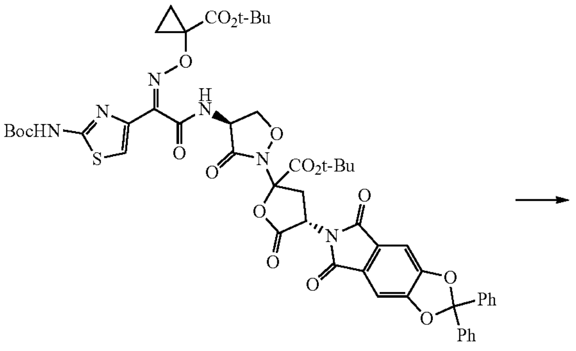

7

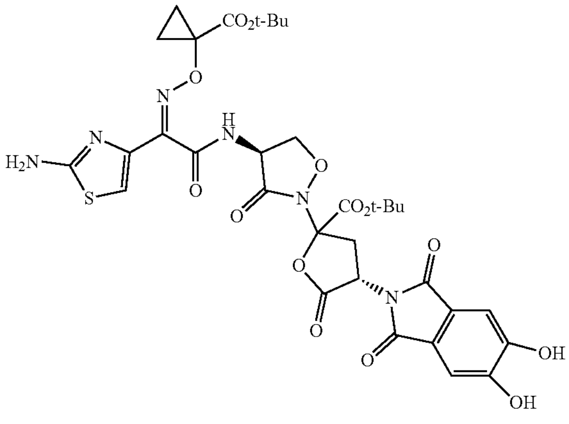

Compound 1

To a solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 7 (562 mg, 0.54 mmol) in anhydrous DCM (20 mL) was added dropwise a $BCl_3$ solution (1.0 M in DCM, 4.34 mL, 4.34 mmol) at −50° C. The reaction mixture was stirred at a temperature between −50° C. to −35° C. for 2.5 h. A mixture of $NaHCO_3$ (873 mg) and $Na_2HPO_4$ (273.5 mg) dissolved in water (47 mL) was then added to the reaction mixture at −50° C. The cold bath was replaced with an ice-water bath, the resulting heterogeneous mixture was stirred at 0 to 5° C. until the aqueous phase thawed (~40 min), and the phases were carefully separated. The aqueous layer was filtered using a 1.0 μm syringe filter and immediately subjected to C18 reverse phase column chromatography using a Biotage system and a 0 to 30% gradient of 0.1% formic acid in acetonitrile and 0.1% formic acid in water. The product-containing fractions were combined and lyophilized to afford Compound 1 (182 mg, 51%) as an off-white solid.

$^1$H NMR (400 MHz, a mixture of $D_2O$ and $CD_3CN$) δ 7.25 (s, 2H), 7.15-7.10 (m, 1H), 5.45-5.18 (m, 1H), 5.18-5.02 (m, 1H), 4.77-4.66 (m, 1H), 4.31-4.19 (m, 1H), 3.60-3.24 (m, 1H), 2.92-2.65 (m, 1H), 1.55-1.45 (m, 2H), 1.45-1.33 (m, 2H). Exchangeable protons were not observed in $D_2O$.

MS (ESI) m/z: $[M+1]^+$ 661.1

Example 2

(4S)-2-[(4S)-4-{[(2Z)-2-(2-amino-1,3-thiazol-4-yl)-2-{[(1-carboxycyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 4, Table 1)

Compound 4

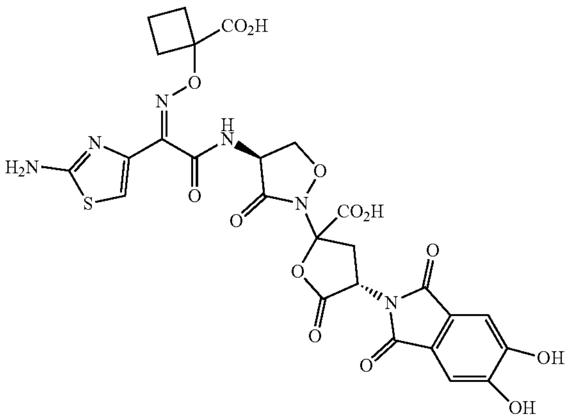

Step 1: tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclobutane-1-carboxylate (9)

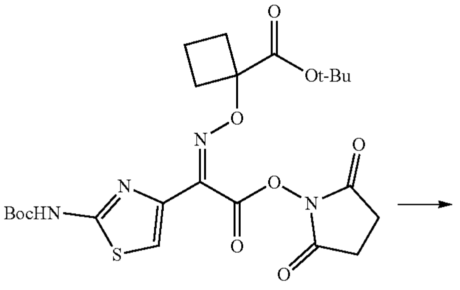

8

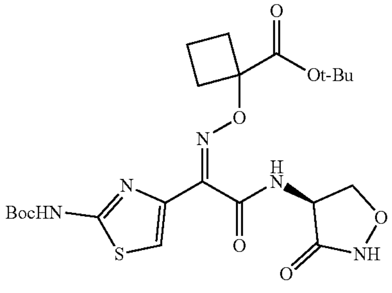

9

To a stirred solution of tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}cyclobutane-1-carboxylate 8 (11.0 g, 20.42 mmol, prepared as described in WO 2012/073138) and L-cycloserine (2.5 g, 24.51 mmol) in anhydrous DMF (110 mL) was added DIPEA (4.23 mL, 24.51 mmol) at room temperature. The reaction mixture was heated at 45° C. overnight and then concentrated to dryness under reduced pressure. The residue was subjected to silica gel column chromatography using a gradient of 0 to 3% MeOH in DCM, and afforded tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclobutane-1-carboxylate 9 (4.5 g, 42%) as an off-white solid.

$^1$H NMR (400 MHz, DMSO-$d_6$) δ 11.83 (s, 1H), 11.59 (s, 1H), 9.10 (d, J=7.9 Hz, 1H), 7.43 (s, 1H), 4.92 (br s, 1H), 4.60 (t, J=8.4 Hz, 1H), 4.12-4.03 (m, 1H), 2.46-2.33 (m, 2H), 2.32-2.14 (m, 2H), 1.94-1.70 (m, 2H), 1.45 (s, 9H), 1.40 (s, 9H).

Step 2: tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclobutyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (10)

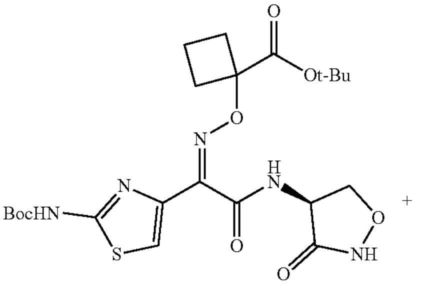

9

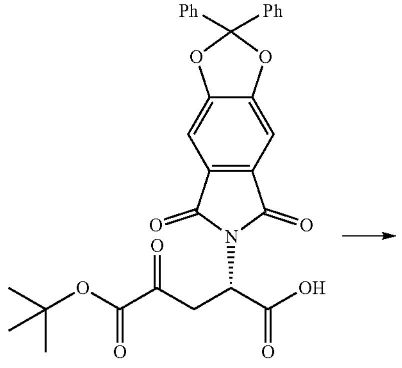

6

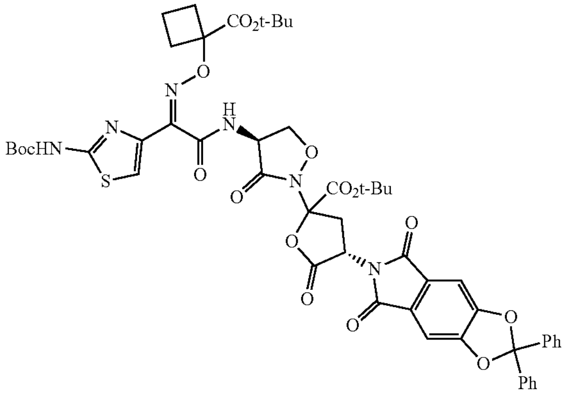

10

To a stirred solution of tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclobutane-1-carboxylate 9 (1.0 g, 1.84 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (1.06 g, 2.02 mmol, prepared as described in J. Med. Chem., 2014, Vol. 57, pp. 3845-3855) in anhydrous DCM (30 mL) was added DCC (0.53 g, 2.58 mmol) at room temperature. The reaction mixture was stirred at room temperature overnight and then filtered to remove the precipitated solids. The filtrate was concentrated to dryness under reduced pressure and the residue was purified by silica gel column chromatography using a gradient of 0 to 35% ethyl acetate in hexanes to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclobutyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 10 (1.0 g, 57%) as a gray colored solid.

$^1$H NMR (400 MHz, $CDCl_3$) δ 8.33-8.25 (m, 1H), 7.57-7.49 (m, 4H), 7.45-7.36 (m, 6H), 7.30 (s, 1H), 7.26 (s, 2H), 5.44-5.31 (m, 1H), 5.19-4.95 (m, 1H), 4.94-4.81 (m, 1H), 4.23 (m, 1H), 3.49-3.24 (m, 1H), 2.94-2.74 (m, 1H), 2.65-2.43 (m, 4H), 2.14-1.90 (m, 2H), 1.58-1.50 (m, 18H), 1.48 (s, 9H).

MS (ESI) m/z: $[M+1]^+$ 1073.4

Step 3: (4S)-2-[(4S)-4-{[(2Z)-2-(2-amino-1,3-thiazol-4-yl)-2-{[(1-carboxycyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 4, Table 1)

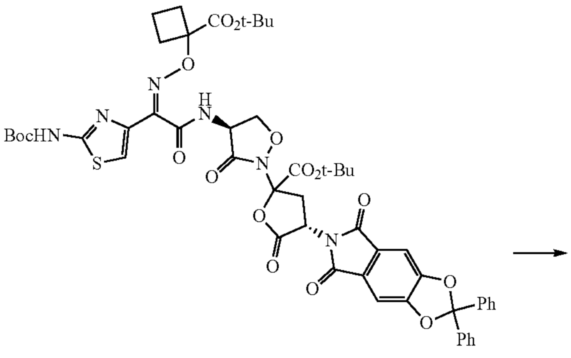

10

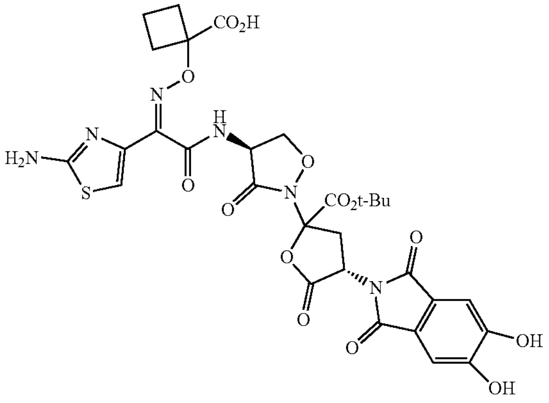

Compound 4

A stirred solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclobutyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 10 (300 mg, 0.28 mmol) in anhydrous DCM (10 ml) was cooled to −50° C. under nitrogen atmosphere. After 10 minutes, a solution of $BCl_3$ in DCM (1.0 M, 2.28 mL, 2.28 mmol) was added dropwise over 10 minutes maintaining the external temperature at −50° C. The reaction mixture was stirred at −50° C. to −40° C. for 2.5 h and then 25.2 mL of a buffer solution (prepared by dissolving 776 mg of $NaHCO_3$ and 243 mg of $Na_2HPO_4$ in 42 mL DI water) was added at −50° C. The cold bath was replaced with an ice-water bath, the resulting heterogeneous mixture was stirred at 0 to 5° C. until the aqueous phase thawed (~30 min), and the phases were carefully separated. The aqueous layer was filtered using a 1.0 μm syringe filter and immediately subjected to C18 reverse phase column chromatography using a Biotage system and a 0 to 30% gradient of 0.1% formic acid in acetonitrile and 0.1% formic acid in water. The product-containing fractions were combined and lyophilized to afford Compound 4 (105 mg, 55%) as a pale-yellow solid.

$^1$H NMR (400 MHz, a mixture of $D_2O$ and $CD_3CN$) δ 7.43 (s, 2H), 7.29 (s, 1H), 5.62-5.52 (m, 1H), 5.33 (m, 1H), 4.92 (m, 1H), 4.53-4.40 (m, 1H), 3.51 (m, 1H), 2.92 (m, 1H), 2.79-2.63 (m, 2H), 2.58-2.41 (m, 2H), 2.21-1.96 (m, 2H). Exchangeable protons were not observed in $D_2O$.

MS (ESI) m/z: $[M+1]^+$ 675

Example 3

(4S)-2-[(4S)-4-{[(2Z)-2-(2-amino-1,3-thiazol-4-yl)-2-{[(3-carboxyoxetan-3-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 5, Table 1) and (4S)-2-[(4S)-4-{[(2Z)-2-(2-amino-1,3-thiazol-4-yl)-2-{[(2-carboxy-1-chloro-3-hydroxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 6, Table 1)

Compound 5

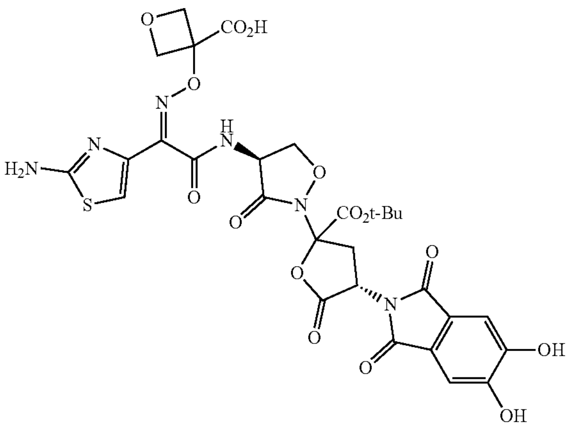

-continued

Compound 6

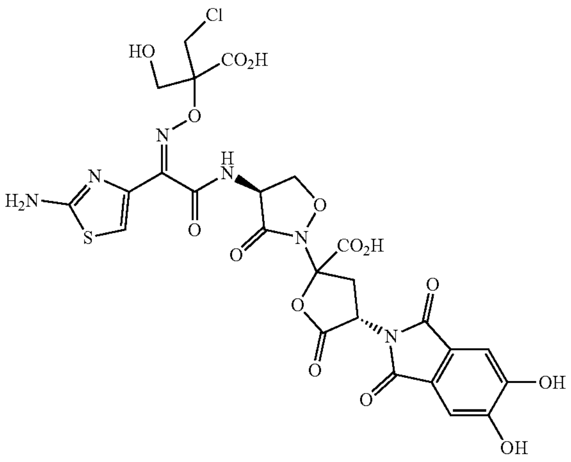

Step 1: 3-[(trimethylsilyl)oxy]oxetane-3-carbonitrile (12)

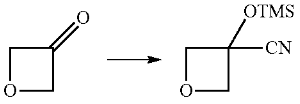

11 12

To $LiClO_4$ (14.70 g, 138.18 mmol) was added oxetan-3-one 11 (8.10 mL, 138.18 mmol), followed by TMSCN (22.0 ml, 175.85 mmol). The resulting mixture was stirred at room temperature for 2 h, then diluted with DCM and filtered. The filtrate was washed with water, dried over sodium sulfate, filtered and concentrated under reduced pressure. The crude 3-[(trimethylsilyl)oxy]oxetane-3-carbonitrile 12 (22.05 g, 93%) was obtained as a brown oil and used in the next step without further purification.

$^1H$ NMR (400 MHz, $CDCl_3$) δ 4.95-4.84 (m, 2H), 4.78-4.64 (m, 2H), 0.43-0.20 (s, 9H).

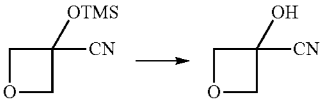

12 13

Step 2: 3-hydroxyoxetane-3-carbonitrile (13)

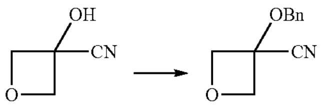

13 14

To a solution of 3-hydroxyoxetane-3-carbonitrile 13 (6.69 g, 67.51 mmol) in THF (200 ml) was added NaOH (powder, 8.10 g, 202.5 mmol). The resulting mixture was stirred at room temperature for 10 min, then cooled to 5-10° C. (cold water bath) and benzyl bromide (12.05 mL, 101.31 mmol) followed by $n-Bu_4NI$ (2.50 g, 6.77 mmol) were added. The reaction mixture was allowed to slowly warm to room temperature and stirred for 19 h. The reaction was then quenched with water and the mixture was extracted with diethyl ether. The combined organic extracts were washed with brine, dried over sodium sulfate, filtered and concentrated under reduced pressure. The residue was purified by silica gel column chromatography using a gradient of 0 to 8% ethyl acetate in hexanes. The obtained product was triturated with hexanes to afford pure 3-(benzyloxy)oxetane-3-carbonitrile 14 (2.61 g, 20%) as a white crystalline solid.

$^1H$ NMR (400 MHz, $CDCl_3$) δ 7.51-7.32 (m, 5H), 4.85 (d, J=8.1 Hz, 2H), 4.74-4.61 (m, 4H).

Step 4: 3-(benzyloxy)oxetane-3-carboxylic acid (15)

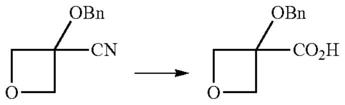

14 15

To a solution of 3-(benzyloxy)oxetane-3-carbonitrile 14 (5.51 g, 29.12 mmol) in MeOH (60 mL) was added an aqueous NaOH solution (2 M, 29.2 mL). The reaction mixture was heated at reflux temperature for 6 h, then cooled to room temperature and concentrated under reduced pressure to remove MeOH. The aqueous solution was cooled to 0° C. and acidified to pH~2 using a 1M aqueous HCl solution. The precipitated white solid was collected by filtration and then dissolved with 10% MeOH in DCM. The resulting solution was dried over sodium sulfate, filtered and concentrated under reduced pressure to afford 3-(benzyloxy)oxetane-3-carboxylic acid 15 (5.30 g, 87%) as a white solid.

$^1H$ NMR (400 MHz, DMSO-$d_6$) δ 13.42 (br s, 1H), 7.46-7.19 (m, 5H), 4.76 (d, J=7.2 Hz, 2H), 4.59 (d, J=7.1 Hz, 2H), 4.47 (s, 2H).

MS (ESI) m/z: $[M-1]^+$ 207.0

Step 5: tert-butyl 3-(benzyloxy)oxetane-3-carboxylate (16)

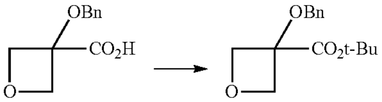

15 16

To a stirred solution of 3-(benzyloxy)oxetane-3-carboxylic acid 15 (5.30 g, 25.46 mmol) in anhydrous THF (80 mL) was slowly added tert-butyl N,N'-diisopropylcarbamimidate (15 mL, 57.6 mmol) at 0° C. The reaction mixture was stirred at 0° C. for 10 min, and then at room temperature for 5 h. The reaction mixture was concentrated under reduced pressure and the residue was treated with 25% DCM in hexanes and filtered. The filtrate was concentrated in vacuo and the crude mixture was purified by silica gel column chromatography using a gradient of 0 to 8% ethyl acetate in hexanes to afford tert-butyl 3-(benzyloxy)oxetane-3-carboxylate 16 (5.65 g, 84%) as a white solid.

$^1$H NMR (500 MHz, $CDCl_3$) δ 7.45-7.30 (m, 5H), 4.92-4.87 (m, 2H), 4.76-4.71 (m, 2H), 4.51 (s, 2H), 1.58 (s, 9H).

Step 6: tert-butyl 3-hydroxyoxetane-3-carboxylate (17)

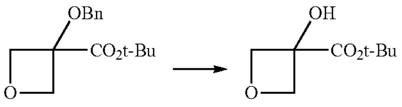

16 17

To a solution of tert-butyl 3-(benzyloxy)oxetane-3-carboxylate 16 (5.65 g, 21.38 mmol) in a mixture of ethyl acetate and MeOH (1:1, 120 mL) was added $Pd(OH)_2$ (20 wt %, 1.30 g). The reaction mixture was purged with hydrogen three times, then shaken at room temperature under hydrogen pressure (50 psi) for 5 h and filtered through a pad of Celite. The filtrate was concentrated under reduced pressure and the residue was purified by silica gel column chromatography using a gradient of 10 to 30% ethyl acetate in hexanes to afford tert-butyl 3-hydroxyoxetane-3-carboxylate 17 (3.31 g, 89%) as a white solid.

$^1$H NMR (500 MHz, $CDCl_3$) δ 4.88 (d, J=6.9 Hz, 2H), 4.75 (d, J=7.3 Hz, 2H), 3.75 (s, 1H), 1.60 (s, 9H).

Step 7: tert-butyl 3-(aminooxy)oxetane-3-carboxylate (18)

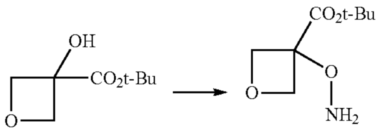

17 18

To a solution of tert-butyl 3-hydroxyoxetane-3-carboxylate 17 (3.31 g, 19.0 mmol) and O-diphenylphosphinylhydroxylamine (5.32 g, 22.81 mmol) in anhydrous THF (90 ml) was added sodium tert-butoxide (2.19 g, 22.79 mmol) at 0-5° C. The reaction mixture was stirred at 0-5° C. for 2 h, then brine (50 mL) and hexanes (30 mL) were added and the resulting mixture was stirred at 15-25° C. for 30 min. The precipitated solids were removed by filtration and washed with 30% ethyl acetate in hexanes. The two layers of the biphasic filtrate were separated, and the aqueous layer was further extracted with ethyl acetate. The combined organic extracts were washed with brine, dried over sodium sulfate, filtered and concentrated under reduced pressure. The residue was treated with hexanes, the resulting mixture filtered, and the filtrate was concentrated in vacuo to afford tert-butyl 3-(aminooxy)oxetane-3-carboxylate 18 (3.41 g, 95%) as a yellow solid.

$^1$H NMR (500 MHz, $CDCl_3$) δ 4.88 (dd, J=7.2, 0.8 Hz, 2H), 4.76-4.64 (m, 2H), 1.62-1.55 (m, 9H).

Step 8: (2Z)-{2-[(tert-butoxycarbonyl)amino]-1,3-thiazol-4-yl}({[3-(tert-butoxycarbonyl)oxetan-3-yl]oxy}imino)acetic acid (19)

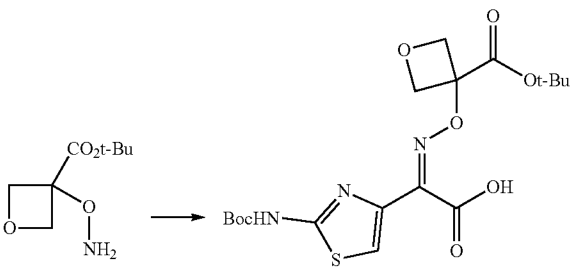

18 19

To a solution of tert-butyl 3-(aminooxy)oxetane-3-carboxylate 18 (3.41 g, 18.02 mmol) in MeOH (50 ml) was added {2-[(tert-butoxycarbonyl)amino]-1,3-thiazol-4-yl}(oxo)acetic acid (4.46 g, 16.38 mmol) and the reaction mixture was stirred at room temperature for 4 h. Water (100 mL) and an aqueous HCl solution (0.1 M, 100 ml) were then added and the mixture was extracted with ethyl acetate. The combined organic extracts were washed with brine, dried over sodium sulfate, filtered and concentrated under reduced pressure. The residue was treated with 5% diethyl ether in hexanes and the resulting suspension was stirred for 1 h then filtered to afford (2Z)-{2-[(tert-butoxycarbonyl)amino]-1,3-thiazol-4-yl}({[3-(tert-butoxycarbonyl)oxetan-3-yl]oxy}imino)acetic acid 19 (6.96 g, 96%) as a white solid.

$^1$H NMR (400 MHz, DMSO-$d_6$) δ 11.81 (s, 1H), 7.43 (s, 1H), 4.95-4.78 (m, 2H), 4.76-4.54 (m, 2H), 1.60-1.43 (m, 9H), 1.41 (s, 9H).

MS(ESI) m/z: $[M+1]^+$ 443.8

Step 9: tert-butyl 3-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}oxetane-3-carboxylate (20)

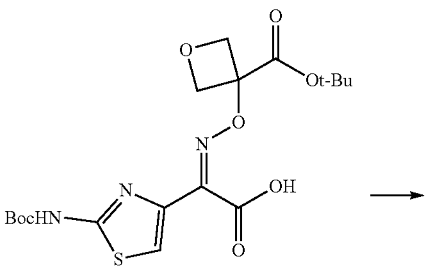

19

-continued

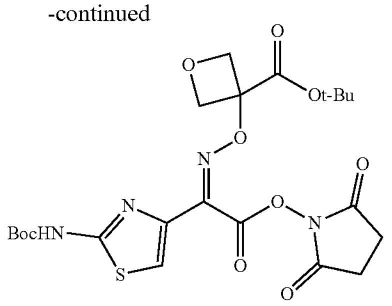

20

To a solution of (2Z)-{2-[(tert-butoxycarbonyl)amino]-1,3-thiazol-4-yl}({[3-(tert-butoxycarbonyl)oxetan-3-yl]oxy}imino)acetic acid 19 (6.96 g, 15.69 mmol) and NHS (2.17 g, 18.85 mmol) in anhydrous DCM (80 ml) was slowly added DIC (2.82 mL, 18.21 mmol) at 0° C. The reaction mixture was stirred for 15 min at 0° C., and then at room temperature for 3 h. The resulting suspension was filtered and the solid rinsed with DCM. The filtrate was concentrated under reduced pressure and the residue was treated with a mixture of methanol (20 mL) and n-heptane (20 ml). The obtained mixture was stirred at room temperature for 30 min, then at ~10° C. for 30 min and subsequently filtered to afford tert-butyl 3-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}oxetane-3-carboxylate 20 (7.69 g, 91%) as a white solid.

$^1H$ NMR (400 MHz, $CDCl_3$) δ 8.51 (br s, 1H), 7.61 (s, 1H), 5.09-5.03 (m, 2H), 4.94-4.88 (m, 2H), 3.05-2.77 (m, 4H), 1.65-1.53 (m, 9H), 1.53-1.47 (m, 9H).

MS (ESI) m/z: $[M+1]^+$ 541.1

Step 10: tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxetane-3-carboxylate (21)

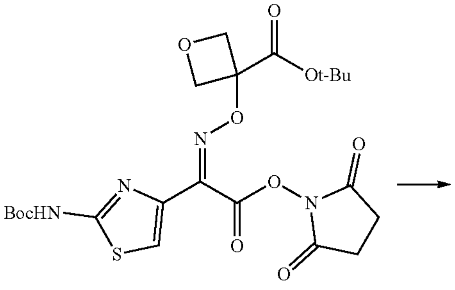

20

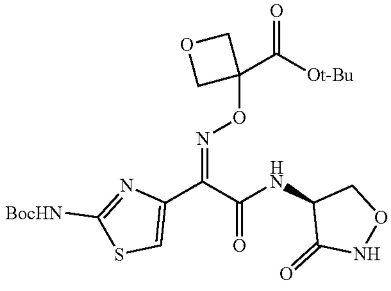

21

To a mixture of tert-butyl 3-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}oxetane-3-carboxylate 20 (7.69 g, 14.23 mmol) and L-cycloserine (1.74 g, 17.05 mmol) in anhydrous DMF (80 mL) was added DIPEA (2.97 mL, 17.05 mmol) at room temperature. The reaction mixture was stirred at 45° C. for 18 h, then cooled to room temperature and concentrated to dryness under reduced pressure. The crude mixture was subjected to silica gel column chromatography purification using a gradient of 0 to 2.5% methanol in DCM. The product containing fractions were combined, concentrated in vacuo, and the residue was further purified by trituration using diethyl ether and hexanes to afford tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxetane-3-carboxylate 21 (2.37 g, 32%) as a white solid.

$^1H$ NMR (400 MHz, DMSO-$d_6$) δ 11.85 (s, 1H), 11.63 (s, 1H), 9.26 (d, J=7.8 Hz, 1H), 7.49 (s, 1H), 4.95 (br s, 1H), 4.81 (d, J=7.3 Hz, 2H), 4.62 (dd, J=12.3, 7.4 Hz, 3H), 4.10 (t, J=9.1 Hz, 1H), 1.45 (s, 9H), 1.43 (s, 9H).

MS (ESI) m/z: $[M+1]^+$ 528.0

Step 11: tert-butyl (4S)-2-[(4S)-4-{[(2Z)-2-{2-[(tert-butoxycarbonyl)amino]-1,3-thiazol-4-yl}-2-({[3-(tert-butoxycarbonyl)oxetan-3-yl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (22)

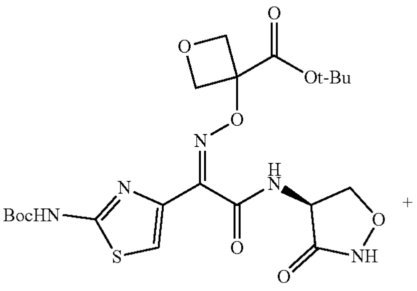

21

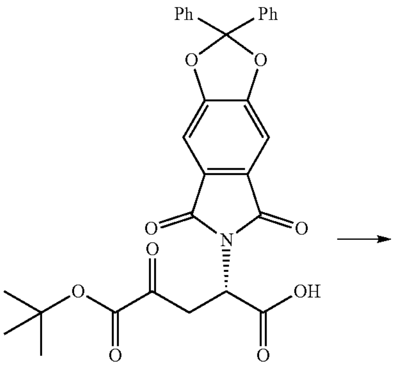

6

-continued

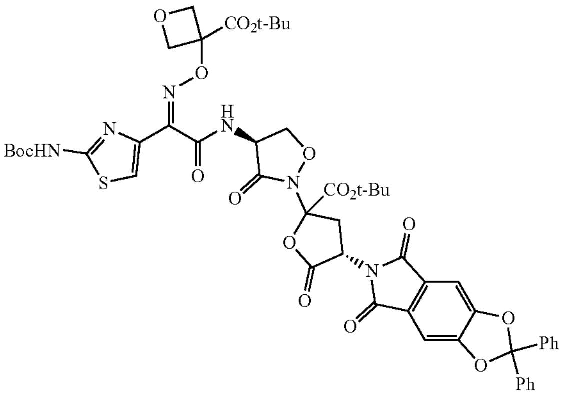

22

To a stirred mixture of tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxetane-3-carboxylate 21 (444 mg, 0.84 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (457 mg, 0.84 mmol, prepared as described in J. Med. Chem., 2014, Vol. 57, pp. 3845-3855) in anhydrous THE (17 mL) was added DMAP (21 mg, 0.17 mmol), followed by DCC (243 mg, 1.18 mmol) at 0° C. The reaction mixture was allowed to slowly warm to room temperature and stirred for 18 h. The mixture was then concentrated under reduced pressure and the residue was treated with 30% DCM in hexanes. The solids were removed by filtration, the filtrate was concentrated, and the residue was purified by silica gel column chromatography using a gradient of 10 to 40% ethyl acetate in hexanes to afford tert-butyl (4S)-2-[(4S)-4-{[(2Z)-2-{2-[(tert-butoxycarbonyl)amino]-1,3-thiazol-4-yl}-2-({[3-(tert-butoxycarbonyl)oxetan-3-yl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 22 (550 mg, 62%) as a white foam.

$^1$H NMR (400 MHz, $CDCl_3$) δ 8.46 (br s, 1H), 8.13-7.91 (m, 1H), 7.63-7.52 (m, 4H), 7.47-7.38 (m, 7H), 7.33 (d, J=1.6 Hz, 2H), 5.38 (m, 1H), 5.25-4.86 (m, 6H), 4.39-4.20 (m, 1H), 3.75-3.24 (m, 1H), 2.93-2.72 (m, 1H), 1.62-1.49 (m, 27H).

MS (ESI) m/z: $[M+Na]^+$ 1075.4

Step 12: (4S)-2-[(4S)-4-{[(2Z)-2-(2-amino-1,3-thiazol-4-yl)-2-{[(3-carboxyoxetan-3-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 5, Table 1) and (4S)-2-[(4S)-4-{((2Z)-2-(2-amino-1,3-thiazol-4-yl)-2-{[(2-carboxy-1-chloro-3-hydroxypropan-2-yl)oxy]imino}acetyl]amino}-3-oxo-1,2-oxazolidin-2-yl)-4-(5,6-dihydroxy-1,3-dioxo-1,3-dihydro-2H-isoindol-2-yl)-5-oxooxolane-2-carboxylic acid (Compound 6, Table 1)

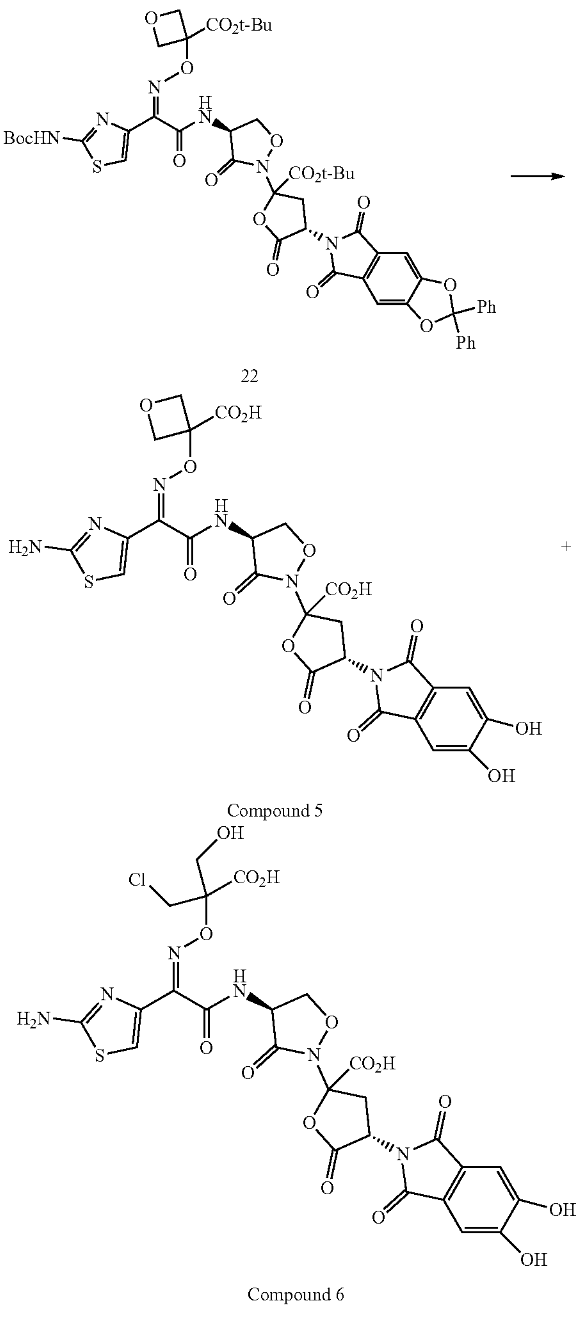

22

Compound 5

+

Compound 6

To a solution of tert-butyl (4S)-2-[(4S)-4-{[(2)-2-(2-[(tert-butoxycarbonyl)amino]-1,3-thiazol-4-yl)-2-({[3-(tert-butoxycarbonyl)oxetan-3-yl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 22 (150 mg, 0.14 mmol) in anhydrous DCM (7 ml) was added dropwise a $BCl_3$ solution (1.0 M in DCM, 1.14 ml, 1.14 mmol) at −78° C. the reaction mixture was stirred at −78° C. for 2.5 h and then a solution of $NaHCO_3$ (233 mg) and $Na_2HPO_4$ (73 mg) dissolved in water (12.6 mL) was added at −78° C. The cold bath was replaced with an ice-water bath, the resulting heterogeneous mixture was stirred at 0 to 5° C. until the aqueous phase thawed (~30 min), and the phases were carefully separated. The aqueous layer was filtered using a 1.0 μm syringe filter and immediately subjected to C18 reverse phase column chromatography using a Biotage system and a 0 to 30% gradient of 0.1% formic acid in acetonitrile and 0.1% formic acid in water. The fractions containing pure products were lyophilized to afford Compound 5 (8.5 mg, 9%) and Compound 6 (38 mg, 19%) as off-white solids.

For Compound 5:

$^1H$ NMR (400 MHz, a mixture of $D_2O$ and $CD_3CN$) δ 10.05 (s, 2H), 10.01-9.95 (m, 1H), 8.23-8.05 (m, 1H), 8.02-7.88 (m, 1H), 7.80 (d, J=7.8 Hz, 2H), 7.65-7.49 (m, 3H), 7.14-7.05 (m, 1H), 6.38-6.10 (m, 1H), 5.76-5.52 (m, 1H). Exchangeable protons were not observed in $D_2O$.

MS (ESI) m/z: $[M+1]^+$ 677.1

For Compound 6:

$^1H$ NMR (400 MHz, a mixture of $D_2O$ and $CD_3CN$) δ 10.05 (s, 2H), 9.98 (s, 1H), 8.28-8.03 (m, 1H), 8.03-7.83 (m, 1H), 7.60-7.46 (m, 1H), 7.14-7.07 (m, 1H), 6.89-6.72 (m, 5H), 6.38-6.07 (m, 1H), 5.75-5.49 (m, 1H). Exchangeable protons were not observed in $D_2O$.

MS (ESI) m/z: $[M+1]^+$ 713.0

Example 4

3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)azetidine-3-carboxylic acid (Compound 7, Table 1)

Compound 7

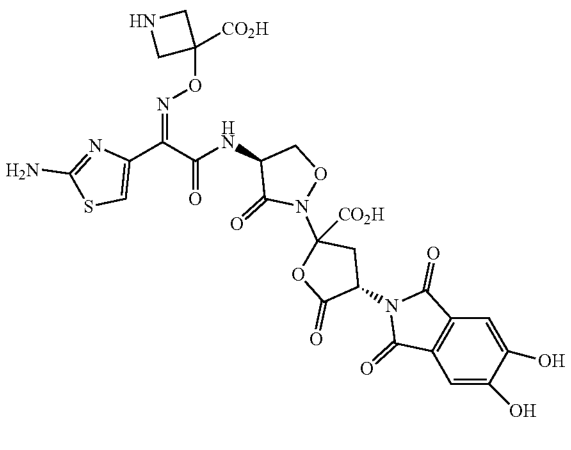

Step 1: di-tert-butyl 3-hydroxyazetidine-1,3-dicarboxylate (24)

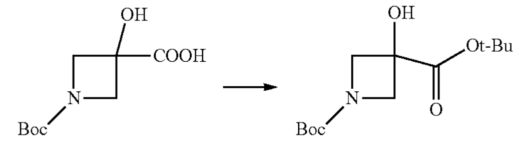

23 24

To a solution of 1-(tert-butoxycarbonyl)-3-hydroxyazetidine-3-carboxylic acid 23 (4.33 g, 19.93 mmol, prepared as described in WO2013/96771 A1) in anhydrous THF (100 ml), was added tert-butyl N,N'-diisopropylcarbamimidate (7.4 ml, ~39.86 mmol) and the reaction mixture was stirred at room temperature for 14 h. The precipitated solids were removed by filtration and washed with THF. The filtrate was concentrated under reduced pressure and the residue was treated with a mixture of DCM and hexanes (1:1, 100 ml). The resulting suspension was stirred at ~5° C. for 10 minutes, the solid was filtered off and washed with a mixture of DCM and hexanes (1:1, 20 ml). The filtrate was collected, concentrated in vacuo, and the residue was purified by silica gel column chromatography using a gradient of 10 to 20% ethyl acetate in hexanes to afford di-tert-butyl 3-hydroxyazetidine-1,3-dicarboxylate 24 as off-white solid (4.35 g, 80% yield).

$^1H$ NMR (400 MHz, $CDCl_3$): δ 4.21 (d, J=13.7 Hz, 2H), 3.97 (d, J=13.7 Hz, 2H), 1.53 (s, 9H), 1.44 (s, 9H).

Step 2: di-tert-butyl 3-(aminooxy)azetidine-1,3-dicarboxylate (25)

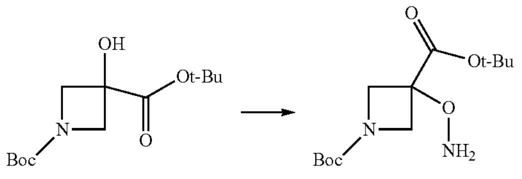

24 25

To a solution of di-tert-butyl 3-hydroxyazetidine-1,3-dicarboxylate 24 (4.33 g, 15.84 mmol) in anhydrous THF (100 ml) was added O-diphenylphosphinylhydroxylamine (4.43 g, 19.0 mmol). The resulting heterogeneous mixture was cooled to 0° C. and sodium tert-butoxide (1.83 g, 19.0 mmol) was added. The reaction mixture was stirred at 0° C. for 2 h, then a 5% aqueous NaCl solution (200 ml) was added and the mixture was stirred at 10-15° C. for 30 min. Subsequently, ethyl acetate (200 ml) was added and the mixture was stirred for 15 min. The organic phase was separated, and the aqueous layer was further extracted with ethyl acetate (100 ml). The combined organic extracts were washed with brine, dried over sodium sulfate, filtered and concentrated under reduced pressure to afford di-tert-butyl 3-(aminooxy)azetidine-1,3-dicarboxylate 25 as thick yellow oil (4.08 g, 89% yield).

$^1H$ NMR (400 MHz, $CDCl_3$): δ 4.15 (d, J=9.5 Hz, 2H), 3.94 (d, J=9.54 Hz, 2H), 1.52 (s, 9H), 1.45 (s, 9H).

Step 3: (2Z)-({[1,3-bis(tert-butoxycarbonyl)azetidin-3-yl]oxy}imino){2-[(tert-butoxycarbonyl)amino]-1,3-thiazol-4-yl}acetic acid (26)

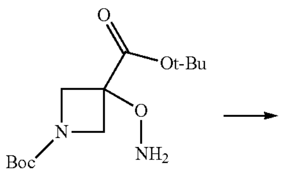

25

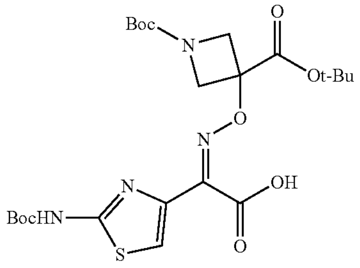

26

To a solution of di-tert-butyl 3-(aminooxy)azetidine-1,3-dicarboxylate 25 (3.97 g, 13.77 mmol) in anhydrous MeOH (40 mL) was added 2-(2-(tert-butoxycarbonylamino)thiazol-4-yl)-2-oxoacetic acid (3.41 g, 12.51 mmol) and the reaction mixture was stirred at room temperature for 3 h. The majority of methanol was removed under reduced pressure and the residue was dissolved in 200 mL of ethyl acetate. The organic phase was washed with a dilute HCl solution (100 mL water and 13 mL of 1M HCl), then brine (100 mL), dried over sodium sulfate, filtered and concentrated in vacuo to afford (2Z)-({[1,3-bis(tert-butoxycarbonyl)azetidin-3-yl]oxy}imino){2-[(tert-butoxycarbonyl)amino]-1,3-thiazol-4-yl}acetic acid 26 as an off-white foamy solid (7.19 g, crude).

$^1$H NMR (400 MHz, DMSO-$d_6$): δ 7.45 (s, 1H), 4.21 (d, J=9.6 Hz, 2H), 3.90 (d, J=9.6 Hz, 2H), 1.45 (s, 9H), 1.41 (s, 9H), 1.38 (s, 9H).

Step 4: di-tert-butyl 3-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}azetidine-1,3-dicarboxylate (27)

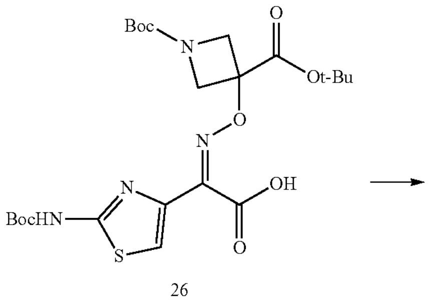

26

-continued

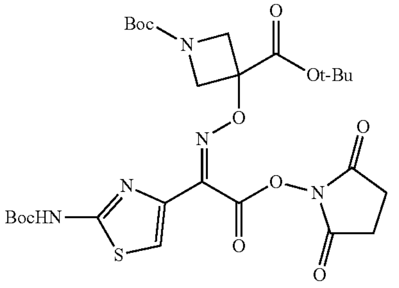

27

A solution of (2Z)-({[1,3-bis(tert-butoxycarbonyl)azetidin-3-yl]oxy}imino){2-[(tert-butoxycarbonyl)amino]-1,3-thiazol-4-yl}acetic acid 26 (7.19 g crude, ~13.25 mmol) and NHS (1.83 g, 15.90 mmol) in anhydrous DCM (140 ml) was cooled to 0° C. N,N'-diisopropylcarbodiimide (2.00 g, 15.90 mmol) was added dropwise and the reaction mixture was stirred at 0° C. for 15 minutes and then at room temperature for 3 h. The precipitated solids were filtered off and the filtrate was concentrated under reduced pressure. The residue was dissolved in 20 ml methanol, the mixture was concentrated to a volume of 5 mL and n-heptane (20 mL) was added. The mixture was stirred for 30 minutes at room temperature, then cooled to ~10° C. and stirred for a further 15 min. The precipitate was collected by filtration, washed with heptane and dried under vacuum to afford di-tert-butyl 3-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}azetidine-1,3-dicarboxylate 27 as an off-white solid (8.41 g, 99% yield).

$^1$H NMR (400 MHz, $CDCl_3$): δ 8.24 (br s, 1H), 7.57 (s, 1H), 4.36 (d, J=9.8 Hz, 2H), 4.20 (d, J=9.8 Hz, 2H), 2.91 (s, 4H), 1.53 (s, 9H), 1.45 (s, 9H), 1.44 (s, 9H).

Step 5: di-tert-butyl 3-{[(Z)-(1-(2-[(tert-butoxycarbonyl)amino]-1,3-thiazol-4-yl}-2-oxo-2-{[(4S)-3-oxo-1,2-oxazolidin-4-yl]amino)ethylidene)amino]oxy}azetidine-1,3-dicarboxylate (28)

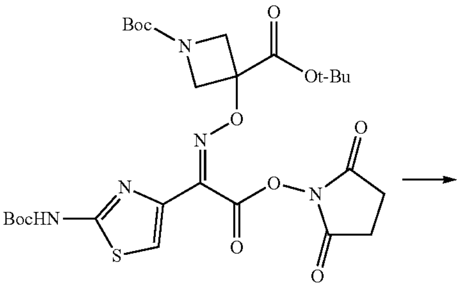

27

-continued

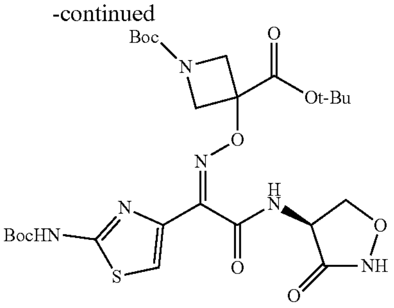

28

To a mixture of di-tert-butyl 3-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}azetidine-1,3-dicarboxylate 27 (8.4 g, 13.1 mmol) and L-cycloserine (1.60 g, 15.7 mmol) in anhydrous DMF (100 ml) was added DIPEA (2.7 mL, 15.7 mmol) at room temperature. The heterogeneous reaction mixture was stirred at 45° C. under nitrogen for 18 h, then cooled to room temperature and concentrated to dryness under reduced pressure. The residue was purified by silica gel column chromatography using 30% acetonitrile in DCM and then 2% MeOH in a 30% acetonitrile-DCM mixture as eluent to afford di-tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}azetidine-1,3-dicarboxylate 28 as a white solid (3.1 g, 37% yield).

$^{1}$H NMR (400 MHz, DMSO-$d_6$): δ 9.23 (d, J=8.0 Hz, 1H), 7.46 (s, 1H), 5.45 (d, J=7.4 Hz, 1H), 4.92 (br s, 1H), 4.63-4.60 (m, 1H), 4.21-4.17 (m, 2H), 4.01-3.85 (m, 2H), 1.45 (s, 9H), 1.42 (s, 9H), 1.38 (s, 9H).

MS (ESI) m/z: $[M+1]^+$ 627.0

Step 6: di-tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)azetidine-1,3-dicarboxylate (29)

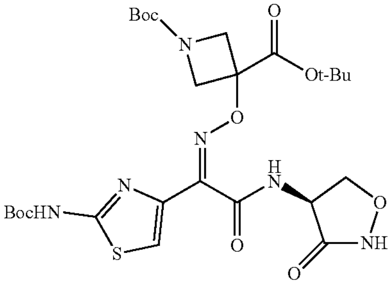

28

+

-continued

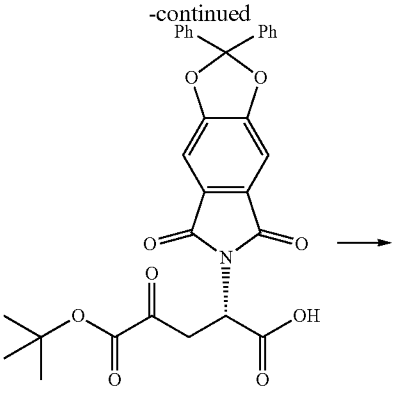

6

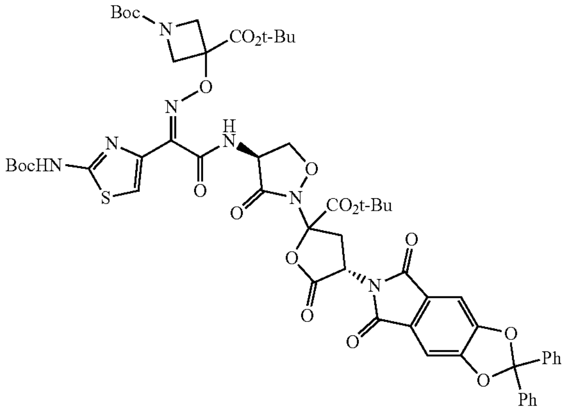

29

A mixture of (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (1.09 g, 2.0 mmol, prepared as described in *J. Med. Chem.*, 2014, Vol. 57, pp. 3845-3855) and di-tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}azetidine-1,3-dicarboxylate 28 (1.25 g, 2.0 mmol) in anhydrous THF (30 ml) was cooled to 0° C. DMAP (50 mg, 0.40 mmol) followed by DCC (0.58 g, 2.80 mmol) were added, the reaction mixture was stirred at 5-10° C. for 1 h and then at room temperature overnight. The mixture was concentrated under reduced pressure at 25° C. and the residue was taken up in 40% DCM in hexanes (25 ml). The precipitated solids were filtered off, washed with 30% DCM in hexanes (25 ml) and then with hexanes. The filtrate was concentrated in vacuo and the crude product was purified by silica gel column chromatography using a gradient of 10 to 35% ethyl acetate in hexanes to afford di-tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)azetidine-1,3-dicarboxylate 29 as an off-white foamy solid (1.44 g, 62% yield).

$^{1}$H NMR (400 MHz, $CDCl_3$): δ 8.03 (d, J=6.0 Hz, 1H), 7.58-7.53 (m, 4H), 7.47-7.40 (m, 6H), 7.35-7.31 (m, 2H), 5.42-5.34 (m, 1H), 5.05-4.85 (m, 1H), 4.42-4.19 (m, 5H), 3.55-3.25 (m, 1H), 2.93-2.81 (m, 1H), 2.00-1.91 (m, 1H), 1.77-1.68 (m, 1H), 1.59 (m, 9H), 1.56 (m, 9H), 1.53 (m, 9H), 1.48 (m, 9H).

Step 7: 3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)azetidine-3-carboxylic acid (Compound 7, Table 1)

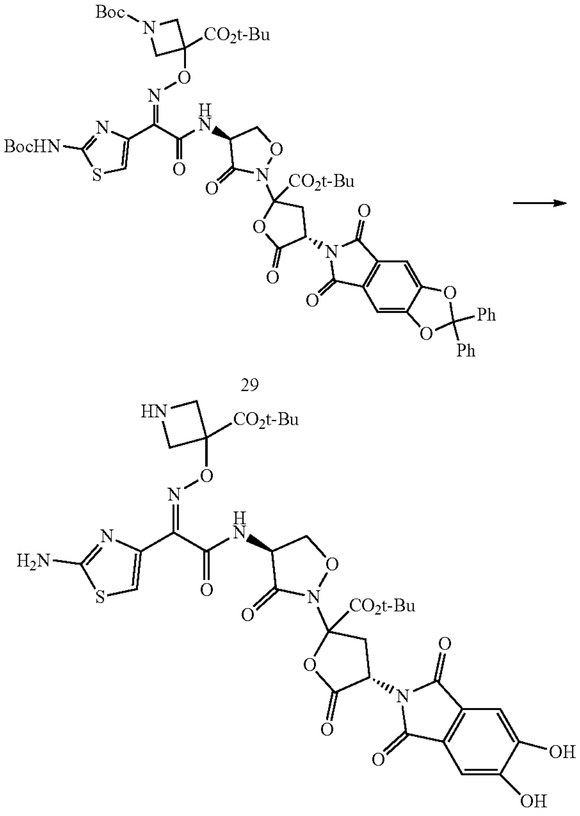

29

Compound 7

To a solution of di-tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)azetidine-1,3-dicarboxylate 29 (240 mg, 0.21 mmol) in anhydrous DCM (15 ml) was added dropwise a solution of boron trichloride (1.0 M solution in DCM, 1.7 mL, 1.7 mmol) at −50° C. The reaction mixture was stirred at −50 to −35° C. for 2.5 h, then cooled to −50° C. and quenched by the addition of 18.3 mL of a buffer solution (prepared by dissolving 776 mg of $NaHCO_3$ and 243 mg of $Na_7HPO_4$ in 42 mL of water). The cold bath was replaced with an ice-water bath, the resulting heterogeneous mixture was stirred at 0 to 5° C. until the aqueous phase thawed (~30 min), and the phases were carefully separated. The aqueous layer was filtered using a 1.0 μm syringe filter and Immediately subjected to C18 reverse phase column chromatography using a Biotage system and a 0 to 30% gradient of 0.1% formic acid in acetonitrile and 0.1% formic acid in water. The fractions containing pure product were lyophilized to afford Compound 7 (40.5 mg, 29%) as a pale yellow foamy solid.

$^1H$ NMR (400 MHz, a mixture of $D_2O$ and $CD_3CN$): δ 7.53 (s, 2H), 7.40 (s, 1H), 5.73-5.58 (m, 1H), 5.51-5.37 (m, 1H), 5.02 (m, 1H), 4.84-4.73 (m, 3H), 4.55-4.45 (m, 2H), 3.68-3.53 (m, 1H), 3.07-2.94 (m, 1H). Exchangeable protons were not observed in $D_2O$.

MS (ESI) m/z: $[M+1]^-$ 676.1

Example 5

4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid (Compound 8, Table 1)

Compound 8

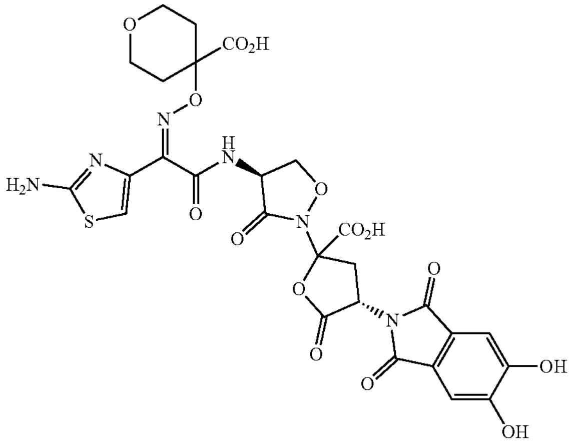

Step 1: 4-[(trimethylsilyl)oxy]oxane-4-carbonitrile (31)

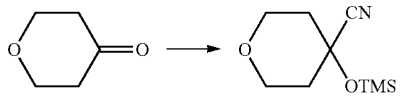

30 31

To $LiClO_4$ (11.57 g, 108.75 mmol) was added oxan-4-one 30 (10.0 mL, 108.29 mmol) followed by TMSCN (17.20 mL, 137.48 mmol) and the resulting mixture was stirred at room temperature for 3.5 h. The reaction mixture was then diluted with DCM and filtered. The filtrate was washed with water, dried over sodium sulfate, filtered and concentrated under reduced pressure. The crude 4-[(trimethylsilyl)oxy]oxane-4-carbonitrile 31 (20.69 g, 96%) was obtained as a colorless oil and used in the next step without further purification.

$^1H$ NMR (400 MHz, $CDCl_3$) δ 3.95-3.85 (m, 2H), 3.66-3.61 (m, 2H), 2.13-2.02 (m, 2H), 1.90-1.81 (m, 2H), 0.48-0.08 (m, 9H).

MS (ESI) m/z: $[M+1]^+$ 200.1

Step 2: 4-hydroxyoxane-4-carboxylic acid (32)

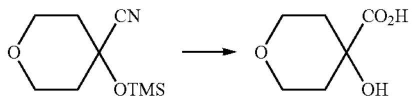

31 32

A stirred mixture of 4-[(trimethylsilyl)oxy]oxane-4-carbonitrile 31 (20.69 g, 103.80 mmol) and glacial AcOH (45 ml) was cooled to 0° C. Concentrated HCl (37%, 45 ml) was added dropwise at 0° C., the cooling bath was then removed, and the resulting mixture was heated at 90° C. for 4 h. Subsequently, the reaction mixture was cooled to room temperature and concentrated under reduced pressure. The residue was diluted with water (80 mL) and the aqueous phase was extracted with ethyl acetate (4×120 ml). The aqueous layer was then saturated with solid NaCl and further extracted with ethyl acetate (4×120 ml). The combined organic extracts were dried over sodium sulfate, filtered and concentrated in vacuo. Trace amounts of solvents were removed by co-evaporation with toluene to afford 4-hydroxyoxane-4-carboxylic acid 32 (15.05 g, 99%) as a light brown solid.

$^1$H NMR (400 MHz, DMSO-$d_6$) δ 5.26 (br s, 1H), 3.68-3.56 (m, 4H), 1.96-1.79 (m, 2H), 1.55-1.42 (m, 2H).

MS (ESI) m/z: $[M-1]^-$ 145.0

Step 3: tert-butyl 4-hydroxyoxane-4-carboxylate (33)

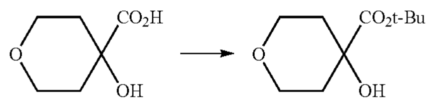

32 33

To a solution of 4-hydroxyoxane-4-carboxylic acid 32 (8.08 g, 55.29 mmol) in anhydrous THF (150 mL) was added slowly tert-butyl N,N'-diisopropylcarbamimidate (32 mL, 122.9 mmol) at 0° C. The reaction mixture was stirred at 0° C. for 10 min, the cooling bath was then removed and stirring at room temperature was continued for 5 h. The reaction mixture was concentrated under reduced pressure, the residue was treated with 30% DCM in hexanes and the urea by-product was filtered off. The filtrate was concentrated in vacuo and the residue was purified by silica gel column chromatography using a gradient of 0 to 20% ethyl acetate in hexanes to afford tert-butyl 4-hydroxyoxane-4-carboxylate 33 (9.42 g, 84%) as a white solid.

$^1$H NMR (400 MHz, $CDCl_3$) δ 3.88-3.74 (m, 4H), 3.16 (s, 1H), 2.16-2.03 (m, 2H), 1.53-1.43 (m, 11H).

MS (ESI) m/z: $[M+Na]^+$ 225.1

Step 4: tert-butyl 4-(aminooxy)oxane-4-carboxylate (34)

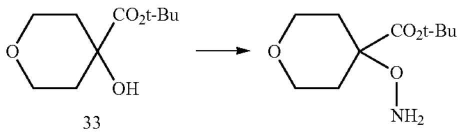

33 34

To a mixture of tert-butyl 4-hydroxyoxane-4-carboxylate 33 (5.00 g, 24.72 mmol) and 0-diphenylphosphinylhydroxylamine (8.65 g, 37.09 mmol) in anhydrous THF (120 mL) was added sodium tert-butoxide (3.56 g, 37.08 mmol) at 0° C. The reaction mixture was stirred at 0-10° C. for 6 h. Brine (65 ml) followed by hexanes (40 mL) were then added and the resulting mixture was stirred at 15-25° C. for 30 min. The two layers were separated, and the aqueous phase was extracted with ethyl acetate. The combined organic extracts were washed with brine, dried over sodium sulfate, filtered and concentrated under reduced pressure. The residue was purified by silica gel column chromatography using a gradient of 0 to 40% ethyl acetate in hexanes to afford tert-butyl 4-(aminooxy)oxane-4-carboxylate 34 (4.14 g, 77%) as an off-white solid.

$^1$H NMR (400 MHz, $CDCl_3$) δ 5.57 (br s, 2H), 3.79-3.62 (m, 4H), 2.10-1.97 (m, 2H), 1.94-1.83 (m, 2H), 1.49 (s, 9H).

Step 5: (2Z)-{2-[(tert-butoxycarbonyl)amino]-1,3-thiazol-4-yl}({[4-(tert-butoxycarbonyl)oxan-4-yl]oxy}imino)acetic acid (35)

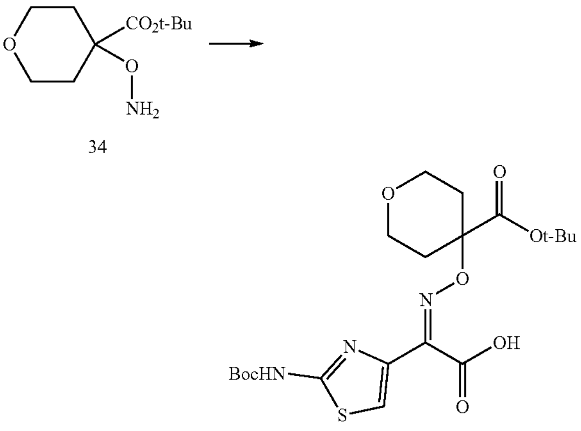

34 35

To a solution of tert-butyl 4-(aminooxy)oxane-4-carboxylate 34 (4.12 g, 18.96 mmol) in MeOH (50 ml) was added 2-(2-(tert-butoxycarbonylamino)thiazol-4-yl)-2-oxoacetic acid (4.70 g, 17.26 mmol) at room temperature. The reaction mixture was stirred at room temperature for 4 h, water (75 mL) and aqueous HCl solution (0.1 M, 80 mL) were then added and the resulting mixture was extracted with ethyl acetate. The combined organic extracts were washed with brine, dried over sodium sulfate, filtered and concentrated under reduced pressure. The residue was triturated using 5% diethyl ether in hexanes to afford (2Z)-{2-[(tert-butoxycarbonyl)amino]-1,3-thiazol-4-yl}({[4-(tert-butoxycarbonyl)oxan-4-yl]oxy}imino)acetic acid 35 (7.94 g, 98%) as a white solid.

$^1$H NMR (400 MHz, DMSO-$d_6$) δ 11.76 (s, 1H), 7.37 (s, 1H), 3.69-3.48 (m, 4H), 2.03-1.89 (m, 2H), 1.83 (m, 2H), 1.45 (s, 9H), 1.39 (s, 9H).

MS (ESI) m/z: $[M+1]^+$ 472.1

Step 6: tert-butyl 4-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}oxane-4-carboxylate (36)

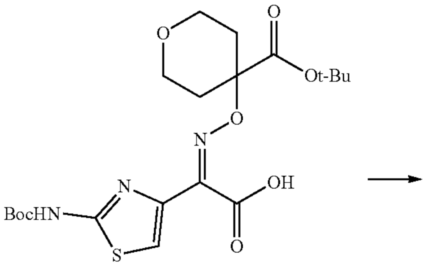

35

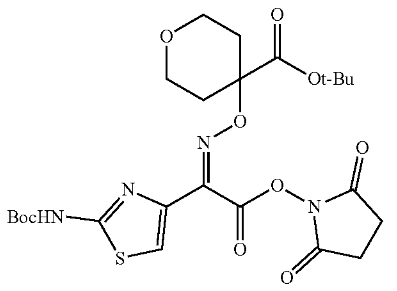

36

To a mixture of (2Z)-{2-[(tert-butoxycarbonyl)amino]-1,3-thiazol-4-yl}({[4-(tert-butoxycarbonyl)oxan-4-yl]oxy}imino)acetic acid 35 (7.94 g, 16.84 mmol) and NHS (2.33 g, 20.24 mmol) in anhydrous DCM (90 ml) was added slowly DIC (3.03 mL, 19.57 mmol) at 0° C. The reaction mixture was stirred for 15 min at 0° C., the cooling bath was removed, and stirring was continued at room temperature for 3 h. The precipitated solids were removed by filtration and washed with DCM. The filtrate was concentrated under reduced pressure and the residue was taken up in a mixture of methanol (20 mL) and n-heptane (20 ml). The resulting suspension was stirred at room temperature for 30 min, then at ~10° C. for an additional 30 min, and was filtered to afford tert-butyl 4-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}oxane-4-carboxylate 36 (8.83 g, 92%) as a white solid.

$^1$H NMR (400 MHz, $CDCl_3$) δ 8.07 (br s, 1H), 7.50 (s, 1H), 3.92-3.67 (m, 4H), 3.06-2.77 (m, 4H), 2.29-2.06 (m, 4H), 1.53 (s, 9H), 1.43 (s, 9H).

MS (ESI) m/z: $[M+1]^+$ 569.0

Step 7: tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxane-4-carboxylate (37)

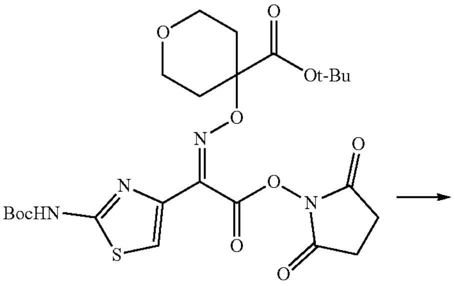

36

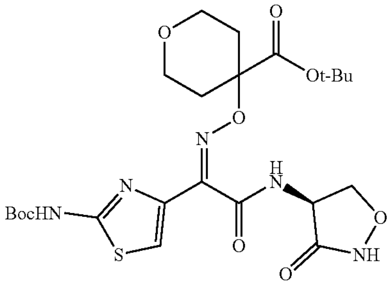

37

To a mixture of tert-butyl 4-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}oxane-4-carboxylate 36 (8.83 g, 15.53 mmol) and L-cycloserine (1.91 g, 18.67 mmol) in anhydrous DMF (75 mL) was added DIPEA (3.25 mL, 18.66 mmol) at room temperature. The reaction mixture was stirred at 45° C. for 18 h and was then concentrated under reduced pressure. The residue was purified by silica gel column chromatography using a gradient of 0 to 30% acetonitrile in DCM, followed by a gradient of 0 to 2% methanol in a 30% mixture of acetonitrile in DCM to afford tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxane-4-carboxylate 37 (3.16 g, 37%) as a white foamy solid.

$^1$H NMR (400 MHz, DMSO-$d_6$) δ 11.69 (s, 1H), 11.48 (s, 1H), 9.05 (d, J=7.8 Hz, 1H), 7.29 (s, 1H), 4.82 (br s, 1H), 4.49 (t, J=8.4 Hz, 1H), 3.97 (t, J=9.0 Hz, 1H), 3.66-3.38 (m, 4H), 1.91-1.66 (m, 4H), 1.35 (s, 9H), 1.28 (s, 9H).

MS (ESI) m/z: $[M+1]^+$ 556.0

Step 8: tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)oxane-4-carboxylate (38)

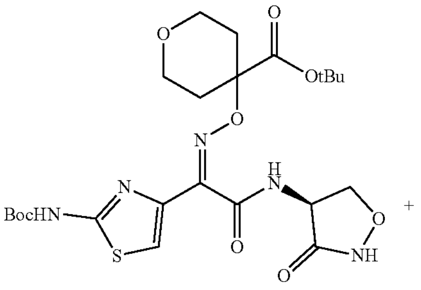

37

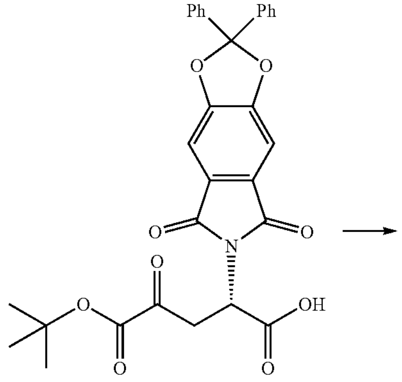

6

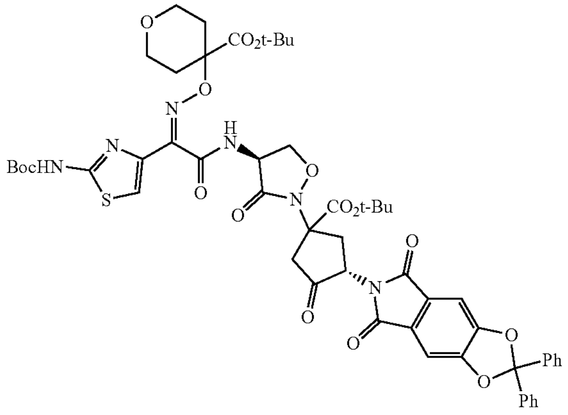

38

To a solution of tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxane-4-carboxylate 37 (556 mg, 1.00 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (571 mg, 1.05 mmol) in anhydrous THF (20 ml) was added DMAP (25 mg, 0.20 mmol), followed by DCC (289 mg, 1.40 mmol) at 0° C. The reaction mixture was allowed to warm gradually to room temperature and stirred for 18 h. The mixture was then concentrated under reduced pressure, the residue was treated with 30% DCM in hexanes and filtered. The filtrate was concentrated in vacuo and the crude product was purified by silica gel column chromatography using a gradient of 10 to 40% ethyl acetate in hexanes to afford tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)oxane-4-carboxylate 38 (756 mg, 70%) as an off-white foam.

$^1$H NMR (400 MHz, $CDCl_3$) δ 8.23-7.96 (m, 2H), 7.58-7.49 (m, 4H), 7.45-7.36 (m, 6H), 7.35-7.31 (m, 1H), 7.30 (s, 2H), 5.42-5.31 (m, 1H), 5.22-4.83 (m, 2H), 4.38-4.16 (m, 1H), 3.92-3.65 (m, 4H), 3.63-3.24 (m, 1H), 2.91-2.69 (m, 1H), 2.31-2.07 (m, 4H), 1.63-1.48 (m, 18H), 1.48-1.34 (m, 9H).

MS (ESI) m/z: $[M+Na]^+$ 1103.4

Step 9: 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid (Compound 8, Table 1)

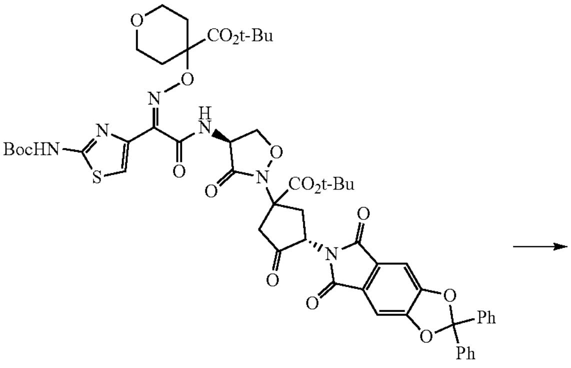

38

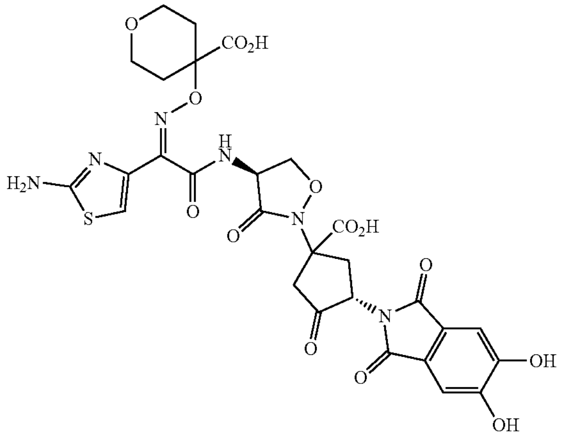

Compound 8

To a solution of tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)oxane-4-carboxylate 38 (100 mg, 0.092 mmol) in anhydrous DCM (5 mL) was added dropwise a boron trichloride solution (1.0 M in DCM, 0.74 mL, 0.74 mmol) at −50° C. The reaction mixture was stirred at −50° C. to −35° C. for 2.5 h, then cooled to −50° C. and a solution of $NaHCO_3$ (152 mg) and $Na_2HPO_4$ (48 mg) in water (8.2 mL) was added at −50° C. The cold bath was replaced with an ice-water bath, the resulting heterogeneous mixture was stirred at 0 to 5° C. until the aqueous phase thawed (~20 min), and the phases were carefully separated. The aqueous layer was filtered using a 1.0 μm syringe filter and immediately subjected to C18 reverse phase column chromatography using a Biotage system and a 0 to 30% gradient of 0.1% formic acid in acetonitrile and 0.1% formic acid in water. The fractions containing pure product were lyophilized to afford Compound 8 (46 mg, 71%) as an off-white solid.

$^1$H NMR (400 MHz, a mixture of $D_2O$ and $CD_3CN$) δ 7.25 (s, 2H), 7.20-7.09 (m, 1H), 5.46-5.24 (m, 1H), 5.21-5.08 (m, 1H), 4.75 (m, 1H), 4.35-4.26 (m, 1H), 3.83-3.73 (m, 2H), 3.64-3.26 (m, 3H), 2.88-2.70 (m, 1H), 2.18-1.99 (m, 4H). Exchangeable protons were not observed in $D_2O$.

MS (ESI) m/z: $[M+1]^+$ 705.1

Example 6

4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-1-methylpiperidine-4-carboxylic acid (Compound 9, Table 1)

Compound 9

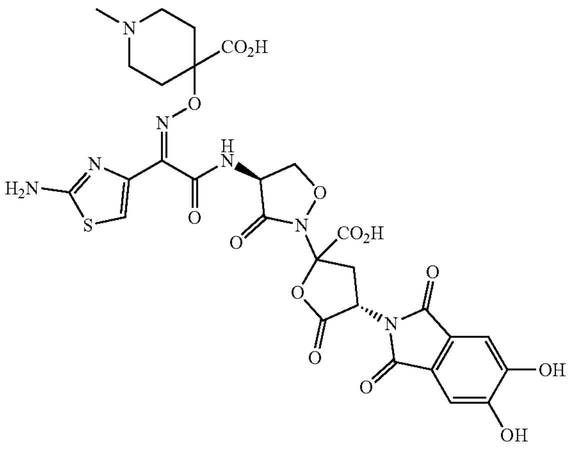

Step 1: 1-methyl-4-[(trimethylsilyl)oxy]piperidine-4-carbonitrile (40)

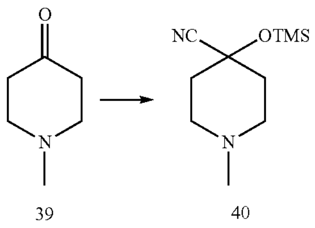

To a stirred solution of 1-methylpiperidin-4-one (39) (11.0 mL, 90.0 mmol) in anhydrous THF (60 mL) was added trimethylsilyl cyanide (12.4 mL, 99.0 mmol) at room temperature. The reaction mixture was heated at 65° C. for 5 h under a nitrogen atmosphere, then allowed to cool to room temperature and stirred overnight. The volatiles were removed under reduced pressure and the residue was further dried under high vacuum to afford 1-methyl-4-((trimethylsilyl)oxy)piperidine-4-carbonitrile 40 as a brown colored oil (20.64 g, quantitative yield) which was used directly in the next step.

$^1$H-NMR (400 MHz; $CDCl_3$): δ 2.76-2.54 (m, 2H), 2.41-2.28 (m, 2H), 2.31 (s, 3H), 2.10-1.99 (m, 2H), 1.93-1.79 (m, 2H), 0.22 (s, 9H).

Step 2: 4-hydroxy-1-methylpiperidine-4-carboxylic acid hydrochloride (41)

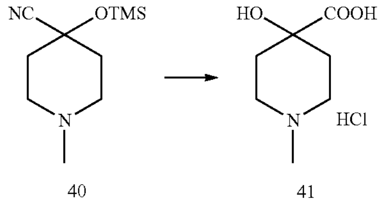

A mixture of 1-methyl-4-((trimethylsilyl)oxy)piperidine-4-carbonitrile 40 (20.64 g, ~90 mmol) and glacial acetic acid (50 mL) was cooled to 0° C. and a concentrated hydrochloric acid solution (50 mL) was added dropwise over a period of 15 minutes. The resulting reaction mixture was stirred at 0° C. for 15 minutes and then at room temperature for 15 minutes.

Subsequently, the reaction mixture was heated and stirred at 110° C. for 4 h. The mixture was allowed to cool to room temperature, the volatiles were removed under reduced pressure and the residue was further dried under high vacuum. The crude product was triturated with ethyl acetate (3×75 mL), filtered and dried under high vacuum to afford 4-hydroxy-1-methylpiperidine-4-carboxylic acid hydrochloride (41) as a light brown solid (24.1 g, crude) which was used in the next step without further purification.

$^1$H-NMR (400 MHz; $D_2O$): δ 3.39-3.36 (m, 2H), 3.21-3.14 (m, 2H), 2.79 (s, 3H), 2.22-2.14 (m, 2H), 1.97-1.85 (m, 2H).

MS (ESI) m/z: $[M+1]^+$ 160.2

Step 3: tert-butyl 4-hydroxy-1-methylpiperidine-4-carboxylate (42)

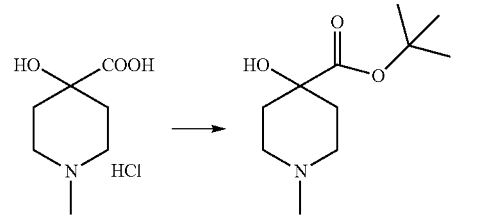

41 42

To a stirred suspension of 4-hydroxy-1-methylpiperidine-4-carboxylic acid hydrochloride 41 (12.01 g, crude, ~45 mmol) in anhydrous THF (200 mL) was added triethylamine (12.5 ml, 90 mmol). The resulting mixture was stirred at room temperature for 15 minutes and then tert-butyl N,N'-diisopropylcarbamimidate (prepared as described in EP2471792A1, 27 mL, ~135 mmol) was added. The reaction mixture was stirred at room temperature for 14 h, additional tert-butyl N,N'-diisopropylcarbamimidate (20 ml) was added and the stirring was continued for another 24 h. The precipitated solid was removed by filtration, washed with THF, and the combined filtrates were concentrated under reduced pressure. The residue was taken up in a mixture of DCM and hexanes (1:1, 200 mL) and the resulting suspension was cooled using an ice-water bath for 10 minutes. The solid was filtered off and washed with a mixture of DCM and hexanes (1:1, 50 ml). The filtrates were combined and concentrated under reduced pressure. The crude product was purified by silica gel column chromatography using a gradient of 0-6% methanol in DCM followed by 6% methanolic ammonia solution (7N) in DCM as eluents to afford tert-butyl 4-hydroxy-1-methylpiperidine-4-carboxylate 42 (5.41 g, 56% yield) as light brown color solid.

$^1$H-NMR (400 MHz; $CDCl_3$): δ 3.18-3.06 (m, 1H), 2.71-2.69 (m, 2H), 2.37-2.33 (m, 5H), 2.10 (td, J=12.9, 4.4 Hz, 2H), 1.58 (dd, J=13.6, 2.6 Hz, 2H), 1.47 (s, 9H).

MS (ESI) m/z: $[M+1]^+$ 216.2

Step 4: tert-butyl 4-(aminooxy)-1-methylpiperidine-4-carboxylate (43)

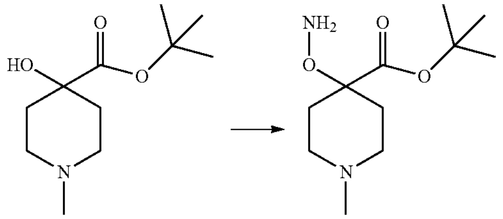

42 43

To a solution of tert-butyl 4-hydroxy-1-methylpiperidine-4-carboxylate 42 (4.89 g, 22.7 mmol) in anhydrous THF (300 ml) was added sodium tert-butoxide (3.27 g, 34.0 mmol) and the resulting mixture was stirred at room temperature until a clear solution was obtained. O-diphenylphosphinylhydroxylamine (6.35 g, 27.2 mmol) was added and the heterogeneous mixture was stirred at room temperature for 4 h. Additional portions of sodium tert-butoxide (1.63 g, 17.0 mmol) and O-diphenylphosphinylhydroxylamine (3.17 g, 13.6 mmol) were then added and the stirring at room temperature was continued overnight. The addition of sodium tert-butoxide (1.63 g, 17.0 mmol) and O-diphenylphosphinylhydroxylamine (3.17 g, 13.6 mmol) was repeated once more and the mixture was stirred at room temperature for 14 h to complete the reaction. The majority of THF was removed under reduced pressure and the residue was taken in DCM (300 ml). Saturated aqueous ammonium chloride solution (20 mL) was added, the organic phase was separated and concentrated under reduced pressure. The residue was passed through a silica gel pad eluting with 6% methanolic ammonia solution (7N) in DCM to afford tert-butyl 4-(aminooxy)-1-methylpiperidine-4-carboxylate 43 (2.32 g, crude) as a brown colored liquid.

$^1$H-NMR (400 MHz; $CDCl_3$): δ 5.28 (bs, 2H), 2.60-2.55 (m, 2H), 2.27 (s, 3H), 2.25-2.16 (m, 2H), 2.02-1.96 (m, 4H), 1.46 (s, 9H).

MS (ESI) m/z: $[M+1]^+$ 231.2

Step 5: (2Z)-{2-[(tert-butoxycarbonyl)amino]-1,3-thiazol-4-yl}({[4-(tert-butoxycarbonyl)-1-methylpiperidin-4-yl]oxy}imino)acetic acid (44)

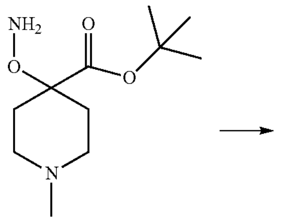

43

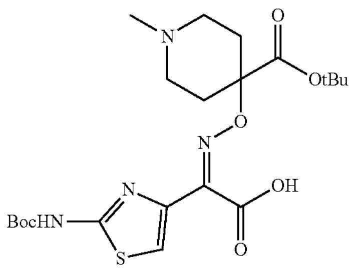

44

To a solution of tert-butyl 4-(aminooxy)-1-methylpiperidine-4-carboxylate 43 (2.33 g, 10.14 mmol) in anhydrous MeOH (40 ml) was added {2-[(tert-butoxycarbonyl)amino]-1,3-thiazol-4-yl}(oxo)acetic acid (1.38 g, 5.07 mmol) followed by glacial acetic acid (0.3 mL, 5.2 mmol) at room temperature. The reaction mixture was stirred at room temperature for 14 h and then concentrated under reduced pressure. The crude product was purified by C18 reverse phase column chromatography using 0.1% formic acid in water and 0.1% formic acid acetonitrile as eluents. The product containing fractions were combined and lyophilized to afford (2Z)-{2-[(tert-butoxycarbonyl)amino]-1,3-thiazol-4-yl}({[4-(tert-butoxycarbonyl)-1-methylpiperidin-4-yl]oxy}imino)acetic acid 44 (1.27 g, 52%) as white solid.

$^1$H-NMR (400 MHz; DMSO-$d_6$): δ 11.66 (s, 1H), 7.18 (s, 1H), 3.14-2.91 (m, 2H), 2.67 (s, 3H), 2.13-1.99 (m, 4H), 1.44 (s, 9H), 1.41 (s, 9H).

MS (ESI) m/z: $[M+1]^+$ 485.6 and $[M-1]^-$ 483.4

Step 6: tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-1-methylpiperidine-4-carboxylate

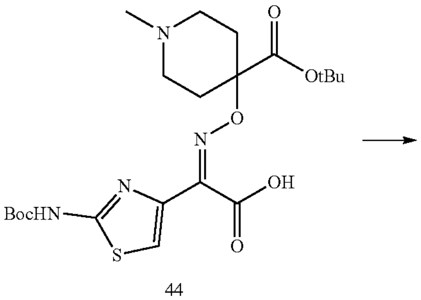

44

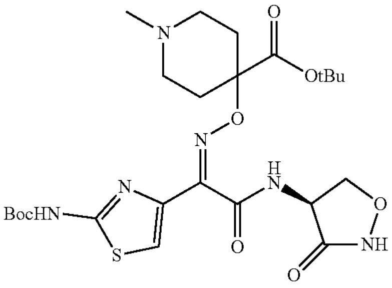

45

To a suspension of (2Z)-{2-[(tert-butoxycarbonyl)amino]-1,3-thiazol-4-yl}({[4-(tert-butoxycarbonyl)-1-methylpiperidin-4-yl]oxy}imino)acetic acid 44 (0.73 g, 1.51 mmol) in anhydrous DMF (10 ml) was added N,N-diisopropylethylamine (0.39 mL, 2.26 mmol) and the resulting mixture was stirred for at room temperature 10 minutes. HATU (0.57 g, 1.51 mmol) was then added and the stirring at room temperature was continued for 14 h. Subsequently, anhydrous DMF (15 mL) and N,N-diisopropylethylamine (1.05 mL, 6.02 mmol) were added and the mixture was stirred at room temperature for 10 minutes before the addition of L-cycloserine (0.23 g, 2.26 mmol). The reaction mixture was stirred for 1 h at room temperature and then concentrated under reduced pressure. The crude mixture was purified by C18 reverse phase column chromatography using 0.1% formic acid in water and 0.1% formic acid acetonitrile as eluents. The product containing fractions were combined and lyophilized to afford tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-1-methylpiperidine-4-carboxylate 45 (702 mg, 76%) as a white solid.

$^1$H-NMR (400 MHz; DMSO-$d_6$): δ 11.77-11.66 (m, 2H), 9.28 (d, J=8.0 Hz, 1H), 7.42 (s, 1H), 4.97 (q, J=8.5 Hz, 1H), 4.61 (t, J=8.5 Hz, 1H), 4.08 (t, J=9.0 Hz, 1H), 3.25-2.99 (m, 4H), 2.76 (s, 3H), 2.17-2.07 (m, 4H), 1.45 (s, 9H), 1.40 (s, 9H).

MS (ESI) m/z: $[M+1]^+$ 569.2

Step 7: tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino)oxy}-1-methylpiperidine-4-carboxylate (46)

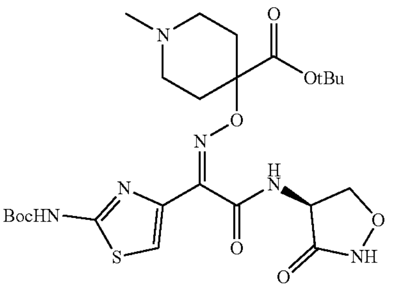

45

+

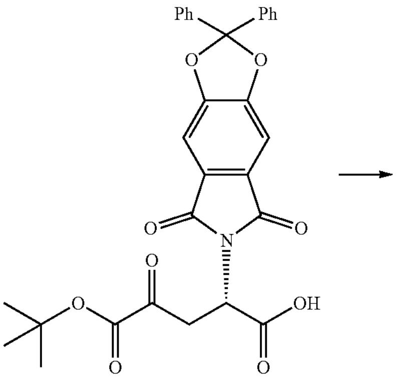

6

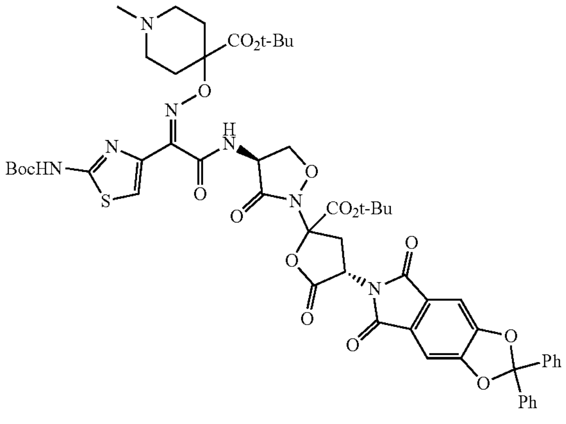

46

To a stirred mixture of tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-1-methylpiperidine-4-carboxylate 45 (455 mg, 0.80 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (435 mg, 0.80 mmol) in anhydrous THF (20 ml) was added DMAP (50 mg, 0.40 mmol) followed by DCC (231 mg, 1.12 mmol) at 0° C. The reaction mixture was stirred at 0° C. for 1 h and then at room temperature overnight. The mixture was concentrated under reduced pressure at 25° C. and the residue was dissolved in DCM (15 mL). Hexanes (15 ml) were then added, the precipitated solids were removed by filtration and washed sequentially with 50% DCM in hexanes (25 mL) and hexanes. The filtrates were combined and concentrated under reduced pressure. The crude product was purified by silica gel column chromatography using a gradient of 0 to 5% MeOH in DCM as eluent to afford tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-1-methylpiperidine-4-carboxylate 46 (435 mg, 50%) as beige colored solid.

$^1$H-NMR (400 MHz; $CDCl_3$): δ 7.53 (dd, J=5.5, 2.7 Hz, 4H), 7.40 (t, J=3.1 Hz, 6H), 7.33-7.29 (m, 3H), 5.39 (td, J=10.0, 4.0 Hz, 1H), 5.25-5.03 (m, 1H), 4.86-4.73 (m, 1H), 4.41-4.24 (m, 1H), 3.32-3.29 (m, 2H), 2.89-2.75 (m, 5H), 2.52-2.42 (m, 4H), 1.54 (m, 18H), 1.44 (s, 9H).

Step 8: 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-1-methylpiperidine-4-carboxylic acid (Compound 9, Table 1)

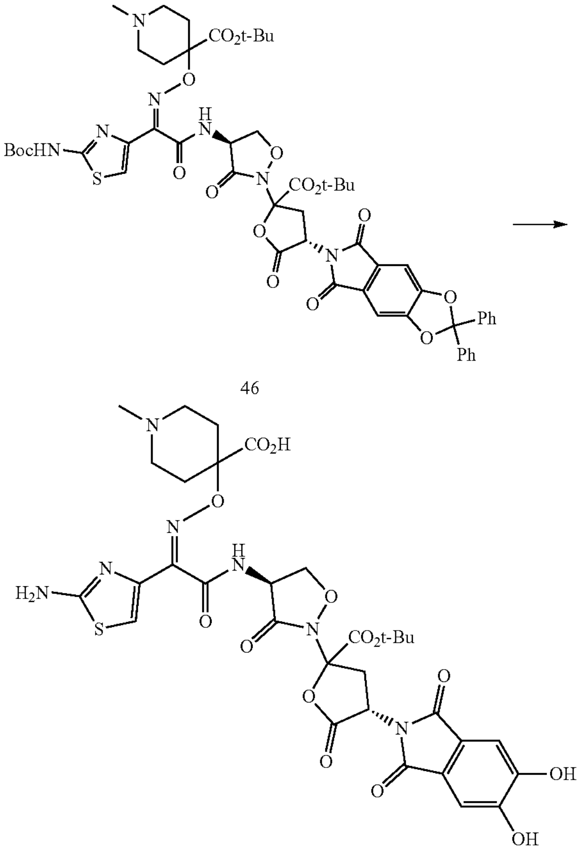

46

Compound 9

To a solution of tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-1-methylpiperidine-4-carboxylate 46 (422 mg, 0.386 mmol) in anhydrous DCM (15 ml) was added drop-wise boron trichloride (1.0 M solution in DCM, 3.1 mL, 3.09 mmol) at −50° C. The reaction mixture was stirred at −45 to −35° C. for 3 h, then cooled to −50° C. and a buffer solution (34 mL, prepared by dissolving 776 mg of $NaHCO_3$ and 243 mg of $Na_2HPO_4$ in 42 ml of water) was added. The cold bath was replaced with an ice-water bath and the heterogeneous mixture was stirred until the aqueous phase thawed. The phases were carefully separated and the aqueous layer was immediately subjected to C18 reverse phase chromatography using 0.1% formic acid in acetonitrile and 0.1% formic acid in water as eluents to afford 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-1-methylpiperidine-4-carboxylic acid Compound 9 (32 mg, 12%) a pale yellow solid.

$^1$H-NMR (400 MHz, a mixture of $D_2O$ and $CD_3CN$): δ 7.25 (s, 2H), 6.99 (s, 1H), 5.41 (t, J=10.0 Hz, 1H), 5.20-5.08 (m, 1H), 4.74 (t, J=8.6 Hz, 1H), 3.49-3.26 (m, 3H), 3.17-3.01 (m, 2H), 2.85-2.70 (m, 4H), 2.45-2.27 (m, 2H), 2.27-2.07 (m, 2H). Exchangeable protons were not observed in $D_2O$.

MS (ESI) m/z: $[M+1]^+$ 718.1

Example 7

(4S)-2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 10, Table 1), (4S)-2-[(4S)-4-{(2Z)-2-(2-amino-1,3-thiazol-4-yl)-2-{[(1-carboxy-4-chloro-4-fluorocyclohexyl)oxy]imino}acetyl]amino}-3-oxo-1,2-oxazolidin-2-yl)-4-(5,6-dihydroxy-1,3-dioxo-1,3-dihydro-2H-isoindol-2-yl)-5-oxooxolane-2-carboxylic acid (Compound 11, Table 1) and (4S)-2-[(4S)-4-{[(2Z)-2-(2-amino-1,3-thiazol-4-yl)-2-{[(1-carboxy-4,4-dichlorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 12, Table 1)

Compound 10

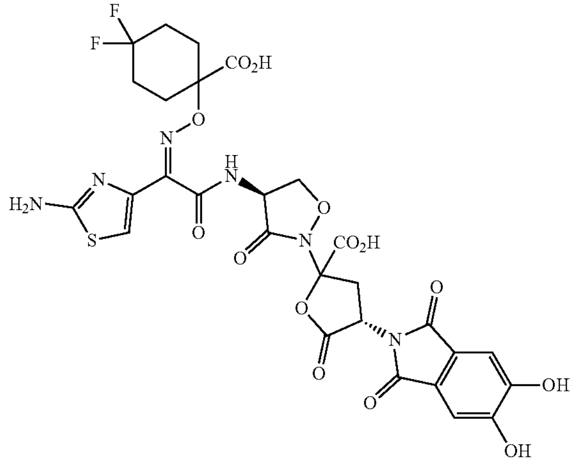

-continued

Compound 11

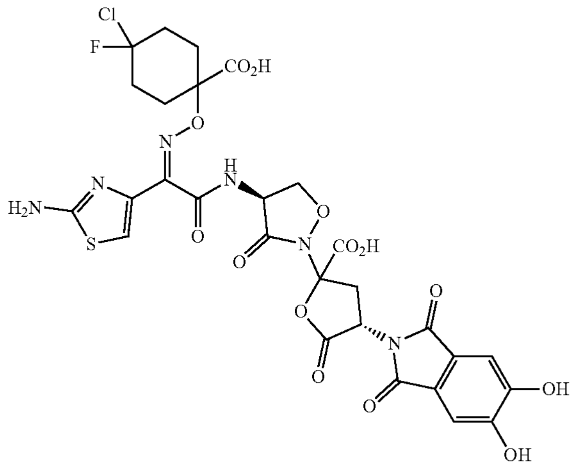

Compound 12

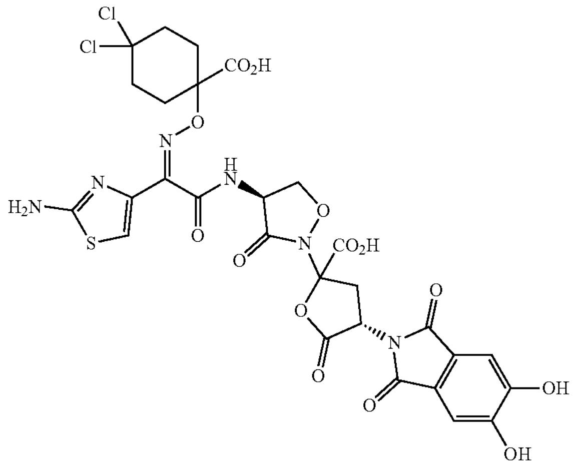

Step 1. tert-butyl 4,4-difluoro-1-hydroxycyclohexane-1-carboxylate (48)

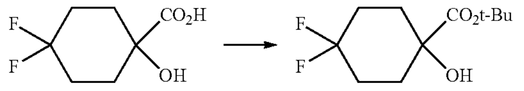

47 48

To a solution of 4,4-difluoro-1-hydroxycyclohexane-1-carboxylic acid 47 (5.19 g, 28.8 mmol) in anhydrous THF (80 ml) was slowly added tert-butyl N,N'-diisopropylcarbamimidate (23 ml, ~90 mmol) at 0° C. The reaction mixture was stirred at 0° C. for 10 min and then at room temperature for 5 h before being concentrated under reduced pressure. The residue was treated with 30% DCM in hexanes and the precipitated solid was removed by filtration. The filtrate was concentrated, and the crude product was purified by silica gel column chromatography using a gradient of 0% to 8% ethyl acetate in hexanes to afford tert-butyl 4,4-difluoro-1-hydroxycyclohexane-1-carboxylate 48 (5.63 g, 83%) as an off-white solid.

$^1$H NMR (400 MHz, $CDCl_3$) δ 3.13 (s, 1H), 2.24-1.97 (m, 6H), 1.75-1.67 (m, 2H), 1.49 (s, 9H).

Step 2: tert-butyl 1-(aminooxy)-4,4-difluorocyclohexane-1-carboxylate (49)

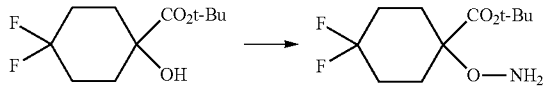

48 49

To a stirred mixture of tert-butyl 4,4-difluoro-1-hydroxycyclohexane-1-carboxylate 48 (3.03 g, 12.8 mmol) and O-diphenylphosphinylhydroxylamine (3.59 g, 15.4 mmol) in anhydrous THF (120 ml) was added sodium tert-butoxide (1.48 g, 15.4 mmol) at 0-5° C. The reaction mixture was stirred at 0-10° C. for 1 h and then additional O-diphenylphosphinylhydroxylamine (2.39 g, 10.3 mmol) followed by sodium tert-butoxide (990 mg, 10.3 mmol) were added at 0-10° C. The stirring was continued at 0-10° C. for 1 h, additional portions of O-diphenylphosphinylhydroxylamine (1.50 g, 6.43 mmol) and sodium tert-butoxide (620 mg, 6.45 mmol) were added at 0-10° C., and the reaction mixture was stirred for 1 h. Brine (40 mL) and hexanes (30 mL) were then added and the resulting mixture was stirred at 15-25° C. for 30 min. The two layers were separated, and the aqueous layer was extracted with ethyl acetate. The combined organic extracts were washed with brine, dried over sodium sulfate, filtered and concentrated under reduced pressure. The residue was purified by silica gel column chromatography using a gradient of 0 to 15% ethyl acetate in hexanes to afford tert-butyl 1-(aminooxy)-4,4-difluorocyclohexane-1-carboxylate 49 (2.99 g, 93%) as a white solid.

$^1$H NMR (400 MHz, $CDCl_3$) δ 5.34 (s, 2H), 2.17-2.13 (m, 2H), 2.00-1.91 (m, 6H), 1.49 (s, 9H).

Step 3: (2Z)-{2-[(tert-butoxycarbonyl)amino]-1,3-thiazol-4-yl}({[1-(tert-butoxycarbonyl)-4,4-difluorocyclohexyl]oxy}imino)acetic acid (50)

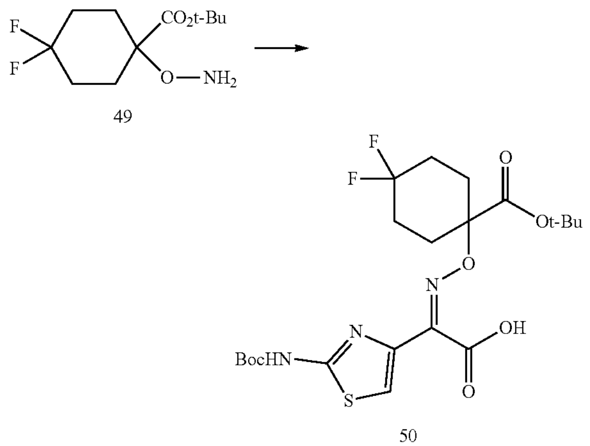

49

50

To solution of tert-butyl 1-(aminooxy)-4,4-difluorocyclohexane-1-carboxylate 49 (2.99 g, 11.9 mmol) in MeOH (32 ml) was added {2-[(tert-butoxycarbonyl)amino]-1,3-thiazol-4-yl}(oxo)acetic acid (2.95 g, 10.83 mmol) at room temperature. The reaction mixture was stirred at room temperature for 3 h, and then water (60 ml) and an aqueous hydrochloric acid solution (0.5 M, 40 ml) were added. The resulting mixture was extracted with ethyl acetate, and the combined organic extracts were washed with brine, dried over sodium sulfate, filtered and concentrated under reduced pressure. The residue was triturated using 5% diethyl ether in hexanes to afford (2Z)-{2-[(tert-butoxycarbonyl)amino]-1,3-thiazol-4-yl}({[1-(tert-butoxycarbonyl)-4,4-difluorocyclohexyl]oxy}imino)acetic acid 50 (5.37 g, 98%) as a white solid.

$^1$H NMR (400 MHz, DMSO-$d_6$) δ 11.77 (s, 1H), 7.40 (s, 1H), 2.19-2.05 (m, 2H), 1.98-1.87 (m, 6H), 1.45 (s, 9H), 1.39 (s, 9H).

MS (ESI) m/z: $[M+1]^+$ 506.4

Step 4: tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}-4,4-difluorocyclohexane-1-carboxylate (51)

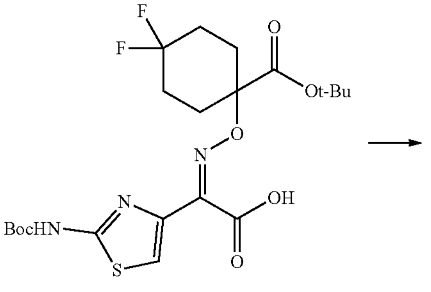

50

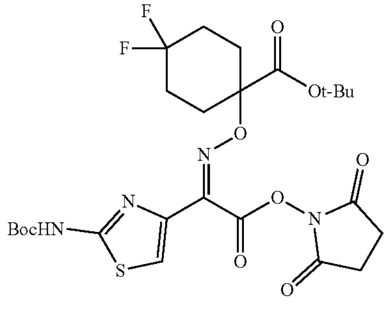

51

To a mixture of (2Z)-{2-[(tert-butoxycarbonyl)amino]-1,3-thiazol-4-yl}({[1-(tert-butoxycarbonyl)-4,4-difluorocyclohexyl]oxy}imino)acetic acid 50 (5.17 g, 10.23 mmol) and N-hydroxysuccinimide (1.41 g, 12.25 mmol) in anhydrous DCM (60 ml) was slowly added DIC (1.84 ml, 11.88 mmol) at 0° C. The reaction mixture was stirred for 15 min at 0° C. and then at room temperature for 3 h. The precipitated solids were removed by filtration and rinsed with DCM. The filtrate was concentrated under reduced pressure and the residue was purified by silica gel column chromatography using a gradient of 0 to 20% ethyl acetate in hexanes to afford tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}-4,4-difluorocyclohexane-1-carboxylate 51 (5.96 g, 97%) as a white foam.

$^1$H NMR (400 MHz, $CDCl_3$) δ 8.13 (bs, 1H), 7.51 (s, 1H), 2.91 (s, 4H), 2.38-2.36 (m, 2H), 2.17-1.99 (m, 6H), 1.53 (s, 9H), 1.42 (s, 9H).

MS (ESI) m/z: $[M+1]^+$ 603.4

Step 5: tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-4,4-difluorocyclohexane-1-carboxylate (52)

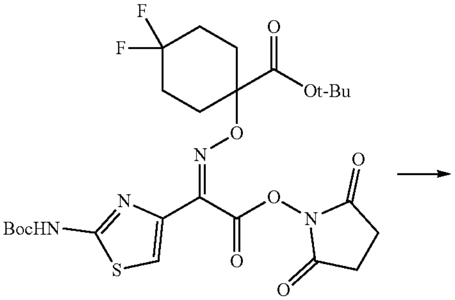

51

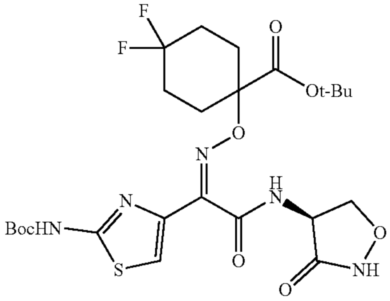

52

To a mixture of tert-butyl 1-{[(Z)-(1-{2-[(tert-butoxycarbonyl)amino]-1,3-thiazol-4-yl}-2-[(2,5-dioxopyrrolidin-1-yl)oxy]-2-oxoethylidene)amino]oxy}-4,4-difluorocyclohexane-1-carboxylate 51 (5.96 g, 9.89 mmol) and L-cycloserine (1.21 g, 11.85 mmol) in anhydrous DMF (50 ml) was added DIPEA (2.07 ml, 11.88 mmol) at room temperature. The reaction mixture was stirred at 45° C. for 18 h and then concentrated under reduced pressure. The residue was dissolved in a mixture of diethyl ether and ethyl acetate (6:4), and the organic phase was washed with water and brine, dried over sodium sulfate, filtered and concentrated. The crude mixture was purified by silica gel column chromatography using a gradient of 0 to 30% acetonitrile in DCM to afford tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-4,4-difluorocyclohexane-1-carboxylate 52 (1.87 g, 32%) as a white foam.

$^1$H NMR (400 MHz, DMSO-$d_6$) δ 11.79 (s, 1H), 11.59 (s, 1H), 9.20 (d, J=8.0 Hz, 1H), 7.41 (s, 1H), 4.96-4.88 (m, 1H), 4.58 (t, J=8.4 Hz, 1H), 4.04 (t, J=9.0 Hz, 1H), 2.16-1.82 (m, 8H), 1.45 (s, 9H), 1.38 (s, 9H).

MS (ESI) m/z: $[M+1]^+$ 590.2

Step 6: tert-butyl (4S)-2-[(4S)-4-{[(2Z)-2-{2-[(tert-butoxycarbonyl)amino]-1,3-thiazol-4-yl}-2-({[1-(tert-butoxycarbonyl)-4,4-difluorocyclohexyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (53)

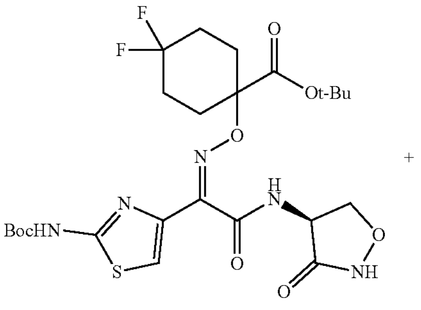

52

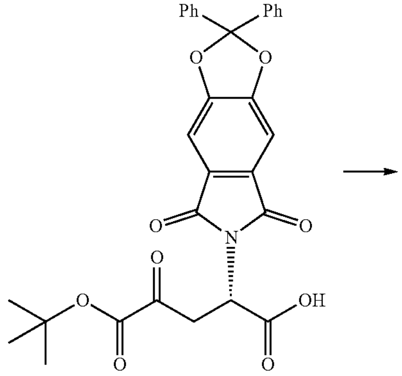

6

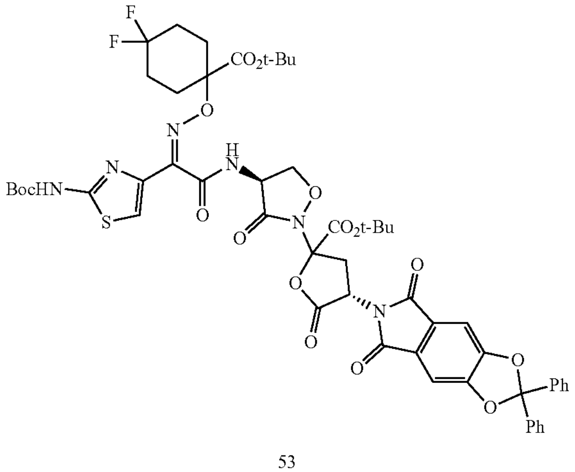

53

To a mixture of tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-4,4-difluorocyclohexane-1-carboxylate 52 (199 mg, 0.34 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (188 mg, 0.35 mmol) in anhydrous THF (6 ml) was added DMAP (9 mg, 0.074 mmol), followed by DCC (98 mg, 0.47 mmol) at 0° C. The reaction mixture was allowed to slowly warm up to room temperature and was stirred for 18 h. The mixture was then concentrated under reduced pressure and the residue was taken up in 25% DCM in hexanes. Insoluble material was removed by filtration, the filtrate was concentrated and the crude product was purified by silica gel column chromatography using a gradient of 0 to 30% ethyl acetate in hexanes to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)-4,4-difluorocyclohexyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (53) (215 mg, 57%) as a light brown foam.

$^1$H NMR (400 MHz, $CDCl_3$) δ 8.15-8.09 (m, 2H), 7.55-7.51 (m, 4H), 7.42-7.39 (m, 6H), 7.34 (d, J=3.8 Hz, 1H), 7.30 (d, J=1.2 Hz, 2H), 5.36 (td, J=10.1, 3.0 Hz, 1H), 5.23-4.87 (m, 2H), 4.37-4.18 (m, 1H), 3.66-3.26 (m, 1H), 2.88-2.71 (m, 1H), 2.51-2.31 (m, 2H), 2.18-1.87 (m, 6H), 1.60-1.58 (m, 9H), 1.51-1.49 (m, 9H), 1.48-1.41 (m, 9H).

Step 7: (4S)-2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 10), (4S)-2-[(4S)-4-{[(2Z)-2-(2-amino-1,3-thiazol-4-yl)-2-{[(1-carboxy-4-chloro-4-fluorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 11) and (4S)-2-[(4S)-4-{[(2Z)-2-(2-amino-1,3-thiazol-4-yl)-2-{[(1-carboxy-4,4-dichlorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 12)

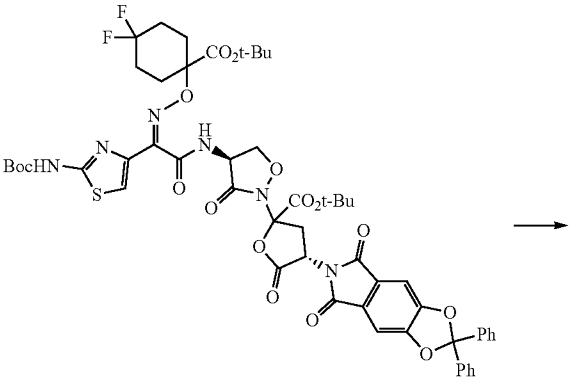

53

-continued

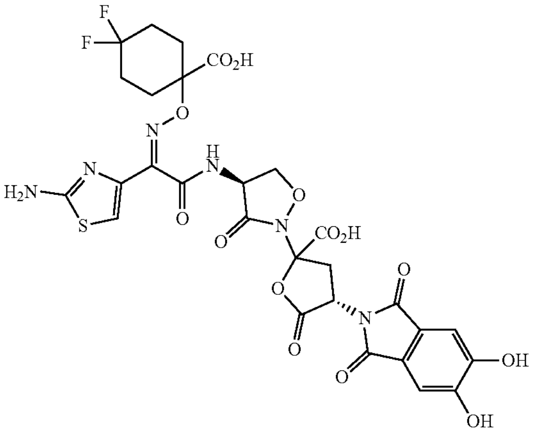

+

Compound 10

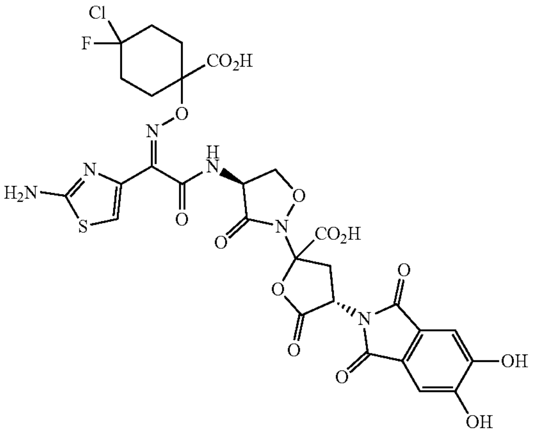

+

Compound 11

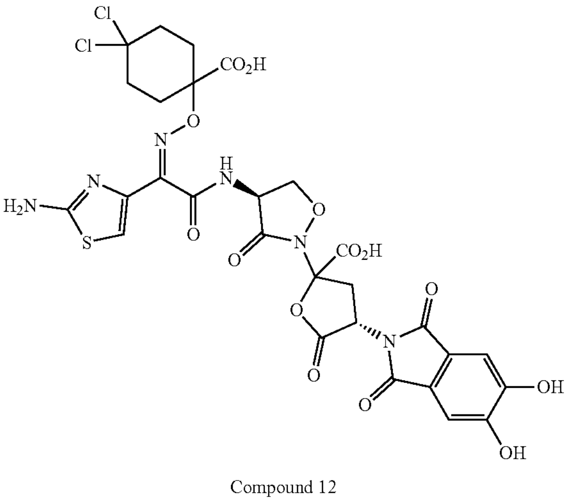 [SMILES: Nc1nc(/C(=N/OC2(C(=O)O)CCC(Cl)(Cl)CC2)C(=O)N[C@H]2CON(C3(C(=O)O)C[C@H](N4C(=O)c5cc(O)c(O)cc5C4=O)C(=O)O3)C2=O)cs1]

Compound 12

To a solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)-4,4-difluorocyclohexyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 53 (215 mg, 0.19 mmol) in anhydrous DCM (10 mL) was added dropwise boron trichloride (1M in DCM, 1.54 ml., 1.54 mmol) at −50° C. The reaction mixture was stirred at −50° C.-−35° C. for 2.5 h, and then quenched by addition of a $NaHCO_3$ (314 mg) and $Na_2HPO_4$ (98 mg) solution in $H_2O$ (17 ml) at −50° C. Subsequently, the mixture was stirred at 0-5° C. (ice-water bath) for 20 min, and then at room temperature until the aqueous phase thawed. The obtained suspension was filtered through a 1.0 μm syringe filter and the phases were carefully separated. The aqueous solution was immediately subjected to C-18 reverse phase column chromatography using a Biotage system, and 0.1% formic acid in acetonitrile and 0.1% formic acid in water as eluents. The fractions containing pure products were collected and lyophilized to afford (4S)-2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 10 (32 mg, 22%), (4S)-2-[(4S)-4-{[(2Z)-2-(2-amino-1,3-thiazol-4-yl)-2-{[(1-carboxy-4-chloro-4-fluorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 11 (41 mg, 28%) and (4S)-2-[(4S)-4-{[(2Z)-2-(2-amino-1,3-thiazol-4-yl)-2-{[(1-carboxy-4,4-dichlorocyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 12 (17 mg, 11%) as off-white solids.

For Compound 10 (Table 1):

$^1H$ NMR (400 MHz, a mixture of $D_2O$ and $CD_3CN$) δ 7.25 (s, 2H), 7.11-7.08 (m, 1H), 5.45-5.24 (m, 1H), 5.18-5.09 (m, 1H), 4.76-4.68 (m, 1H), 4.31-4.24 (m, 1H), 3.58-3.26 (m, 1H), 2.88-2.70 (m, 1H), 2.29-1.76 (m, 8H). Exchangeable protons were not observed in $D_2O$.

MS (ESI) m/z: $[M+1]^+$ 739.1

For Compound 11 (Table 1):

$^1H$ NMR (400 MHz, a mixture of $D_2O$ and $CD_3CN$) δ 7.25 (s, 2H), 7.12-7.09 (m, 1H), 5.44-5.24 (m, 1H), 5.18-5.08 (m, 1H), 4.76-4.68 (m, 1H), 4.30-4.24 (m, 1H), 3.57-3.27 (m, 1H), 2.88-2.70 (m, 1H), 2.32-2.05 (m, 8H). Exchangeable protons were not observed in $D_2O$.

MS (ESI) m/z: $[M+1]^+$ 755.0

For Compound 12 (Table 1):

$^1H$ NMR (400 MHz, a mixture of D-O and $CD_3CN$) δ 7.25 (s, 2H), 7.10-7.08 (m, 1H), 5.45-5.24 (m, 1H), 5.18-5.08 (m, 1H), 4.76-4.69 (m, 1H), 4.32-4.24 (m, 1H), 3.59-3.28 (m, 1H), 2.88-2.70 (m, 1H), 2.46-2.10 (m, 8H). Exchangeable protons were not observed in $D_2O$.

MS (ESI) m/z: $[M+1]^+$ 771.0

Example 8

3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid (Compound 13, Table 1)

Compound 13

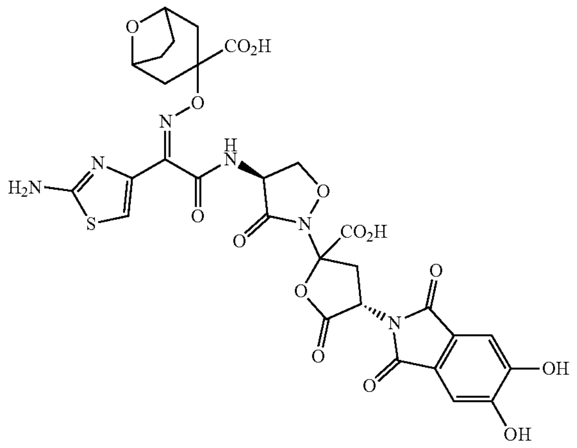

Step 1: 3-[(trimethylsilyl)oxy]-8-oxabicyclo[3.2.1]octane-3-carbonitrile 55

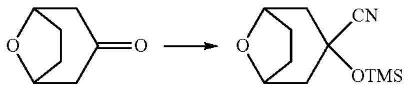

54 55

Zinc iodide (174 mg, 0.55 mmol) was placed in a dry round bottom flask and dried under high vacuum with gentle heating for 30 minutes. A solution of oxabicyclo[3.2.1]octan-3-one 54 (3.44 g, 27.25 mmol) in anhydrous DCM (60 ml) was added and the resulting mixture was cooled to 0° C. Trimethylsilyl cyanide (4.09 mL, 32.7 mmol) was added slowly at 0° C., the reaction mixture was then allowed to warm up to room temperature and stirred for 5 h. The mixture was concentrated under reduced pressure and the residue was taken up in 10% DCM in hexanes (75 mL). The solids were removed by filtration, the filtrate was concentrated under reduced pressure and the obtained brown oil was further dried under high vacuum to afford 3-((trimethylsilyl)oxy)-8-oxabicyclo[3.2.1]octane-3-carbonitrile 55 (6.41 g, quantitative yield).

$^1$H-NMR (400 MHz; $CDCl_3$): δ 4.47-4.43 (m, 2H), 2.38 (d, J=4.3 Hz, 1H), 2.34 (d, J=4.3 Hz, 1H), 2.20 (s, 1H), 2.18 (s, 1H), 2.05-2.02 (m, 2H), 1.94-1.90 (m, 2H), 0.29 (s, 9H).

Step 2: 3-hydroxy-8-oxabicyclo[3.2.1]octane-3-carboxylic acid (56)

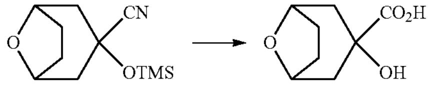

55 56

A mixture of 3-((trimethylsilyl)oxy)-8-oxabicyclo[3.2.1]octane-3-carbonitrile 55 (6.4 g crude, ~27 mmol) and glacial acetic acid (30 ml) was cooled at 0° C. and a concentrated hydrochloric acid solution (30 mL) was added dropwise over a period of 10 minutes. The reaction mixture was stirred at 0° C. for 15 minutes, then at room temperature for 15 minutes and was subsequently stirred and heated at 110° C. for 4 h. The reaction mixture was allowed to cool to room temperature, the volatiles were removed under reduced pressure and the residue was further dried under high vacuum. The residue was dissolved in water (100 mL) and the aqueous phase was saturated using solid NaCl and extracted with ethyl acetate (2×150 ml). The extracts were combined and washed with water and brine, dried over sodium sulfate, filtered, concentrated in vacuo and dried under high vacuum to afford 3-hydroxy-8-oxabicyclo[3.2.1]octane-3-carboxylic acid 56 (2.43 g, 52% yield) as a brown colored solid.

$^1$H-NMR (400 MHz; DMSO-$d_6$): δ 12.50-12.34 (m, 1H), 4.29-4.25 (m, 2H), 2.18-2.13 (m, 2H), 2.07 (d, J=4.3 Hz, 1H), 2.03 (d, J=3.4 Hz, 1H), 1.72-1.66 (m, 2H), 1.58 (s, 1H), 1.54 (s, 1H).

MS (ESI) m/z: $[M-1]^-$ 171.0

Step 3: tert-butyl 3-hydroxy-8-oxabicyclo[3.2.1]octane-3-carboxylate (57)

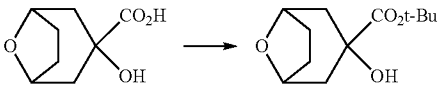

56 57

To a solution of 3-hydroxy-8-oxabicyclo[3.2.1]octane-3-carboxylic acid 56 (2.44 g, 14.18 mmol) in anhydrous THF (50 ml) was added tert-butyl N,N'-diisopropylcarbamimidate (11.4 mL, 56.72 mmol, prepared as described in EP2471792A1) and the reaction mixture was stirred at room temperature for 16 h. The precipitated solids were removed by filtration and rinsed with THF. The filtrates were combined and concentrated under reduced pressure. The residue was triturated using a mixture of DCM and hexanes (1:2, 90 mL) at 0-4° C., the precipitate was filtered off and washed with a mixture of DCM and hexanes (1:2, 50 ml). The filtrate was collected and concentrated under reduced pressure, and the crude product was purified by silica gel column chromatography using a gradient of 10 to 40% ethyl acetate in hexanes to give tert-butyl 3-hydroxy-8-oxabicyclo[3.2.1]octane-3-carboxylate 57 (2.31 g, 71% yield) as a light yellow solid.

$^1$H-NMR (400 MHz; $CDCl_3$): δ 4.48-4.45 (m, 2H), 3.40 (s, 1H), 2.37 (d, J=4.3 Hz, 1H), 2.35-2.33 (m, 3H), 1.96-1.90 (m, 2H), 1.59 (t, J=1.1 Hz, 1H), 1.55 (t, J=1.1 Hz, 1H), 1.49 (s, 9H).

MS (ESI) m/z: $[M-1]^-$ 226.8

Step 4: tert-butyl 3-(aminooxy)-8-oxabicyclo[3.2.1]octane-3-carboxylate (58)

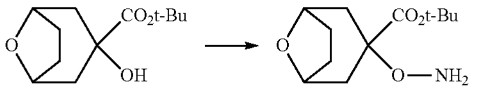

57 58

To a solution of tert-butyl 3-hydroxy-8-oxabicyclo[3.2.1]octane-3-carboxylate 57 (1.74 g, 7.62 mmol) in anhydrous THF (75 mL) was added sodium hydride (60% in mineral oil, 0.46 g, 11.43 mmol) portion-wise at 0° C. The mixture was stirred for 15 min, then O-diphenylphosphinylhydroxylamine (2.67 g, 11.43 mmol) was added, and stirring at 0° C. was continued for 30 min. The reaction mixture was allowed to warm to room temperature and was stirred for 17 h. Subsequently, additional sodium hydride (60% in mineral oil, 0.23 g, 5.72 mmol) and O-diphenylphosphinylhydroxylamine (1.33 g, 5.72 mmol) were added, and the resulting mixture was stirred at room temperature for 24 h. The majority of THF was then removed under reduced pressure, brine (75 mL) was added and the mixture was extracted with ethyl acetate (2×150 ml). The combined organic phase was dried over sodium sulfate, filtered, concentrated in vacuo and further dried under high vacuum. The residue was subjected to silica gel column chromatography using a gradient of 10 to 30% ethyl acetate in hexanes and afforded tert-butyl 3-(aminooxy)-8-oxabicyclo[3.2.1]octane-3-carboxylate 58 (1.06 g, 57% yield) as white solid.

$^{1}$H-NMR (400 MHz; $CDCl_3$): δ 5.29 (bs, 2H), 4.42-4.39 (m, 2H), 2.23 (d, J=4.3 Hz, 1H), 2.20 (d, J=4.4 Hz, 1H), 2.04-1.97 (m, 4H), 1.96-1.88 (m, 2H), 1.49 (s, 9H)

Step 5: (2Z)-{2-[(tert-butoxycarbonyl)amino]-1,3-thiazol-4-yl}({[3-(tert-butoxycarbonyl)-8-oxabicyclo[3.2.1]octan-3-yl]oxy}imino)acetic acid (59)

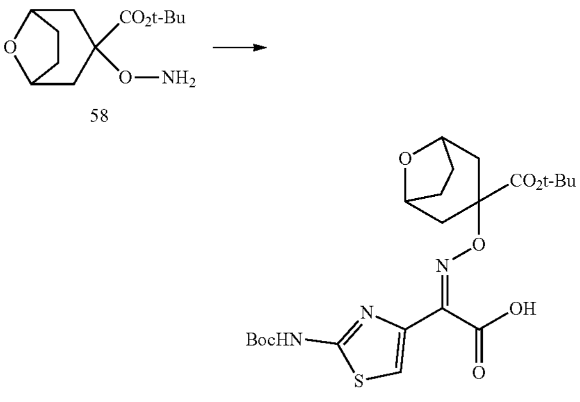

58

59

To a solution of tert-butyl 3-(aminooxy)-8-oxabicyclo[3.2.1]octane-3-carboxylate 58 (0.42 g, 1.73 mmol) in anhydrous MeOH (10 ml) was added {2-[(tert-butoxycarbonyl)amino]-1,3-thiazol-4-yl}(oxo)acetic acid (0.47 g, 1.73 mmol) and the reaction mixture was stirred at room temperature for 17 h. The reaction mixture was then concentrated under reduced pressure and the crude product was further dried under high vacuum to afford (2Z)-{2-[(tert-butoxycarbonyl)amino]-1,3-thiazol-4-yl}({[3-(tert-butoxycarbonyl)-8-oxabicyclo[3.2.1]octan-3-yl]oxy}imino)acetic acid 59 (0.86 g, 100%) as a white solid.

$^{1}$H-NMR (400 MHz; $CDCl_3$): δ 7.37 (s, 1H), 4.41-4.40 (m, 2H), 2.33-2.23 (m, 4H), 2.05-2.00 (m, 2H), 1.86-1.81 (m, 2H), 1.55 (s, 9H), 1.44 (s, 9H).

MS (ESI) m/z: $[M+1]^+$ 498.1

Step 6: tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-8-oxabicyclo[3.2.1]octane-3-carboxylate (60)

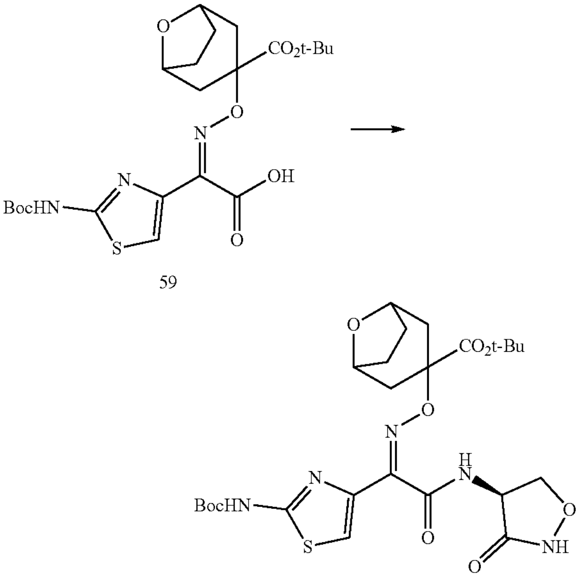

59

60

To a solution of (2Z)-{2-[(tert-butoxycarbonyl)amino]-1,3-thiazol-4-yl}({[3-(tert-butoxycarbonyl)-8-oxabicyclo[3.2.1]octan-3-yl]oxy}imino)acetic acid 59 (0.60 g, 1.20 mmol) in anhydrous DMF (8 mL) was added N,N-diisopropylethylamine (0.31 mL, 1.80 mmol) and the resulting mixture was stirred for 10 minutes at room temperature. HATU (0.46 g, 1.20 mmol) was then added and stirring at room temperature was continued for 14 h. The reaction mixture was subsequently diluted with anhydrous DMF (8 ml) and DIPEA (0.84 ml, 4.80 mmol) followed by L-cycloserine (184 mg, 1.80 mmol) was added. The mixture was stirred at room temperature for 1 h and then concentrated under reduced pressure. The residue was dissolved in DCM (50 ml) and the organic phase was washed with water (20 mL) and brine (20 ml), dried over sodium sulfate, filtered, and concentrated under reduced pressure. The crude product was purified by silica gel column chromatography using a gradient of 0 to 3% MeOH in DCM to afford tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-8-oxabicyclo[3.2.1]octane-3-carboxylate 60 (0.69 g, 98%) as off-white solid.

$^{1}$H-NMR (400 MHz; DMSO-$d_6$): δ 11.84 (bs, 1H), 11.55 (bs, 1H), 9.09 (d, J=7.8 Hz, 1H), 7.46 (s, 1H), 4.98-4.90 (m,

1H), 4.59 (t, J=8.5 Hz, 1H), 4.34-4.27 (m, 2H), 4.13 (dd, J=9.9, 8.4 Hz, 1H), 2.16-2.06 (m, 2H), 1.94-1.89 (m, 4H), 1.71-1.66 (m, 2H), 1.47 (s, 9H), 1.36 (s, 9H).

MS (ESI) m/z: $[M+1]^+$ 582.2

Step 7: tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylate (61)

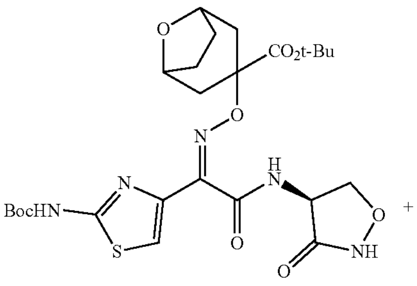

60

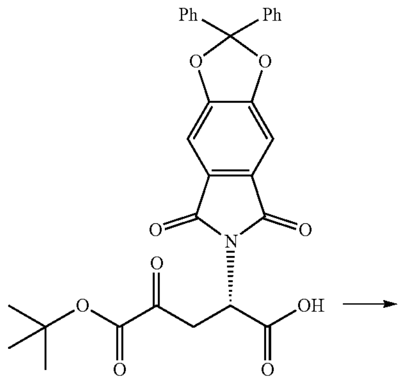

6

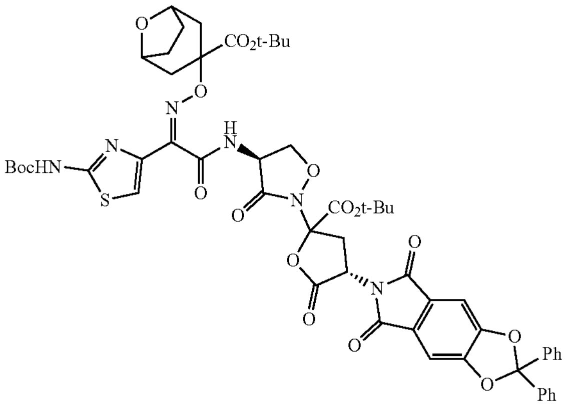

61

To a mixture of tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-8-oxabicyclo[3.2.1]octane-3-carboxylate 60 (0.38 g, 0.65 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (0.353 g, 0.65 mmol) In anhydrous THF (15 mL), DMAP (16 mg, 0.13 mmol) followed by DCC (188 mg, 0.91 mmol) was added at 0° C. The reaction mixture was stirred at 0° C. for 1 h, then at room temperature overnight and concentrated under reduced pressure at 25° C. The residue was triturated using 30% DCM in hexanes (20 ml) and the precipitated solids were removed by filtration and rinsed with 30% DCM in hexanes (15 mL) and hexanes (15 ml). The filtrates were combined and concentrated under reduced pressure, and the crude product was purified by silica gel column chromatography using a gradient of 10 to 50% ethyl acetate in hexanes to afford tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylate 61 (355 mg, 49%) as a tan solid.

${}^1$H-NMR (400 MHz; $CDCl_3$): δ 7.57-7.54 (m, 4H), 7.45-7.42 (m, 6H), 7.36 (m, 1H), 7.33 (m, 2H), 5.42-5.36 (m, 1H), 5.22-4.89 (m, 2H), 4.49-4.45 (m, 2H), 4.29-4.22 (m, 1H), 3.54-3.47 (m, 1H), 3.43-3.31 (m, 1H), 2.91-2.84 (m, 1H), 2.44-2.28 (m, 4H), 2.03-1.88 (m, 4H), 1.75-1.69 (m, 1H), 1.59-1.42 (m, 27H).

Step 8: 3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid (Compound 13)

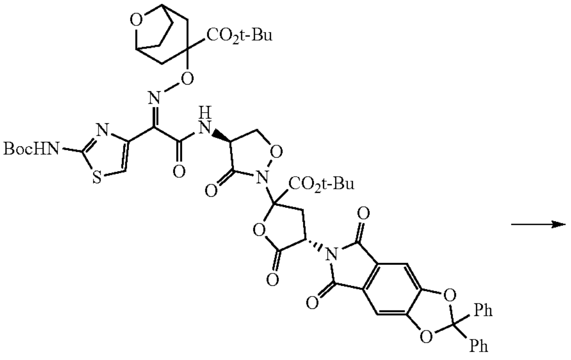

61

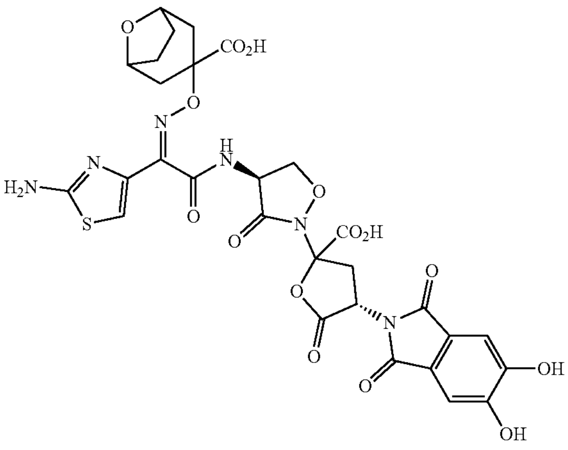

Compound 13

To a solution of tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylate 61 (345 mg, 0.31 mmol) in anhydrous DCM (16 ml) was added dropwise boron trichloride (1.0M in DCM, 2.5 mL, 2.50 mmol) at −50° C. The reaction mixture was stirred at −45 to −35° C. for 3 h, then cooled to −50° C., and 31 mL of a buffer solution (prepared by dissolving 776 mg of $NaHCO_3$ and 243 mg of $Na_2HPO_4$ in 42 mL of water) was added. The cold bath was replaced with an ice-water bath and the resulting mixture was stirred until the aqueous layer thawed and the phases separated. The organic phase was carefully removed and the collected aqueous phase immediately subjected to C18 reverse phase column chromatography using a Biotage system and 0.1% formic acid in acetonitrile and 0.1% formic acid in water as mobile phases to afford 3-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid Compound 13 (100 mg, 44%) as a pale yellow foamy solid.

$^1$H-NMR (400 MHz; a mixture of $D_2O$ and $CD_3CN$): δ 7.25 (s, 2H), 7.08 (s, 1H), 5.41-5.33 (m, 1H), 5.16-5.06 (m, 1H), 4.76-4.66 (m, 1H), 4.32-4.24 (m, 2H), 3.35-3.27 (m, 1H), 2.79-2.68 (m, 1H), 2.32-2.18 (m, 2H), 2.11-2.01 (m, 2H), 1.86-1.71 (m, 4H). Exchangeable protons were not observed in $D_2O$.

MS (ESI) m/z: $[M+H]^+$ 731.0

Example 9

(4S)-2-[(4S)-4-{[(2Z)-2-(5-amino-1,2,4-thiadiazol-3-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-S-oxooxolane-2-carboxylic acid (Compound 18, Table 1)

Compound 18

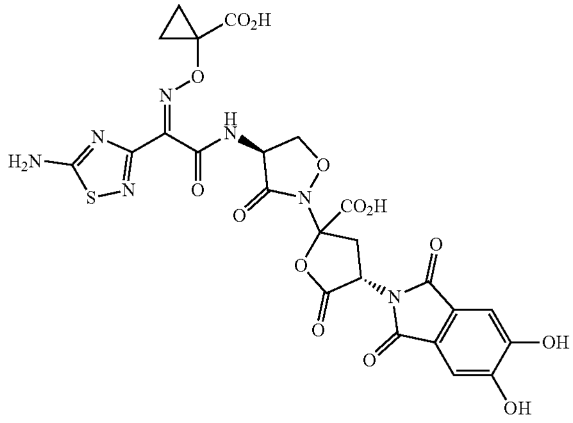

Step 1: (2Z)-{5-[(tert-butoxycarbonyl)amino]-1,2,4-thiadiazol-3-yl}({[1-(tert-butoxycarbonyl)cyclopropyl]oxy}imino)acetic acid (63)

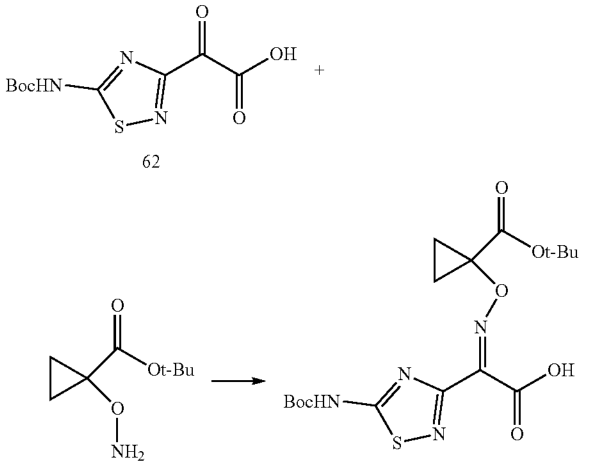

62

2

63

To a solution of tert-butyl 1-(aminooxy)cyclopropane-1-carboxylate 2 (364 mg, 2.10 mmol, prepared as described in Example 1, step 1) in anhydrous MeOH (10 ml) was added {5-[(tert-butoxycarbonyl)amino]-1,2,4-thiadiazol-3-yl}(oxo)acetic acid 62 (546 mg, 2.00 mmol, prepared as described in WO 2017/155765). The reaction mixture was stirred at room temperature for 14 h and then concentrated under reduced pressure. The residue was taken up in diethyl ether (50 ml) and the organic phase was washed with 0.1 M hydrochloric acid solution (33 ml) and brine (30 ml), dried over sodium sulfate, filtered and concentrated under reduced pressure. The crude product was further dried under high vacuum to afford (2Z)-{5-[(tert-butoxycarbonyl)amino]-1,2,4-thiadiazol-3-yl}({[1-(tert-butoxycarbonyl)cyclopropyl]oxy}imino)acetic acid 63 (696 mg, 81%) as a pale yellow solid.

$^1$H-NMR (400 MHz; DMSO-$d_6$): δ 12.62 (s, 1H), 12.51 (s, 1H), 1.49 (s, 9H), 1.36 (m, 11H), 1.28 (m, 2H).

Step 2: tert-butyl 1-{[(Z)-(1-{5-[(tert-butoxycarbonyl)amino]-1,2,4-thiadiazol-3-yl}-2-oxo-2-{[(4S)-3-oxo-1,2-oxazolidin-4-yl]amino}ethylidene)amino]oxy}cyclopropane-1-carboxylate (64)

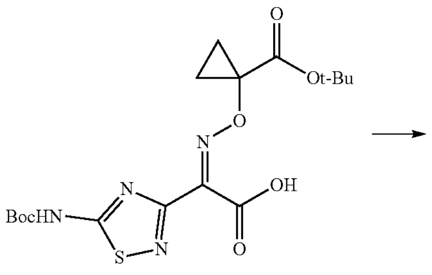

63

-continued

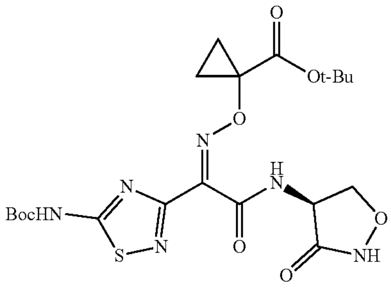

64

To a solution of (2Z)-{5-[(tert-butoxycarbonyl)amino]-1,2,4-thiadiazol-3-yl}({[1-(tert-butoxycarbonyl)cyclopropyl]oxy}imino)acetic acid 63 (514 mg, 1.20 mmol) in anhydrous DMF (8 ml) was added N,N-diisopropylethylamine (0.31 mL, 1.80 mmol) and the resulting mixture was stirred for 10 minutes at room temperature. HATU (456 mg, 1.20 mmol) was then added and stirring at room temperature was continued for 14 h. Subsequently, anhydrous DMF (10 mL) and N,N-diisopropylethylamine (0.84 mL, 4.8 mmol) followed by L-cycloserine (184 mg, 1.80 mmol) were added and the reaction mixture was stirred at room temperature for 1 h. The volatiles were then removed under reduced pressure and the residue was taken up in DCM (30 ml). The organic phase was washed with water, dried over sodium sulfate, filtered and concentrated. The crude product was purified by silica gel column chromatography using a gradient of 0 to 3% methanol in DCM to afford tert-butyl 1-{[(Z)-(1-{5-[(tert-butoxycarbonyl)amino]-1,2,4-thiadiazol-3-yl}-2-oxo-2-{[(4S)-3-oxo-1,2-oxazolidin-4-yl]amino}ethylidene)amino]oxy}cyclopropane-1-carboxylate 64 (204 mg, 33%) as off-white solid.

$^1$H-NMR (400 MHz; DMSO-$d_6$): δ 12.59 (s, 1H), 11.57 (s, 1H), 9.07 (d, J=7.6 Hz, 1H), 4.91-4.78 (m, 1H), 4.59 (t, J=8.3 Hz, 1H), 3.91 (t, J=8.8 Hz, 1H), 1.49 (s, 9H), 1.38 (s, 9H), 1.34 (m, 2H), 1.24 (m, 2H)

Step 3: tert-butyl (4S)-2-[(4S)-4-{[(2Z)-2-{5-[(tert-butoxycarbonyl)amino]-1,2,4-thiadiazol-3-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (65)

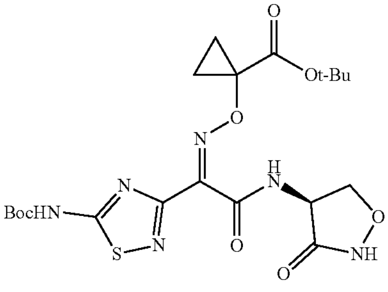

64

+

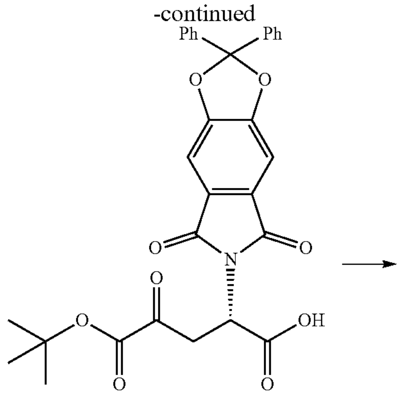

6

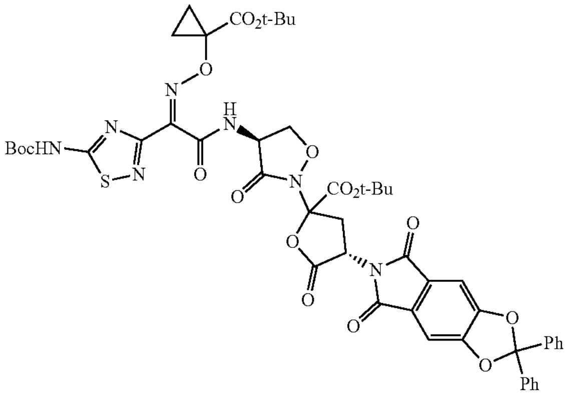

65

A stirred mixture of tert-butyl 1-{[(Z)-(1-{5-[(tert-butoxycarbonyl)amino]-1,2,4-thiadiazol-3-yl}-2-oxo-2-{[(4S)-3-oxo-1,2-oxazolidin-4-yl]amino}ethylidene)amino]oxy}cyclopropane-1-carboxylate 64 (196 mg, 0.38 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (207 mg, 0.38 mmol) in anhydrous THF (20 mL) was cooled to 0° C. DMAP (14 mg, 0.11 mmol) followed by DCC (110 mg, 0.53 mmol) was added and the reaction mixture was stirred at 0° C. for 1 h, then at room temperature overnight and concentrated under reduced pressure at 25° C. The residue was treated with 40% DCM in hexanes (25 ml), the precipitated solids were removed by filtration and rinsed with 40% DCM in hexanes (25 mL) and hexanes (15 mL). The filtrates were combined and concentrated under reduced pressure, and the crude product was purified by silica gel column chromatography using a gradient of 10 to 40% ethyl acetate in hexanes to afford tert-butyl (4S)-2-[(4S)-4-{[(2Z)-2-{5-[(tert-butoxycarbonyl)amino]-1,2,4-thiadiazol-3-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 65 (197 mg, 50%) as a white solid.

$^1$H-NMR (400 MHz; $CDCl_3$): δ 8.56 (s, 1H), 8.18 (dd, J=8.1, 5.0 Hz, 1H), 7.54-7.51 (m, 4H), 7.41 (q, J=3.3 Hz, 6H), 7.30 (s, 2H), 5.38 (td, J=10.0, 8.3 Hz, 1H), 5.16-4.96 (m, 2H), 4.30-4.22 (m, 1H), 3.49-3.29 (m, 1H), 2.88-2.82 (m, 1H), 1.57-1.53 (m, 22H), 1.43 (d, J=2.7 Hz, 9H).

Step 4: (4S)-2-[(4S)-4-{[(2Z)-2-(5-amino-1,2,4-thiadiazol-3-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 18, Table 1)

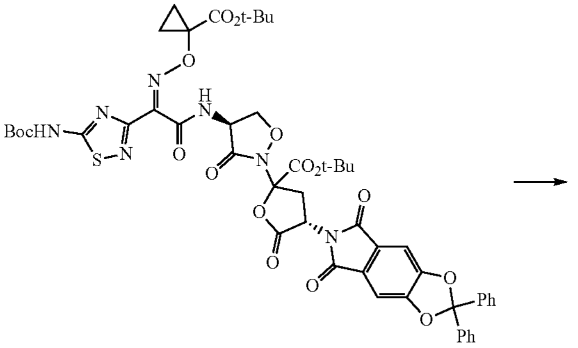

65

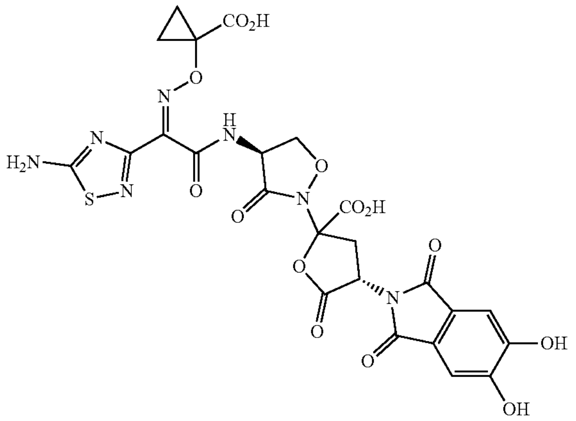

Compound 18

A solution of tert-butyl (4S)-2-((S)-4-((2)-2-(5-((tert-butoxycarbonyl)amino)-1,2,4-thiadiazol-3-yl)-2-((1-(tert-butoxycarbonyl)cyclopropoxy)imino)acetamido)-3-oxoisoxazolidin-2-yl)-4-(5,7-dioxo-2,2-diphenyl-5,7-dihydro-6H-[1,3]dioxolo[4,5-f]isoindol-6-yl)-5-oxotetrahydrofuran-2-carboxylate 65 (190 mg, 0.183 mmol) in anhydrous DCM (10 mL) was cooled to −50° C. and boron trichloride (1.0M in DCM, 1.46 mL, 1.46 mmol) was added dropwise. The reaction mixture was stirred at −45 to −35° C. for 3 h, then cooled to −50° C. and 16.5 mL of a buffer solution (prepared by dissolving 776 mg of $NaHCO_3$ and 243 mg of $Na_2HPO_4$ in 42 mL of water) was added. The cold bath was replaced with an ice-water bath and the resulting mixture was stirred until the aqueous layer thawed. The organic phase was carefully separated and the aqueous phase was immediately subjected to C18 reverse phase chromatography using a Biotage system and 0.1% formic acid in acetonitrile and 0.1% formic acid in water as eluents to afford (4S)-2-[(4S)-4-{[(2Z)-2-(5-amino-1,2,4-thiadiazol-3-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 18 (50 mg, 41%) as a pale yellow foamy solid.

$^1$H-NMR (400 MHz; a mixture of $D_2O$ and $CD_3CN$): δ 7.25 (s, 2H), 5.44-5.34 (m, 1H), 5.15-5.04 (m, 1H), 4.73 (q, J=8.4 Hz, 1H), 4.32-4.14 (m, 1H), 3.45-3.31 (m, 1H), 2.91-2.73 (m, 1H), 1.55-1.45 (m, 2H), 1.45-1.42 (m, 2H). Exchangeable protons were not observed in $D_2O$.

MS (ESI) m/z: $[M+H]^+$ 662.1

Example 10

(4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid (Compound 36, Table 1)

Compound 36

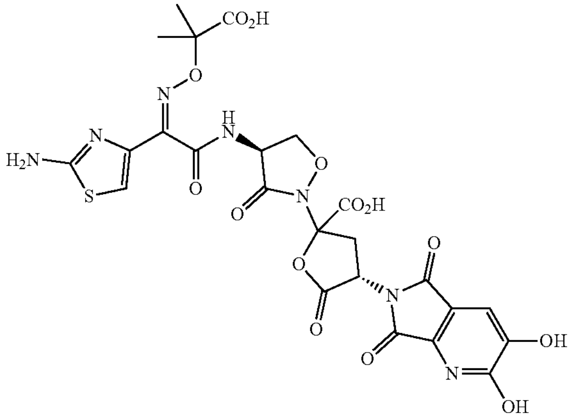

Step 1: Diethyl 2,2-diphenyl-2H-[1,3]dioxolo[4,5-b]pyridine-5,6-dicarboxylate (66)

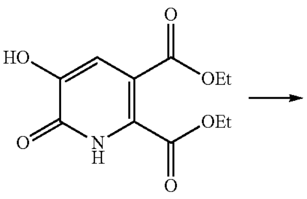

66

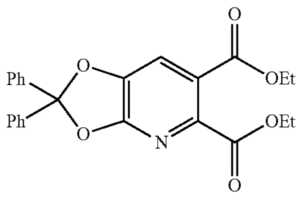

67

A stirred mixture of diethyl 5-hydroxy-6-oxo-1,6-dihydropyridine-2,3-dicarboxylate 66 (6.83 g, 26.76 mmol, prepared as described in U.S. Pat. No. 5,252,538 (A), 1993) and potassium carbonate (4.07 g, 29.45 mmol) in anhydrous DMA (60 ml) was heated to 100° C. and a solution of 1,1'-(dichloromethylene)dibenzene (5.65 mL, 29.43 mmol) in DMA (20 mL) was added dropwise. The reaction mixture was then heated to 170° C. and stirred at 170° C. for 20 h. Subsequently, the reaction mixture was cooled to room temperature and water was added. The resulting mixture was extracted with a mixture of diethyl ether and ethyl acetate (2:1). The combined organic extracts were washed with brine, dried over sodium sulfate, filtered and concentrated under reduced pressure. The residue was purified by silica gel column chromatography using a gradient of 0 to 16% ethyl acetate in hexanes. The obtained product was further purified by recrystallization from diethyl ether and hexanes to afford diethyl 2,2-diphenyl-2H-[1,3]dioxolo[4,5-b]pyridine-5,6-dicarboxylate 67 (1.66 g, 15%) was a white solid.

$^1$H NMR (400 MHz, $CDCl_3$) δ 7.57-7.53 (m, 4H), 7.45 (s, 1H), 7.41-7.38 (m, 6H), 4.40 (q, J=7.2 Hz, 2H), 4.34 (q, J=7.1 Hz, 2H), 1.38 (t, J=7.2 Hz, 3H), 1.34 (t, J=7.1 Hz, 3H).

Step 2: 2,2-diphenyl-2H-[1,3]dioxolo[4,5-b]pyridine-5,6-dicarboxylic acid (68)

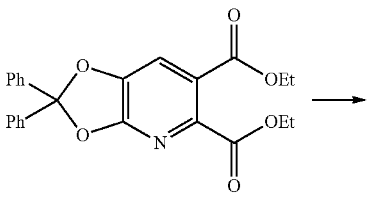

67

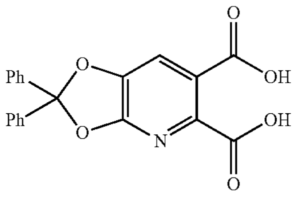

68

To a stirred suspension of diethyl 2,2-diphenyl-2H-[1,3]dioxolo[4,5-b]pyridine-5,6-dicarboxylate 67 (1.75 g, 4.17 mmol) in a mixture of MeOH, THF and water (1:1:1, 30 ml) was added a sodium hydroxide solution (835 mg, 20.88 mmol, in 10 mL of water) at room temperature. The reaction mixture was heated at 80° C. for 5 h, then cooled to room temperature and concentrated under reduced pressure to remove THF and MeOH. The aqueous phase was washed twice with diethyl ether, cooled to 0° C. and acidified to pH=1. The resulting mixture was extracted with ethyl acetate and the combined organic extracts were dried over sodium sulfate, filtered and concentrated under reduced pressure to afford crude 2,2-diphenyl-2H-[1,3]dioxolo[4,5-b]pyridine-5,6-dicarboxylic acid 68 (1.46 g, 96%) as a white solid which was used directly in the next step without further purification.

$^1$H NMR (400 MHz, DMSO-$d_6$) δ 7.78 (s, 1H), 7.56-7.52 (m, 4H), 7.49-7.45 (m, 6H).

Step 3: 2,2-diphenyl-2H-[1,3]dioxolo[4,5-b]furo[3,4-e]pyridine-5,7-dione (69)

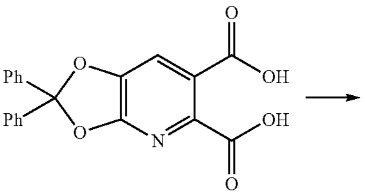

68

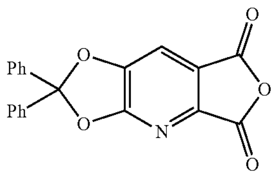

69

Acetic anhydride (16 mL) was added to 2,2-diphenyl-2H-[1,3]dioxolo[4,5-b]pyridine-5,6-dicarboxylic acid 68 (1.46 g, 4.02 mmol) at room temperature. The resulting mixture was heated to 100° C. and stirred for 3 h. The reaction mixture was then cooled to room temperature and concentrated under reduced pressure. Traces of volatiles were removed by co-evaporation with toluene (3×) and the residue was further dried under high vacuum to afford 2,2-diphenyl-2H-[1,3]dioxolo[4,5-b]furo[3,4-e]pyridine-5,7-dione 69 (1.27 g, 92%) as an off-white foam, which was directly used in the next step.

$^1$H NMR (400 MHz, DMSO-$d_6$) δ 8.08 (s, 1H), 7.58-7.55 (m, 4H), 7.52-7.49 (m, 6H).

Step 4: (2S)-5-tert-butoxy-2-(5,7-dioxo-2,2-diphenyl-5,7-dihydro-2H,6H-[1,3]dioxolo[4,5-b]pyrrolo[3,4-e]pyridin-6-yl)-4,5-dioxopentanoic acid (71)

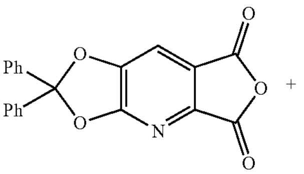

69

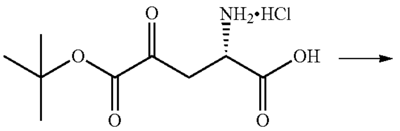

70

-continued

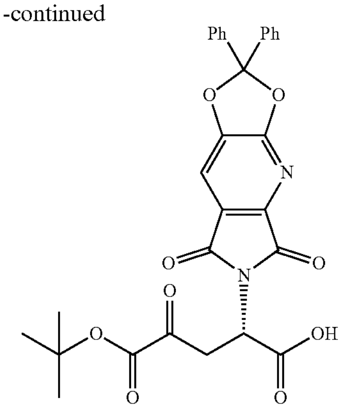

71

-continued

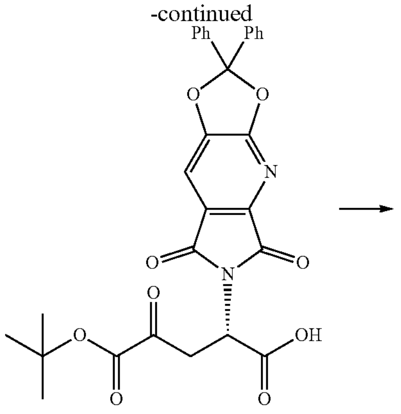

71

To (2S)-2-amino-5-tert-butoxy-4,5-dioxopentanoic acid hydrochloride 70 (2.03 g, 7.68 mmol, prepared as described in J. Med. Chem. 2014, 57, 3845-3855) was added a solution of 2,2-diphenyl-2H-[1,3]dioxolo[4,5-b]furo[3,4-e]pyridine-5,7-dione 69 (crude, 1.27 g, 3.68 mmol) in anhydrous pyridine (25 ml) at room temperature. The reaction mixture was stirred and heated at 90° C. for 2.5 h, then cooled to room temperature and concentrated under reduced pressure. The residue was dissolved in DCM (10 ml) and water (120 ml) was added. The mixture was extracted with ethyl acetate and the combined organic extracts were washed with brine, dried over sodium sulfate, filtered and concentrated under reduced pressure. The crude product was purified by silica gel column chromatography using a gradient of 0 to 16% acetonitrile in DCM to afford (2S)-5-tert-butoxy-2-(5,7-dioxo-2,2-diphenyl-5,7-dihydro-2H,6H-[1,3]dioxolo[4,5-b]pyrrolo[3,4-e]pyridin-6-yl)-4,5-dioxopentanoic acid 71 (390 mg, 19%) as a brown foam.

$^1$H NMR (400 MHz, DMSO-$d_6$) δ 7.93 (s, 1H), 7.57-7.53 (m, 4H), 7.51-7.47 (m, 6H), 5.19-5.16 (m, 1H), 3.71-3.62 (m, 1H), 3.37-3.34 (m, 1H), 1.44 (s, 9H).

MS (ESI) m/z: $[M+1]^+$ 545.2

Step 5: tert-butyl (4S)-2-[(4S)-4-([(2Z)-2-{2-[(tert-butoxycarbonyl)amino]-1,3-thiazol-4-yl)-2-{[(1-tert-butoxy-2-methyl-1-oxopropan-2-yl)oxy]imino}acetyl]amino}-3-oxo-1,2-oxazolidin-2-yl]-4-(5,7-dioxo-2,2-diphenyl-5,7-dihydro-2H,6H-[1,3]dioxolo[4,5-b]pyrrolo[3,4-e]pyridin-6-yl)-5-oxooxolane-2-carboxylate (73)

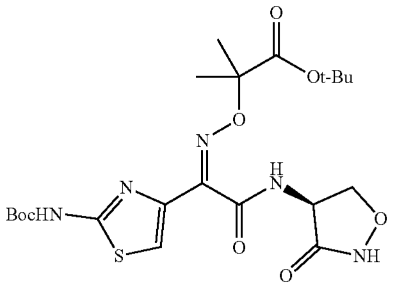

+

72

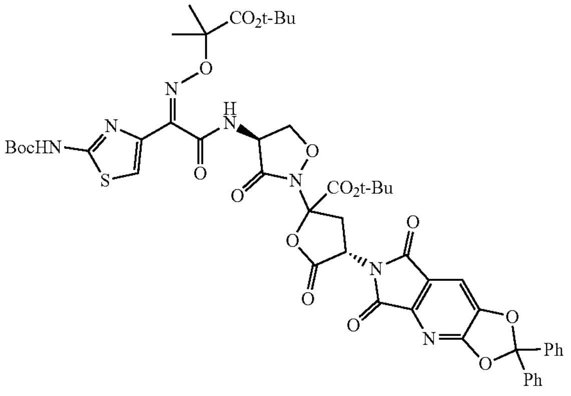

73

To a mixture of (2S)-5-tert-butoxy-2-(5,7-dioxo-2,2-diphenyl-5,7-dihydro-2H,6H-[1,3]dioxolo[4,5-b]pyrrolo[3,4-e]pyridin-6-yl)-4,5-dioxopentanoic acid 71 (390 mg, 0.72 mmol) and tert-butyl 2-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2-methylpropanoate 72 (368 mg, 0.72 mmol, prepared as described in *J. Med. Chem.,* 2014, 57, 3845-3855) in anhydrous THF (20 mL) was added DMAP (18 mg, 0.15 mmol), followed by DCC (207 mg, 1.0 mmol) at 0° C. The reaction mixture was allowed to slowly warm up to room temperature and was stirred for 18 h. The mixture was then concentrated under reduced pressure and the residue was triturated with 30% DCM in hexanes. The precipitated solids were removed by filtration, the filtrate was concentrated in vacuo and the residue was purified by silica gel column chromatography using a gradient of 10 to 35% ethyl acetate in hexane to afford tert-butyl (4S)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-4-(5,7-dioxo-2,2-diphenyl-5,7-dihydro-2H,6H-[1,3]dioxolo[4,5-b]pyrrolo[3,4-e]pyridin-6-yl)-5-oxooxolane-2-carboxylate 73 (375 mg, 50%) as a brown foam.

$^1$H NMR (400 MHz, $CDCl_3$) 8.44-8.39 (m, 1H), 7.57-7.54 (m, 4H), 7.44-7.40 (m, 8H), 5.45-5.39 (m, 1H), 5.18-4.85 (m, 2H), 4.38-4.21 (m, 1H), 3.68-3.33 (m, 1H), 2.89-2.77 (m, 1H), 1.66-1.65 (m, 6H), 1.57-1.55 (m, 9H), 1.54-1.52 (m, 9H), 1.45-1.44 (m, 9H).

Step 6: (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylicacid (Compound 36, Table 1)

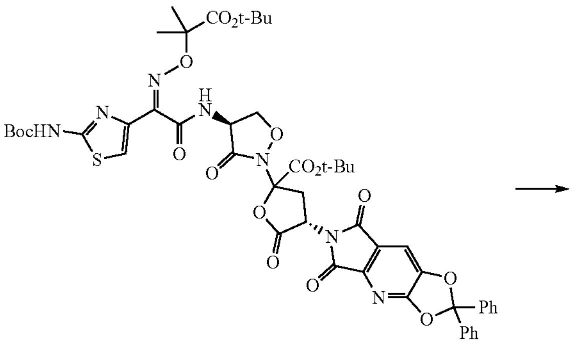

73

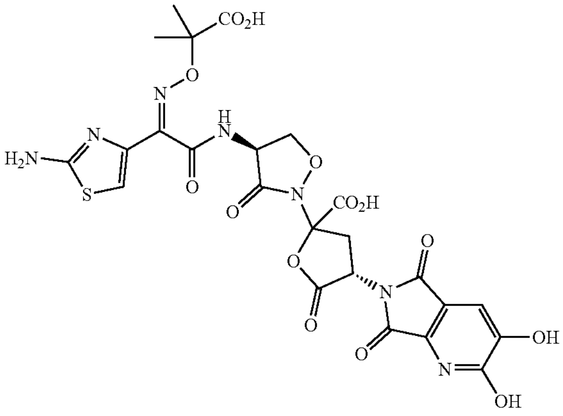

Compound 36

To a solution of tert-butyl (4S)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-4-(5,7-dioxo-2,2-diphenyl-5,7-dihydro-2H,6H-[1,3]dioxolo[4,5-b]pyrrolo[3,4-e]pyridin-6-yl)-5-oxooxolane-2-carboxylate 73 (100 mg, 0.096 mmol) in anhydrous DCM (5 mL) was added dropwise boron trichloride (1.0 M in DCM, 0.77 ml, 0.77 mmol) at −50° C. The reaction mixture was stirred at −50° C. to −35° C. for 2.5 h and then a solution of $NaHCO_3$ (157 mg) and $Na_2HPO_4$ (49 mg) in $H_2O$ (8.5 ml) was added at −50° C. The cold bath was replaced with an ice-water bath and the mixture was stirred for 20 min. Subsequently, the heterogenous mixture was stirred at room temperature until the aqueous phase thawed fully. The resulting mixture was filtered through a 1 μm syringe filter and the organic layer was carefully removed. The aqueous phase was immediately subjected to C-18 reverse phase chromatography using a Biotage system and 0.1% formic acid in acetonitrile and 0.1% formic acid in water as eluents. The product containing fractions were combined and lyophilized to afford (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid Compound 36 (23 mg, 36%) as a yellow solid.

$^1H$ NMR (400 MHz, a mixture of $D_2O$ and $CD_3CN$) δ 7.09-7.08 (m, 1H), 7.08-7.06 (m, 1H), 5.42-5.22 (m, 1H), 5.17-5.08 (m, 1H), 4.76-4.68 (m, 1H), 4.34-4.23 (m, 1H), 3.53-3.29 (m, 1H), 2.88-2.64 (m, 1H), 1.53-1.45 (m, 6H). Exchangeable protons were not observed in $D_2O$.

MS (ESI) m/z: $[M+1]^+$ 664.1

Example 11

(4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid (Compound 3, Table 1)

Compound 3

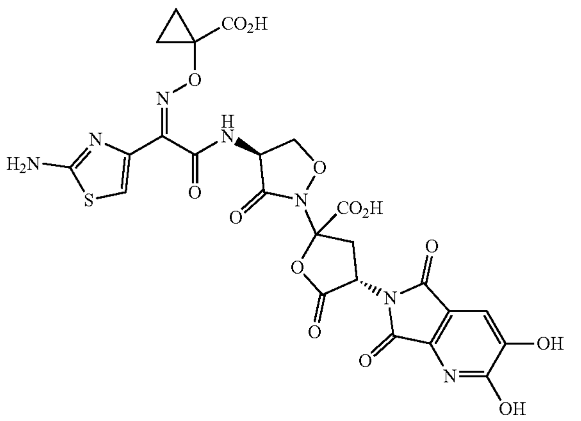

Step 1: tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-b]pyrrolo[3,4-e]pyridin-6-yl)-5-oxooxolane-2-carboxylate (74)

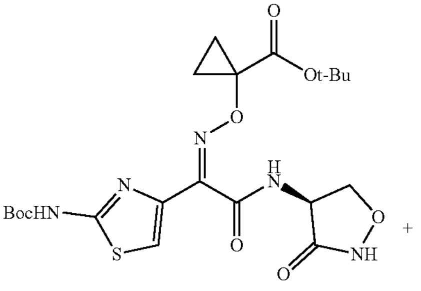

5

-continued

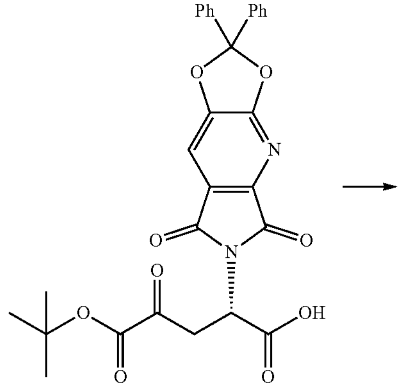

71

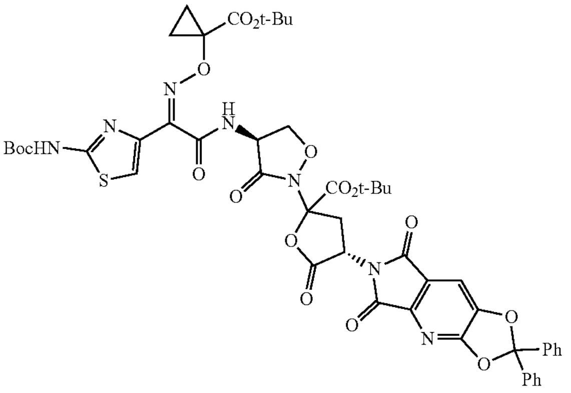

74

To a mixture of (2S)-5-tert-butoxy-2-(5,7-dioxo-2,2-diphenyl-5,7-dihydro-2H,6H-[1,3]dioxolo[4,5-b]pyrrolo[3,4-e]pyridin-6-yl)-4,5-dioxopentanoic acid 71 (105 mg, 0.2 mmol, prepared as described in Example 10, Step 4) and tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclopropane-1-carboxylate 5 (100 mg, 0.2 mmol, prepared as described in Example 1, Step 4) in anhydrous THE (2 mL) was added DMAP (5 mg, 0.04 mmol), followed by DCC (56 mg, 0.27 mmol) at 0° C. The reaction mixture was allowed to gradually warm up to room temperature and stirring was continued for 18 h. The reaction mixture was then concentrated under reduced pressure and the residue was triturated with 25% DCM in hexanes. The insoluble material was filtered off and the filtrate concentrated. The crude product was purified by silica gel column chromatography using a gradient of 10 to 40% ethyl acetate in hexanes to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-b]pyrrolo[3,4-e]pyridin-6-yl)-5-oxooxolane-2-carboxylate 74 (50 mg, 25%) as a white foam.

$^1$H-NMR (599 MHz; $CDCl_3$) δ 8.59 (t, J=7.5 Hz, 1H), 8.20-8.05 (bs, 1H) 7.58-7.52 (m, 4H), 7.43-7.40 (m, 7H), 5.43 (dt, J=19.8, 10.0 Hz, 1H), 5.15-5.12 (m, 1H), 4.90 (dt, J=26.1, 8.4 Hz, 1H), 4.30-4.21 (m, 1H), 3.50-3.32 (m, J=9.8 Hz, 1H), 2.86 (dd, J=13.3, 11.3 Hz, 1H), 1.59-1.57 (m, 9H), 1.55-1.51 (m, 13H), 1.44 (s, 9H).

Step 2: (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylicacid (Compound 3)

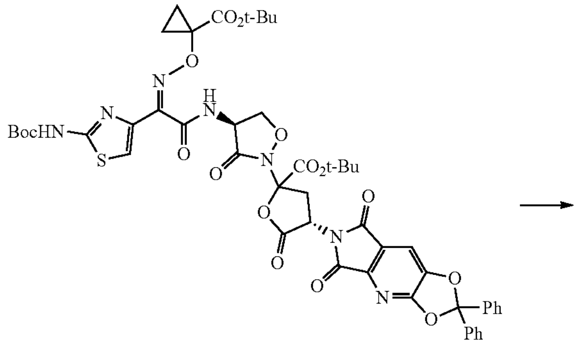

74

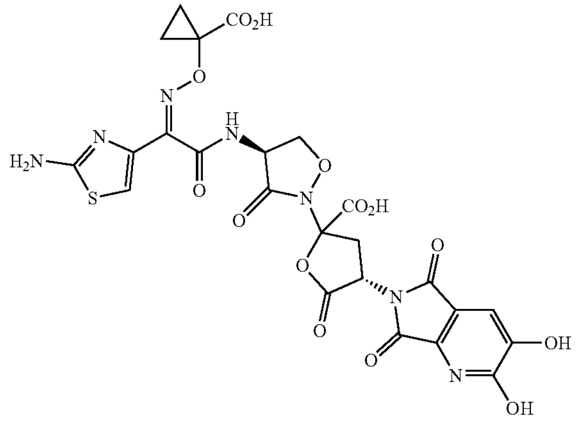

Compound 3

A solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-b]pyrrolo[3,4-e]pyridin-6-yl)-5-oxooxolane-2-carboxylate 74 (50 mg, 0.05 mmol) in anhydrous DCM (4 mL) was cooled to −50° C. and a boron trichloride solution (1.0 M in DCM, 0.39 mL, 0.39 mmol) was added dropwise. The reaction mixture was stirred at −30° C. to −25° C. for 2.5 h, then cooled to −50° C. before a solution of $NaHCO_3$ (75 mg) and $Na_2HPO_4$ (24 mg) in $H_2O$ (4 ml) was added. The resulting heterogeneous mixture was stirred for 20 min at 0-5° C. (ice-water bath) and then at room temperature until the aqueous phase thawed. The layers were allowed to separate, and the organic layer was carefully removed. The aqueous solution was then subjected to purification by C-18 reverse phase column chromatography using a Biotage system and a mixture of 0.1% formic acid in acetonitrile and 0.1% formic acid in water as mobile phases. The fractions containing pure product were collected and lyophilized to afford (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(2,3-dihydroxy-5,7-dioxo-5,7-dihydro-6H-pyrrolo[3,4-b]pyridin-6-yl)-5-oxooxolane-2-carboxylic acid Compound 3 (8 mg, 25%) as a yellow solid.

$^1$H-NMR (599 MHz; a mixture of $D_2O$ and $CD_3CN$) δ 7.06 (s, 1H), 7.04 (s, 1H), 5.40-5.16 (m, 1H), 5.14-5.03 (m, 1H), 4.69 (dt, J=17.4, 8.7 Hz, 1H), 4.29-4.18 (m, 1H), 3.52-3.26 (m, 1H), 2.87-2.63 (m, 1H), 1.42 (s, 2H), 1.34 (s, 2H). Exchangeable protons were not observed in $D_2O$.

MS (ESI) m/z: $[M+H]^+$ 662.0

Example 12

4-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)oxane-4-carboxylic acid (Compound 26, Table 1)

Compound 26

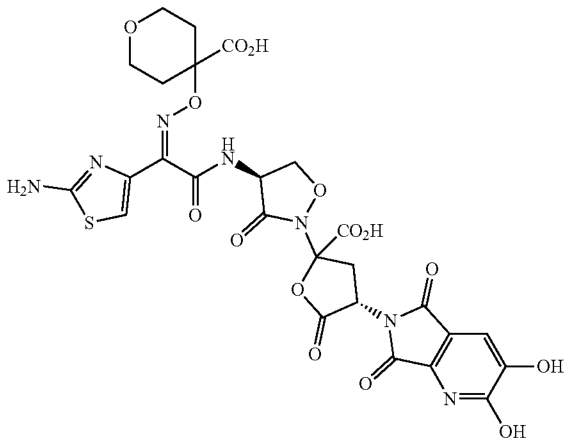

Step 1: tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-b]pyrrolo[3,4-e]pyridin-6-yl)-5-oxooxolan-2-yl]-3-oxo-1,2-oxazolidin-4-yl}amino)-2-oxoethylidene]amino}oxy)oxane-4-carboxylate (75)

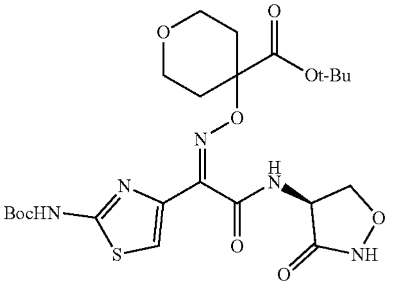

+

-continued

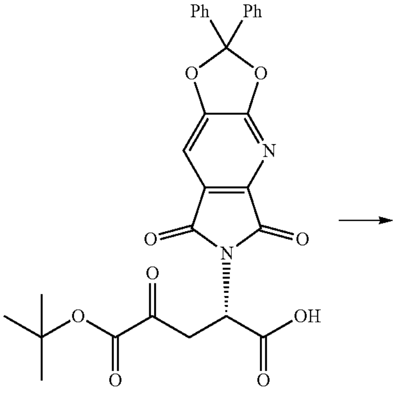

71

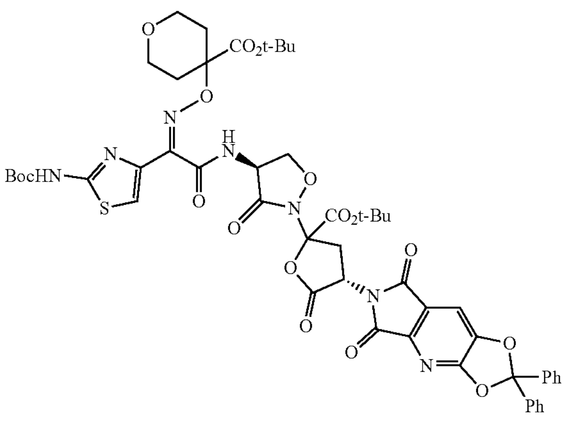

75

To a mixture of tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxane-4-carboxylate 71 (316 mg, 0.58 mmol, prepared as described in Example 5, Step 7) and (2S)-5-tert-butoxy-2-(5,7-dioxo-2,2-diphenyl-5,7-dihydro-2H,6H-[1,3]dioxolo[4,5-b]pyrrolo[3,4-e]pyridin-6-yl)-4,5-dioxopentanoic acid 37 (293 mg, 0.53 mmol, prepared as described in Example 10, Step 4) in anhydrous THF (9 ml) was added DMAP (14 mg, 0.11 mmol), followed by DCC (153 mg, 0.74 mmol) at 0° C. The reaction mixture was allowed to slowly warm up to room temperature and stirred for 18 h. The mixture was then concentrated, and the residue was treated with 30% DCM in hexanes and the precipitated solids were removed by filtration. The filtrate was concentrated under reduced pressure and the crude product was purified by silica gel column chromatography using a gradient of 10 to 40% ethyl acetate in hexanes to afford tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-b]pyrrolo[3,4-e]pyridin-6-yl)-5-oxooxolan-2-yl]-3-oxo-1,2-oxazolidin-4-yl}amino)-2-oxoethylidene]amino}oxy)oxane-4-carboxylate 75 (238 mg, 42%) as a light brown foam.

$^1$H NMR (400 MHz, $CDCl_3$) δ 8.26-8.01 (m, 2H), 7.59-7.56 (m, 4H), 7.46-7.42 (m, 7H), 7.37-7.34 (m, 1H), 5.46-4.88 (m, 3H), 4.39-4.21 (m, 1H), 3.89-3.33 (m, 5H), 2.91-2.77 (m, 1H), 2.26-2.12 (m, 4H), 1.60-1.57 (m, 9H), 1.56-1.51 (m, 9H), 1.49-1.42 (m, 9H).

Step 2: 4-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)oxane-4-carboxylicacid (Compound 26)

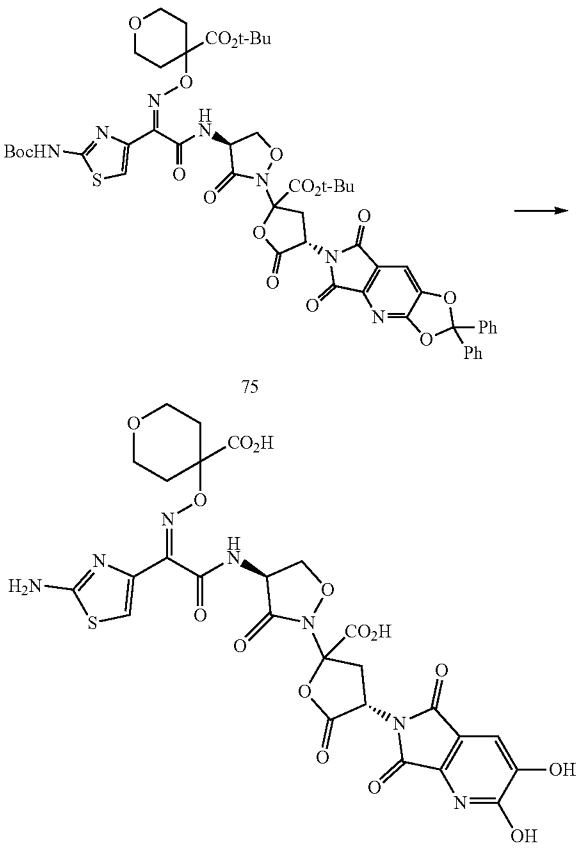

75

Compound 26

To a solution of tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-b]pyrrolo[3,4-e]pyridin-6-yl)-5-oxooxolan-2-yl]-3-oxo-1,2-oxazolidin-4-yl}amino)-2-oxoethylidene]amino}oxy)oxane-4-carboxylate 75 (238 mg, 0.22 mmol) in anhydrous DCM (17 ml) was added dropwise a boron trichloride solution (1.0 M in DCM, 1.76 mL, 1.76 mmol) at −50° C. The reaction mixture was stirred at −50° C. to −25° C. for 2.5 h and then a solution of $NaHCO_3$ (362 mg) and $Na_2HPO_4$ (114.5 mg) in water (19.6 ml) was added at −50° C. The resulting heterogenous mixture was stirred at 0-5° C. (ice-water bath) for 20 min, and then at room temperature until the aqueous phase thawed. The mixture was filtered through a syringe filter and the organic layer was carefully separated. The aqueous layer was then subjected to C-18 reverse phase chromatography purification using a Biotage system and a mixture of 0.1% formic acid in acetonitrile and 0.1% formic acid in water as mobile phases. The product containing fractions were collected and lyophilized to afford 4-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)oxane-4-carboxylic acid Compound 26 (47 mg, 30%) as a yellow solid.

$^1H$ NMR (400 MHz, a mixture of $D_2O$ and $CD_3CN$) δ 7.07-7.06 (m, 2H), 5.39-5.07 (m, 2H), 4.74-4.67 (m, 1H), 4.30-4.23 (m, 1H), 3.78-3.72 (m, 2H), 3.60-3.28 (m, 3H), 2.86-2.64 (m, 1H), 2.12-1.96 (m, 4H). Exchangeable protons were not observed in $D_2O$.

MS (ESI) m/z: $[M+1]^+$ 706.0

Example 13

3-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid (Compound 27, Table 1)

Compound 27

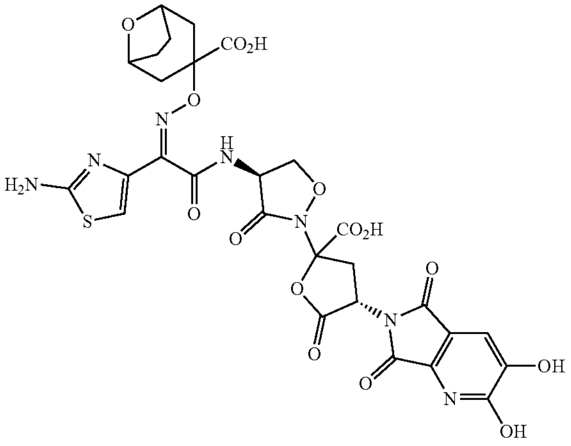

Step 1: tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-b]pyrrolo[3,4-e]pyridin-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylate (76)

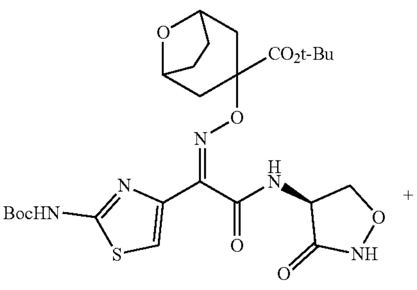

60

-continued

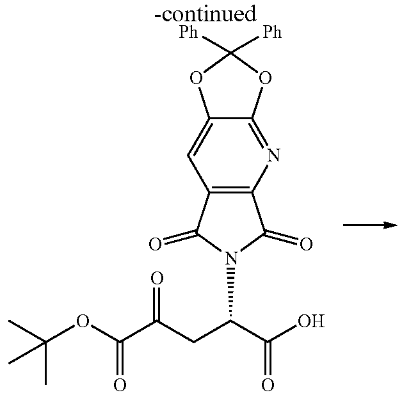

71

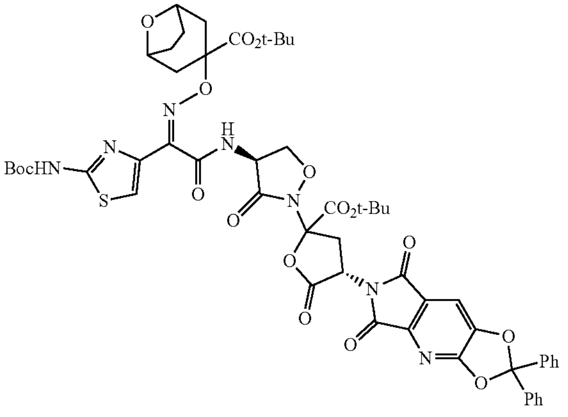

76

To a mixture of tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-8-oxabicyclo[3.2.1]octane-3-carboxylate 60 (337 mg, 0.62 mmol, prepared as described in Example 8, Step 6) and (2S)-5-tert-butoxy-2-(5,7-dioxo-2,2-diphenyl-5,7-dihydro-2H,6H-[1,3]dioxolo[4,5-b]pyrrolo[3,4-e]pyridin-6-yl)-4,5-dioxopentanoic acid 71 (343 mg, 0.59 mmol, prepared as described in Example 1, Step 4) in THF (9 mL) was added DMAP (15 mg, 0.12 mmol), followed by DCC (171 mg, 0.83 mmol) at 0° C. The reaction mixture was allowed to gradually warm to room temperature and stirred for 18 h. Subsequently, the mixture was concentrated, and the residue was triturated with 30% DCM in hexanes and filtered. The filtrate was concentrated under reduced pressure and the crude product was purified by silica gel column chromatography using a gradient of 10 to 40% ethyl acetate in hexanes to afford tert-butyl 3-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-b]pyrrolo[3,4-e]pyridin-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylate 76 (274 mg, 42%) as a light brown foam.

$^1$H NMR (400 MHz, $CDCl_3$) δ 8.19-8.01 (m, 2H), 7.60-7.54 (m, 4H), 7.47-7.42 (m, 7H), 7.36 (d, J=4.2 Hz, 1H), 5.47-4.89 (m, 3H), 4.50-4.22 (m, 3H), 3.71-3.34 (m, 1H), 2.92-2.79 (m, 1H), 2.44-2.19 (m, 4H), 2.05-1.87 (m, 4H), 1.61-1.53 (m, 18H), 1.46-1.44 (m, 9H).

Step 2: 3-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid (Compound 27)

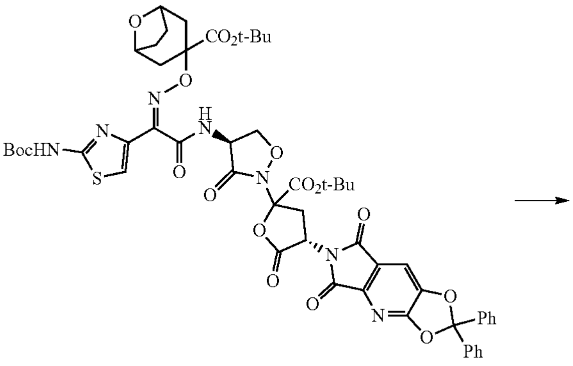

76

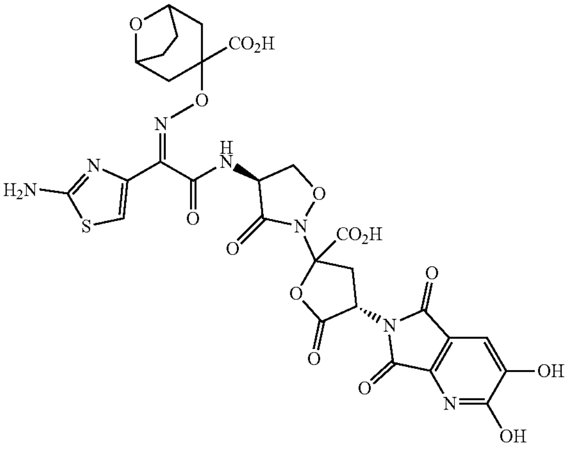

Compound 27

To a solution of tert-butyl 3-({(Z)-[1-(2-[(tert-butoxycarbonyl)amino]-1,3-thiazol-4-yl)-2-({(4S)-2-[(4S)-2-(tert-butoxycarbonyl)-4-(5,7-dioxo-2,2-diphenyl-5,7-dihydro-2H,6H-[1,3]dioxolo[4,5-b]pyrrolo[3,4-e]pyridin-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylate 76 (265 mg, 0.24 mmol) in anhydrous DCM (17 mL) was added dropwise a boron trichloride solution (1.0 M in DCM, 1.91 mL, 1.91 mmol) at −50° C. The reaction mixture was stirred at −50° C.–−25° C. for 2.5 h and then a solution of $NaHCO_3$ (393 mg) and $Na_2HPO_4$ (124 mg) in $H_2O$ (21.3 mL) was added at −50° C. The cold bath was replaced with an ice-water bath, the resulting heterogenous mixture was stirred for 20 min at 5-10° C. and then at room temperature until the aqueous phase thawed completely. The mixture was filtered through a syringe filter and the organic layer was carefully separated. The aqueous solution was immediately subjected to C-18 reverse phase column chromatography using a Biotage system and 0.1% formic acid in acetonitrile and 0.1% formic acid in water as eluents. The fractions containing pure product were combined and lyophilized to afford 3-({(Z)-[1-(2-amino-1,3-thiazol-4-yl)-2-({(4S)-2-[(4S)-2-carboxy-4-(2,3-dihydroxy-5,7-dioxo-5,7-dihydro-6H-pyrrolo[3,4-b]pyridin-6-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid Compound 27 (95 mg, 54%) as a yellow solid.

$^1$H NMR (400 MHz, a mixture of $D_2O$ and $CD_3CN$) δ 7.13-7.11 (m, 1H), 7.07-7.06 (m, 1H), 5.38-5.24 (m, 1H), 5.14-5.07 (m, 1H), 4.74-4.68 (m, 1H), 4.42-4.39 (m, 2H), 4.34-4.24 (m, 1H), 3.48-3.28 (m, 1H), 2.87-2.66 (m, 1H), 2.30-2.23 (m, 2H), 2.09-2.04 (m, 2H), 1.83-1.70 (m, 4H). Exchangeable protons were not observed in $D_2O$.

MS (ESI) m/z: $[M+1]^+$ 732.0

Example 14

(4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid (Compound 35, Table 1)

Compound 35

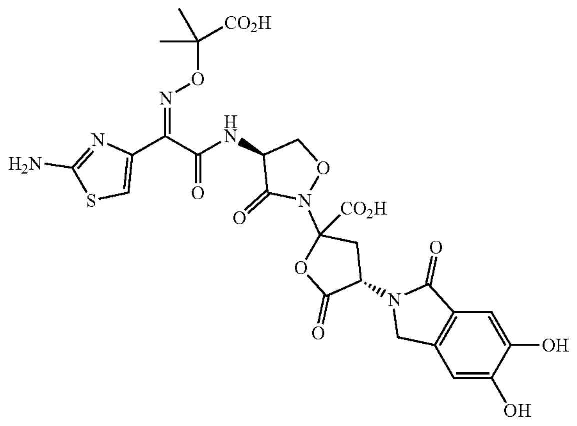

Step 1: Methyl 6-methyl-2,2-diphenyl-2H-1,3-benzodioxole-5-carboxylate (78)

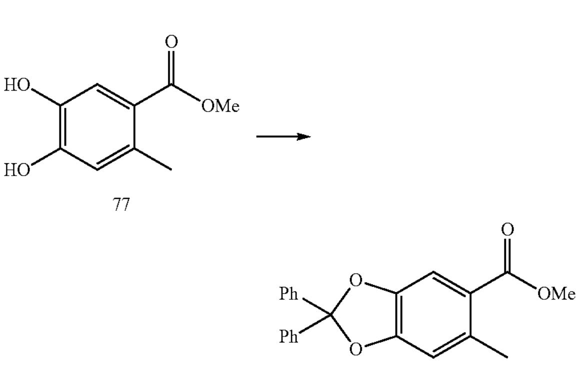

77

78

A mixture of methyl 4,5-dihydroxy-2-methylbenzoate 77 (7.45 g, 40.90 mmol) and 1,1'-(dichloromethylene)dibenzene (7.86 mL, 40.94 mmol) was heated to 170° C. and stirred at 170° C. for 30 min. The reaction mixture was then cooled and concentrated under reduced pressure. The crude product was purified by silica gel column chromatography using a gradient of 0 to 6% ethyl acetate in hexanes, followed by trituration with hexanes to afford methyl 6-methyl-2,2-diphenyl-2H-1,3-benzodioxole-5-carboxylate 78 (12.37 g, 87%) as a white solid.

$^1$H NMR (400 MHz, $CDCl_3$) δ 7.54-7.50 (m, 4H), 7.45 (s, 1H), 7.36-7.32 (m, 6H), 6.72 (s, 1H), 3.81 (s, 3H), 2.50 (s, 3H).

MS (ESI) m/z: $[M+1]^+$ 347.1

Step 2: Methyl 6-(bromomethyl)-2,2-diphenyl-2H-1,3-benzodioxole-5-carboxylate (79)

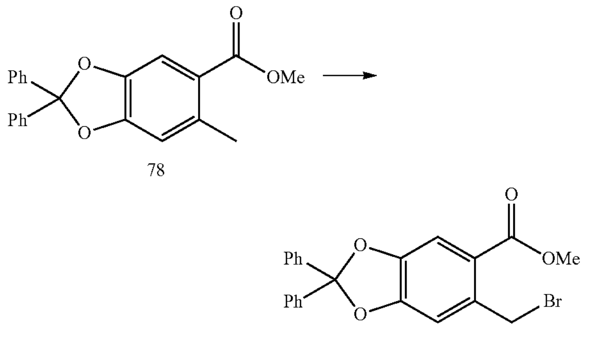

78

79

To a mixture of methyl 6-methyl-2,2-diphenyl-2H-1,3-benzodioxole-5-carboxylate 78 (12.37 g, 35.71 mmol) and NBS (7.0 g, 39.33 mmol) in carbon tetrachloride (120 ml) was added AIBN (587 mg, 3.57 mmol) at room temperature. The reaction mixture was heated to 70° C. and stirred at 70° C. overnight, then was cooled and concentrated under reduced pressure. The residue was triturated with hexanes and the Insoluble material was filtered off. The filtrate was concentrated and the crude product was purified by silica gel column chromatography using a gradient of 0 to 4% ethyl acetate in hexanes to afford methyl 6-(bromomethyl)-2,2-diphenyl-2H-1,3-benzodioxole-5-carboxylate 79 (9.83 g, 65%) as a colorless sticky oil.

$^1$H NMR (400 MHz, $CDCl_3$) δ 7.56-7.53 (m, 4H), 7.51 (s, 1H), 7.40-7.36 (m, 6H), 6.96 (s, 1H), 4.93 (s, 2H), 3.89 (s, 3H).

Step 3: 4-tert-butyl 1-methyl (2S)-2-(5-oxo-2,2-diphenyl-5,7-dihydro-2H,6H-[1,3]dioxolo[4,5-f]isoindol-6-yl)butanedioate (81)

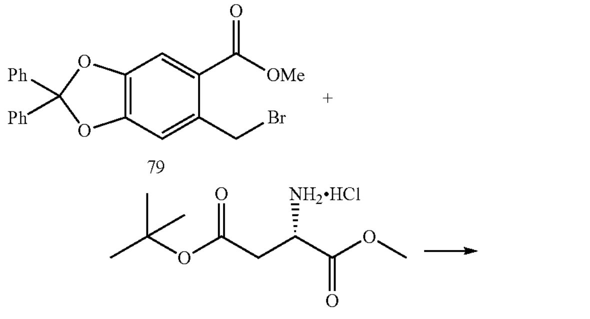

79

80

-continued

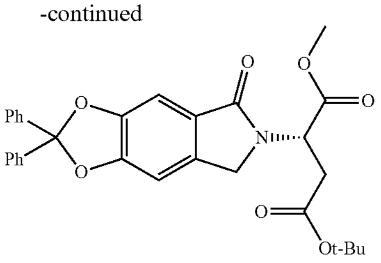

81

To a mixture of methyl 6-(bromomethyl)-2,2-diphenyl-2H-1,3-benzodioxole-5-carboxylate 79 (5.28 g, 12.42 mmol) and 4-tert-butyl 1-methyl L-aspartate hydrochloride 80 (3.28 g, 13.68 mmol) in anhydrous acetonitrile (60 ml) was added dropwise DIPEA (4.76 ml, 27.33 mmol) at 0° C. The reaction mixture was stirred at 0° C. for 10 min and then at room temperature for 1 h. Subsequently, the reaction mixture was heated to reflux, stirred at reflux temperature for 20 h, then cooled and concentrated. The residue was treated with ethyl acetate, the solids were removed by filtration and the filtrate was concentrated. The crude product was purified by silica gel column chromatography using a gradient of 0 to 4% ethyl acetate in hexanes to afford 4-tert-butyl 1-methyl (2S)-2-(5-oxo-2,2-diphenyl-5,7-dihydro-2H,6H-[1,3]dioxolo[4,5-f]isoindol-6-yl)butanedioate 81 (5.08 g, 79%) as a white foam.

$^1$H NMR (400 MHz, $CDCl_3$) δ 7.59-7.54 (m, 4H), 7.42-7.35 (m, 6H), 7.30 (s, 1H), 6.91 (d, J=0.3 Hz, 1H), 5.30 (dd, J=8.5, 5.7 Hz, 1H), 4.45-4.28 (m, 2H), 3.71 (s, 3H), 3.01-2.84 (m, 2H), 1.39 (s, 9H).

MS (ESI) m/z: $[M+1]^+$ 516.2

Step 4: (3S)-4-methoxy-4-oxo-3-(5-oxo-2,2-diphenyl-5,7-dihydro-2H,6H-[1,3]dioxolo[4,5-f]isoindol-6-yl)butanoic acid (82)

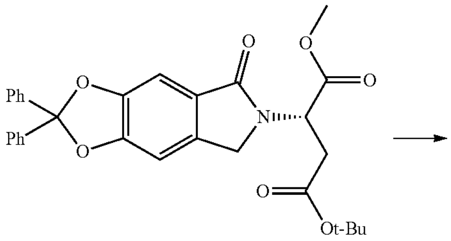

81

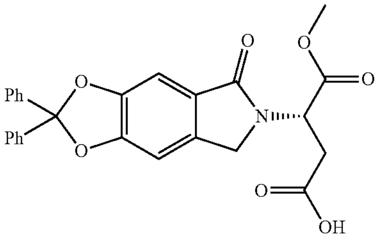

82

To solution of 4-tert-butyl 1-methyl (2S)-2-(5-oxo-2,2-diphenyl-5,7-dihydro-2H,6H-[1,3]dioxolo[4,5-f]isoindol-6-yl)butanedioate 81 (245 mg, 0.475 mmol) in anhydrous DCM (12 ml) was added dropwise a boron trichloride solution (1.0 M in DCM, 0.86 mL, 0.86 mmol) at −78° C. The reaction mixture was stirred for 30 min at −78° C. and then gradually warmed up to −45° C. Subsequently the reaction mixture was diluted with ethyl acetate and water was added at −50° C. The resulting mixture was stirred until the aqueous phase thawed, then the organic layer was separated, dried over sodium sulfate, filtered and concentrated under reduced pressure. The residue was triturated with a mixture of ethyl acetate and hexanes and the precipitated solid was collected by filtration and further dried under high vacuum to afford (3S)-4-methoxy-4-oxo-3-(5-oxo-2,2-diphenyl-5,7-dihydro-2H,6H-[1,3]dioxolo[4,5-f]isoindol-6-yl)butanoic acid 82 (154 mg, 71%) as a white solid.

$^1$H NMR (400 MHz, DMSO-$d_6$) δ 12.52 (bs, 1H), 7.54-7.50 (m, 4H), 7.47-7.40 (m, 6H), 7.26 (s, 1H), 7.25 (s, 1H), 5.08 (t, J=7.0 Hz, 1H), 4.33 (s, 2H), 3.60 (s, 3H), 2.99-2.83 (m, 2H).

MS (ESI) m/z: $[M+1]^+$ 460.1

Step 5: methyl (2S)-5-cyano-4-oxo-2-(5-oxo-2,2-diphenyl-5,7-dihydro-2H,6H-[1,3]dioxolo[4,5-f]isoindol-6-yl)-5-(1λ$^4$-thiolan-1-ylidene)pentanoate (83)

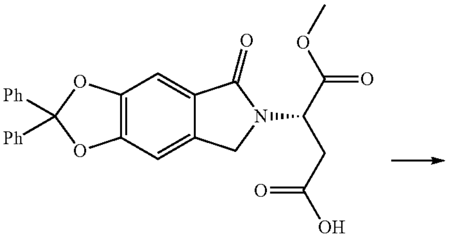

82

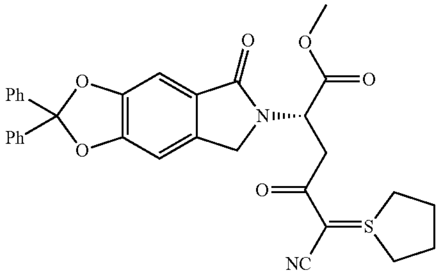

83

To a solution of (3S)-4-methoxy-4-oxo-3-(5-oxo-2,2-diphenyl-5,7-dihydro-2H,6H-[1,3]dioxolo[4,5-f]isoindol-6-yl)butanoic acid 82 (189 mg, 0.41 mmol) in anhydrous DMF (4 ml) was added HATU (172 mg, 0.45 mmol) at room temperature. The resulting mixture was cooled to 0° C. and DIPEA (0.22 ml, 1.26 mmol) was added, followed by 1-(cyanomethyl)thiolan-1-ium bromide (112 mg, 0.54 mmol). The reaction mixture was stirred at 0° C. for 30 min, then allowed to slowly warm to room temperature and stirred overnight. Subsequently, the reaction was quenched by addition of a saturated ammonium chloride solution at 0° C. and the mixture was diluted with water and extracted with ethyl acetate. The combined organic extracts were washed with brine, dried over sodium sulfate, filtered and concentrated under reduced pressure. The residue was purified by silica gel column chromatography using a gradient of 0 to 40% acetone in ethyl acetate to afford (2S)-5-cyano-4-oxo- 2-(5-oxo-2,2-diphenyl-5,7-dihydro-2H,6H-[1,3]dioxolo[4,5-f]isoindol-6-yl)-5-(1$\lambda^4$-thiolan-1-ylidene)pentanoate 83 (247 mg, quantitative) as a white foam.

$^1$H NMR (400 MHz, $CDCl_3$) δ 7.59-7.53 (m, 4H), 7.42-7.36 (m, 6H), 7.27 (s, 1H), 6.95-6.91 (m, 1H), 5.55-5.50 (m, 1H), 4.51-4.36 (m, 2H), 3.77-3.71 (m, 3H), 3.55-3.12 (m, 6H), 2.53-2.40 (m, 2H), 2.12-2.00 (m, 2H).

Step 6: (4S)-5-methoxy-2,5-dioxo-4-(5-oxo-2,2-diphenyl-5,7-dihydro-2H,6H-[1,3]dioxolo[4,5-f]isoindol-6-yl)pentanoic acid (84)

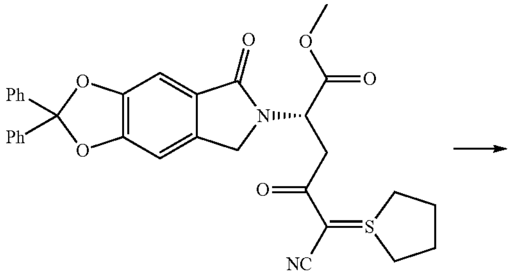

83

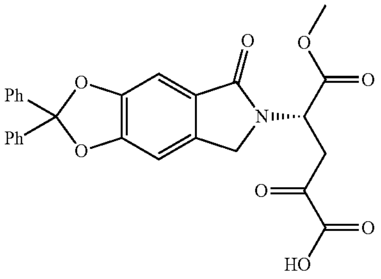

84

To a solution of methyl (2S)-5-cyano-4-oxo-2-(5-oxo-2,2-diphenyl-5,7-dihydro-2H,6H-[1,3]dioxolo[4,5-f]isoindol-6-yl)-5-(1-thiolan-1-ylidene)pentanoate 83 (244 mg, 0.41 mmol) in a mixture of THF and water (1:1, 9 ml) was added OXONE (264 mg, 0.86 mmol) and the reaction mixture was stirred at room temperature for 2 h. An additional portion of OXONE (132 mg, 0.43 mmol) and water (2 ml) were then added and stirring was continued at room temperature for 1 h. The reaction mixture was concentrated to remove THF and the aqueous phase was extracted with ethyl acetate. The combined organic extracts were dried over sodium sulfate, filtered and concentrated under reduced pressure to afford (4S)-5-methoxy-2,5-dioxo-4-(5-oxo-2,2-diphenyl-5,7-dihydro-2H,6H-[1,3]dioxolo[4,5-f]isoindol-6-yl)pentanoic acid 84 (220 mg) as a white foam, which was used in the next step.

$^1$H NMR (400 MHz, $CDCl_3$) δ 7.56-7.53 (m, 4H), 7.39-7.36 (m, 6H), 7.28 (s, 1H), 6.88 (s, 1H), 5.38-5.34 (m, 1H), 4.43-4.27 (m, 2H), 3.74 (dd, J=17.8, 6.3 Hz, 1H), 3.70 (s, 3H), 3.46 (dd, J=17.8, 7.7 Hz, 1H).

Step 7: 1-tert-butyl 5-methyl (4S)-2-oxo-4-(5-oxo-2,2-diphenyl-5,7-dihydro-2H,6H-[1,3]dioxolo[4,5-f]isoindol-6-yl)pentanedioate (85)

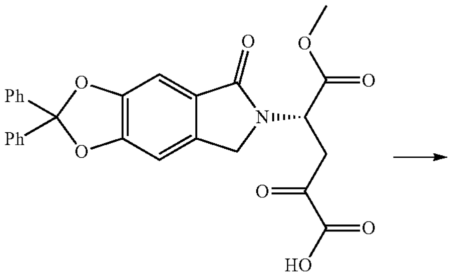

84

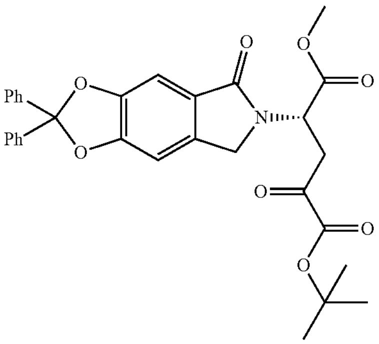

85

To a solution of (4S)-5-methoxy-2,5-dioxo-4-(5-oxo-2,2-diphenyl-5,7-dihydro-2H,6H-[1,3]dioxolo[4,5-f]isoindol-6-yl)pentanoic acid 84 (220 mg, 0.41 mmol) in anhydrous THF (5 mL) was slowly added tert-butyl N,N'-di(propan-2-yl)carbamimidate (0.4 mL, 1.54 mmol) at 0° C. The reaction mixture was stirred at 0° C. for 10 min and then at room temperature for 3 h. The mixture was concentrated under reduced pressure and the residue was triturated with 25% DCM in hexanes. The insoluble material was removed by filtration, the filtrate was concentrated and the crude product was purified by silica gel column chromatography using a gradient of 10 to 30% ethyl acetate in hexanes to afford 1-tert-butyl 5-methyl (4S)-2-oxo-4-(5-oxo-2,2-diphenyl-5,7-dihydro-2H,6H-[1,3]dioxolo[4,5-f]isoindol-6-yl)pentanedioate 85 (181 mg, 81% over 2 steps) as a white solid.

$^1$H NMR (400 MHz, $CDCl_3$) δ 7.57-7.54 (m, 4H), 7.40-7.36 (m, 6H), 7.28 (s, 1H), 6.90 (s, 1H), 5.24 (dd, J=7.5, 5.6 Hz, 1H), 4.45 (d, J=16.5 Hz, 1H), 4.27 (d, J=16.5 Hz, 1H), 3.71 (s, 3H), 3.63 (dd, J=18.5, 5.6 Hz, 1H), 3.49 (dd, J=18.5, 7.5 Hz, 1H), 1.53 (s, 9H).

MS (ESI) m/z: $[M+1]^+$ 544.2

Step 8: (2S)-5-tert-butoxy-4,5-dioxo-2-(5-oxo-2,2-diphenyl-5,7-dihydro-2H,6H-[1,3]dioxolo[4,5-f]isoindol-6-yl)pentanoic acid (86)

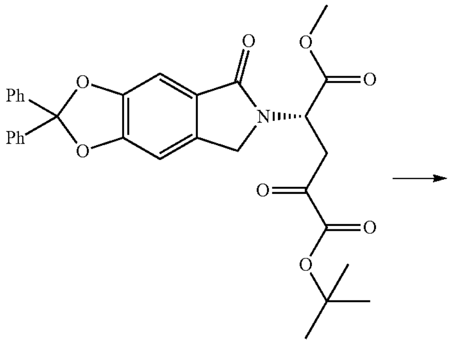

85

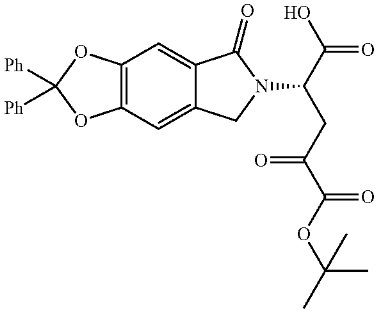

86

A solution of 1-tert-butyl 5-methyl (4S)-2-oxo-4-(5-oxo-2,2-diphenyl-5,7-dihydro-2H,6H-[1,3]dioxolo[4,5-f]isoindol-6-yl)pentanedioate 85 (181 mg, 0.33 mmol) in a mixture of THE and water (1:1, 4 ml) was cooled to 0° C. and $LiOH \cdot H_2O$ (14 mg, 0.33 mmol) was added. The reaction mixture was stirred at 0° C. for 40 min and then at room temperature for 10 min. Subsequently, the reaction mixture was cooled to 0° C. and 1 M HCl (0.33 ml) was added. The resulting mixture was diluted with water and extracted with ethyl acetate. The combined organic extracts were dried over sodium sulfate, filtered and concentrated under reduced pressure. The residue was purified by silica gel column chromatography using 30% ethyl acetate in hexanes, followed by a gradient of 0 to 5% MeOH in DCM to afford (2S)-5-tert-butoxy-4,5-dioxo-2-(5-oxo-2,2-diphenyl-5,7-dihydro-2H,6H-[1,3]dioxolo[4,5-f]isoindol-6-yl)pentanoic acid 86 (115 mg, 65%) as a white foam.

$^1H$ NMR (400 MHz, DMSO-$d_6$) δ 7.58-7.54 (m, 4H), 7.42-7.36 (m, 6H), 7.32-7.27 (m, 1H), 6.93-6.87 (m, 1H), 5.63-5.51 (m, 1H), 4.39-4.23 (m, 2H), 3.01-2.85 (m, 1H), 2.63-2.35 (m, 1H), 1.57-1.52 (m, 9H).

MS (ESI) m/z: $[M+1]^+$ 530.2

Step 9: tert-butyl (4S)-2-[(4S)-4-{[(2Z)-2-(2-[(tert-butoxycarbonyl)amino]-1,3-thiazol-4-yl)-2-{[(1-tert-butoxy-2-methyl-1-oxopropan-2-yl)oxy]imino}acetyl]amino}-3-oxo-1,2-oxazolidin-2-yl]-5-oxo-4-(5-oxo-2,2-diphenyl-5,7-dihydro-2H,6H-[1,3]dioxolo[4,5-f]isoindol-6-yl)oxolane-2-carboxylate (87)

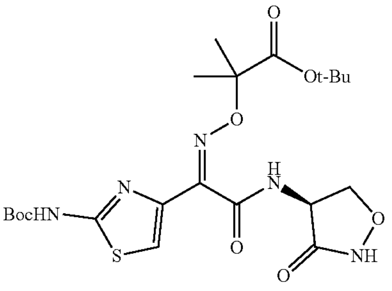

72

+

86

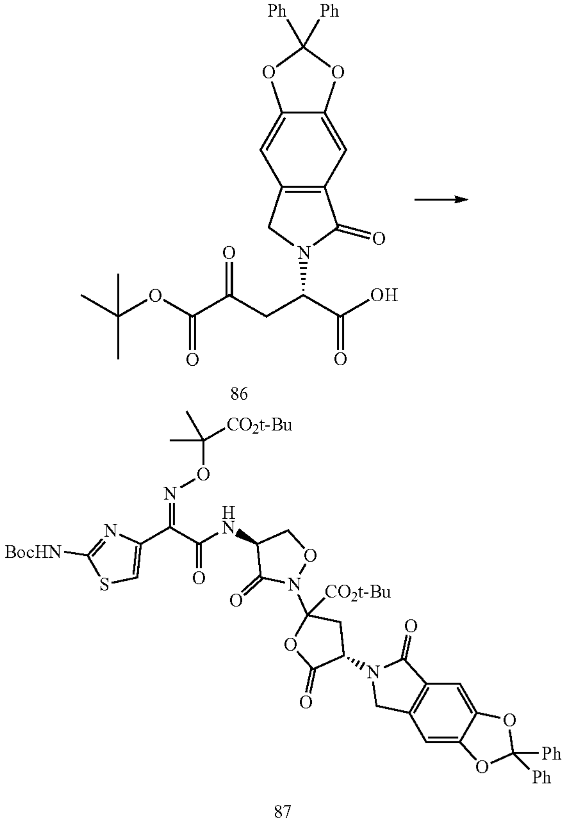

87

To a mixture of (2S)-5-tert-butoxy-4,5-dioxo-2-(5-oxo-2,2-diphenyl-5,7-dihydro-2H,6H-[1,3]dioxolo[4,5-f]isoindol-6-yl)pentanoic acid 86 (112 mg, 0.21 mmol) and tert-butyl 2-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2-methylpropanoate 72 (109 mg, 0.21 mmol) in anhydrous THF (4 ml) was added DMAP (6 mg, 0.049 mmol), followed by DCC (62 mg, 0.30 mmol) at 0° C. The reaction mixture was allowed to gradually warm up to room temperature and was stirred for 18 h. The mixture was then concentrated, and the residue was treated with 25% DCM in hexanes and filtered. The filtrate was concentrated under reduced pressure and the crude product was purified by silica gel column chromatography using a gradient of 10 to 40% ethyl acetate in hexanes to afford tert-butyl (4S)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-5-oxo-4-(5-oxo-2,2-diphenyl-5,7-dihydro-2H,6H-[1,3]dioxolo[4,5-f]isoindol-6-yl)oxolane-2-carboxylate 87 (132 mg, 61%) as a white foam.

$^1$H NMR (400 MHz, $CDCl_3$) δ 8.21-8.18 (m, 1H), 7.57-7.52 (m, 4H), 7.41-7.34 (m, 7H), 7.30-7.29 (m, 1H), 6.92-6.90 (m, 1H), 5.47-5.39 (m, 1H), 5.20-4.85 (m, 2H), 4.34-4.21 (m, 3H), 3.51-3.31 (m, 1H), 2.93-2.49 (m, 1H), 1.61-1.58 (m, 6H), 1.55-1.52 (m, 18H), 1.43 (s, 9H).

Step 10: (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid (Compound 35)

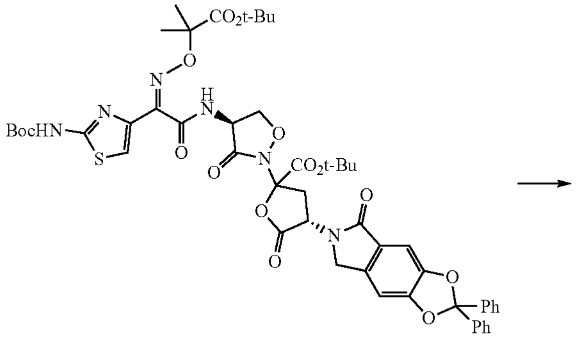

87

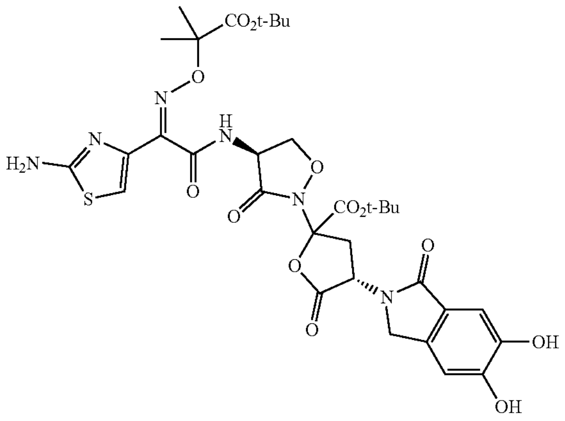

Compound 35

A stirred solution of tert-butyl (4S)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-5-oxo-4-(5-oxo-2,2-diphenyl-5,7-dihydro-2H,6H-[1,3]dioxolo[4,5-f]isoindol-6-yl)oxolane-2-carboxylate 87 (132 mg, 0.13 mmol) in anhydrous DCM (7 mL) was cooled to −50° C. and a boron trichloride solution (1.0 M in DCM, 1.03 mL, 1.03 mmol) was added dropwise. The reaction mixture was stirred at −50° C.-−35° C. for 2.5 h and then cooled to −50° C. before a solution of $NaHCO_3$ (212 mg) and $Na_2HPO_4$ (67 mg) in water (11.4 ml) was added. The cold bath was replaced with an ice-water bath and the heterogenous mixture was stirred at 5-10° C. for 10 min and then at ambient temperature until the aqueous layer thawed. The mixture was filtered through a syringe filter and the organic layer was carefully removed. The aqueous solution was then immediately subjected to C18 reverse phase chromatography using a Biotage system and a mixture of 0.1% formic acid in acetonitrile and 0.1% formic acid in water as mobile phases. The pure fractions were collected and lyophilized to afford (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid Compound 35 (27 mg, 32%) as a white solid.

$^1$H NMR (400 MHz, a mixture of $D_2O$ and $CD_3CN$) δ 7.15-7.13 (m, 1H), 7.10-7.06 (m, 1H), 7.00-6.98 (m, 1H), 5.46-5.08 (m, 2H), 4.77-4.68 (m, 1H), 4.42-4.23 (m, 3H), 3.46-3.32 (m, 1H), 2.91-2.62 (m, 1H), 1.53-1.47 (m, 6H). Exchangeable protons were not observed in $D_2O$.

MS (ESI) m/z: $[M+1]^+$ 649.1

Example 15

(4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid (Compound 28, Table 1)

Compound 28

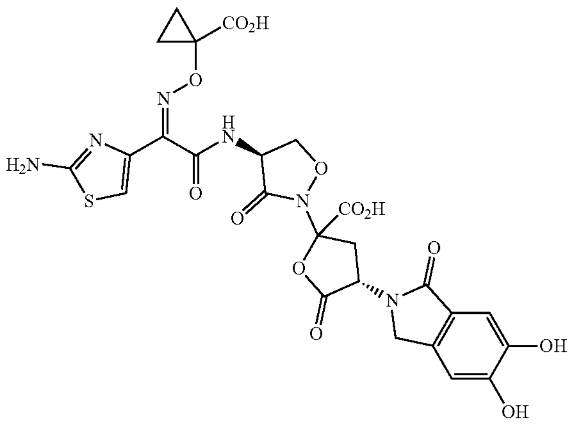

Step 1: tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-5-oxo-4-(5-oxo-2,2-diphenyl-5,7-dihydro-2H,6H-[1,3]dioxolo[4,5-f]isoindol-6-yl)oxolane-2-carboxylate (88)

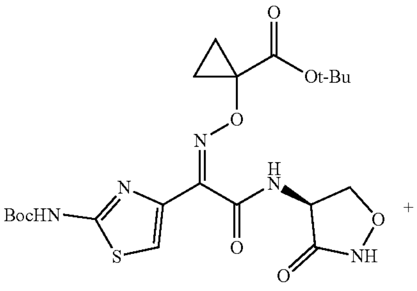

5

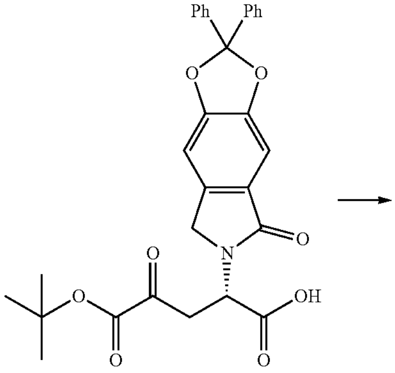

86

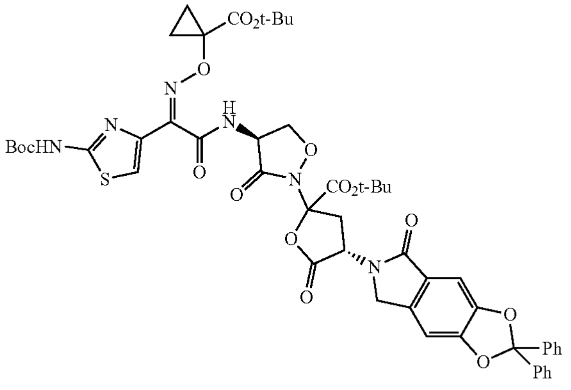

88

A mixture of tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}cyclopropane-1-carboxylate 5 (358 mg, 0.70 mmol, prepared as described in Example 1, Step 4) and (2S)-5-tert-butoxy-4,5-dioxo-2-(5-oxo-2,2-diphenyl-5,7-dihydro-2H,6H-[1,3]dioxolo[4,5-f]isoindol-6-yl)pentanoic acid 86 (370 mg, 0.70 mmol, prepared as described in Example 14, Step 8) in anhydrous THF (20 ml) was cooled to 0° C. DMAP (17 mg, 0.14 mmol) followed by DCC (202 mg, 0.98 mmol) were added and the reaction mixture was stirred at 0° C. for 1 h and then at room temperature overnight. The solvent was evaporated at 25° C. and the residue was triturated with 25% DCM in hexanes (25 ml). The precipitated solids were filtered off, washed with 25% DCM in hexanes (15 ml) and hexanes. The combined filtrates were concentrated under reduced pressure and the crude product was purified by silica gel column chromatography using a gradient of 10 to 50% ethyl acetate in hexanes as eluent to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-5-oxo-4-(5-oxo-2,2-diphenyl-5,7-dihydro-2H,6H-[1,3]dioxolo[4,5-f]isoindol-6-yl)oxolane-2-carboxylate 88 (460 mg, 64% yield) as off-white solid.

$^1$H-NMR (400 MHz; $CDCl_3$) δ 8.59 (d, J=6.1 Hz, 1H), 8.17 (bs, 1H), 7.60-7.55 (m, 4H), 7.42-7.39 (m, 6H), 7.32 (s, 1H), 6.93 (s, 1H), 5.49-5.43 (m, 1H), 5.23-5.17 (m, 1H), 4.94 (t, J=8.3 Hz, 1H), 4.37-4.25 (m, 3H), 3.45-3.35 (m, 1H), 2.60 (dd, J=14.0, 10.4 Hz, 1H), 1.58-1.51 (m, 22H), 1.45 (s, 9H).

Step 2: (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid (Compound 28)

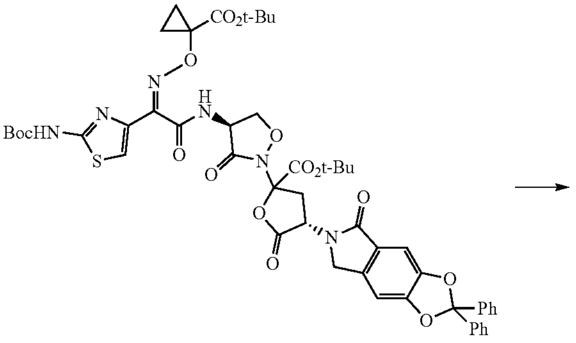

88

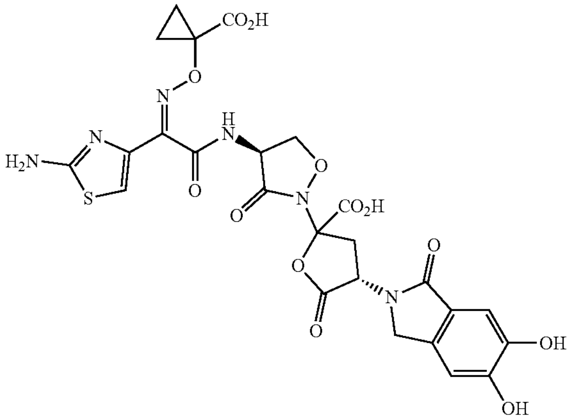

Compound 28

A solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)cyclopropyl]oxy}imino)acetyl]amino}-3-oxo-1,2-oxazolidin-2-yl]-5-oxo-4-(5-oxo-2,2-diphenyl-5,7-dihydro-2H,6H-[1,3]dioxolo[4,5-f]isoindol-6-yl)oxolane-2-carboxylate 88 (450 mg, 0.44 mmol) in anhydrous DCM (22 mL) was cooled to −50° C. A solution of boron trichloride (1.0M in DCM, 3.52 mL, 3.52 mmol) was added dropwise at −50° C. and the reaction mixture was stirred at −45 to −30° C. for 2.5 h. Subsequently the reaction mixture was cooled to −50° C. and 40 mL of a buffer solution (prepared by dissolving 776 mg of $NaHCO_3$ and 243 mg of $Na_2HPO_4$ in 42 mL of water) was added. The cold bath was replaced with an ice-water bath to allow the frozen heterogenous mixture to thaw and to separate into two layers. The organic phase was carefully removed, and the aqueous phase was collected and immediately purified by C18 reverse phase chromatography using a Biotage system and a mixture of 0.1% formic acid in acetonitrile and 0.1% formic acid in water as mobile phases. The product containing fractions were combined and lyophilized to afford (4S)-2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1-oxo-1,3-dihydro-2H-isoindol-2-yl)-5-oxooxolane-2-carboxylic acid Compound 28 (70 mg, 24%) as off-white foamy.

$^1$H-NMR (400 MHz; a mixture of $D_2O$ and $CD_3CN$) δ 7.12 (s, 1H), 7.09 (s, 1H), 6.97 (s, 1H), 5.40 (t, J=10.1 Hz, 1H), 5.15-5.06 (m, 1), 4.73-4.64 (m, 1H), 4.35-4.21 (m, 3H), 3.37-3.30 (m, 1H), 2.64 (dd, J=14.2, 11.1 Hz, 1H), 1.49-1.44 (m, 2H), 1.42-1.37 (m, 2H). Exchangeable protons were not observed in $D_2O$.

MS (ESI) m/z: $[M+1]^+$ 647.0

Example 16

4-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid (Compound 29, Table 1)

Compound 29

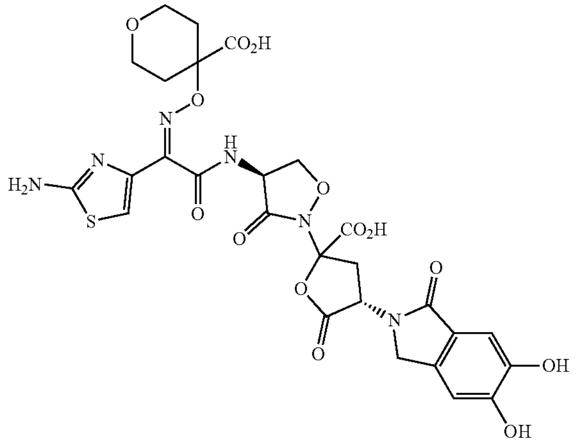

Step 1: tert-butyl 4-({(Z)-[1-{2-[(tert-butoxycarbonyl)amino]-1,3-thiazol-4-yl}-2-({(4S)-2-[(4S)-2-(tert-butoxycarbonyl)-5-oxo-4-(5-oxo-2,2-diphenyl-5,7-dihydro-2H,6H-[1,3]dioxolo[4,5-f]isoindol-6-yl)oxolan-2-yl]-3-oxo-1,2-oxazolidin-4-yl}amino)-2-oxoethylidene]amino}oxy)oxane-4-carboxylate (89)

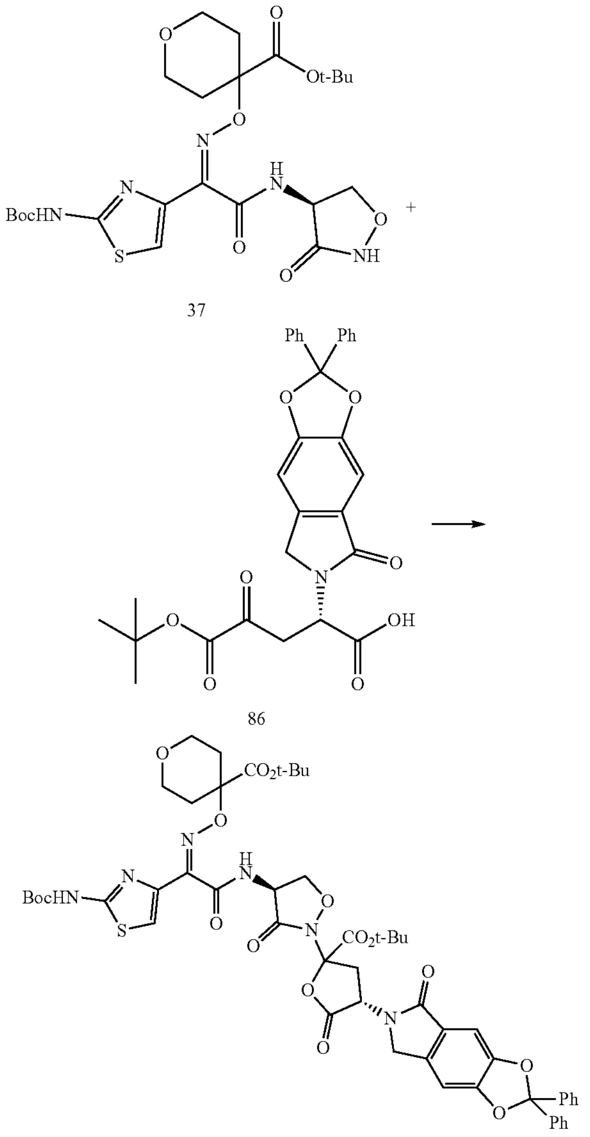

37

86

89

To a stirred mixture of (2S)-5-tert-butoxy-4,5-dioxo-2-(5-oxo-2,2-diphenyl-5,7-dihydro-2H,6H-[1,3]dioxolo[4,5-f]isoindol-yl)pentanoic acid 86 (400 mg, 0.76 mmol, prepared as described in Example 14, Step 8) and tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}oxane-4-carboxylate 37 (420 mg, 0.76 mmol) in anhydrous THF (10 ml) was added DMAP (19 mg, 0.16 mmol), followed by DCC (219 mg, 1.06 mmol) at 0° C. The reaction mixture was allowed to gradually warm to room temperature and was stirred for 18 h. The mixture was then concentrated, and the residue was treated with 50% DCM in hexanes and the precipitated solids were filtered off. The filtrate was concentrated under reduced pressure and the residue was purified by silica gel column chromatography using a gradient of 20 to 45% ethyl acetate in hexanes to afford tert-butyl 4-({(Z)-[1-{2-[(tert-butoxycarbonyl)amino]-1,3-thiazol-4-yl}-2-({(4S)-2-[(4S)-2-(tert-butoxycarbonyl)-5-oxo-4-(5-oxo-2,2-diphenyl-5,7-dihydro-2H,6H-[1,3]dioxolo[4,5-f]isoindol-6-yl)oxolan-2-yl]-3-oxo-1,2-oxazolidin-4-yl}amino)-2-oxoethylidene]amino}oxy)oxane-4-carboxylate 89 (545 mg, 68%) as a white foam.

$^1$H NMR (400 MHz, $CDCl_3$) δ 8.14-8.03 (m, 2H), 7.57-7.52 (m, 4H), 7.41-7.36 (m, 6H), 7.34-7.32 (m, 1H), 7.30-7.28 (m, 1H), 6.92-6.89 (m, 1H), 5.49-5.37 (m, 1H), 5.23-4.84 (m, 2H), 4.36-4.18 (m, 3H), 3.85-3.66 (m, 4H), 3.49-3.29 (m, 1H), 2.92-2.48 (m, 1H), 2.24-2.09 (m, 4H), 1.56-1.52 (m, 18H), 1.44-1.40 (m, 9H).

Step 2: 4-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid (Compound 29)

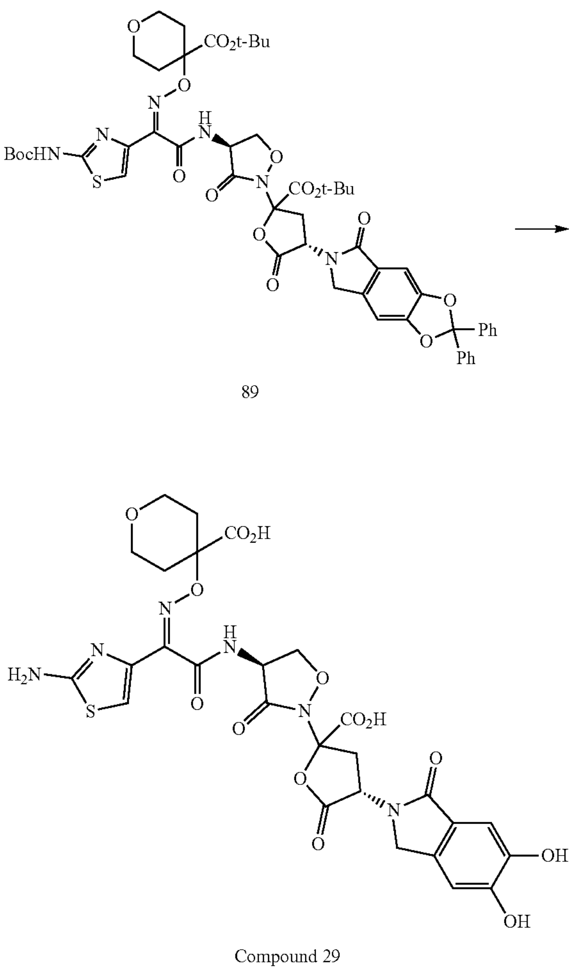

89

Compound 29

To a solution of tert-butyl 4-({(Z)-[1-{2-[(tert-butoxycarbonyl)amino]-1,3-thiazol-4-yl}-2-({(4S)-2-[(4S)-2-(tert-butoxycarbonyl)-5-oxo-4-(5-oxo-2,2-diphenyl-5,7-dihydro- 2H,6H-dioxolo[4,5-f]isoindol-6-yl)oxolan-2-yl]-3-oxo-1,2-oxazolidin-4-yl}amino)-2-oxoethylidene]amino}oxy)oxane-4-carboxylate 89 (541 mg, 0.51 mmol) in anhydrous DCM (30 mL) was added dropwise a boron trichloride solution (1.0 M in DCM, 4.06 mL, 4.06 mmol) at −50° C. The reaction mixture was stirred at −50° C.–−25° C. for 2.5 h, then cooled to −50° C. before a solution of $NaHCO_3$ (835 mg) and $Na_2HPO_4$ (264 mg) in water (45.2 mL) was added. The resulting heterogeneous mixture was stirred at 5-10° C. (ice-water bath) for 10 min and then at ambient temperature until the aqueous phase thawed and two layers separated. The mixture was filtered through a 1 μm syringe filter and the organic layer was carefully removed. The aqueous solution was then subjected to purification by C18 reverse phase chromatography using a Biotage system and a mixture of 0.1% formic acid in acetonitrile and 0.1% formic acid in water as eluents. The pure fractions were collected and lyophilized to afford 4-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)oxane-4-carboxylic acid Compound 29 (161 mg, 46%) as a white solid.

$^1$H NMR (400 MHz, a mixture of $D_2O$ and $CD_3CN$) δ 7.13-7.06 (m, 21H), 6.97-6.96 (m, 1H), 5.44-5.06 (m, 2H), 4.76-4.67 (m, 1H), 4.40-4.22 (m, 3H), 3.78-3.72 (m, 2H), 3.60-3.52 (m, 2H), 3.44-3.29 (m, 1H), 2.90-2.61 (m, 1H), 2.14-1.96 (m, 4H). Exchangeable protons were not observed in $D_2O$.

MS (ESI) m/z: $[M+1]^+$ 691.0

Example 17

3-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid (Compound 30, Table 1)

Compound 30

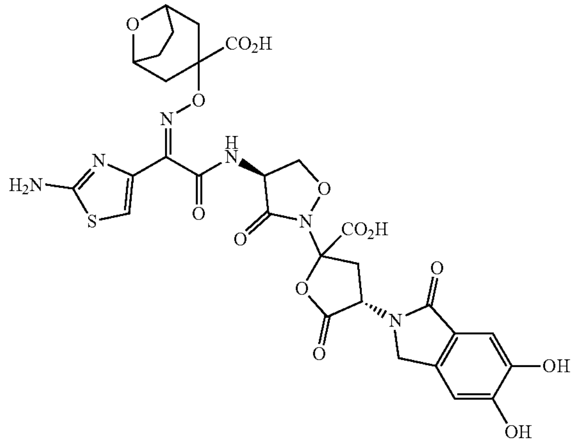

Step 1: tert-butyl 3-({(Z)-[1-{2-[(tert-butoxycarbonyl)amino]-1,3-thiazol-4-yl}-2-({(4S)-2-[(4S)-2-(tert-butoxycarbonyl)-5-oxo-4-(5-oxo-2,2-diphenyl-5,7-dihydro-2H,6H-[1,3]dioxolo[4,5-f]isoindol-6-yl)oxolan-2-yl]-3-oxo-1,2-oxazolidin-4-yl}amino)-2-oxoethylidene]amino}oxy)-8-oxabicyclo[3.2.1]octane-3-carboxylate (90)

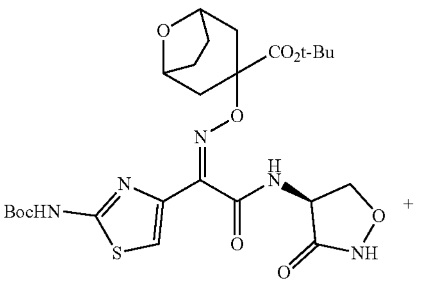

72

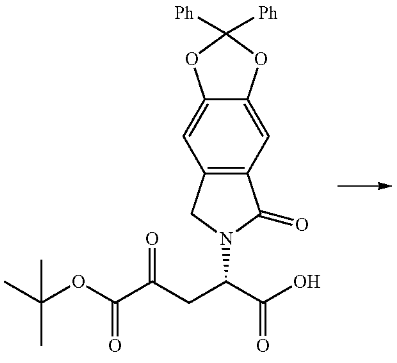

86

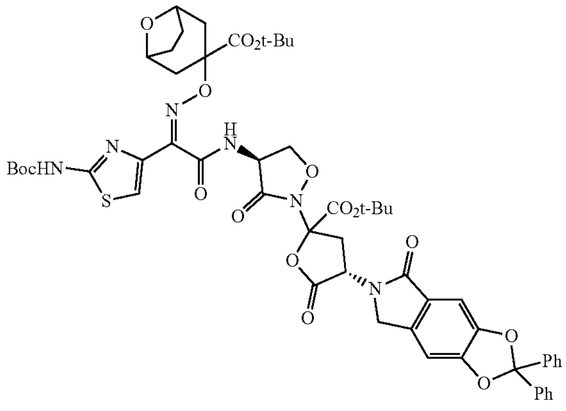

90

To a mixture of (2S)-5-tert-butoxy-4,5-dioxo-2-(5-oxo-2,2-diphenyl-5,7-dihydro-2H,6H-[1,3]dioxolo[4,5-f]isoindol-6-yl)pentanoic acid 86 (461 mg, 0.87 mmol, prepared as described in Example 14, Step 8) and tert-butyl 3-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-8-oxabicyclo[3.2.1]octane-3-carboxylate 60 (507 mg, 0.87 mmol, prepared as described in Example 8, Step 6) in anhydrous THF (4 ml) was added DMAP (21 mg, 0.17 mmol), followed by DCC (252 mg, 1.2 mmol) at 0° C. The reaction mixture was allowed to slowly warm to room temperature and was stirred for 18 h. The mixture was then concentrated, and the residue was treated with 25% DCM in hexanes. The solids were filtered off and the filtrate was concentrated under reduced pressure. The crude product was purified by silica gel column chromatography using a gradient of 10 to 40% ethyl acetate in hexanes to afford tert-butyl 3-({(Z)-[1-{2-[(tert-butoxycarbonyl)amino]-1,3-thiazol-4-yl}-2-({(4S)-2-[(4S)-2-(tert-butoxycarbonyl)-5-oxo-4-(5-oxo-2,2-diphenyl-5,7-dihydro-2H,6H-[1,3]dioxolo[4,5-f]isoindol-6-yl)oxolan-2-yl]-3-oxo-1,2-oxazolidin-4-yl}amino)-2-oxoethylidene]amino}oxy)-8-oxabicyclo[3.2.1]octane-3-carboxylate 90 (460 mg, 48%) as a white foam.

$^1$H-NMR (400 MHz; $CDCl_3$) δ 8.27-8.25 (m, 1H), 8.06 (d, J=6.3 Hz, 1H), 7.64-7.51 (m, 4H), 7.45-7.37 (m, 6H), 7.35 (s, 1H), 7.32 (s, 1H), 6.93 (s, 1H), 5.51-5.43 (m, 1H), 5.27-5.15 (m, J=6.3 Hz, 1H), 4.97 (t, J=8.3 Hz, 1H), 4.52-4.42 (m, 2H), 4.36-4.22 (m, 3H), 3.44-3.34 (m, 1H), 2.58 (dd, J=14.0, 10.4 Hz, 1H), 2.43-2.25 (m, 4H), 2.03-1.88 (m, 4H), 1.69 (s, 2H), 1.58-1.55 (m, 18H), 1.44 (s, 9H).

Step 2: 3-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid (Compound 30)

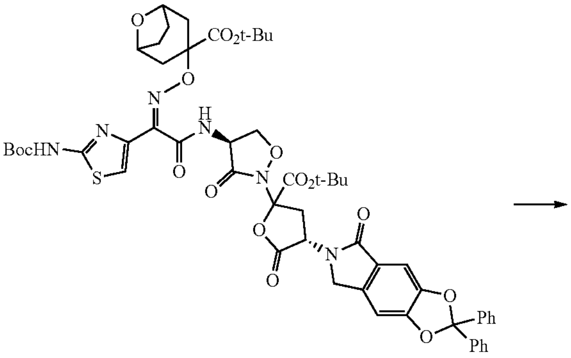

90

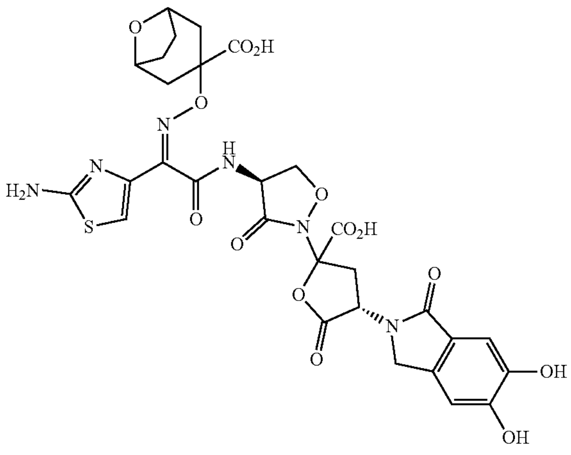

Compound 30

To a solution of tert-butyl 3-({(Z)-[1-{2-[(tert-butoxycarbonyl)amino]-1,3-thiazol-4-yl}-2-({(4S)-2-[(4S)-2-(tert-butoxycarbonyl)-5-oxo-4-(5-oxo-2,2-diphenyl-5,7-dihydro- 2H,6H-[1,3]dioxolo[4,5-f]isoindol-6-yl)oxolan-2-yl]-3-oxo-1,2-oxazolidin-4-yl}amino)-2-oxoethylidene]amino}oxy)-8-oxabicyclo[3.2.1]octane-3-carboxylate 90 (338 mg, 0.31 mmol) in anhydrous DCM (25 mL) was dropwise added a boron trichloride solution (1.0 M in DCM, 2.48 mL, 2.48 mmol) at −50° C. The reaction mixture was stirred at −30° C.–−25° C. for 2.5 h, then cooled to −50° C. and a buffer solution (prepared by dissolving $NaHCO_3$ (514 mg) and $Na_2HPO_4$ (163 mg) in 28 mL of water) was added. The reaction flask was transferred to an ice-water bath and the heterogenous mixture was stirred at 0-5° C. for 20 min, and then at room temperature until the aqueous phase thawed completely and two layers separated. The organic layer was carefully removed, and the aqueous solution was immediately subjected to purification by C18 reverse phase chromatography using a Biotage system and a mixture of 0.1% formic acid in acetonitrile and 0.1% formic acid in water as eluents. The pure fractions were combined and lyophilized to afford 3-({(Z)-[1-(2-amino-1,3-thiazol-4-yl)-2-({(4S)-2-[(4S)-2-carboxy-4-(5,6-dihydroxy-1-oxo-1,3-dihydro-2H-isoindol-2-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid Compound 30 (95 mg, 43%) as a green tinged solid.

1H-NMR (599 MHz; a mixture of $D_2O$ and $CD_3CN$) δ 7.12 (s, 1H), 7.02 (s, 1H), 6.97 (s, 1H), 5.44-5.41 (m, 1H), 5.15-5.08 (m, 1H), 4.75-4.68 (m, 1H), 4.43-−4.34 (m, 5H), 4.34-4.23 (m, 3H), 3.45-3.28 (m, 1H), 2.89-2.59 (m, 1H), 2.26-2.20 (m, 2H), 2.07-1.98 (m, 2H), 1.79-1.72 (m, 4H). Exchangeable protons were not observed in $D_2O$.

MS (ESI) m/z: $[M+1]^+$ 717.0

Example 18

(4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid (Compound 37, Table 1)

Compound 37

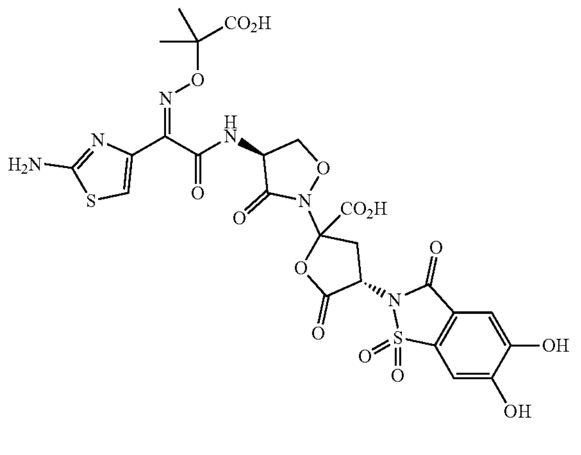

Step 1: 4-tert-butyl 1-(prop-2-en-1-yl) N-{[(9H-fluoren-9-yl)methoxy]carbonyl}-L-aspartate (92)

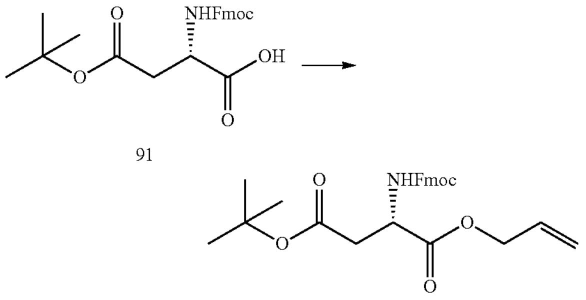

91

92

To a solution of allyl bromide (16 mL, 184.9 mmol) and DIPEA (12.7 mL, 72.9 mmol) in anhydrous acetonitrile (75 ml) was added (2S)-4-tert-butoxy-2-({[(9H-fluoren-9-yl)methoxy]carbonyl}amino)-4-oxobutanoic acid 91 (15.0 g, 36.5 mmol). The reaction mixture was heated to 40° C. and stirred at 40° C. for 4 h, then cooled and concentrated in vacuo. The residue was taken up in EtOAc and the organic phase was washed consecutively with 0.5 M aqueous hydrochloric acid, saturated aqueous sodium bicarbonate solution and brine. The organic layer was then dried over sodium sulfate, filtered and concentrated under reduced pressure. The crude product was purified by silica gel column chromatography using a gradient of 5% to 20% ethyl acetate in hexanes to afford 4-tert-butyl 1-(prop-2-en-1-yl) N-{[(9H-fluoren-9-yl)methoxy]carbonyl}-L-aspartate 92 (15.19 g, 92%) as a white solid.

$^1H$ NMR (400 MHz, $CDCl_3$) δ 7.80-7.78 (m, 2H), 7.64-7.61 (m, 2H), 7.45-7.40 (m, 2H), 7.33 (td, J=7.5, 1.2 Hz, 2H), 5.94-5.92 (m, 1H), 5.85-5.82 (m, 1H), 5.38-5.34 (m, 1H), 5.29-5.26 (m, 1H), 4.71-4.64 (m, 3H), 4.46-4.43 (m, 1H), 4.39-4.34 (m, 1H), 4.29-4.26 (m, 1H), 2.98-2.97 (m, 1H), 2.83-2.82 (m, 1H), 1.48-1.46 (m, 9H).

Step 2: 4-tert-butyl 1-(prop-2-en-1-yl) L-aspartate (93)

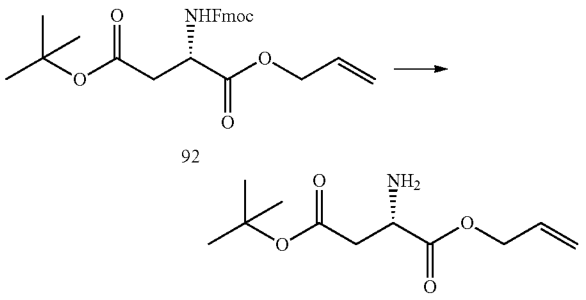

92

93

To a solution of 4-tert-butyl 1-(prop-2-en-1-yl) N-{[(9H-fluoren-9-yl)methoxy]carbonyl}-L-aspartate 92 (15.19 g, 33.64 mmol) in anhydrous DCM (80 ml) was added diethylamine (80 mL). The reaction mixture was stirred at room temperature for 3 h, and then concentrated under reduced pressure. The residue was purified by silica gel column chromatography using a gradient of 5% to 100% ethyl acetate in hexanes to afford 4-tert-butyl 1-(prop-2-en-1-yl) L-aspartate 93 (7.84 g, quantitative) as a light-yellow oil.

$^1$H NMR (400 MHz, $CDCl_3$) δ 5.95-5.86 (m, 1H), 5.35-5.29 (m, 1H), 5.26-5.23 (m, 1H), 4.67-4.58 (m, 2H), 3.77 (dd, J=6.8, 4.8 Hz, 1H), 2.69 (qd, J=14.3, 5.8 Hz, 2H), 1.71-1.67 (m, 3H).

Step 3: methyl 6-bromo-2,2-diphenyl-2H-1,3-benzodioxole-5-carboxylate (95)

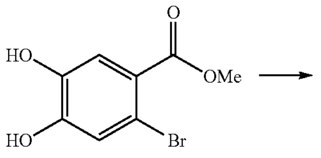

94

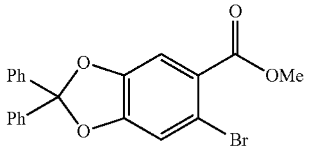

95

A mixture of methyl 2-bromo-4,5-dihydroxybenzoate 94 (9.53 g, 38.58 mmol) and 1,1'-(dichloromethylene)dibenzene (7.41 mL, 38.59 mmol) was heated to 170° C. and stirred at 170° C. for 50 min. The reaction mixture was then cooled to room temperature and concentrated under reduced pressure. The residue was purified by silica gel column chromatography using a gradient of 0% to 10% ethyl acetate in hexanes to afford methyl 6-bromo-2,2-diphenyl-2H-1,3-benzodioxole-5-carboxylate 95 (15.01 g, 95%) as a white solid.

$^1$H NMR (400 MHz, $CDCl_3$) δ 7.57-7.53 (m, 4H), 7.43-7.39 (m, 7H), 7.18 (s, 1H), 3.90 (s, 3H).

Step 4: methyl 6-(benzylsulfanyl)-2,2-diphenyl-2H-1,3-benzodioxole-5-carboxylate (96)

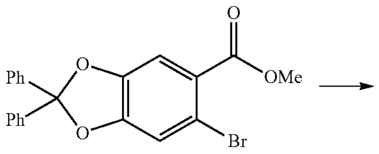

95

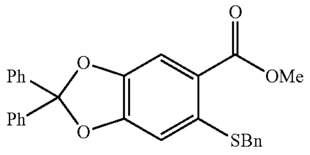

96

To a suspension of NaH (60% in mineral oil, 1.67 g, 41.75 mmol) in anhydrous THF (120 ml) was added dropwise benzenemethanethiol (4.30 mL, 36.63 mmol) at 0° C. and the resulting solution was stirred at 0° C. for 10 min. Methyl 6-bromo-2,2-diphenyl-2H-1,3-benzodioxole-5-carboxylate 95 (14.30 g, 34.77 mmol) was then added and the reaction mixture was heated to 45° C. and stirred at 45° C. for 13 h. The reaction mixture was cooled to room temperature, diluted with a mixture of ethyl acetate and hexanes (7:3) and water was then added. The organic phase was separated, and the aqueous layer was further extracted with a mixture of ethyl acetate and hexanes (7:3). The combined organic extracts were washed with brine, dried over sodium sulfate, filtered and concentrated under reduced pressure. The residue was purified by silica gel column chromatography using a gradient of 0% to 8% ethyl acetate in hexanes to afford methyl 6-(benzylsulfanyl)-2,2-diphenyl-2H-1,3-benzodioxole-5-carboxylate 96 (7.88 g, 50%) as a white foam.

$^1$H NMR (400 MHz, $CDCl_3$) δ 7.57-7.53 (m, 5H), 7.42-7.39 (m, 8H), 7.35-7.25 (m, 3H), 6.92 (s, 1H), 4.12 (d, J=2.4 Hz, 2H), 3.87 (s, 3H).

Step 5: methyl 6-(chlorosulfonyl)-2,2-diphenyl-2H-1,3-benzodioxole-5-carboxylate (97)

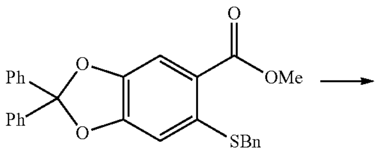

96

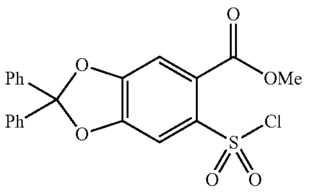

97

To a stirred suspension of methyl 6-(benzylsulfanyl)-2,2-diphenyl-2H-1,3-benzodioxole-5-carboxylate 96 (7.88 g, 17.34 mmol) in a mixture of acetonitrile (170 ml), acetic acid (6.3 mL) and water (4.25 ml) was added 1,3-dichloro-5,5-dimethylimidazolidine-2,4-dione (6.84 g, 34.72 mmol) in small portions at 0° C. The reaction mixture was stirred at 0 to 5° C. for 2 h, and then concentrated in vacuo. The residue was taken up in DCM (110 mL), the obtained solution was cooled to 0° C. and saturated aqueous sodium bicarbonate solution (110 mL) was added slowly while the temperature was maintained below 10° C. The resulting mixture was stirred between 0 and 5° C. for 15 min, then the aqueous phase was separated, and the organic layer was washed with pre-cooled brine (<10° C.). The organic layer was dried over sodium sulfate, filtered and concentrated under reduced pressure. The residue was purified by silica gel column chromatography using a gradient of 0% to 10% ethyl acetate in hexanes to afford methyl 6-(chlorosulfonyl)-2,2-diphenyl-2H-1,3-benzodioxole-5-carboxylate 97 (7.40 g, 99%) as a white foam.

$^1$H NMR (400 MHz, $CDCl_3$) δ 7.64 (s, 1H), 7.56-7.53 (m, 4H), 7.46-7.43 (m, 6H), 7.20 (s, 1H), 3.97 (s, 3H).

Step 6: 4-tert-butyl 1-(prop-2-en-1-yl) N-[6-(methoxycarbonyl)-2,2-diphenyl-2H-1,3-benzodioxole-5-sulfonyl]-L-aspartate (98)

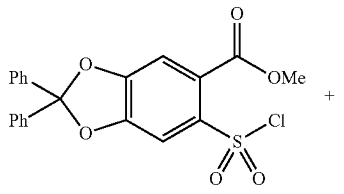

97

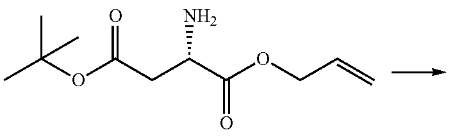

93

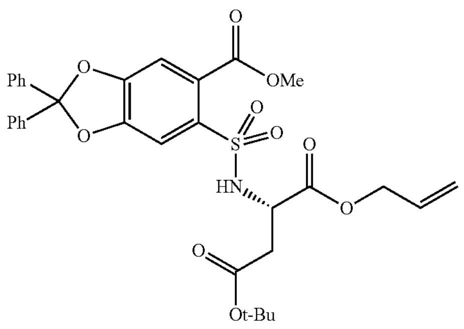

98

A solution of methyl 6-(chlorosulfonyl)-2,2-diphenyl-2H-1,3-benzodioxole-5-carboxylate 97 (7.40 g, 17.17 mmol) in anhydrous DCM (150 ml) was cooled to 0° C. Triethylamine (2.90 ml, 20.81 mmol), a solution of 4-tert-butyl 1-(prop-2-en-1-yl) L-aspartate 93 (4.33 g, 18.89 mmol) in DCM (25 mL) and DMAP (210 mg, 1.72 mmol) were then added sequentially at 0 T, and the reaction mixture was stirred at 0° C. for 10 min. Subsequently, the reaction mixture was stirred at room temperature for 4 h and concentrated under reduced pressure. The residue was dissolved in ethyl acetate, and the organic phase was washed with water and brine, dried over sodium sulfate, filtered and concentrated in vacuo. The residue was purified by silica gel column chromatography using a gradient of 0% to 20% ethyl acetate in hexanes to afford 4-tert-butyl 1-(prop-2-en-1-yl) N-[6-(methoxycarbonyl)-2,2-diphenyl-2H-1,3-benzodioxole-5-sulfonyl]-L-aspartate 98 (8.43 g, 79%) as a white foam.

$^1$H NMR (400 MHz, $CDCl_3$) δ 7.60 (s, 1H), 7.58-7.53 (m, 4H), 7.44-7.41 (m, 7H), 7.27 (d, J 8.6 Hz, 1H), 5.64-5.54 (m, 1H), 5.10-5.00 (m, 2H), 4.39-4.31 (m, 3H), 3.96 (s, 3H), 2.96 (dd, J=16.9, 4.7 Hz, 1H), 2.82 (dd, J=16.9, 5.0 Hz, 1H), 1.44 (s, 9H).

Step 7: 4-tert-butyl 1-(prop-2-en-1-yl) (2S)-2-(1,1,3-trioxo-6,6-diphenyl-1,3-dihydro-2H,6H-1λ$^6$-[1,3]dioxolo[4,5-f][1,2]benzothiazol-2-yl)butanedioate (99)

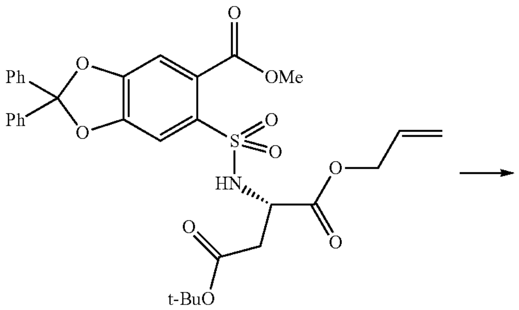

98

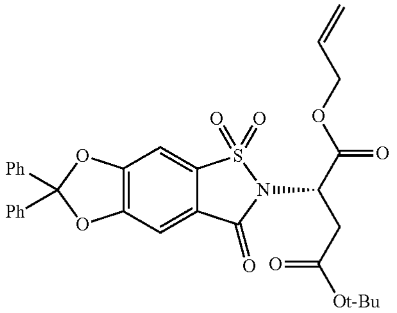

99

To a solution of 4-tert-butyl 1-(prop-2-en-1-yl) N-[6-(methoxycarbonyl)-2,2-diphenyl-2H-1,3-benzodioxole-5-sulfonyl]-L-aspartate 98 (9.25 g, 14.83 mmol) in anhydrous toluene (400 mL) were added DMAP (544 mg, 4.45 mmol) and triethylamine (5.80 mL, 41.61 mmol) at room temperature. The resulting mixture was stirred at reflux temperature for 120 h, then cooled and concentrated in vacuo. The residue was taken up in ethyl acetate, and the organic phase was washed with water and brine, dried over sodium sulfate, filtered and concentrated under reduced pressure. The residue was purified by silica gel column chromatography using a gradient of 0% to 15% ethyl acetate in hexanes to afford 4-tert-butyl 1-(prop-2-en-1-yl) (2S)-2-(1,1,3-trioxo-6,6-diphenyl-1,3-dihydro-2H,6H-1λ$^6$-[1,3]dioxolo[4,5-f][1,2]benzothiazol-2-yl)butanedioate 99 (6.26 g, 71%) as an off-white foam.

$^1$H NMR (400 MHz, $CDCl_3$) δ 7.53-7.51 (m, 4H), 7.43-7.41 (m, 7H), 7.30 (d, J=0.4 Hz, 1H), 5.88-5.78 (m, 1H), 5.30-5.24 (m, 2H), 5.20-5.16 (m, 1H), 4.69-4.59 (m, 2H), 3.35 (dd, J=16.8, 7.6 Hz, 1H), 2.98 (dd, J=16.8, 7.1 Hz, 1H), 1.45 (s, 9H).

Step 8: (3S)-4-oxo-4-[(prop-2-en-1-yl)oxy]-3-(1,1,3-trioxo-6,6-diphenyl-1,3-dihydro-2H,6H-1$\lambda^6$-[1,3]dioxolo[4,5-f][1,2]benzothiazol-2-yl)butanoic acid (100)

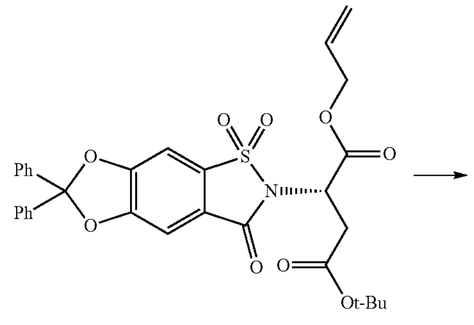

99

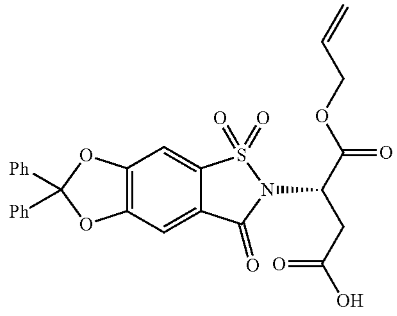

100

To solution of 4-tert-butyl 1-(prop-2-en-1-yl) (2S)-2-(1,1,3-trioxo-6,6-diphenyl-1,3-dihydro-2H,6H-1$\lambda^6$-[1,3]dioxolo[4,5-f][1,2]benzothiazol-2-yl)butanedioate 99 (1.08 g, 1.83 mmol) in anhydrous DCM (42 ml) was added dropwise a boron trichloride solution (1.0 M in DCM, 3.29 mL, 3.29 mmol) at −78° C. The reaction mixture was stirred at −78° C. for 1 h and then at −78° C. to −45° C. for 30 min. Subsequently, the reaction mixture was diluted with ethyl acetate and water was added at −50° C. The heterogeneous mixture was stirred at room temperature until the layers separated, and the organic phase was dried over sodium sulfate, filtered and concentrated under reduced pressure. The residue was initially subjected to purification by C18 reverse phase chromatography using mixtures of 0.1% formic acid in acetonitrile and 0.1% formic acid in water as eluents, and the product containing fractions were combined and concentrated under reduced pressure. The obtained product was further purified by silica gel column chromatography using a gradient of 0% to 4% methanol in DCM to afford (3S)-4-oxo-4-[(prop-2-en-1-yl)oxy]-3-(1,1,3-trioxo-6,6-diphenyl-1,3-dihydro-2H,6H-1$\lambda^6$-[1,3]dioxolo[4,5-f][1,2]benzothiazol-2-yl)butanoic acid 100 (395 mg, 40%) as a white foam.

$^1$H NMR (400 MHz, $CDCl_3$) δ 7.57-7.52 (m, 4H), 7.48-7.41 (m, 7H), 7.33 (s, 1H), 5.90-5.80 (m, 1H), 5.32-5.27 (m, 2H), 5.23-5.20 (m, 1H), 4.72-4.63 (m, 2H), 3.53 (dd, J=17.1, 7.8 Hz, 1H), 3.11 (dd, J=17.1, 6.7 Hz, 1H).

Step 9: prop-2-en-1-yl (2S)-5-cyano-4-oxo-5-(1$\lambda^4$-thiolan-1-ylidene)-2-(1,1,3-trioxo-6,6-diphenyl-1,3-dihydro-2H,6H-1$\lambda^6$-[1,3]dioxolo[4,5-f][1,2]benzothiazol-2-yl)pentanoate (101)

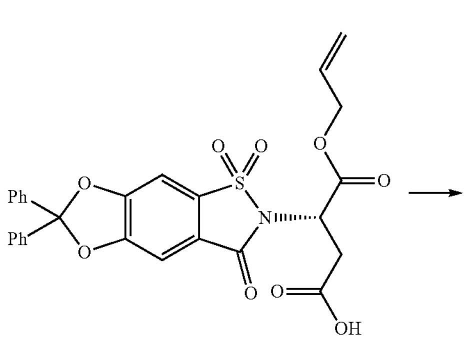

100

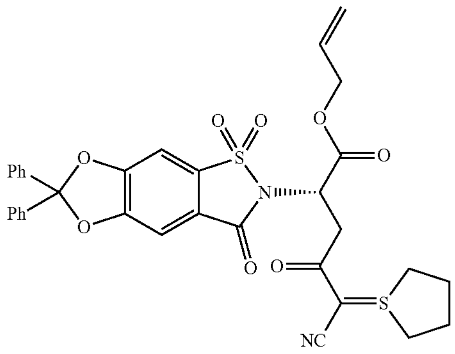

101

To a solution of (35)-4-oxo-4-[(prop-2-en-1-yl)oxy]-3-(1,1,3-trioxo-6,6-diphenyl-1,3-dihydro-2H,6H-1$\lambda^6$-[1,3]dioxolo[4,5-f][1,2]benzothiazol-2-yl)butanoic acid 100 (783 mg, 1.46 mmol) in anhydrous DCM (14 mL) was added HATU (612 mg, 1.61 mmol) at room temperature. The resulting mixture was cooled to 0° C. and DIPEA (0.76 ml, 4.36 mmol) followed by 1-(cyanomethyl)thiolan-1-ium bromide (396 mg, 1.90 mmol) were added. The reaction mixture was stirred at 0° C. for 5 min, and then at room temperature for 1 h. The mixture was cooled to 0° C. and an aqueous saturated ammonium chloride solution was added. Subsequently, the mixture was diluted with water and extracted with ethyl acetate. The combined organic extracts were washed with brine, dried over sodium sulfate, filtered and concentrated under reduced pressure. The residue was purified by silica gel column chromatography using a gradient of 50% to 100% ethyl acetate in hexanes to afford prop-2-en-1-yl (2S)-5-cyano-4-oxo-5-(1$\lambda^4$-thiolan-1-ylidene)-2-(1,1,3-trioxo-6,6-diphenyl-1,3-dihydro-2H,6H-1$\lambda^6$-[1,3]dioxolo[4,5-f][1,2]benzothiazol-2-yl)pentanoate 101 (970 mg, crude) as a white foam.

$^1$H NMR (400 MHz, $CDCl_3$) δ 7.57-7.52 (m, 4H), 7.47-7.42 (m, 7H), 7.30 (s, 1H), 5.91-5.81 (m, 1H), 5.36 (dd, 1=8.1, 5.9 Hz, 1H), 5.32-5.27 (m, 1H), 5.21-5.18 (m, 1H), 4.71-4.61 (m, 2H), 3.55-3.30 (m, 6H), 2.65-2.56 (m, 2H), 2.10-2.00 (m, 2H).

Step 10: (4S)-2,5-dioxo-5-[(prop-2-en-1-yl)oxy]-4-(1,1,3-trioxo-6,6-diphenyl-1,3-dihydro-2H,6H-1λ$^6$-[1,3]dioxolo[4,5-f][1,2]benzothiazol-2-yl)pentanoic acid (102)

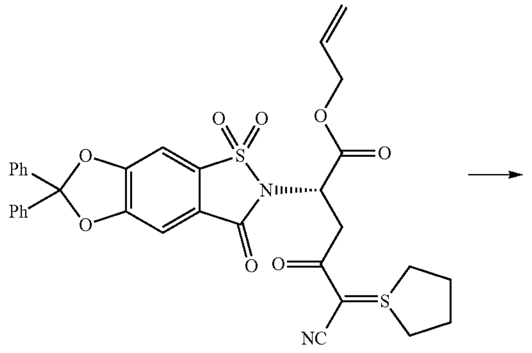

101

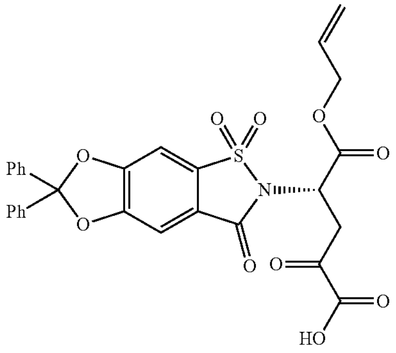

102

To a solution of prop-2-en-1-yl (2S)-5-cyano-4-oxo-5-(1λ$^4$-thiolan-1-ylidene)-2-(1,1,3-trioxo-6,6-diphenyl-1,3-dihydro-2H,6H-1λ$^6$-[1,3]dioxolo[4,5-f][1,2]benzothiazol-2-yl)pentanoate 101 (970 mg, ~1.46 mmol) in THF (11 mL) was added water (11 ml), followed by OXONE (898 mg, 2.92 mmol). The reaction mixture was stirred at room temperature for 1 h, an additional OXONE (898 mg, 2.92 mmol) was added in two portions over 1 h and stirring at room temperature was continued for 2 h. The majority of THF was removed under reduced pressure and the aqueous solution was extracted with ethyl acetate. The combined organic extracts were dried over sodium sulfate, filtered and concentrated to afford crude (4S)-2,5-dioxo-5-[(prop-2-en-1-yl)oxy]-4-(1,1,3-trioxo-6,6-diphenyl-1,3-dihydro-2H,6H-1λ$^6$-[1,3]dioxolo[4,5-f][1,2]benzothiazol-2-yl)pentanoic acid 102 (900 mg, crude) as a white foam which was directly used in the next step.

$^1$H NMR (400 MHz, $CDCl_3$) δ 7.56-7.53 (m, 4H), 7.47-7.43 (m, 7H), 7.33 (s, 1H), 5.87-5.79 (m, 1H), 5.43-5.39 (m, 1H), 5.32-5.22 (m, 2H), 4.72-4.62 (m, 2H), 4.14-4.08 (m, 1H), 3.59-3.52 (m, 1H).

Step 11: 1-tert-butyl 5-(prop-2-en-1-yl) (4S)-2-oxo-4-(1,1,3-trioxo-6,6-diphenyl-1,3-dihydro-2H,6H-1λ$^6$-[1,3]dioxolo[4,5-f][1,2]benzothiazol-2-yl)pentanedioate (103)

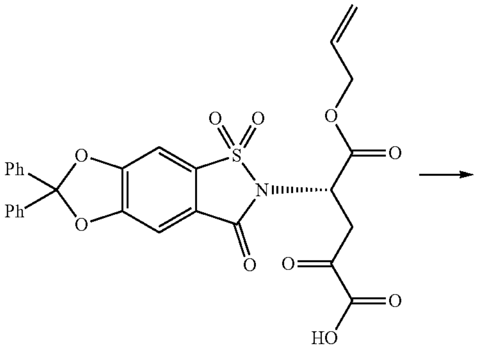

102

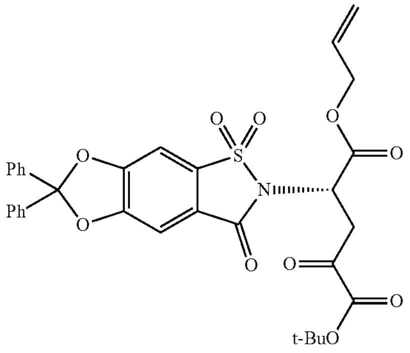

103

To a solution of (4S)-2,5-dioxo-5-[(prop-2-en-1-yl)oxy]-4-(1,1,3-trioxo-6,6-diphenyl-1,3-dihydro-2H,6H-1λ$^6$-[1,3]dioxolo[4,5-f][1,2]benzothiazol-2-yl)pentanoic acid 102 (900 mg, crude) in anhydrous THF (10 ml) was added slowly tert-butyl N,N'-diisopropylcarbamimidate (0.38 ml, 1.52 mmol) at 0° C. The reaction mixture was stirred at 0° C. for 5 min, the cooling bath was removed and stirring was continued at room temperature for 1 h. Additional tert-butyl N,N'-diisopropylcarbamimidate (0.42 mL, 1.68 mmol) was added in small portions over 2 h, and stirring at room temperature was continued for 1 h. The majority of THF was removed under reduced pressure and the mixture was treated with 30% DCM in hexanes. The precipitated solids were filtered off and the filtrate was concentrated in vacuo. The residue was purified by silica gel column chromatography using a gradient of 0% to 20% ethyl acetate in hexanes to afford 1-tert-butyl 5-(prop-2-en-1-yl) (4S)-2-oxo-4-(1,1,3-trioxo-6,6-diphenyl-1,3-dihydro-2H,6H-1λ$^6$-[1,3]dioxolo[4,5-f][1,2]benzothiazol-2-yl)pentanedioate 103 (341 mg, 38% over 3 steps) as a white foam.

$^1$H NMR (400 MHz, $CDCl_3$) δ 7.53-7.50 (m, 4H), 7.44-7.40 (m, 7H), 7.29 (s, 1H), 5.86-5.77 (m, 1H), 5.41-5.37 (m, 1H), 5.29-5.17 (m, 2H), 4.68-4.59 (m, 2H), 3.93 (dd, J=18.4, 7.6 Hz, 1H), 3.46 (dd, J=18.4, 6.8 Hz, 1H), 1.54 (s, 9H).

Step 12: (2S)-5-tert-butoxy-4,5-dioxo-2-(1,1,3-trioxo-6,6-diphenyl-1,3-dihydro-2H,6H-1λ$^6$-[1,3]dioxolo[4,5-f][1,2]benzothiazol-2-yl)pentanoic acid (104)

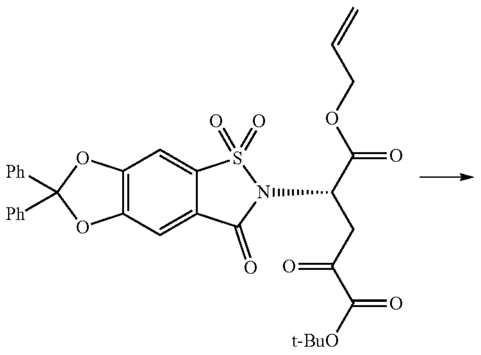

103

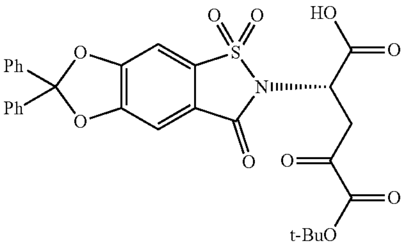

104

To a solution of 1-tert-butyl 5-(prop-2-en-1-yl) (4S)-2-oxo-4-(1,1,3-trioxo-6,6-diphenyl-1,3-dihydro-2H,6H-1λ$^6$-[1,3]dioxolo[4,5-f][1,2]benzothiazol-2-yl)pentanedioate 103 (239 mg, 0.39 mmol) in anhydrous THF (7 mL) was added morpholine (0.10 mL, 1.14 mmol) at −5° C. The mixture was purged with nitrogen for 10 min, $Pd(PPh_3)_4$ (23 mg, 0.02 mmol) was added and the reaction mixture was stirred at −5° C.-0° C. under nitrogen atmosphere for 2 h. The reaction mixture was diluted with diethyl ether and the organic phase was washed with 1 M HCl and brine, then dried over sodium sulfate, filtered and concentrated to afford (2S)-5-tert-butoxy-4,5-dioxo-2-(1,1,3-trioxo-6,6-diphenyl-1,3-dihydro-2H,6H-1λ$^6$-[1,3]dioxolo[4,5-f][1,2]benzothiazol-2-yl)pentanoic acid 104 (231 mg, crude) as a yellow foam which was used directly in the next step.

$^1$H NMR (400 MHz, DMSO-$d_6$) δ 8.11 (s, 1H), 7.74 (s, 1H), 7.54-7.45 (m, 10H), 5.12 (t, J=7.3 Hz, 1H), 3.75-3.68 (m, 1H), 3.44-3.38 (m, 1H), 1.45 (s, 9H).

Step 13: tert-butyl (4S)-2-[(4S)-4-{[(2Z)-2-(2-[(tert-butoxycarbonyl)amino]-1,3-thiazol-4-yl)-2-{[(1-tert-butoxy-2-methyl-1-oxopropan-2-yl)oxy]imino}acetyl]amino}-3-oxo-1,2-oxazolidin-2-yl]-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate (105)

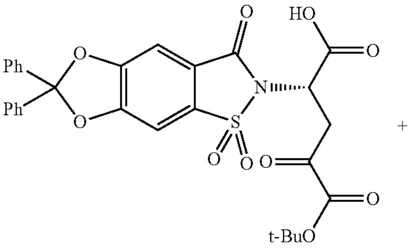

104

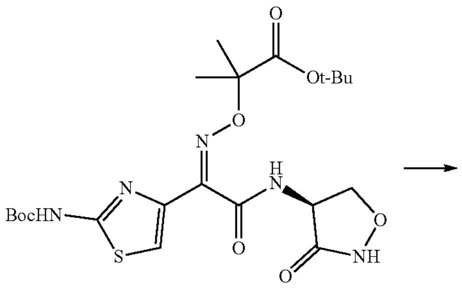

72

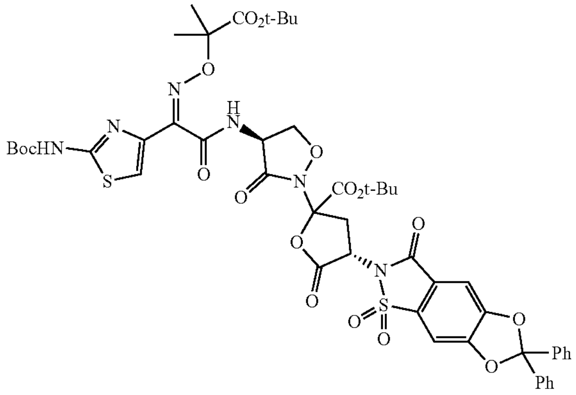

105

To a mixture of (2S)-5-tert-butoxy-4,5-dioxo-2-(1,1,3-trioxo-6,6-diphenyl-1,3-dihydro-2H,6H-1λ$^6$-[1,3]dioxolo[4,5-f][1,2]benzothiazol-2-yl)pentanoic acid 104 (231 mg, crude) and tert-butyl 2-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2-methylpropanoate 72 (189 mg, 0.37 mmol) in anhydrous THF (7 mL) was added DMAP (9 mg, 0.074 mmol), followed by DCC (99 mg, 0.48 mmol) at 0° C. The reaction mixture was allowed to slowly warm to room temperature and was stirred for 18 h. The mixture was then concentrated under reduced pressure and the residue was treated with 25% DCM in hexanes. The precipitated solids were removed by filtration and the filtrate was concentrated in vacuo. The residue was purified by silica gel column chromatography using a gradient of 10% to 30% ethyl acetate in hexanes to afford tert-butyl (4S)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate 105 (209 mg, 53%) as a light-yellow foam.

$^1$H NMR (400 MHz, $CDCl_3$) δ 8.23-8.04 (m, 2H), 7.56-7.51 (m, 4H), 7.47-7.43 (m, 7H), 7.35 (m, 2H), 5.34-4.82 (m, 3H), 4.38-4.21 (m, 1H), 3.78-3.42 (m, 1H), 3.00-2.88 (m, 1H), 1.63-1.60 (m, 6H), 1.58-1.54 (m, 9H), 1.55 (s, 9H), 1.47-1.44 (m, 9H).

Step 14: (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid (Compound 37)

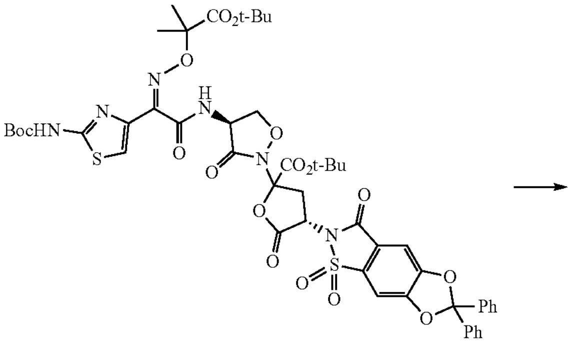

105

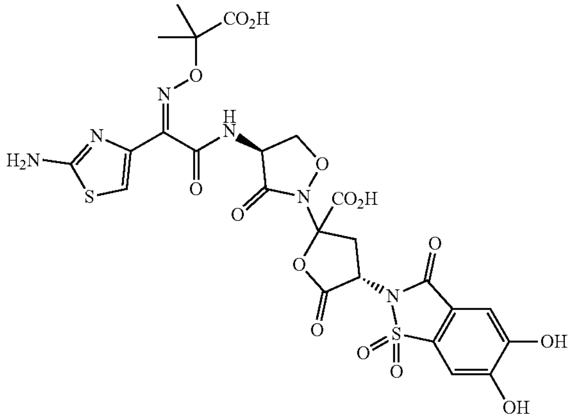

Compound 37

To a solution of tert-butyl (4S)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate 105 (209 mg, 0.19 mmol) in anhydrous DCM (7 mL) was added dropwise a boron trichloride solution (1.0 M in DCM, 1.56 mL, 1.56 mmol) at −50° C. The reaction mixture was stirred at −50° C.-−25° C. for 2.5 h and then a solution of $NaHCO_3$ (320 mg) and $Na_2HPO_4$ (100 mg) in water (17.3 ml) was added at −50° C. The mixture was then stirred at 0° C.-5° C. (ice-water bath) for 10 min and subsequently at room temperature until the aqueous phase thawed. The mixture was filtered through a 1 μm syringe filter and the organic layer was carefully separated. The aqueous solution was then subjected to purification by C18 reverse phase column chromatography using a Biotage system and mixtures of 0.1% formic acid in acetonitrile and 0.1% formic acid in water as eluents. The product containing fractions were combined and lyophilized to afford (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid Compound 37 (45 mg, 33%) as an off-white solid.

$^1$H NMR (400 MHz, a mixture of $D_2O$ and $CD_3CN$) δ 7.43 (s, 1H), 7.36-7.34 (m, 1H), 7.08-7.06 (m, 1H), 5.27-5.07 (m, 2H), 4.74-4.67 (m, 1H), 4.32-4.22 (m, 1H), 3.67-3.35 (m, 1H), 2.98-2.78 (m, 1H), 1.48 (s, 6H). Exchangeable protons were not observed in $D_2O$.

MS (ESI) m/z: $[M+1]^+$ 699.0

Example 19

(4S)-2-[(4S)-4-{[(2Z)-2-(2-amino-5-chloro-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 24, Table 1)

Compound 24

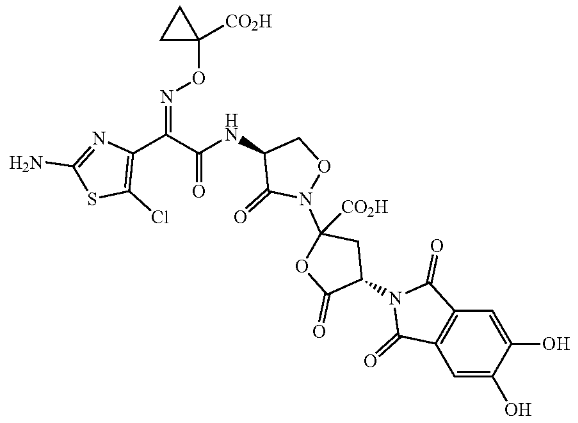

Step 1: {2-[(tert-butoxycarbonyl)amino]-5-chloro-1,3-thiazol-4-yl}(oxo)acetic acid (107)

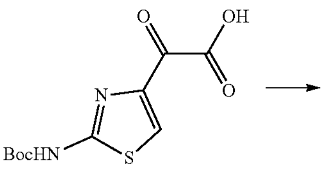

106

-continued

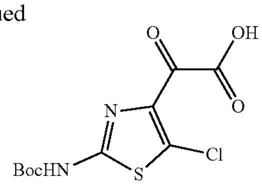

107

To a solution of {2-[(tert-butoxycarbonyl)amino]-1,3-thiazol-4-yl}(oxo)acetic acid 106 (5.0 g, 18.4 mmol) in anhydrous 1,4-dioxane (35 mL) was added NCS (2.7 g, 20.2 mmol) at room temperature. The reaction mixture was heated to and stirred at 40° C. for 6 hours, then cooled and concentrated under reduced pressure. The crude mixture was triturated using a mixture of diethyl ether (40 mL) and hexanes (20 ml). The resulting precipitate was removed by filtration and the filtrate was concentrated under reduced pressure. The residue was further dried under high vacuum and then triturated with hexanes. The precipitated off-white powder was collected by filtration to afford {2-[(tert-butoxycarbonyl)amino]-5-chloro-1,3-thiazol-4-yl}(oxo)acetic acid 107 (5.7 g, quantitative yield).

$^1$H-NMR (400 MHz; DMSO-$d_6$) δ 12.21 (s, 1H), 1.46 (s, 9H).

Step 2: (2Z)-{2-[(tert-butoxycarbonyl)amino]-5-chloro-1,3-thiazol-4-yl}({[1-(tert-butoxycarbonyl)cyclopropyl]oxy}imino)acetic acid (108)

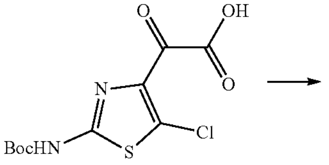

107

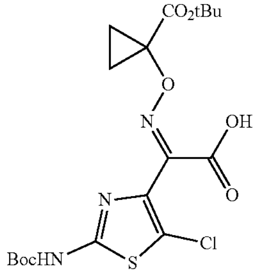

108

To a solution of {2-[(tert-butoxycarbonyl)amino]-5-chloro-1,3-thiazol-4-yl}(oxo)acetic acid 107 (5.6 g, 18.4 mmol) in methanol (150 ml) was added tert-butyl 1-(aminooxy)cyclopropane-1-carboxylate 2 (3.5 g, 20.2 mmol). The reaction mixture was stirred at room temperature for 3 h and then was concentrated under reduced pressure. The traces of methanol were co-evaporated with hexane (3×50 ml), and the residue was further dried under high vacuum. The crude product was treated with 5% diethyl ether in hexanes and the resulting suspension was stirred overnight. The precipitated solid was collected by filtration to afford (2Z)-{2-[(tert-butoxycarbonyl)amino]-5-chloro-1,3-thiazol-4-yl}({[1-(tert-butoxycarbonyl)cyclopropyl]oxy}imino)acetic acid 108 (8.3 g, 98%) as an off-white powder.

$^1$H-NMR (400 MHz; $CDCl_3$) δ 2.81 (s, 1H), 1.64-1.61 (m, 2H), 1.60-1.51 (m, 11H), 1.48 (s, 9H).

Step 3: tert-butyl 1-{[(Z)-(1-{2-[(tert-butoxycarbonyl)amino]-5-chloro-1,3-thiazol-4-yl}-2-oxo-2-{[(4S)-3-oxo-1,2-oxazolidin-4-yl]amino}ethylidene)amino]oxy}cyclopropane-1-carboxylate (109)

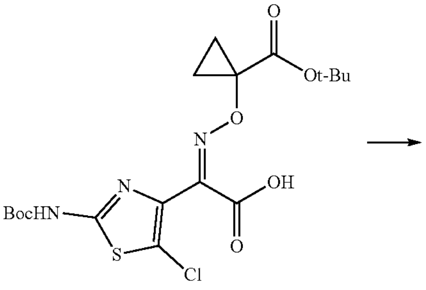

108

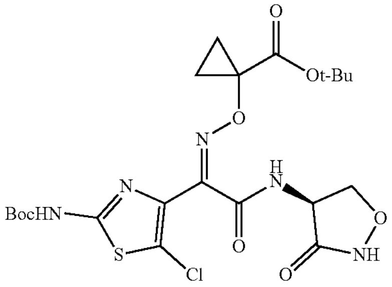

109

To a solution of (2Z)-{2-[(tert-butoxycarbonyl)amino]-5-chloro-1,3-thiazol-4-yl}({[1-(tert-butoxycarbonyl)cyclopropyl]oxy}imino)acetic acid 108 (8.3 g, 18.0 mmol) in anhydrous DMF (100 mL) was added DIPEA (4.7 mL, 26.9 mmol) at room temperature. The resulting mixture was stirred at room temperature for 5 min, then HATU was added and stirring was continued at room temperature for 2 h. The reaction mixture was then diluted with anhydrous DMF (100 ml), and DIPEA (4.7 mL, 26.9 mmol) followed by L-cycloserine (2.2 g, 21.6 mmol) were added. The reaction mixture was stirred at room temperature overnight and then concentrated to dryness under reduced pressure. The residue was purified by silica gel chromatography using a gradient of 0 to 4% methanol in DCM to afford tert-butyl 1-{[(Z)-(1-{2-[(tert-butoxycarbonyl)amino]-5-chloro-1,3-thiazol-4-yl}-2-oxo-2-{[(4S)-3-oxo-1,2-oxazolidin-4-yl]amino}ethylidene)amino]oxy}cyclopropane-1-carboxylate 109 (7.5 g, 76%) as an amorphous white solid.

$^1$H-NMR (400 MHz; DMSO-$d_6$) δ 12.04 (s, 1H), 11.58 (s, 1H), 9.02 (m, 1H), 3.95 (t, J=8.8 Hz, 1H), 1.45 (s, 9H), 1.39 (s, 9H), 1.34-1.26 (m, 4H).

Step 4: tert-butyl (4S)-2-[(4S)-4-{[(2Z)-2-{2-[(tert-butoxycarbonyl)amino]-5-chloro-1,3-thiazol-4-yl}-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (110)

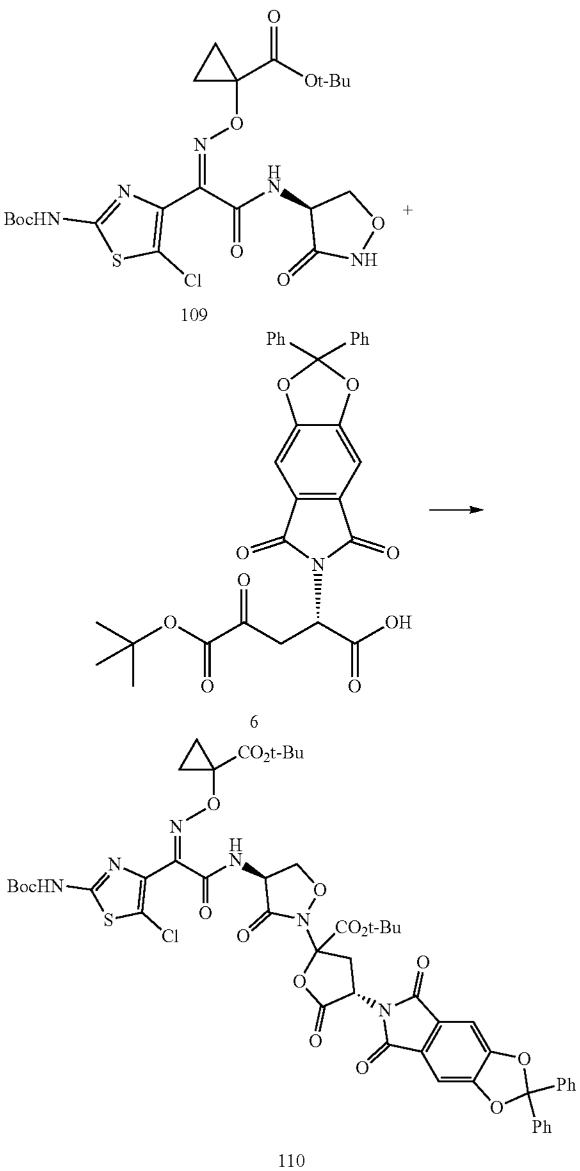

109

6

110

To a mixture of tert-butyl 1-{[(Z)-(1-{2-[(tert-butoxycarbonyl)amino]-5-chloro-1,3-thiazol-4-yl}-2-oxo-2-{[(4S)-3-oxo-1,2-oxazolidin-4-yl]amino}ethylidene)amino]oxy}cyclopropane-1-carboxylate 109 (402 mg, 0.74 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (400 mg, 0.74 mmol) in anhydrous THF (10 mL) was added DMAP (18 mg, 0.15 mmol) at 0° C. The resulting mixture was stirred for 5 min, then DCC (212 mg, 1.0 mmol) was added at 0° C. The reaction mixture was allowed to gradually warm to room temperature and was stirred overnight. Subsequently, the reaction mixture was concentrated under reduced pressure and the residue was triturated with 30% DCM in hexanes (20 ml). The precipitated solids were removed by filtration and the filtrate was concentrated in vacuo. The crude mixture was purified by silica gel column chromatography using a gradient of 0 to 30% ethyl acetate in hexanes, and the obtained product was treated with 25% ethyl acetate in hexanes (20 ml). The separated solids were removed by filtration, and the filtrate was concentrated to afford tert-butyl (4S)-2-[(4S)-4-([(2Z)-2-{2-[(tert-butoxycarbonyl)amino]-5-chloro-1,3-thiazol-4-yl)-2-({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 110 (450 mg, 57%) as an off-white foam.

$^1$H-NMR (400 MHz; $CDCl_3$) δ 8.39-8.30 (m, 1H), 7.97-7.93 (m, 1H), 7.57-7.54 (m, 4H), 7.43 (t, J=3.2 Hz, 6H), 7.33 (s, 2H), 5.41 (q, J=10.0 Hz, 1H), 5.11-4.93 (m, 2H), 4.28-4.23 (m, 1H), 3.49-3.29 (m, 1H), 2.88 (dd, J=13.7, 10.4 Hz, 1H), 1.63-1.58 (m, 9H), 1.58-1.50 (m, 13H), 1.49-1.44 (m, 9H).

Step 5: (4S)-2-[(4S)-4-{[(2Z)-2-(2-amino-5-chloro-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 24)

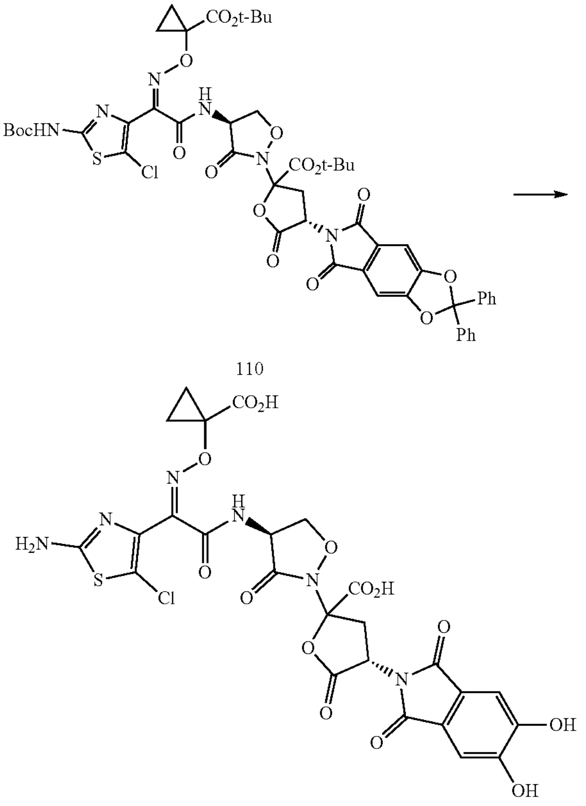

110

Compound 24

To a solution of tert-butyl (4S)-2-[(4S)-4-{[(2Z)-2-{2-[(tert-butoxycarbonyl)amino]-5-chloro-1,3-thiazol-4-yl}-2-

({[1-(tert-butoxycarbonyl)cyclopropyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 110 (200 mg, 0.19 mmol) in anhydrous DCM (16 mL) was added dropwise a boron trichloride solution (1.0 M in DCM, 1.49 ml, 1.49 mmol) at −50° C. The reaction mixture was stirred at −35° C.--30° C. for 2.5 h, then cooled to −50° C. and a solution of $NaHCO_3$ (300 mg) and $Na_2HPO_4$ (100 mg) in water (16 mL) was added. The cold bath was replaced with an ice-water bath, the heterogenous mixture was stirred at 5° C.-10° C. for 20 min, and then at room temperature until the aqueous layer thawed and the layers separated. The organic layer was carefully removed and the aqueous solution was subjected to purification by C18 reverse phase column chromatography using a Biotage system and mixtures of 0.1% formic acid in acetonitrile and 0.1% formic acid in water as eluents. The pure fractions were collected and lyophilized to afford (4S)-2-[(4S)-4-{[(2Z)-2-(2-amino-5-chloro-1,3-thiazol-4-yl)-2-{[(1-carboxycyclopropyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 24 (70 mg, 54%) as an off-white solid.

$^1$H-NMR (400 MHz; $CD_3CN$ with $D_2O$ as co-solvent) δ 7.23 (s, 2H), 5.45-5.30 (m, 1H), 5.19-5.01 (m, 1H), 4.72-4.65 (m, 1H), 4.24-4.17 (m, 1H), 3.59-3.27 (m, 1H), 2.86-2.61 (m, 1H), 1.47 (s, 2H), 1.43 (s, 2H). Exchangeable protons were not observed in $D_2O$.

MS (ESI) m/z: $[M+1]^+$ 695.0

Example 20

(4S)-2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 38, Table 1)

Compound 38

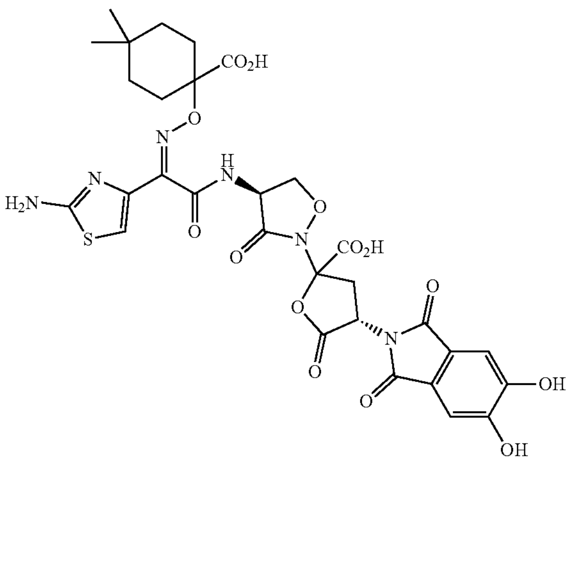

Step 1: 4,4-dimethyl-1-[(trimethylsilyl)oxy]cyclohexane-1-carbonitrile (112)

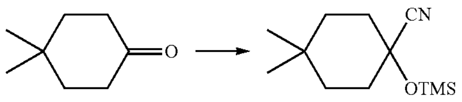

111 112

Zinc Iodide (160 mg, 0.5 mmol) was placed in a dry round-bottom flask and was dried under high vacuum (with gentle heating) for 30 minutes. A solution of 4,4-dimethylcyclohexan-1-one 111 (3.16 g, 25.0 mmol) in anhydrous DCM (60 ml) was added and the reaction mixture was cooled to 0° C. Trimethylsilyl cyanide (3.75 ml, 30.0 mmol) was added slowly at 0° C., then the ice-water bath was removed, stirring was continued at room temperature for 1 h. The reaction mixture was concentrated under reduced pressure and the residue was triturated using 10% DCM in hexanes (100 ml). The precipitated solids were removed by filtration and the filtrate was collected and concentrated in vacuo to afford 4,4-dimethyl-1-[(trimethylsilyl)oxy]cyclohexane-1-carbonitrile 112 (5.18 g, 92%) as a light yellow oil.

$^1$H-NMR (400 MHz; $CDCl_3$) δ 2.00-1.94 (m, 2H), 1.83-1.76 (m, 2H), 1.47 (t, J=6.2 Hz, 4H), 0.98 (s, 3H), 0.95 (s, 3H), 0.26 (s, 9H).

Step 2: 1-hydroxy-4,4-dimethylcyclohexane-1-carboxylic acid (113)

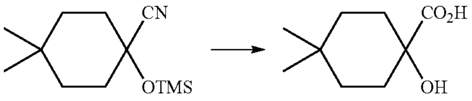

112 113

A solution of 4,4-dimethyl-1-[(trimethylsilyl)oxy]cyclohexane-1-carbonitrile 112 (5.1 g, 22.6 mmol) in glacial acetic acid (25 ml) was cooled to 0° C. Concentrated HCl (25 mL) was added dropwise over a period of 10 minutes and the reaction mixture was stirred at 0° C. for 15 minutes and then at room temperature for 15 minutes. Subsequently, the reaction mixture was heated to and stirred at 100° C. for 4 h. The resulting mixture was allowed to cool to room temperature and the volatiles were removed under reduced pressure. The residue was further dried under high vacuum and then taken up in water (100 ml). The aqueous phase was saturated using solid sodium chloride and extracted with ethyl acetate (2×150 mL). The combined organic extracts were washed with water and brine, dried over sodium sulfate, filtered, and concentrated under reduced pressure to afford 1-hydroxy-4,4-dimethylcyclohexane-1-carboxylic acid 113 (3.79 g, 97%) as a yellow solid.

$^1$H-NMR (400 MHz; DMSO-$d_6$) δ 12.25 (s, 1H), 4.79 (s, 1H), 1.80-1.72 (m, 2H), 1.48-1.40 (m, 4H), 1.13-1.08 (m, 2H), 0.87 (s, 3H), 0.85 (s, 3H).

Step 3: tert-butyl 1-hydroxy-4,4-dimethylcyclohexane-1-carboxylate (114)

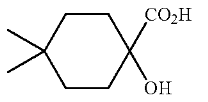

113 114

To a solution of 1-hydroxy-4,4-dimethylcyclohexane-1-carboxylic acid 113 (3.71 g, 21.54 mmol) in anhydrous THF (100 ml) was added tert-butyl N,N'-diisopropylcarbamimidate (17.3 ml, 86.16 mmol, prepared as described in EP2471792A1) and the reaction mixture was stirred at room temperature for 14 h. The separated solid was filtered off and washed with THF. The combined filtrates were collected and concentrated in vacuo. The residue was taken up in a mixture of DCM and hexanes (1:3, 100 mL) and the resulting suspension was cooled in an ice-water bath for 10 min. The precipitates were removed by filtration, rinsed with DCM and hexanes (1:3, 30 mL), and the filtrates were combined and concentrated under reduced pressure. The crude product was purified by silica gel column chromatography using a gradient of 0 to 5% ethyl acetate in hexanes to afford tert-butyl 1-hydroxy-4,4-dimethylcyclohexane-1-carboxylate 114 as a yellow solid (4.12 g, 84%).

$^1$H-NMR (400 MHz; $CDCl_3$) δ 2.96 (s, 1H), 1.92 (td, J=13.1, 4.2 Hz, 2H), 1.63-1.56 (m, 2H), 1.54-1.49 (m, 11H), 1.31-1.26 (m, 2H), 0.96 (s, 3H), 0.96 (s, 3H).

Step 4: tert-butyl 1-(aminooxy)-4,4-dimethylcyclohexane-1-carboxylate (115)

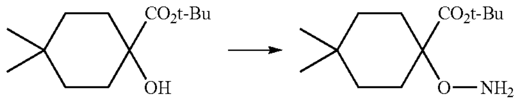

114 115

A solution of tert-butyl 1-hydroxy-4,4-dimethylcyclohexane-1-carboxylate 114 (1.57 g, 6.88 mmol) in anhydrous THF (50 mL) was cooled to 0° C. under nitrogen atmosphere. Sodium hydride (60% in mineral oil, 0.41 g, 10.32 mmol) was added in small portions and the resulting mixture was stirred for 15 minutes at 0° C. O-diphenylphosphinylhydroxylamine (2.40 g, 10.32 mmol) was then added at 0° C. and stirring continued for 30 minutes. The reaction mixture was allowed to gradually warm to room temperature and was stirred for 4 h. Additional 0-diphenylphosphinylhydroxylamine (0.5 g, 2.14 mmol) was added and stirring continued for 14 h. The majority of THF was removed under reduced pressure and the residue was taken up in saturated sodium chloride solution (75 mL). The aqueous phase was extracted with ethyl acetate (2×150 ml), and the combined organic extracts were dried over sodium sulfate, filtered, concentrated and dried under high vacuum. The crude product was purified by silica gel column chromatography using a gradient of 5% to 15% ethyl acetate in hexanes to afford tert-butyl 1-(aminooxy)-4,4-dimethylcyclohexane-1-carboxylate 115 as an off-white solid (1.11 g, 66% yield).

$^1$H-NMR (400 MHz; $CDCl_3$): δ 5.26 (s, 2H), 1.92-1.80 (m, 4H), 1.51 (s, 9H), 1.46-1.39 (m, 2H), 1.26-1.20 (m, 2H), 0.95 (s, 3H), 0.94 (s, 3H).

Step 5: (2Z)-{2-[(tert-butoxycarbonyl)amino]-1,3-thiazol-4-yl}({[1-(tert-butoxycarbonyl)-4,4-dimethylcyclohexyl]oxy}imino)acetic acid (116)

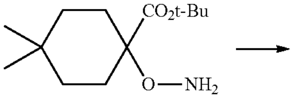

115

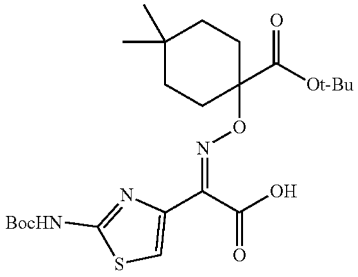

116

To a solution of tert-butyl 1-(aminooxy)-4,4-dimethylcyclohexane-1-carboxylate 115 (1.06 g, 4.35 mmol) in anhydrous MeOH (25 ml) was added 2-(2-(tert-butoxycarbonylamino)thiazol-4-yl)-2-oxoacetic acid (1.06 g, 3.92 mmol) and the reaction mixture was stirred at room temperature for 16 h. The reaction mixture was concentrated under reduced pressure and the residue was further dried under high vacuum to afford (2Z)-{2-[(tert-butoxycarbonyl)amino]-1,3-thiazol-4-yl}({[1-(tert-butoxycarbonyl)-4,4-dimethylcyclohexyl]oxy}imino)acetic acid 116 as a white solid (2.07 g, crude).

$^1$H-NMR (400 MHz; DMSO-$d_6$) δ 11.75 (s, 1H), 7.33 (s, 1H), 1.83-1.80 (m, 4H), 1.45 (s, 9H), 1.40-1.35 (m, 11H), 1.17-1.13 (m, 2H), 0.88 (s, 3H), 0.86 (s, 3H).

Step 6: tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-4,4-dimethylcyclohexane-1-carboxylate (117)

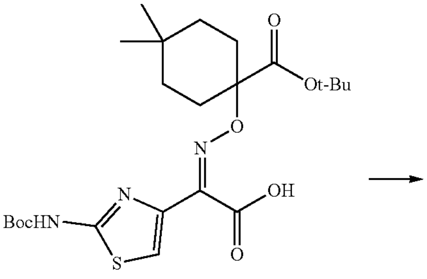

116

-continued

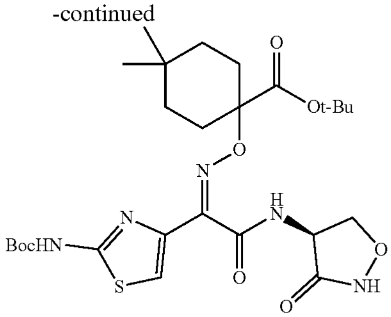

117

To a solution of (2Z)-{2-[(tert-butoxycarbonyl)amino]-1,3-thiazol-4-yl}({[1-(tert-butoxycarbonyl)-4,4-dimethylcyclohexyl]oxy}imino)acetic acid 116 (1.00 g, 2.00 mmol) in anhydrous DMF (10 mL) was added DIPEA (0.52 mL, 3.00 mmol) and the resulting mixture was stirred at room temperature for 10 min. HATU (0.76 g, 2.00 mmol) was then added and stirring at room temperature continued for 14 h. Subsequently, an additional 15 mL of anhydrous DMF followed by DIPEA (1.4 mL, 8.00 mmol) was added and the mixture was stirred at room temperature for 10 min. To this solution was added L-cycloserine (0.30 g, 3.00 mmol), the reaction mixture was stirred for 2 h and then concentrated under reduced pressure. Traces of DMF were removed by co-evaporation with toluene (3×10 mL) and the residue was dissolved in DCM (100 ml). The organic phase was washed with water (50 ml) and brine (30 ml), dried over sodium sulfate, filtered and concentrated under reduced pressure. The crude product was purified by silica gel column chromatography using a gradient of 0 to 3% MeOH in DCM to afford tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-4,4-dimethylcyclohexane-1-carboxylate 117 as a white solid (1.02 g, 98%).

$^1$H-NMR (400 MHz; DMSO-$d_6$) δ 11.78 (s, 1H), 11.57 (s, 1H), 9.04 (d, J=7.8 Hz, 1H), 7.37 (s, 1H), 4.92-4.86 (m, 1H), 4.57 (t, J=8.5 Hz, 1H), 4.07 (t, J=9.0 Hz, 1H), 1.90-1.71 (m, 4H), 1.45 (s, 9H), 1.39-1.33 (m, 11H), 1.18-1.06 (m, 2H), 0.87 (s, 6H).

Step 7: tert-butyl (4S)-2-[(4S)-4-{[(2Z)-2-{2-[(tert-butoxycarbonyl)amino]-1,3-thiazol-4-yl}-2-({[1-(tert-butoxycarbonyl)-4,4-dimethylcyclohexyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (118)

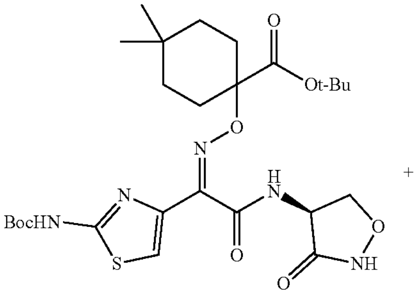

117

+

-continued

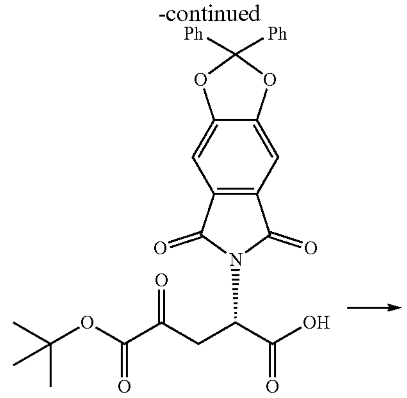

6

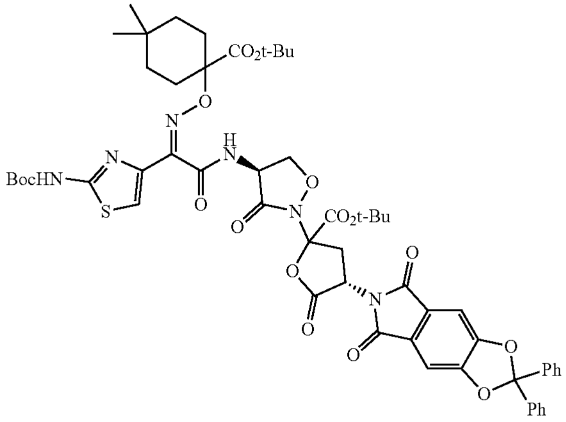

118

A mixture of tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-4,4-dimethylcyclohexane-1-carboxylate 117 (0.38 g, 0.70 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (0.407 g, 0.70 mmol) in anhydrous THF (20 mL) was cooled to 0° C. under nitrogen atmosphere. DMAP (17 mg, 0.14 mmol) followed by DCC (0.202 g, 0.98 mmol) were added and the reaction mixture was stirred at 0° C. for 1 h. The mixture was allowed to gradually warm to room temperature and was stirred overnight. The mixture was then concentrated at 25° C. and the residue was triturated with 30% DCM in hexanes (40 ml). The precipitated solids were filtered off, rinsed with 30% DCM in hexanes (15 ml) and hexanes (15 mL). The filtrates were combined and concentrated under reduced pressure. The crude product was purified by silica gel column chromatography using a gradient of 0 to 30% ethyl acetate in hexanes to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)-4,4-dimethylcyclohexyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 118 as an off-white solid (0.363 g, 47%).

$^1$H-NMR (400 MHz; $CDCl_3$) δ 8.11-8.00 (m, 2H), 7.58-7.53 (m, 4H), 7.45-7.41 (m, 6H), 7.35-7.32 (m, 3H), 5.42-5.32 (m, 1H), 5.17-4.93 (m, 2H), 4.27-4.21 (m, 1H), 3.44-3.31 (m, 1H), 2.90-2.84 (m, 1H), 2.20-1.90 (m, 4H), 1.61-1.57 (s, 9H), 1.57-1.53 (s, 9H), 1.49-1.43 (s, 9H), 1.33- 1.24 (m, 4H), 0.99-0.96 (s, 3M), 0.96-0.92 (s, 3H).

Step 8: ((4S)-2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 38)

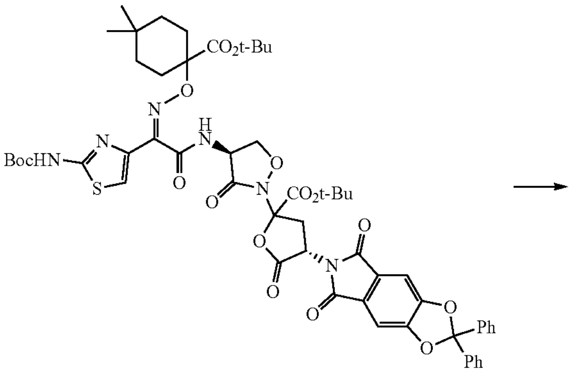

118

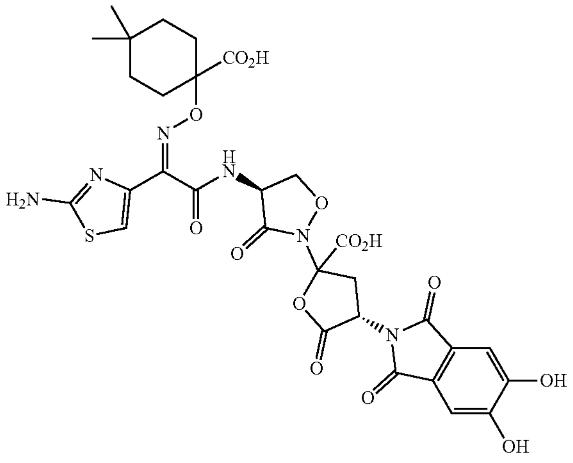

Compound 38

To a solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)-4,4-dimethylcyclohexyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 118 (346 mg, 0.312 mmol) in anhydrous DCM (16 ml), was added dropwise a solution of boron trichloride (1.0 M in DCM, 2.5 mL, 2.5 mmol) at −50° C. The reaction mixture was stirred at −45 to −30° C. for 2.5 h, then cooled to −50° C. and quenched using 30 ml of a buffer solution (prepared by dissolving 776 mg of $NaHCO_3$ and 243 mg of $Na_2HPO_4$ in 42 ml of water). The cold bath was replaced with an ice-water bath and the mixture was stirred until the aqueous layer thawed and two layers separated. The DCM layer was carefully removed and the aqueous phase was collected, filtered, and immediately purified by C18 reverse phase column chromatography using a Biotage system and mixtures of 0.1% formic acid in acetonitrile and 0.1% formic acid in water as eluents to afford ((4S)-2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 38 as a pale yellow foamy solid in 35% yield (80 mg).

$^1$H-NMR (400 MHz; a mixture of $D_2O$ and $CD_3CN$) δ 7.23 (s, 2H), 7.05 (s, 1H), 5.38-5.29 (m, 1H), 5.14-5.04 (m, 1H), 4.74-4.66 (m, 1H), 4.31-4.27 (m, 1H), 3.35-3.26 (m, 1H), 2.80-2.68 (m, 1H), 1.98-1.88 (m, 4H), 1.35-1.24 (m, 2H), 1.24-1.15 (m, 2H), 0.88 (s, 3H), 0.84 (s, 3H). Exchangeable protons were not observed in $D_2O$.

MS (ESI) m/z: $[M+1]^+$ 731.2

Example 21

(4S)-2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 14, Table 1)

Compound 14

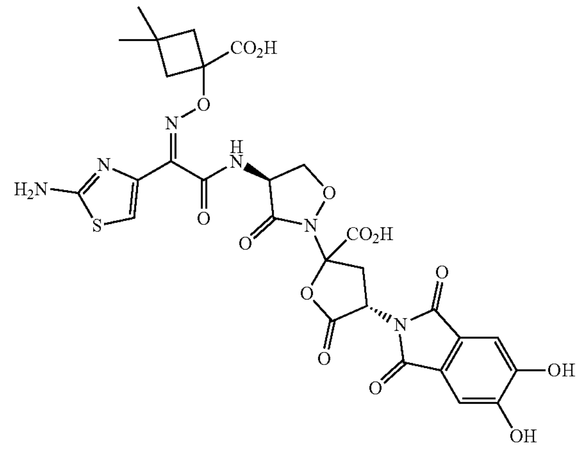

Step 1: 1-bromo-3,3-dimethylcyclobutane-1-carboxylic acid (120)

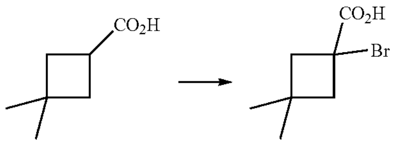

119 120

A mixture of 3,3-dimethylcyclobutane-1-carboxylic acid 119 (5.0 g, 39.0 mmol) and bromine (3 mL, 58.5 mmol) was placed in a round-bottom pressure flask and $PBr_3$ (0.6 mL, 6.5 mmol) was carefully added at room temperature. An ice-water bath was used during the addition to control the temperature of the reaction mixture. The reaction flask was sealed, and the reaction mixture was heated to and stirred at 100° C. overnight. The reaction mixture was then cooled to room temperature and the flask was carefully opened to release some internal pressure buildup. The mixture was diluted with ethyl acetate (100 mL) and washed with 5% $NaHSO_3$ solution (2×30 ml), water (2×30 ml) and brine (30 ml). The organic phase was dried over sodium sulfate, filtered and concentrated to afford 1-bromo-3,3-dimethylcyclobutane-1-carboxylic acid 120 as an off-white solid (8.0 g, quantitative yield).

$^1$H-NMR (599 MHz; $CDCl_3$) δ 2.89-2.86 (m, 2H), 2.56-2.53 (m, 2H), 1.38 (s, 3H), 1.08 (s, 3H).

Step 2: tert-butyl 1-bromo-3,3-dimethylcyclobutane-1-carboxylate (121)

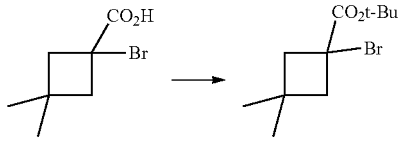

120 121

To a stirred mixture of 1-bromo-3,3-dimethylcyclobutane-1-carboxylic acid 120 (8.0 g, 36.6 mmol), t-BuOH (4.0 g, 54.1 mmol) and DMAP (472 mg, 3.9 mmol) was added triethylamine (11.9 mL, 85.0 mmol) followed by di-tert-butyl dicarbonate (11.0 g, 50.2 mmol) at 0° C. The reaction mixture was allowed to warm to room temperature and stirred for 5 days. The reaction mixture was then partitioned between hexanes (150 mL) and water (50 ml) and the layers were separated. The aqueous phase was further extracted with hexane (4×30 ml). The combined organic extracts were washed with IN HCl (2×30 mL) and water (2×30 mL), and then concentrated under reduced pressure. The crude mixture was purified by silica gel column chromatography using a gradient of 0 to 5% ethyl acetate in hexanes to afford tert-butyl 1-bromo-3,3-dimethylcyclobutane-1-carboxylate 121 as a colorless liquid (6.45 g, 63%).

$^1$H-NMR (400 MHz; $CDCl_3$) δ 2.83-2.80 (m, 2H), 2.53-2.49 (m, 2H), 1.52 (s, 9H), 1.31 (s, 3H), 1.04 (s, 3H).

Step 3: tert-butyl 1-({(Z)-[1-(2-amino-1,3-thiazol-4-yl)-2-ethoxy-2-oxoethylidene]amino}oxy)-3,3-dimethylcyclobutane-1-carboxylate (122)

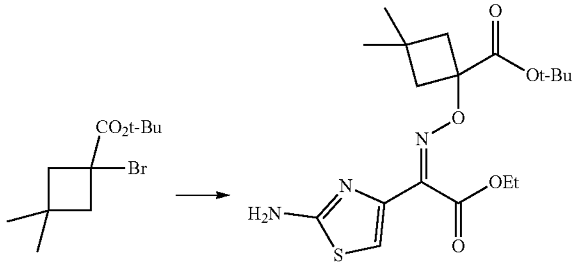

121 122

To a solution of (Z)-2-(2-aminothiazol-4-yl)-2-(hydroxyimino)acetate (200 mg, 0.91 mmol) in anhydrous DMSO (5 ml) was added potassium carbonate (210 mg, 1.5 mmol) at room temperature. The resulting mixture was stirred at 50° C. for 5 min, and tert-butyl 1-bromo-3,3-dimethylcyclobutane-1-carboxylate 121 (200 mg, 0.76 mmol) was added. The reaction mixture was stirred at 50° C. for 2 days, then cooled, diluted with water (30 ml) and extracted with diethyl ether (8×20 mL). The combined organic extracts were dried over sodium sulfate and concentrated under reduced pressure. The residue was purified by silica gel column chromatography using a gradient of 0 to 20% ethyl acetate in hexanes to afford tert-butyl 1-({(Z)-[1-(2-amino-1,3-thiazol-4-yl)-2-ethoxy-2-oxoethylidene]amino}oxy)-3,3-dimethylcyclobutane-1-carboxylate 122 as an off-white solid (150 mg, 50%).

$^1$H-NMR (400 MHz; $CDCl_3$) δ 6.61 (s, 1H), 6.57-6.57 (m, 2H), 4.41 (q, J=7.1 Hz, 2H), 2.41-2.37 (m, 2H), 2.09-2.06 (m, 2H), 1.45 (s, 9H), 1.37 (t, J=7.1 Hz, 3H), 1.20 (s, 3H), 1.15 (s, 3H).

Step 4: tert-butyl 1-{[(Z)-(1-{2-[(tert-butoxycarbonyl)amino]-1,3-thiazol-4-yl}-2-ethoxy-2-oxoethylidene)amino]oxy}-3,3-dimethylcyclobutane-1-carboxylate (123)

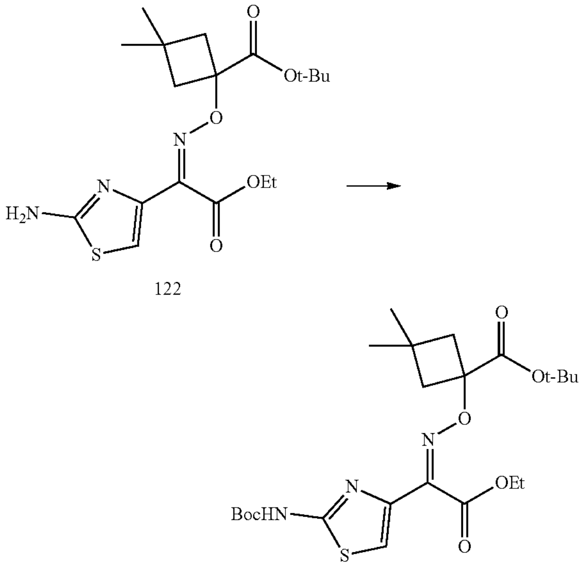

A solution of tert-butyl 1-({(Z)-[1-(2-amino-1,3-thiazol-4-yl)-2-ethoxy-2-oxoethylidene]amino}oxy)-3,3-dimethylcyclobutane-1-carboxylate 122 (1.0 g, 2.5 mmol) in anhydrous THF (10 mL) was cooled to 0° C. TMEDA (0.02 mL, 0.13 mmol) followed by a solution of di-tert-butyl dicarbonate (0.577 g, 2.6 mmol) in THF (5 mL) were added at 0° C. The reaction mixture was stirred at 0° C. for 2 h, and then at room temperature for 48 h. The reaction mixture was concentrated under reduced pressure and traces of solvent were removed by co-evaporation with MeOH (4×30 ml). The residue was purified by silica gel column chromatography using a gradient of 0 to 20% ethyl acetate in hexanes to afford tert-butyl 1-{[(Z)-(1-{2-[(tert-butoxycarbonyl)amino]-1,3-thiazol-4-yl}-2-ethoxy-2-oxoethylidene)amino]oxy}-3,3-dimethylcyclobutane-1-carboxylate 123 as a white foam (1.20 g, 96%).

$^1$H-NMR (400 MHz; $CDCl_3$) δ 7.21 (s, 1H), 4.42 (q, J=7.1 Hz, 2H), 2.41 (d, J=14.0 Hz, 2H), 2.11 (d, J=14.0 Hz, 2H), 1.52 (s, 9H), 1.45 (s, 9H), 1.37 (t, J=7.1 Hz, 3H), 1.21 (s, 3H), 1.16 (s, 3H).

Step 5: (2Z)-{2-[(tert-butoxycarbonyl)amino]-1,3-thiazol-4-yl}({[1-(tert-butoxycarbonyl)-3,3-dimethylcyclobutyl]oxy}imino)acetic acid (124)

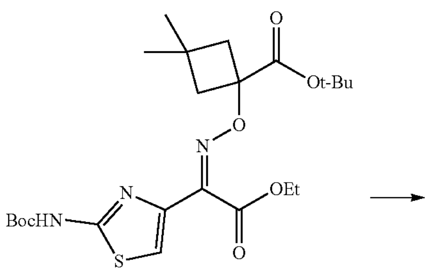

123

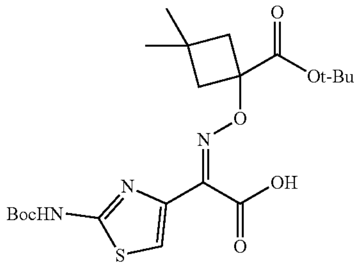

124

To a solution of tert-butyl 1-{[(Z)-(1-{2-[(tert-butoxycarbonyl)amino]-1,3-thiazol-4-yl}-2-ethoxy-2-oxoethylidene)amino]oxy}-3,3-dimethylcyclobutane-1-carboxylate 123 (3.2 g, 6.4 mmol) in MeOH (25 mL) was added LiOH monohydrate (0.81 g, 19.3 mmol) in $H_2O$ (10 ml) at room temperature. The reaction mixture was heated to and stirred at 55° C. overnight. The reaction mixture was then concentrated under reduced pressure to remove methanol and the pH of the aqueous solution was acidified to pH~4 using IN HCl (~20 mL). The aqueous solution was then extracted with ethyl acetate (6×20 ml), and the combined organic extracts were washed with brine (2×20 ml), dried over sodium sulfate, filtered and concentrated under reduced pressure to afford (2Z)-{2-[(tert-butoxycarbonyl)amino]-1,3-thiazol-4-yl}({[1-(tert-butoxycarbonyl)-3,3-dimethylcyclobutyl]oxy}imino)acetic acid 124 as an off-white foam (3.0 g, 99%). The obtained product was used in the next step without further purification.

$^1$H-NMR (400 MHz; $CDCl_3$) δ 7.43 (s, 1H), 2.42-2.32 (s, 4H), 1.55 (s, 9H), 1.51 (s, 9H), 1.36-1.35 (m, 2H), 1.31-1.30 (m, 2H), 1.26 (s, 3H), 1.22 (s, 3H).

Step 6: tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-3,3-dimethylcyclobutane-1-carboxylate (125)

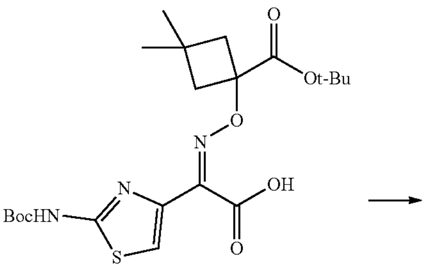

124

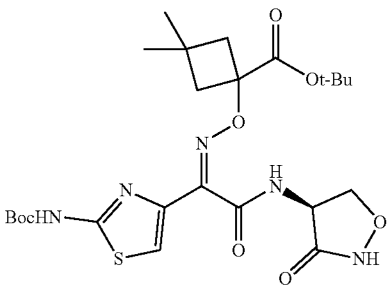

125

To a solution of compound (2Z)-{2-[(tert-butoxycarbonyl)amino]-1,3-thiazol-4-yl}({[1-(tert-butoxycarbonyl)-3,3-dimethylcyclobutyl]oxy}imino)acetic acid 124 (3.0 g, 6.4 mmol) in anhydrous DMF (35 ml) were added DIPEA (1.67 ml, 9.6 mmol) and HATU (2.43 g, 6.4 mmol) at room temperature. The reaction mixture was stirred at room temperature for 4 h and then DIPEA (1.67 mL, 9.6 mmol) and DMF (35 ml) followed by L-cycloserine (0.783 g, 7.7 mmol) were added. The resulting mixture was stirred at room temperature overnight and then diluted with ethyl acetate (150 ml). The organic phase was washed with water (6×30 ml) and the aqueous layers were combined and re-extracted with diethyl ether (5×30 ml). The organic extracts were combined, washed with brine (2×30 ml), dried over sodium sulfate and concentrated under reduced pressure. The residue was purified by silica gel column chromatography using a gradient of 0 to 5% methanol in DCM to afford tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-3,3-dimethylcyclobutane-1-carboxylate 125 as an off-white solid (1.97 g, 56%).

$^1$H-NMR (400 MHz; DMSO-$d_6$) δ 11.85 (s, 1H), 11.60 (s, 1H), 9.15 (d, J=8.0 Hz, 1H), 7.44 (s, 1H), 5.04-4.87 (br, J=1.1 Hz, 1H), 4.69-4.56 (m, 1H), 4.14-4.05 (m, 1H), 2.36-2.24 (m, 2H), 2.09-1.98 (m, 2H), 1.47 (s, 9H), 1.41 (s, 9H), 1.17 (s, 3H), 1.13 (s, 3H).

Step 7: tert-butyl (4S)-2-[(4S)-4-{[(2Z)-2-{2-[(tert-butoxycarbonyl)amino]-1,3-thiazol-4-yl}-2-({[1-(tert-butoxycarbonyl)-3,3-dimethylcyclobutyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (126)

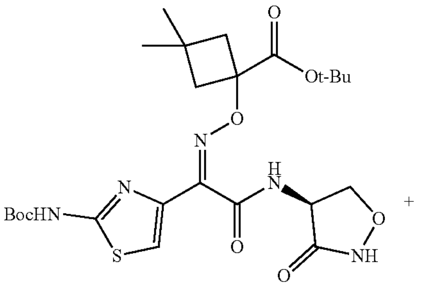

125

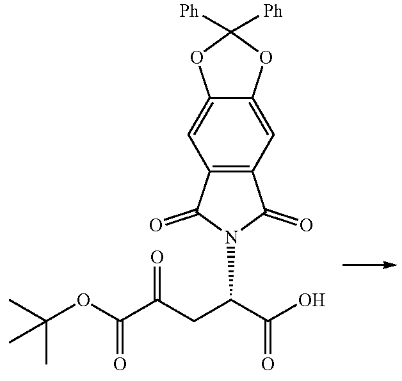

6

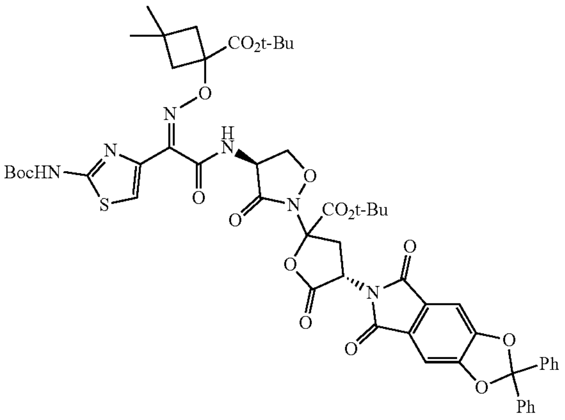

126

A mixture of tert-butyl 1-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-3,3-dimethylcyclobutane-1-carboxylate 125 (408 mg, 0.74 mmol) and (2S)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 6 (400 mg, 0.74 mmol) in anhydrous THF (10 mL) was cooled to 0° C. DMAP (18 mg, 0.15 mmol) followed by DCC (212 mg, 1.0 mmol) was added at 0° C., the resulting mixture was allowed to gradually warm to room temperature and stirred overnight. The reaction mixture was then concentrated under reduced pressure and the residue was triturated with 30% DCM in hexanes (20 ml). The precipitated solids were removed by filtration and the filtrate was concentrated in vacuo. The crude mixture was purified by silica gel column chromatography using a gradient of 0 to 30% ethyl acetate in hexanes and the obtained product was triturated using 25% ethyl acetate in hexanes (20 mL). The precipitate was filtered off and the filtrate was concentrated to afford tert-butyl (4S)-2-[(4S)-4-{[(2Z)-2-{2-[(tert-butoxycarbonyl)amino]-1,3-thiazol-4-yl}-2-({[1-(tert-butoxycarbonyl)-3,3-dimethylcyclobutyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 126 as an off-white foam (520 mg, 65%).

$^1$H-NMR (400 MHz; $CDCl_3$) δ 8.34-8.27 (m, 1H), 8.12-8.00 (m, 1H), 7.57-7.54 (m, 4H), 7.47-7.42 (m, 6H), 7.34-7.31 (m, 2H), 5.44-5.35 (m, 1H), 5.22-4.99 (m, 1H), 4.99-4.86 (m, 1H), 4.29-4.17 (m, 1H), 3.48-3.28 (m, J=9.8 Hz, 1H), 2.90-2.84 (m, 1H), 2.48-2.26 (m, 4H), 1.60-1.57 (m, 9H), 1.56-1.54 (s, 9H), 1.51-1.48 (m, 9H), 1.27-1.24 (m, 3H), 1.24-1.23 (m, 3H).

Step 8: P(4S)-2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 14)

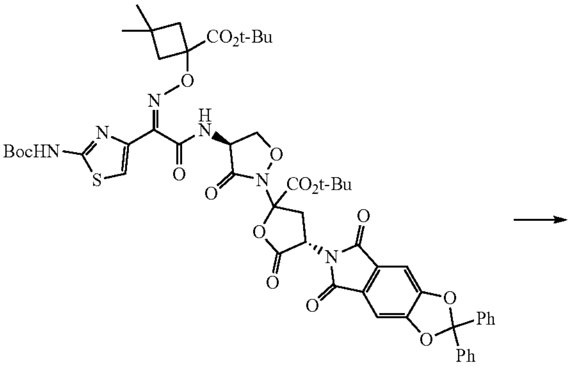

126

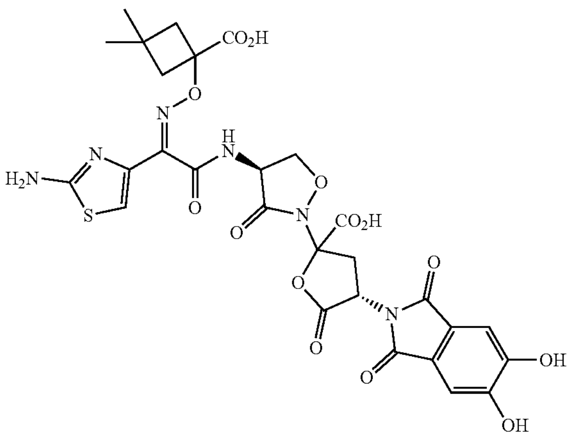

Compound 14

To a solution of tert-butyl (4S)-2-[(4S)-4-{[(2Z)-2-{2-[(tert-butoxycarbonyl)amino]-1,3-thiazol-4-yl}-2-({[1-(tert-butoxycarbonyl)-3,3-dimethylcyclobutyl]oxy}imino)acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 126 (200 mg, 0.19 mmol) in anhydrous DCM (16 mL) was added dropwise a boron trichloride solution (1.0 M in DCM, 1.48 ml, 1.48 mmol) at −50° C. The reaction mixture was stirred at −35° C. to −30° C. for 2.5 h, then cooled to −50° C. and a solution of $NaHCO_3$ (300 mg) and $Na_2HPO_4$ (100 mg) in $H_2O$ (16 mL) was added. The cold bath was replaced with an ice-water bath, the mixture was stirred for 30 min, and then at room temperature until the aqueous layer thawed (~30 min). The layers were allowed to separate, and the organic phase was carefully removed. The aqueous solution was then subjected to purification by C18 reverse phase column chromatography using a Biotage system and mixtures of 0.1% formic acid in acetonitrile and 0.1% formic acid in water as eluents. The product containing fractions were collected and lyophilized to afford (4S)-2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 14 (55 mg, 42%) as an off-white solid.

$^1$H-NMR (400 MHz; a mixture of $CD_3CN$ with $D_2O$) δ 7.23 (s, 2H), 7.10 (s, 1H), 5.42-5.21 (m, 1H), 5.16-5.08 (m, 1H), 4.77-4.66 (m, 1H), 4.32-4.22 (m, 1H), 3.55-3.24 (m, 1H), 2.87-2.67 (m, 1H), 2.39 (d, J=7.2 Hz, 2H), 2.06 (d, J=7.2 Hz, 2H), 1.11 (s, 3H), 1.09 (s, 3H). Exchangeable protons were not observed in $D_2O$.

MS (ESI) m/z: $[M+1]^+$ 703.1

Example 22

(4R)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 40, Table 1)

Compound 40

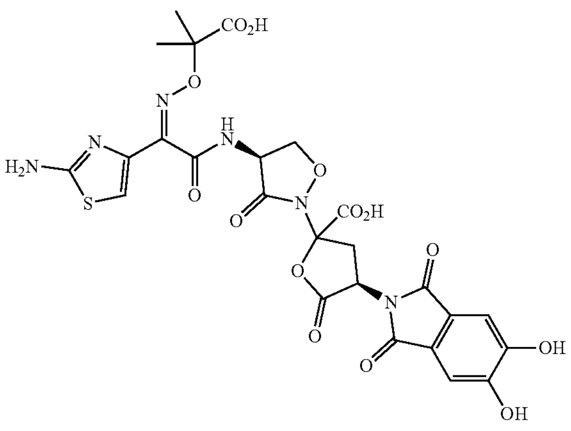

Step 1: tert-butyl (4R)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate (127)

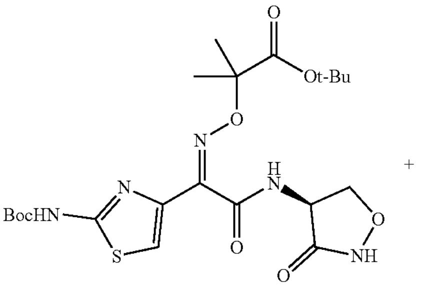

72

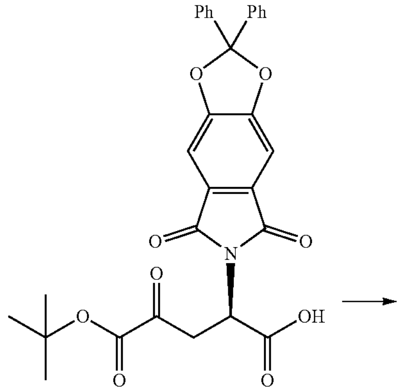

128

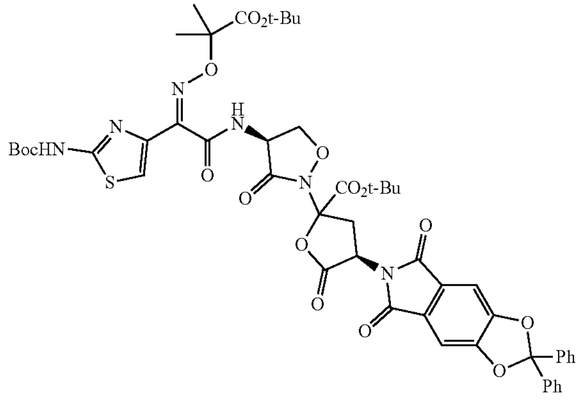

127

(2R)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 128 was prepared in a similar manner as described in *J. Med. Chem.*, 2014, 57, 3845-3855, and starting from 5-tert-butyl 1-methyl N-[(benzyloxy)carbonyl]-4-oxo-D-glutamate and 2,2-diphenyl-2H-furo[3,4-f][1,3]benzodioxole-5,7-dione.

To a mixture of (2R)-5-tert-butoxy-2-(5,7-dioxo-2,2-diphenyl-5,7-dihydro-2H,6H-[1,3]dioxolo[4,5-f]isoindol-6-yl)-4,5-dioxopentanoic acid 128 (200 mg, 0.37 mmol) and tert-butyl 2-{[(Z)-(1-(2-[(tert-butoxycarbonyl)amino]-1,3-thiazol-4-yl}-2-oxo-2-{[(4S)-3-oxo-1,2-oxazolidin-4-yl] amino)ethylidene)amino]oxy}-2-methylpropanoate 72 (189 mg, 0.37 mmol) in anhydrous THF (4 ml) were added DMAP (9 mg, 0.074 mmol) and DCC (107 mg, 0.52 mmol). The reaction mixture was stirred at room temperature overnight and then concentrated under reduced pressure. The residue was triturated with 40% DCM in hexanes (20 ml) and the separated solid was filtered off and washed with hexanes. The combined filtrates were concentrated and the crude product was purified by silica gel column chromatography using a gradient of 10 to 35% ethyl acetate in hexanes to afford tert-butyl (4R)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl]amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 127 (174 mg, 45% yield) as a light brown solid.

$^1$H NMR (400 MHz, $CDCl_3$) δ 8.09 (br. s, 1H), 7.52-7.48 (m, 4H), 7.40-7.37 (m, 6H), 7.27 (s, 2H), 7.23 (s, 1H), 5.41-5.28 (m, 1H), 5.15-4.82 (m, 2H), 4.24-4.15 (m, 1H), 3.50-3.38 (m, 2H), 2.88-2.76 (m, 1H), 1.95-1.85 (m, 1H), 1.72-1.61 (m, 1H), 1.58 (s, 6H), 1.54 (d, 9H), 1.50 (s, 9H), 1.41 (s, 9H)

Step 2: (4R)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid (Compound 38)

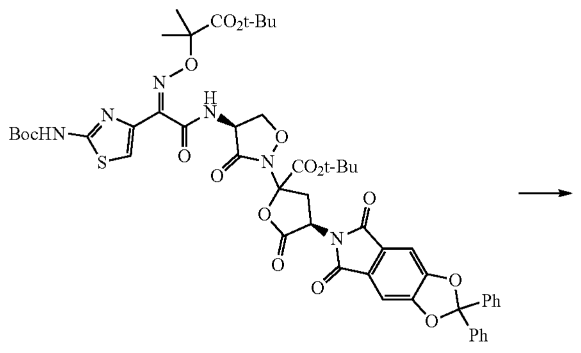

127

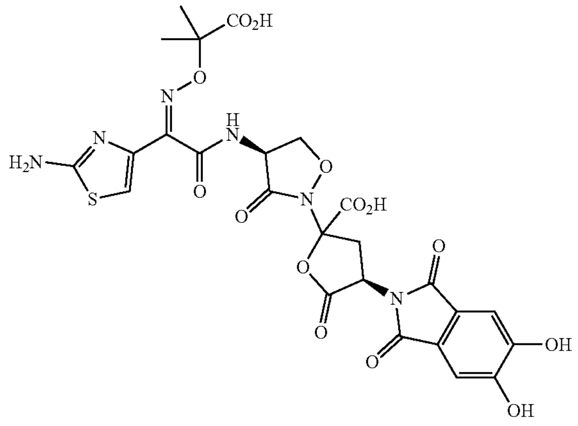

Compound 40

A solution of tert-butyl (4R)-2-[(4S)-4-{[(2Z)-2-{2-[(tert-butoxycarbonyl)amino]-1,3-thiazol-4-yl}-2-{[(1-tert-butoxy-2-methyl-1-oxopropan-2-yl)oxy]imino}acetyl] amino}-3-oxo-1,2-oxazolidin-2-yl]-4-(5,7-dioxo-2,2-diphenyl-5,7-dihydro-2H,6H-[1,3]dioxolo[4,5-f]isoindol-6-yl)-5-oxooxolane-2-carboxylate 127 (170 mg, 0.163 mmol) in anhydrous DCM (10 ml) was cooled to −50° C. and a solution of boron trichloride (1.0M in DCM, 1.3 ml, 1.3 mmol) was added dropwise. The reaction mixture was stirred at −50 to −35° C. for 2.5 h, then cooled to −50° C. before 14.3 mL of a buffer solution (prepared by dissolving 776 mg of $NaHCO_3$ and 243 mg of $Na_2HPO_4$ in 42 mL of water) was added. The cold bath was replaced with an ice-water bath and the heterogenous mixture was stirred until the aqueous phase thawed and two layers separated. The organic layer was carefully removed and the aqueous phase was immediately purified by C18 reverse phase column chromatography using a Biotage system and a mixture of 0.1% formic acid in acetonitrile and 0.1% formic acid in water as eluents to afford (4R)-2-[(4S)-4-{[(2Z)-2-(2-amino-1,3-thiazol-4-yl)-2-{[(2-carboxypropan-2-yl)oxy] imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid Compound 40 (40 mg, 37%) as a pale yellow solid.

$^1$H NMR (400 MHz, a mixture of $D_2O$ and $CD_3CN$) δ 7.35 (s, 2H), 7.18 (s, 1H), 5.54-5.48 (m, 1H), 5.28-5.20 (m, 1H), 4.91-4.76 (m, 1H), 4.45-4.30 (m, 1H), 3.52-3.32 (m, 1H), 2.89-2.76 (m, 1H), 1.58 (s, 6H). Exchangeable protons were not observed in $D_2O$.

MS (ESI) m/z: $[M+1]^+$ 663.1

Example 23

4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene] amino}oxy)-2,2-dimethyloxane-4-carboxylic acid (Compound 41, Table 1)

Compound 41

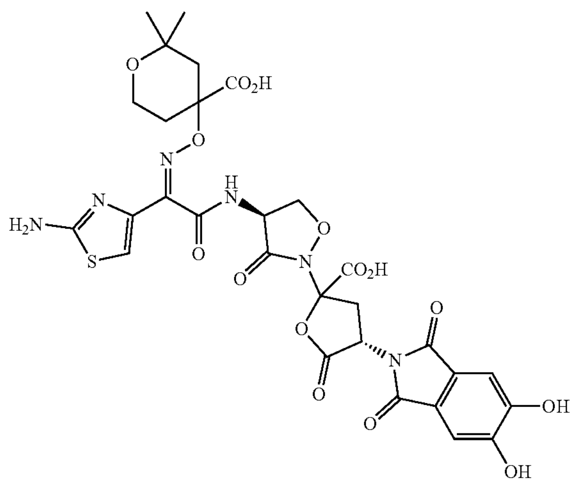

Step 1: 2,2-dimethyl-4-[(trimethylsilyl)oxy]oxane-4-carbonitrile (130)

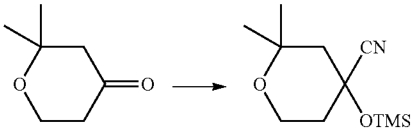

129 130

Zinc iodide (260 mg, 0.8 mmol) was placed in a dry round-bottom flask and dried under high vacuum (with gentle heating) for 30 minutes. A solution of 2,2-dimethyloxan-4-one 129 (5.13 g, 40.0 mmol) in anhydrous DCM (60 mL) was added and the mixture was cooled to 0° C. Trimethylsilyl cyanide (6.00 mL, 48.0 mmol) was added slowly at 0° C. then the ice-bath was removed, and the reaction mixture was stirred at room temperature for 2 h. The reaction mixture was concentrated under reduced pressure and the residue was treated with 10% DCM in hexanes (100 mL). The resulting precipitate was removed by filtration and the filtrate was concentrated and dried under high vacuum to afford 2,2-dimethyl-4-[(trimethylsilyl)oxy]oxane-4-carbonitrile 130 as a light brown oil (8.61 g, crude).

$^1$H-NMR (400 MHz; $CDCl_3$): δ 3.93-3.86 (m, 1H), 3.82-3.73 (m, 1H), 2.15-2.05 (m, 1H), 2.03-1.96 (m, 1H), 1.87-1.77 (m, 2H), 1.33 (s, 3H), 1.32 (s, 3H), 0.29 (s, 9H).

Step 2: 4-hydroxy-2,2-dimethyloxane-4-carboxylic acid (131)

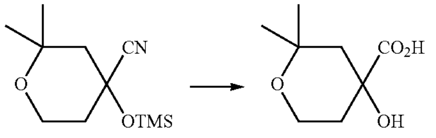

130 131

To 2,2-dimethyl-4-[(trimethylsilyl)oxy]oxane-4-carbonitrile 130 (8.6 g, 37.8 mmol) glacial acetic acid (40 mL) was added and the resulting mixture was cooled to 0° C. Concentrated hydrochloric acid (40 ml) was then added dropwise over a period of 10 minutes. The reaction mixture was stirred at 0° C. for 15 minutes, then at room temperature for 15 minutes and subsequently heated and stirred at 110° C. for 3 h. The reaction mixture was allowed to cool to room temperature and the volatiles were removed under reduced pressure. The residue was further dried under high vacuum and then taken in water (100 ml). The aqueous phase was saturated with solid sodium chloride and then extracted with ethyl acetate (2×150 ml). The combined organic extracts were washed with water and brine, dried over sodium sulfate, filtered and concentrated under reduced pressure to afford 4-hydroxy-2,2-dimethyloxane-4-carboxylic acid 131 as a brown viscous liquid (7.21 g, crude).

$^1$H-NMR (400 MHz; $CDCl_3$): δ 4.01-4.00 (m, 1H), 3.81-3.75 (m, 1H), 2.18-2.08 (m, 2H), 1.66-1.62 (m, 1H), 1.60-1.52 (m, 1H), 1.46 (s, 3H), 1.27-1.24 (m, 3H).

MS (ESI) m/z: $[M-1]^-$ 173.0

Step 3: tert-butyl 4-hydroxy-2,2-dimethyloxane-4-carboxylate (132)

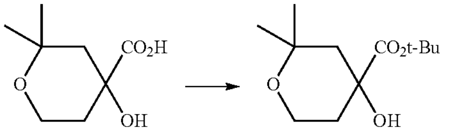

131 132

To a solution of 4-hydroxy-2,2-dimethyloxane-4-carboxylic acid 131 (7.2 g, crude, 41.33 mmol) in anhydrous THF (100 mL) was added slowly tert-butyl N,N'-diisopropylcarbamimidate (prepared as described in EP2471792A1, 33 mL, 165.32 mmol). The reaction mixture was stirred at room temperature for 14 h and the precipitated solids were removed by filtration and washed with THF. The combined filtrates were concentrated under reduced pressure and the residue was treated with a mixture of DCM and hexanes (1:3, 50 ml). The resulting mixture was stirred at 0° C. for 10 minutes, the precipitated solids were removed by filtration and washed with 25% DCM in hexanes (30 ml). The combined filtrates were concentrated, and the residue was purified by silica gel column chromatography using a gradient of 0% to 15% ethyl acetate in hexanes to afford tert-butyl 4-hydroxy-2,2-dimethyloxane-4-carboxylate 132 as yellow oil (4.62 g, 50% yield in three steps).

$^1$H-NMR (400 MHz; $CDCl_3$): δ 4.03-3.97 (m, 1H), 3.73-3.68 (m, 1H), 3.21 (s, 1H), 2.09-1.98 (m, 1H), 1.88-1.85 (m, 1H), 1.53 (d, J=2.1 Hz, 1H), 1.47 (s, 9H), 1.44 (q, J=2.2 Hz, 1H), 1.41 (s, 3H), 1.22 (s, 3H).

Step 4: tert-butyl 4-(aminooxy)-2,2-dimethyloxane-4-carboxylate (133)

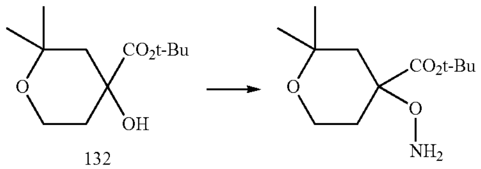

132 133

A solution of tert-butyl 4-hydroxy-2,2-dimethyloxane-4-carboxylate 132 (2.30 g, 10.0 mmol) in anhydrous THE (120 ml) was cooled to 0° C. and sodium hydride (60% in mineral oil, 0.60 g, 15.0 mmol) was added in small portions. The resulting mixture was stirred for 15 minutes at 0° C. and then O-diphenylphosphinylhydroxylamine (3.50 g, 15.0 mmol) was added at 0° C. The reaction mixture was stirred at 0° C. for 30 minutes, then allowed to gradually warm to room temperature and stirred for 14 h. The majority of the THF was removed under reduced pressure and saturated sodium chloride solution (75 ml) was added. The aqueous phase was extracted with ethyl acetate (2×150 ml) and the combined organic extracts were dried over sodium sulfate, filtered and concentrated under reduced pressure. The residue was purified by silica gel column chromatography using a gradient of 10% to 20% ethyl acetate in hexanes to afford tert-butyl 4-(aminooxy)-2,2-dimethyloxane-4-carboxylate 133 as a pale-yellow viscous oil (1.57 g, 64%).

$^1$H-NMR (400 MHz; $CDCl_3$): δ 5.30 (s, 2H), 3.84 (dd, J=11.5, 2.8 Hz, 1H), 3.71-3.66 (m, 1H), 2.00-1.93 (m, 2H), 1.89-1.83 (m, 1H), 1.80-1.76 (m, 1H), 1.51 (s, 9H), 1.33 (s, 3H), 1.22 (s, 3H).

Step 5: (2Z)-{2-[(tert-butoxycarbonyl)amino]-1,3-thiazol-4-yl}({[4-(tert-butoxycarbonyl)-2,2-dimethyloxan-4-yl]oxy}imino)acetic acid (134)

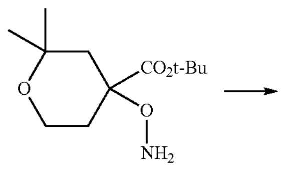

133

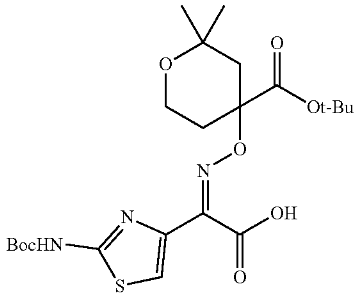

134

To a solution of tert-butyl 4-(aminooxy)-2,2-dimethyloxane-4-carboxylate 133 (0.86 g, 3.50 mmol) in anhydrous MeOH (20 ml) was added 2-(2-(tert-butoxycarbonylamino)thiazol-4-yl)-2-oxoacetic acid (0.90 g, 3.32 mmol) at room temperature. The reaction mixture was stirred at room temperature for 16 h and then concentrated under reduced pressure. The residue was further dried under high vacuum to afford (2Z)-{2-[(tert-butoxycarbonyl)amino]-1,3-thiazol-4-yl}({[4-(tert-butoxycarbonyl)-2,2-dimethyloxan-4-yl]oxy}imino)acetic acid 134 as an off-white solid (1.71 g, crude).

$^1$H-NMR (400 MHz; DMSO-d6): δ 11.77 (s, 1H), 7.34 (s, 1H), 3.69-3.63 (m, 1H), 3.58-3.53 (m, 1H), 1.90-1.83 (m, 2H), 1.69-1.65 (m, 1H), 1.45 (s, 9H), 1.37 (s, 9H), 1.20 (s, 3H), 1.11 (s, 3H).

MS (ESI) m/z: $[M+1]^+$ 499.9

Step 7: tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2,2-dimethyloxane-4-carboxylate

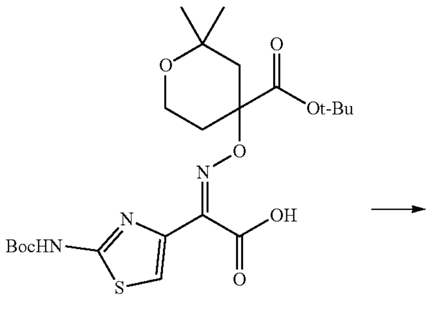

134

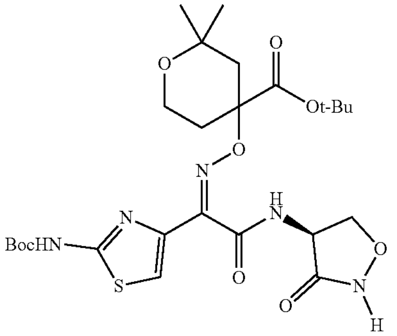

135

To a solution of (2Z)-{2-[(tert-butoxycarbonyl)amino]-1,3-thiazol-4-yl}({[4-(tert-butoxycarbonyl)-2,2-dimethyloxan-4-yl]oxy}imino)acetic acid 134 (1.67 g, 3.34 mmol) in anhydrous DMF (20 ml) was added N,N-diisopropylethyl amine (0.87 mL, 5.00 mmol). The resulting mixture was stirred for 10 minutes at room temperature, HATU (1.27 g, 3.34 mmol) was then added and stirring at room temperature was continued for 14 h. Subsequently, an additional 30 mL of anhydrous DMF followed by N,N-diisopropylethyl amine (2.3 mL, 13.20 mmol) was added, and the mixture was stirred for 10 minutes at room temperature. To this solution was added L-cycloserine (0.51 g, 5.01 mmol) and the reaction mixture was stirred for 2 h. The reaction mixture was then concentrated under reduced pressure and traces of DMF were removed by co-evaporation with toluene (3×10 ml). The residue was dissolved in DCM (100 ml) and the organic phase was washed with water (50 ml) and brine (30 ml), dried over sodium sulfate, filtered and concentrated under reduced pressure. The crude product was purified by silica gel column chromatography using a gradient of 0% to 4% methanol in dichloromethane to afford tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2,2-dimethyloxane-4-carboxylate 135 as an off-white solid (1.30 g, 67%).

$^1$H-NMR (400 MHz; DMSO-d6): δ 11.80 (d, J=5.7 Hz, 1H), 11.61-11.57 (m, 1H), 9.15 (t, J=7.1 Hz, 1H), 7.45 (s, 1H), 4.56-4.49 (m, 1H), 4.17-4.01 (m, 1H), 3.72-3.66 (m, 1H), 3.62-3.51 (m, 2H), 3.14-3.11 (m, 1H), 1.90-1.80 (m, 2H), 1.64-1.58 (m, 1H), 1.46 (s, 9H), 1.36 (s, 9H), 1.17 (s, 3H), 1.09 (s, 3H).

MS (ESI) m/z: $[M+1]^+$ 583.9

Step 8: tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-2,2-dimethyloxane-4-carboxylate (136)

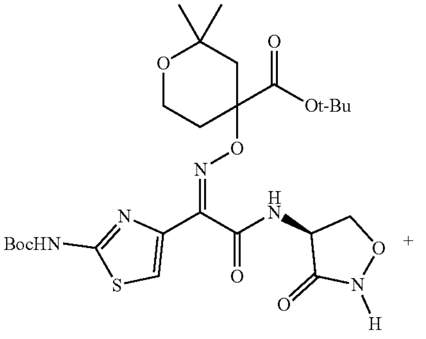

135

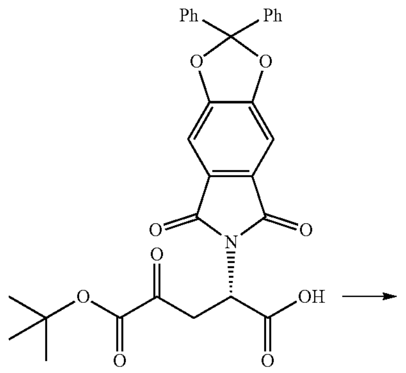

6

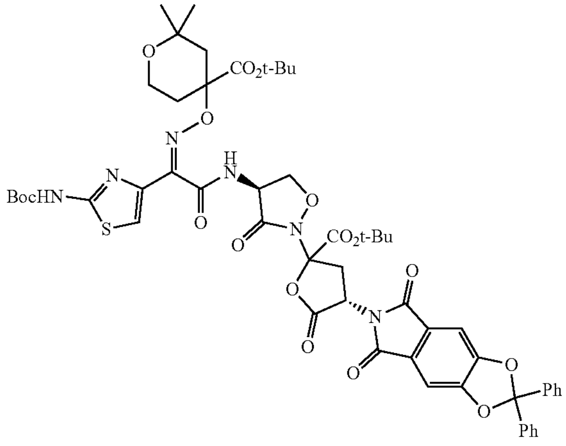

136

A mixture of tert-butyl 4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2,2-dimethyloxane-4-carboxylate 135 (0.435 g, 0.80 mmol) and (S)-5-(tert-butoxy)-2-(5,7-dioxo-2,2-diphenyl-5,7-dihydro-6H-[1,3]dioxolo[4,5-f]isoindol-6-yl)-4,5-dioxopentanoic acid 6 (0.467 g, 0.80 mmol, prepared as described in *J. Med. Chem.*, 2014, Vol. 57, pp. 3845-3855) in anhydrous THF (25 mL) was cooled to 0° C. DMAP (20 mg, 0.16 mmol) followed by DCC (0.231 g, 1.12 mmol) were added and the reaction mixture was stirred at 0° C. for 1 h. The reaction mixture was allowed to gradually warm to room temperature and was stirred overnight. The mixture was then concentrated under reduced pressure at 25° C. and the residue was triturated using 30% DCM in hexanes (40 mL). The separated urea by-products were removed by filtration and washed with 30% DCM in hexanes (15 mL) and then with hexanes. The combined filtrates were concentrated under reduced pressure and the residue was purified by silica gel column chromatography using a gradient of 10% to 40% ethyl acetate in hexanes to afford tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-2,2-dimethyloxane-4-carboxylate 136 as an off-white solid (0.428 g, 48%).

$^1$H-NMR (400 MHz; $CDCl_3$): δ 8.07-7.96 (m, 2H), 7.92-7.87 (m, 1H), 7.54-7.50 (m, 4H), 7.42-7.37 (m, 6H), 7.35-7.32 (m, 1H), 7.30 (s, 2H), 5.39-5.33 (m, 1H), 5.17-4.89 (m, 2H), 4.24-4.18 (m, 1H), 3.91-3.80 (m, 1H), 3.77-3.64 (m, 1H), 3.53-3.27 (m, 2H), 2.89-2.75 (m, 1H), 2.23-2.09 (m, 2H), 1.98-1.81 (m, 2H), 1.58 (s, 9H), 1.54 (s, 9H), 1.43 (s, 9H), 1.30-1.22 (m, 6H).

MS (ESI) m/z: $[M+1]^+$ 1108.7

Step 9: 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,2-dimethyloxane-4-carboxylic acid (Compound 41)

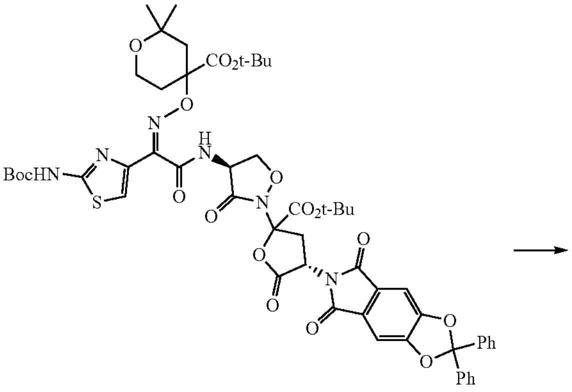

136

-continued

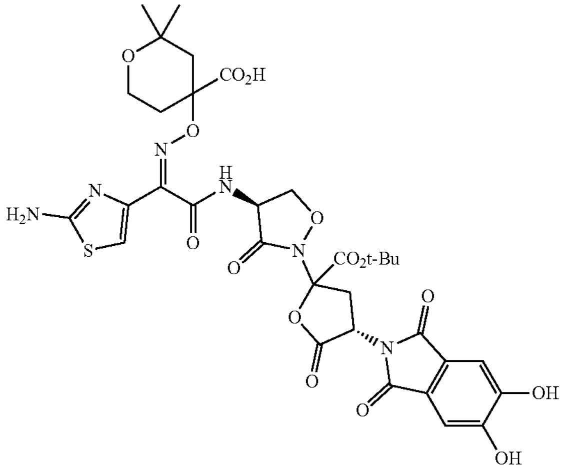

Compound 41

A solution of tert-butyl 4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-2,2-dimethyloxane-4-carboxylate 136 (420 mg, 0.378 mmol) in anhydrous DCM (20 mL) was cooled to −50° C. under a nitrogen atmosphere and boron trichloride (1.0 M in DCM, 3.0 mL, 3.0 mmol) was added dropwise at −50° C. The reaction mixture was stirred at −45° C. to −30° C. for 2.5 h, then cooled to −50° C. and quenched by addition of 36 mL of a buffer solution (prepared by dissolving 776 mg of $NaHCO_3$ and 243 mg of $Na_2HPO_4$ in 42 mL of water). The cold bath was replaced with an ice-water bath to allow the frozen mixture to thaw and separate into two layers. The dichloromethane layer was carefully separated and the aqueous phase was filtered through a 1 μm syringe filter and purified immediately by C18 reverse phase chromatography using a Biotage system and mixtures of 0.1% formic acid in acetonitrile and 0.1% formic acid in water as eluents to afford 4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,2-dimethyloxane-4-carboxylic acid Compound 41 as a pale yellow foamy solid (90 mg, 32%).

$^1$H-NMR (400 MHz; a mixture of $D_2O$ and $CD_3CN$): δ 7.23 (s, 1H), 7.10 (s, 1H), 5.43-5.27 (m, 1H), 5.16-4.98 (m, 1H), 4.76-4.59 (m, 1H), 4.36-4.17 (m, 3H), 3.74-3.62 (m, 2H), 3.41-3.19 (m, 1H), 2.81-2.60 (m, 1H), 2.48-2.31 (m, 2H), 2.08-2.01 (m, 1H), 1.48-1.41 (s, 3H), 1.19-1.10 (s, 3H). 7 exchangeable protons were not observed.

MS (ESI) m/z: $[M+1]^+$ 732.7

Example 24

(2R,6R)-4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,6-dimethyloxane-4-carboxylic acid (Compound 42, Table 1)

Compound 42

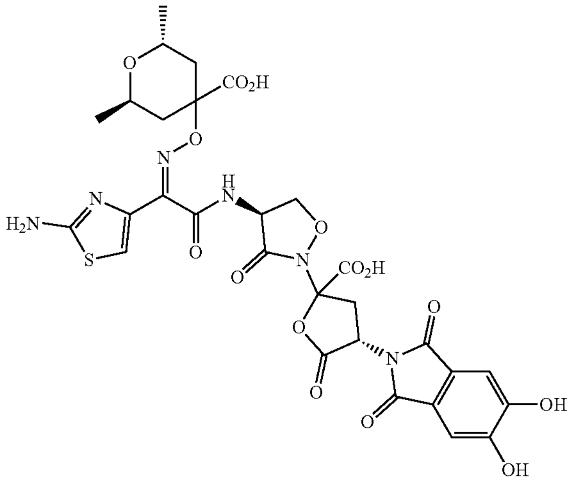

Step 1: (2R,6R)-2,6-dimethyl-4-[(trimethylsilyl)oxy]oxane-4-carbonitrile (138)

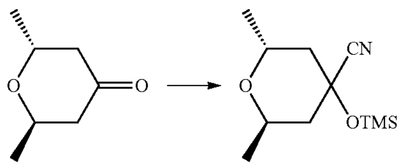

137 138

Zinc iodide (51 mg, 0.16 mmol) was placed in a dry round-bottom flask and dried under high vacuum (with gentle heating) for 30 minutes. A solution of (2R,6R)-2,6-dimethyloxan-4-one 137 (1.02 g, 8.00 mmol, prepared as described in *Org. Process Res. Dev.*, 2015, 19(10), 1360-1368) in anhydrous DCM (20 ml) was added and the resulting mixture was cooled to 0° C. under a nitrogen atmosphere. Trimethylsilyl cyanide (1.20 mL, 9.60 mmol) was added slowly at 0° C., then the ice-bath was removed, and stirring was continued at room temperature for 2 h. The reaction mixture was concentrated under reduced pressure and the residue was triturated with 10% DCM in hexanes (100 mL). The precipitated solids were removed by filtration and the filtrate was collected and concentrated. The residue was further dried under high vacuum to afford (2R,6R)-2,6-dimethyl-4-[(trimethylsilyl)oxy]oxane-4-carbonitrile 138 as a light brown oil (1.89 g, crude).

$^1$H-NMR (400 MHz; $CDCl_3$): δ 4.23-4.08 (m, 2H), 2.15 (ddd, J=13.5, 4.3, 1.0 Hz, 1H), 1.98-1.88 (m, 2H), 1.74-1.68 (m, 1H), 1.34 (d, J=1.9 Hz, 3H), 1.32 (d, J=1.8 Hz, 3H), 0.29-0.27 (s, 9H).

Step 2: (2R,6R)-4-hydroxy-2,6-dimethyloxane-4-carboxylic acid (139)

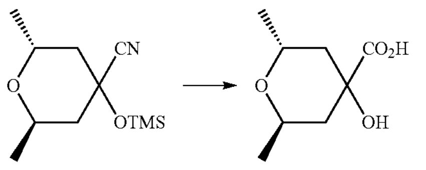

138 139

Glacial acetic acid (10 ml) was added to (2R,6R)-2,6-dimethyl-4-[(trimethylsilyl)oxy]oxane-4-carbonitrile 138 (1.87 g, 8.00 mmol) and the resulting mixture was cooled to 0° C. Concentrated hydrochloric acid (10 ml) was then added dropwise over a period of 10 minutes. The reaction mixture was stirred at 0° C. for 15 minutes, then at room temperature for 15 minutes, and was subsequently heated and stirred at 110° C. for 3 h. The reaction mixture was allowed to cool to room temperature and the volatiles were removed under reduced pressure. The residue was dissolved in water (50 mL) and the aqueous phase was saturated using solid sodium chloride, and then extracted with ethyl acetate (2×50 ml). The combined organic extracts were washed with water and brine, dried over sodium sulfate, filtered and concentrated under reduced pressure. The residue was further dried under high vacuum to afford (2R,6R)-4-hydroxy-2,6-dimethyloxane-4-carboxylic acid 139 as a brown viscous liquid (1.41 g, crude).

$^1$H-NMR (400 MHz; $CDCl_3$): δ 4.35-4.28 (m, 1H), 4.22-4.14 (m, 1H), 2.32-2.27 (m, 1H), 1.88-1.81 (m, 1H), 1.70-1.65 (m, 1H), 1.60-1.56 (m, 1H), 1.47 (d, J=7.0 Hz, 3H), 1.22 (d, J=6.3 Hz, 3H).

MS (ESI) m/z: $[M-1]^-$ 173.0

Step 3: tert-butyl (2R,6R)-4-hydroxy-2,6-dimethyloxane-4-carboxylate (140)

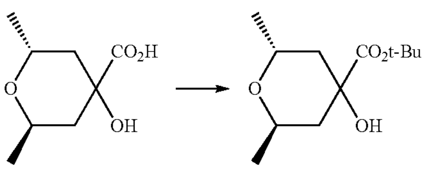

139 140

To a solution of (2R,6R)-4-hydroxy-2,6-dimethyloxane-4-carboxylic acid 139 (1.38 g crude, 8.00 mmol) in anhydrous THF (20 mL) was added tert-butyl N,N'-diisopropylcarbamimidate (4.8 g, 24.0 mmol, prepared as described in EP2471792A1). The reaction mixture was stirred at room temperature for 14 h. The precipitated solids were removed by filtration and washed with THF, and the combined filtrates were concentrated under reduced pressure. The residue was treated with a mixture of DCM and hexanes (1:3, 20 ml) and the resulting suspension was cooled in an ice-water bath for 10 minutes. The precipitated solids were filtered off and washed with 25% DCM in hexanes (20 ml). The filtrates were combined and concentrated. The crude product was purified by silica gel column chromatography using a gradient of 10% to 20% diethyl ether in hexanes to afford tert-butyl (2R,6R)-4-hydroxy-2,6-dimethyloxane-4-carboxylate 140 as a yellow oil (1.10 g, 60% yield for three steps).

$^1$H-NMR (400 MHz; $CDCl_3$): δ 4.30-4.22 (m, 1H), 4.18-4.10 (m, 1H), 3.28 (s, 1H), 2.25-2.16 (m, 1H), 1.73 (dd, J=13.3, 11.0 Hz, 1H), 1.57-1.52 (m, 1H), 1.50 (s, 9H), 1.49-1.47 (m, 1H), 1.46 (d, J=7.0 Hz, 3H), 1.19 (d, J=6.3 Hz, 3H).

Step 4: tert-butyl (2R,6R)-4-(aminooxy)-2,6-dimethyloxane-4-carboxylate (141)

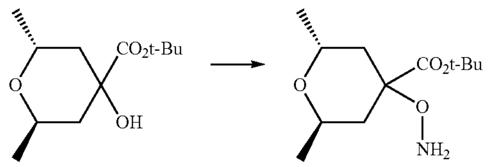

140 141

A solution of tert-butyl (2R,6R)-4-hydroxy-2,6-dimethyloxane-4-carboxylate 140 (1.10 g, 4.77 mmol) in anhydrous THF (80 mL) was cooled to 0° C. and sodium hydride (60% in mineral oil, 0.286 g, 7.16 mmol) was added in small portions. The resulting mixture was stirred for 15 minutes at 0° C. and then O-diphenylphosphinylhydroxylamine (1.67 g, 7.16 mmol) was added. The reaction mixture was stirred at 0° C. for 30 minutes, then allowed to gradually warm to room temperature and stirred for 14 h. To complete the reaction, additional amounts of sodium hydride (95 mg, 2.38 mmol) and O-diphenylphosphinylhydroxylamine (560 mg, 2.40 mmol) were added and the mixture was stirred at room temperature for 2 h. Subsequently, the reaction mixture was concentrated, and the residue was taken in saturated sodium chloride solution (75 ml). The aqueous phase was extracted with ethyl acetate (2×75 ml), and the combined organic extracts were dried over sodium sulfate, filtered, and concentrated under reduced pressure. The crude product was purified by silica gel column chromatography using a gradient of 10% to 20% ethyl acetate in hexanes to afford tert-butyl (2R,6R)-4-(aminooxy)-2,6-dimethyloxane-4-carboxylate 141 as a pale-yellow viscous oil (0.50 g, 42% yield).

$^1$H-NMR (400 MHz; $CDCl_3$): δ 5.28 (s, 2H), 4.19-4.10 (m, 1H), 4.01-3.93 (m, 1H), 2.13-2.08 (m, 1H), 1.99-1.94 (m, 1H), 1.85-1.80 (m, 1H), 1.65-1.56 (m, 1H), 1.48 (s, 9H), 1.34 (t, J=5.5 Hz, 3H), 1.16 (t, J=5.5 Hz, 3H).

Step 5: (2Z)-{2-[(tert-butoxycarbonyl)amino]-1,3-thiazol-4-yl}({[(2R,6R)-4-(tert-butoxycarbonyl)-2,6-dimethyloxan-4-yl]oxy}imino)acetic acid (142)

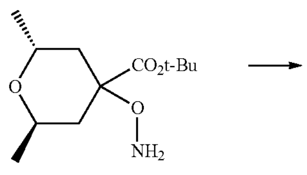

141

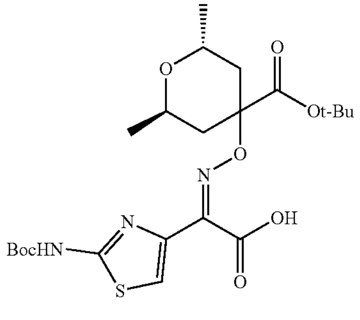

142

To a solution of tert-butyl (2R,6R)-4-(aminooxy)-2,6-dimethyloxane-4-carboxylate 141 (0.49 g, 2.00 mmol) in anhydrous methanol (12 ml) was added 2-(2-(tert-butoxycarbonylamino)thiazol-4-yl)-2-oxoacetic acid (0.52 g, 1.90 mmol) at room temperature. The reaction mixture was stirred at room temperature for 16 h and then concentrated under reduced pressure. The residue was further dried under high vacuum to afford (2Z)-{2-[(tert-butoxycarbonyl)amino]-1,3-thiazol-4-yl}({[(2R,6R)-4-(tert-butoxycarbonyl)-2,6-dimethyloxan-4-yl]oxy}imino)acetic acid 142 as an off-white solid (0.98 g, crude).

$^{1}$H-NMR (400 MHz; DMSO-di): δ 11.33 (bs, 1H), 9.78 (s, 1H), 7.87 (s, 1H), 4.72-4.64 (m, 1H), 4.53-4.45 (m, 1H), 2.70-2.65 (m, 1H), 2.60-2.55 (m, 1H), 2.42-2.37 (m, 1H), 2.29-2.23 (m, 1H), 2.06 (s, 9H), 1.99 (s, 9H), 1.81 (d, J=6.9 Hz, 3H), 1.67 (d, J=6.3 Hz, 3H).

MS (ESI) m/z: $[M+1]^+$ 500.1

Step 7: tert-butyl (2R,6R)-4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2,6-dimethyloxane-4-carboxylate (143)

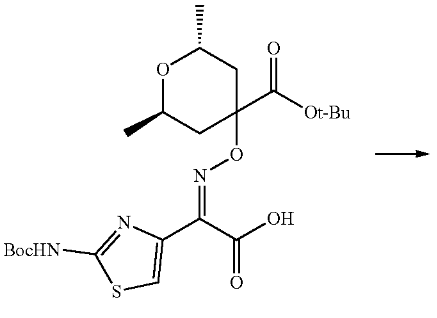

142

-continued

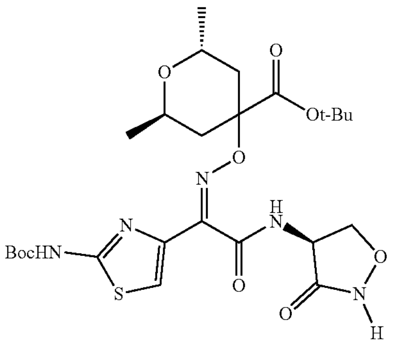

143

To a solution of (2Z)-{2-[(tert-butoxycarbonyl)amino]-1,3-thiazol-4-yl}({[(2R,6R)-4-(tert-butoxycarbonyl)-2,6-dimethyloxan-4-yl]oxy}imino)acetic acid 142 (0.97 g, 1.94 mmol) in anhydrous DMF (12 ml) was added N,N-diisopropylethyl amine (0.5 mL, 2.91 mmol). The resulting mixture was stirred for 10 minutes at room temperature, then HATU (0.74 g, 1.94 mmol) was added and stirring at room temperature was continued for 14 h. An additional 30 ml of anhydrous DMF followed by N,N-diisopropylethyl amine (1.35 mL, 7.76 mmol) was added and the mixture was stirred for 10 minutes at room temperature. Subsequently, L-cycloserine (0.30 g, 2.91 mmol) was added and the reaction mixture was stirred for 2 h, and then concentrated under reduced pressure. Traces of DMF were removed by co-evaporation with toluene (3×10 ml). The residue was dissolved in DCM (100 ml), the organic phase was washed with water (50 mL) and brine (30 mL), dried over sodium sulfate, filtered and concentrated. The crude product was purified by silica gel column chromatography using a gradient of 0% to 5% methanol in dichloromethane to afford tert-butyl (2R,6R)-4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2,6-dimethyloxane-4-carboxylate 143 as an off-white solid (0.604 g, 53%).

$^{1}$H-NMR (400 MHz; DMSO-$d_6$): δ 9.16-9.14 (d, 1H), 7.96 (s, 1H), 7.46 (s, 1H), 4.87-4.78 (m, 1H), 4.57-4.52 (m, 1H), 4.18-4.13 (m, 1H), 4.08-4.00 (m, 1H), 3.97-3.85 (m, 1H), 2.01-1.95 (m, 2H), 1.74-1.70 (m, 1H), 1.64-1.58 (m, 1H), 1.47 (s, 9H), 1.39 (s, 9H), 1.20 (d, J=6.9 Hz, 3H), 1.06 (d, J=6.3 Hz, 3H).

MS (ESI) m/z: $[M+1]^+$ 584.1

Step 8: tert-butyl (2R,6R)-4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-2,6-dimethyloxane-4-carboxylate (144)

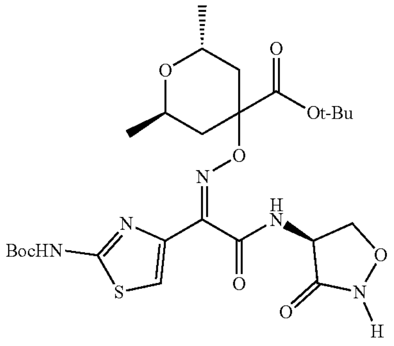

143

+

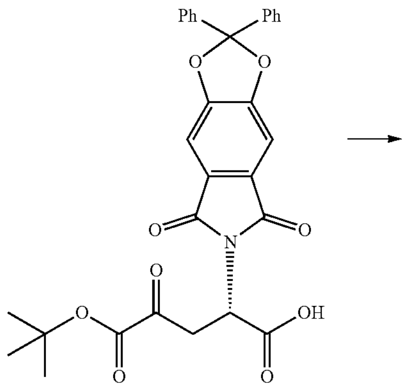

6

-continued

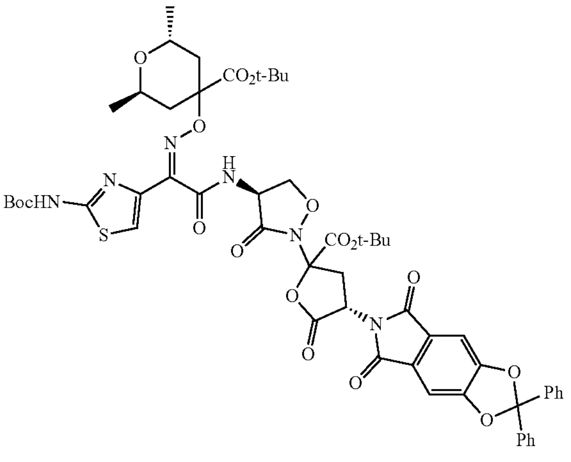

144

A mixture of tert-butyl (2R,6R)-4-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-2,6-dimethyloxane-4-carboxylate 143 (0.60 g, 1.02 mmol) and (S)-5-(tert-butoxy)-2-(5,7-dioxo-2,2-diphenyl-5,7-dihydro-6H-[1,3]dioxolo[4,5-f]isoindol-6-yl)-4,5-dioxopentanoic acid 6 (0.55 g, 1.02 mmol, prepared as described in J. Med. Chem., 2014, Vol. 57, pp. 3845-3855) in anhydrous THF (30 ml) was cooled to 0° C. under nitrogen atmosphere. DMAP (25 mg, 0.20 mmol) followed by DCC (0.29 g, 1.43 mmol) were added and the reaction mixture was stirred at 0° C. for 1 h and then at room temperature overnight. The reaction mixture was concentrated under reduced pressure at 25° C. The residue was triturated with 30% DCM in hexanes (40 ml), the urea by-products were removed by filtration and washed with 30% DCM in hexanes (15 mL) followed by hexanes. The filtrates were combined and concentrated under reduced pressure, and the crude mixture was purified by silica gel column chromatography using 20-40% EtOAc in hexanes to give tert-butyl (2R,6R)-4-({(Z)-[1-{2-[(tert-butoxycarbonyl)amino]-1,3-thiazol-4-yl}-2-({(4S)-2-[(4S)-2-(tert- butoxycarbonyl)-4-(5,7-dioxo-2,2-diphenyl-5,7-dihydro-2H,6H-[1,3]dioxolo[4,5-f]isoindol-6-yl)-5-oxooxolan-2-yl]-3-oxo-1,2-oxazolidin-4-yl}amino)-2-oxoethylidene]amino}oxy)-2,6-dimethyloxane-4-carboxylate 144 as an off-white solid (0.586 g, 52%).

$^1$H-NMR (400 MHz; $CDCl_3$): δ 8.08-8.02 (m, 1H), 8.01-7.97 (m, 1H), 7.58-7.53 (m, 4H), 7.46-7.41 (m, 6H), 7.35 (d, J=4.1 Hz, 1H), 7.34-7.32 (m, 2H), 5.41-5.36 (m, 1H), 5.23-4.92 (m, 3H), 4.28-4.21 (m, 1H), 4.07-4.01 (m, 1H), 3.43-3.30 (m, 1H), 2.90-2.83 (m, 1H), 2.34-2.20 (m, 2H), 2.13-2.07 (m, 1H), 1.82-1.74 (m, 1H), 1.60-1.57 (m, 9H), 1.57-1.53 (m, 9H), 1.47-1.43 (m, 9H), 1.35-1.30 (m, 3H), 1.24-1.19 (m, 3H).

Step 9: (2R,6R)-4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,6-dimethyloxane-4-carboxylic acid (Compound 42)

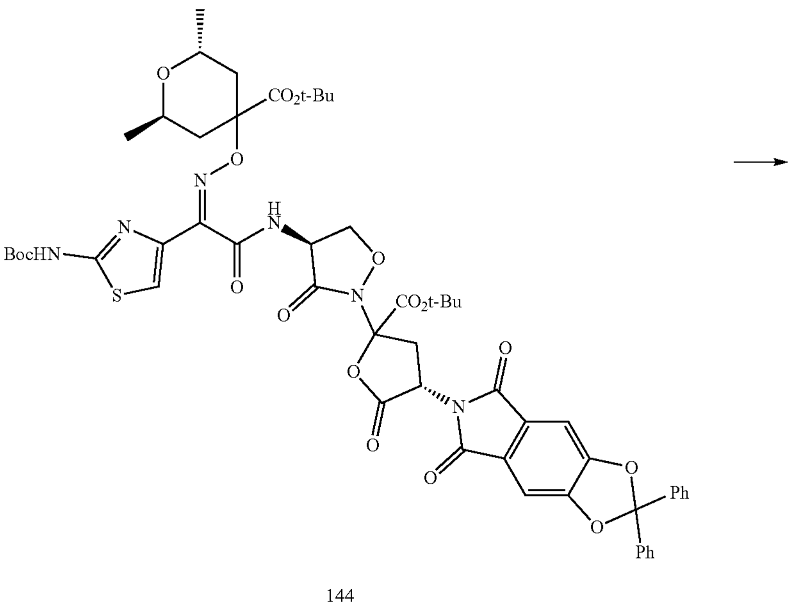

144

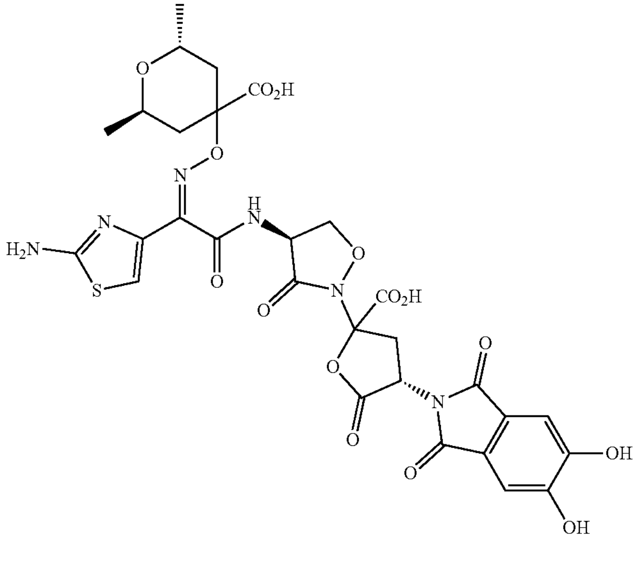

Compound 42

A solution of tert-butyl (2R,6R)-4-({(Z)-[1-{2-[(tert-butoxycarbonyl)amino]-1,3-thiazol-4-yl}-2-({(4S)-2-[(4S)-2-(tert-butoxycarbonyl)-4-(5,7-dioxo-2,2-diphenyl-5,7-dihydro-2H,6H-dioxolo[4,5-f]isoindol-6-yl)-5-oxooxolan-2-yl]-3-oxo-1,2-oxazolidin-4-yl}amino)-2-oxoethylidene]amino}oxy)-2,6-dimethyloxane-4-carboxylate 144 (545 mg, 0.49 mmol) in anhydrous DCM (25 ml) was cooled to −50° C. under nitrogen atmosphere. Boron trichloride (1.0 M in DCM, 4.0 mL, 3.93 mmol) was added dropwise at −50° C. and the reaction mixture was stirred at −45 to −30° C. for 2.5 h. The reaction mixture was cooled to −50° C. and quenched by addition of 50 mL of a buffer solution (prepared by dissolving 776 mg of $NaHCO_3$ and 243 mg of $Na_2HPO_4$ in 42 mL of water). The cold bath was replaced with an ice-water bath to allow the frozen mixture to thaw and the layers to separate. The dichloromethane layer was carefully removed and the aqueous phase was collected, filtered through a 1 μm syringe filter and purified immediately by C18 reverse phase chromatography using a Biotage system and mixtures of 0.1% formic acid in acetonitrile and 0.1% formic acid in water as eluents to afford (2R,6R)-4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,6-dimethyloxane-4-carboxylic acid Compound 42 as a pale-yellow foam (140 mg, 39%).

$^1$H-NMR (400 MHz; a mixture of $D_2O$ and $CD_3CN$): δ 7.25-7.21 (m, 2H), 7.12-7.08 (m, 1H), 5.41-5.31 (m, 1H), 5.17-5.03 (m, 1H), 4.73-4.61 (m, 1H), 4.42-4.35 (m, 1H), 4.32-4.21 (m, 1H), 4.21-4.10 (m, 1H), 3.99-3.86 (m, 1H), 3.41-3.25 (m, 1H), 2.81-2.66 (m, 1H), 2.20-2.04 (m, 2H), 1.75-1.64 (m, 1H), 1.16 (d, J=5.4 Hz, 3H), 1.08 (d, J=6.2 Hz, 3H). 7 exchangeable protons were not observed.

MS (ESI) m/z: $[M+1]^+$ 733.0

Example 25

(4S)-2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid (Compound 43, Table 1)

Compound 43

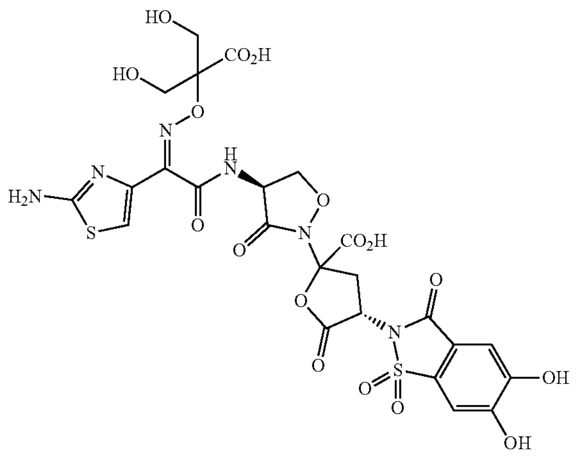

Step 1. tert-butyl 2-(hydroxymethyl)prop-2-enoate (146)

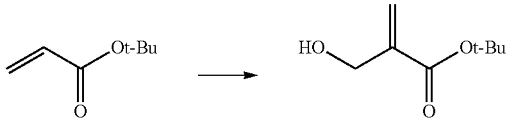

145 146

To a solution of tert-butyl acrylate 145 (22.8 mL, 155.65 mmol) in a mixture of 1,4-dioxane (500 ml) and water (500 mL) was added DABCO (52.4 g, 467.15 mmol) followed by aqueous formaldehyde solution (37% w/w, 38 mL, 510.34 mmol). The reaction mixture was stirred at room temperature for 48 h and then diluted with diethyl ether (600 ml). The layers were separated, and the organic phase was washed with brine (2×400 ml). The combined aqueous layers were re-extracted with diethyl ether (3×400 mL). The combined organic extracts were dried over sodium sulfate, filtered and concentrated under reduced pressure. The residue was purified by silica gel column chromatography using a gradient of 10% to 25% ethyl acetate in hexanes to afford tert-butyl 2-(hydroxymethyl)prop-2-enoate 146 (19.82 g, 80%) as a light-yellow oil.

$^1$H NMR (400 MHz, $CDCl_3$) δ 6.18-6.17 (m, 1H), 5.76 (q, J=1.4 Hz, 1H), 4.32-4.30 (m, 2H), 2.33 (t, J=6.6 Hz, 1H), 1.53 (s, 9H).

Step 2. tert-butyl 2-({[tert-butyl(dimethyl)silyl]oxy}methyl)prop-2-enoate (147)

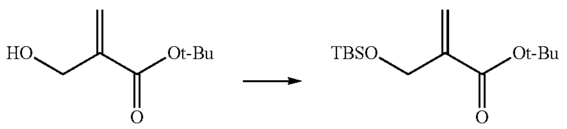

146 147

A solution of tert-butyl 2-(hydroxymethyl)prop-2-enoate 146 (9.01 g, 56.95 mmol) in anhydrous dichloromethane (240 ml) was cooled to 0° C. and then imidazole (5.82 g, 85.49 mmol) followed by a solution of TBSCl (10.30 g, 68.35 mmol) in dichloromethane (60 mL) was added. The reaction mixture was allowed to warm gradually to room temperature and was stirred for 2 h. The reaction mixture was concentrated under reduced pressure and the residue was taken in water. The aqueous phase was extracted with diethyl ether, and the combined organic extracts were dried over sodium sulfate, filtered, and concentrated. The crude product was purified by silica gel column chromatography using a gradient of 0% to 3% ethyl acetate in hexanes to afford tert-butyl 2-({[tert-butyl(dimethyl)silyl]oxy}methyl)prop-2-enoate 147 (14.31 g, 92%) as a colorless oil.

$^1$H NMR (400 MHz, $CDCl_3$) δ 6.17 (q, J=2.0 Hz, 1H), 5.84 (q, J=2.1 Hz, 1H), 4.35 (t, J=2.1 Hz, 2H), 1.51 (s, 9H), 0.94 (s, 9H), 0.11 (s, 6H).

Step 3. tert-butyl 2-({[tert-butyl(dimethyl)silyl]oxy}methyl)-2,3-dihydroxypropanoate (148)

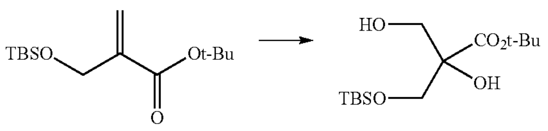

147 148

To a solution of tert-butyl 2-({[tert-butyl(dimethyl)silyl]oxy}methyl)prop-2-enoate 147 (13.40 g, 49.18 mmol) in a mixture of acetone (80 ml) and water (20 ml) was added $K_2OsO_4 \cdot 2H_2O$ (181 mg, 0.49 mmol), followed by NMO (11.52 g, 98.34 mmol). The reaction mixture was stirred at room temperature for 2 h and then quenched with an aqueous solution of sodium thiosulfate (36.70 g, 147.93 mmol). The reaction mixture was concentrated to remove most of the acetone. The aqueous phase was then extracted with ethyl acetate and the combined organic extracts were dried over sodium sulfate, filtered, and concentrated under reduced pressure. The residue was purified by silica gel column chromatography using a gradient of 5% to 25% ethyl acetate in hexanes to afford tert-butyl 2-({[tert-butyl (dimethyl)silyl]oxy}methyl)-2,3-dihydroxypropanoate 148 (14.77 g, 98%) as a light brown solid.

$^1$H NMR (400 MHz, $CDCl_3$) δ 3.83 (d, J=10.0 Hz, 1H), 3.79-3.73 (m, 1H), 3.67-3.61 (m, 2H), 3.60 (s, 1H), 2.14 (dd, J=8.8, 4.9 Hz, 1H), 1.52 (s, 9H), 0.90 (s, 9H), 0.08 (s, 3H), 0.07 (s, 3H).

MS (ESI) m/z: $[M+Na]^+$ 329.1

Step 4. tert-butyl 3-{[tert-butyl(dimethyl)silyl]oxy}-2-({[tert-butyl(dimethyl)silyl]oxy}methyl)-2-hydroxypropanoate (149)

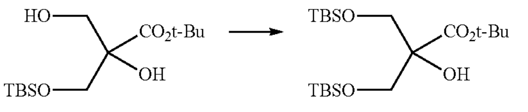

148 149

A solution of tert-butyl 2-({[tert-butyl(dimethyl)silyl]oxy}methyl)-2,3-dihydroxypropanoate 148 (14.77 g, 48.19 mmol) in anhydrous DCM (190 ml) was cooled to 0° C. and imidazole (4.92 g, 72.27 mmol) followed by a solution of TBSCl (8.72 g, 57.86 mmol) in DCM (50 ml) was added. The reaction mixture was stirred at 0° C. for 15 min, then the cooling bath was removed and stirring was continued at room temperature for 6 h. The reaction mixture was concentrated under reduced pressure and the residue was diluted with water. The aqueous phase was extracted with diethyl ether and the combined organic extracts were dried over sodium sulfate, filtered, and concentrated. The crude product was purified by silica gel column chromatography using a gradient of 0% to 3% ethyl acetate in hexanes to afford tert-butyl 3-{[tert-butyl(dimethyl)silyl]oxy}-2-({[tert-butyl(dimethyl)silyl]oxy}methyl)-2-hydroxypropanoate 149 (20.01 g, 99%) as a colorless oil.

$^1$H NMR (400 MHz, $CDCl_3$) δ 3.79-3.77 (m, 2H), 3.61 (d, J=9.9 Hz, 2H), 3.36 (s, 1H), 1.47 (s, 9H), 0.87 (s, 19H), 0.05 (s, 6H), 0.04 (s, 6H).

MS (ESI) m/z: $[M+Na]^+$ 443.2

Step 5. tert-butyl 2-(aminooxy)-3-{[tert-butyl(dimethyl)silyl]oxy}-2-({[tert-butyl(dimethyl)silyl]oxy}methyl)propanoate (150)

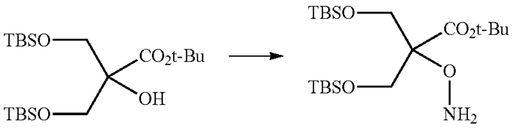

149 150

To a solution of tert-butyl 3-{([tert-butyl(dimethyl)silyl]oxy}-2-({[tert-butyl(dimethyl)silyl]oxy}methyl)-2-hydroxypropanoate 149 (4.91 g, 11.67 mmol) in anhydrous THE (90 mL) was added sodium hydride (60% in mineral oil, 700 mg, 17.50 mmol) at 0° C. The resulting mixture was stirred at 0° C. for 15 min and then O-diphenylphosphinylhydroxylamine (4.08 g, 17.50 mmol) was added. The reaction mixture was allowed to warm gradually to room temperature and stirred for 4 h. To complete the reaction, an additional portion of sodium hydride (60% in mineral oil, 233 mg, 5.83 mmol) was added at 0° C. The mixture was then stirred at 0° C. for 15 min, an additional O-diphenylphosphinylhydroxylamine (1.36 g, 5.83 mmol) was added and stirring was continued at room temperature overnight. The reaction mixture was then cooled to 0° C., and brine (45 ml) and hexanes (45 ml) were added. The resulting mixture was stirred at 15-25° C. for 30 min and the precipitated solid was filtered off. The filtrate was extracted with ethyl acetate, and the combined organic extracts were washed with brine, dried over sodium sulfate, filtered, and concentrated under reduced pressure. The residue was treated with 5% DCM in hexanes and the precipitated solids were removed by filtration. The filtrate was concentrated under reduced pressure to afford crude tert-butyl 2-(aminooxy)-3-{[tert-butyl(dimethyl)silyl]oxy}-2-({[tert-butyl(dimethyl)silyl]oxy}methyl)propanoate 150 (5.41 g, quantitative) as a yellow oil.

$^1$H NMR (400 MHz, $CDCl_3$) δ 5.29 (bs, 2H), 3.94 (d, J=10.0 Hz, 2H), 3.76 (d, J=10.0 Hz, 2H), 1.48 (s, 9H), 0.88 (s, 18H), 0.05 (s, 6H), 0.05 (s, 6H).

MS (ESI) m/z: $[M+1]^+$ 436.2

Step 6. (2Z)-5-(tert-butoxycarbonyl)-2-{2-[(tert-butoxycarbonyl)amino]-1,3-thiazol-4-yl}-5-({[tert-butyl(dimethyl)silyl]oxy}methyl)-8,8,9,9-tetramethyl-4,7-dioxa-3-aza-8-siladec-2-en-1-oic acid (151)

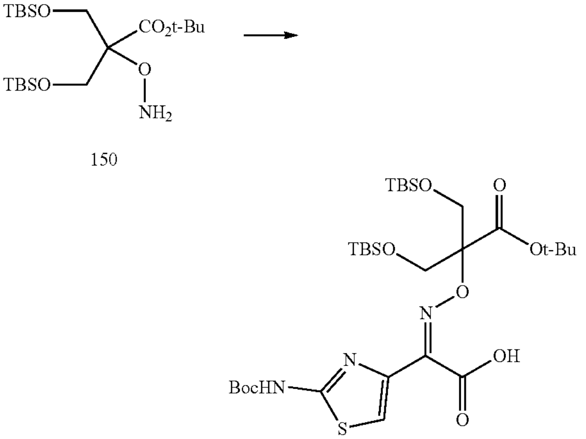

150

151

To solution of tert-butyl 2-(aminooxy)-3-{[tert-butyl(dimethyl)silyl]oxy}-2-({[tert-butyl(dimethyl)silyl]oxy}methyl)propanoate 150 (5.41 g, 11.67 mmol) in anhydrous methanol (35 ml) was added 2-(2-(tert-butoxycarbonylamino)thiazol-4-yl)-2-oxoacetic acid (2.76 g, 10.14 mmol) at room temperature. The reaction mixture was stirred at room temperature for 3 h and then quenched by addition of water (50 mL) and diluted hydrochloric acid (0.1 M, 50 ml). The mixture was extracted with ethyl acetate and the combined organic extracts were washed with brine, dried over sodium sulfate, filtered, and concentrated under reduced pressure. The crude product was treated with 5% diethyl ether in hexanes and the resulting mixture was stirred for 1 h at room temperature. The solids were collected by filtration to afford (2Z)-5-(tert-butoxycarbonyl)-2-{2-[(tert-butoxycarbonyl)amino]-1,3-thiazol-4-yl}-5-({[tert-butyl(dimethyl)silyl]oxy}methyl)-8,8,9,9-tetramethyl-4,7-dioxa-3-aza-8-siladec-2-en-1-oic acid 151 (5.27 g, 75%) as a white solid.

$^1$H NMR (400 MHz, DMSO-$d_6$) δ 13.72 (bs, 1H), 11.75 (s, 1H), 7.34 (d, J=0.7 Hz, 1H), 3.94 (d, J=9.9 Hz, 2H), 3.80 (d, J=9.9 Hz, 2H), 1.45 (s, 9H), 1.35 (s, 9H), 0.82 (s, 18H), −0.00 (s, 6H), −0.01 (s, 6H).

Step 7. tert-butyl 2-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-3-{[tert-butyl(dimethyl)silyl]oxy}-2-({[tert-butyl(dimethyl)silyl]oxy}methyl)propanoate (152)

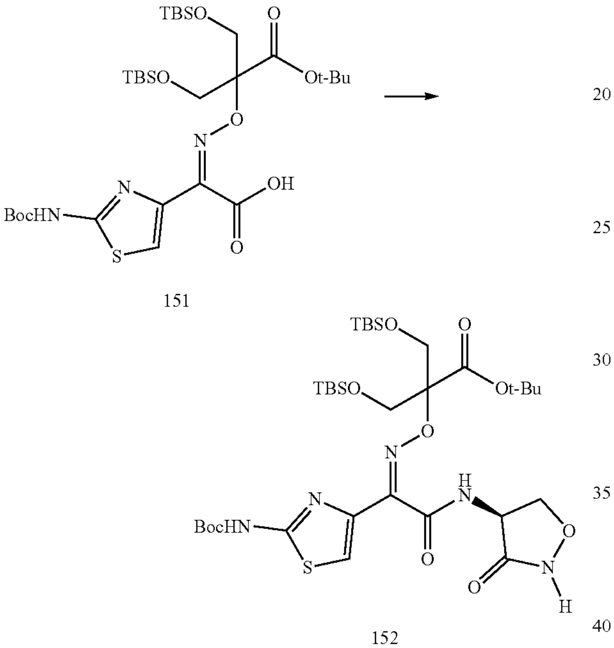

151

152

To a solution of (2Z)-5-(tert-butoxycarbonyl)-2-{2-[(tert-butoxycarbonyl)amino]-1,3-thiazol-4-yl}-5-({[tert-butyl(dimethyl)silyl]oxy}methy)-8,8,9,9-tetramethyl-4,7-dioxa-3-aza-8-siladec-2-en-1-oic acid 151 (5.30 g, 7.68 mmol) in anhydrous DMF (45 mL) was added HATU (2.98 g, 7.84 mmol) followed by DIPEA (2.0 mL, 11.48 mmol) and the reaction mixture was stirred at room temperature for 2 h. The mixture was then diluted with anhydrous DMF (45 ml) and L-cycloserine (863 mg, 8.45 mmol) followed by DIPEA (2.0 mL, 11.48 mmol) was added. The reaction mixture was stirred at room temperature for 21 h and then quenched by addition of water (300 ml). The resulting solution was extracted with a mixture of diethyl ether and ethyl acetate (ratio 3:2). The combined organic extracts were washed with brine, dried over sodium sulfate, filtered, and concentrated under reduced pressure. The residue was purified by silica gel column chromatography using a gradient of 0% to 25% acetonitrile in DCM to afford tert-butyl 2-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-3-([tert-butyl(dimethyl)silyl]oxy)-2-({[tert-butyl(dimethyl)silyl]oxy}methyl)propanoate 152 (3.98 g, 67%) as a white foam.

$^1$H NMR (400 MHz, DMSO-$d_6$) δ 11.80 (s, 1H), 11.59 (s, 1H), 8.81-8.68 (m, 1H), 7.48-7.32 (m, 1H), 4.94-4.87 (m, 1H), 4.59-4.54 (m, 1H), 4.07-3.72 (m, 5H), 1.45 (s, 9H), 1.36-1.32 (m, 9H), 0.83-0.80 (m, 18H), 0.02--0.04 (m, 12H).

MS (ESI) m/z: $[M+1]^+$ 774.2

Step 8. tert-butyl (4S)-2-{(4S)-4-[(2Z)-5-(tert-butoxycarbonyl)-2-{2-[(tert-butoxycarbonyl)amino]-1,3-thiazol-4-yl}-5-({[tert-butyl(dimethyl)silyl]oxy}methyl)-8,8,9,9-tetramethyl-4,7-dioxa-3-aza-8-siladec-2-enamido]-3-oxo-1,2-oxazolidin-2-yl}-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate (153)

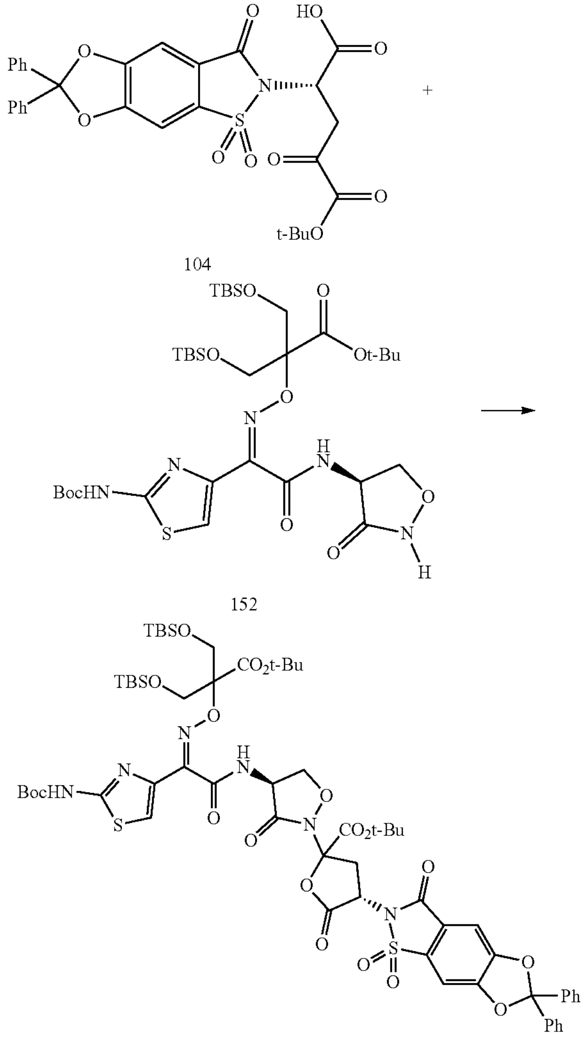

104

152

153

To a mixture of (2S)-5-tert-butoxy-4,5-dioxo-2-(1,1,3-trioxo-6,6-diphenyl-1,3-dihydro-2H,6H-1λ$^6$-[1,3]dioxolo[4,5-f][1,2]benzothiazol-2-yl)pentanoic acid 104 (1.18 g, 1.94 mmol, crude, prepared as described in Example 18) and tert-butyl 2-{[(Z)-(1-{2-[(tert-butoxycarbonyl)amino]-1,3-thiazol-4-yl}-2-oxo-2-{[(4S)-3-oxo-1,2-oxazolidin-4-yl]amino}ethylidene)amino]oxy}-3-{([tert-butyl(dimethyl)silyl]oxy}-2-({[tert-butyl(dimethyl)silyl]oxy}methyl)propanoate 152 (1.41 g, 1.82 mmol) in anhydrous THF (32 mL) was added DMAP (45 mg, 0.37 mmol), followed by DCC (526 mg, 2.55 mmol) at 0° C. The reaction mixture was allowed to gradually warm to room temperature and stirred for 19 h. The mixture was then concentrated under reduced pressure and the residue was treated with 25% DCM in hexanes. The precipitated solids were removed by filtration and the filtrate was concentrated. The residue was purified by silica gel column chromatography using a gradient of 5% to 23% ethyl acetate in hexanes to afford tert-butyl (4S)-2-{(4S)-4-[(2Z)-5-(tert-butoxycarbonyl)-2-{2-[(tert-butoxy-carbonyl)amino]-1,3-thiazol-4-yl}-5-({[tert-butyl(dimethyl)silyl]oxy}methyl)-8,8,9,9-tetramethyl-4,7-dioxa-3-aza-8-siladec-2-enamido]-3-oxo-1,2-oxazolidin-2-yl}-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate 153 (1.55 g, 64%) as a light-yellow foam.

$^1$H NMR (400 MHz, $CDCl_3$) δ 7.98-7.93 (m, 1H), 7.71-7.63 (m, 1H), 7.52-7.48 (m, 4H), 7.42-7.39 (m, 7H), 7.33-7.29 (m, 2H), 5.24-4.80 (m, 3H), 4.34-4.20 (m, 1H), 4.13-

3.93 (m, 4H), 3.75-3.42 (m, 1H), 2.97-2.85 (m, 1H), 1.54-1.48 (m, 18H), 1.44-1.42 (m, 9H), 0.85-0.83 (m, 18H), 0.03-0.01 (m, 12H).

Step 9. tert-butyl (4S)-2-[(4S)-4-{[(2Z)-2-{2-[(tert-butoxycarbonyl)amino]-1,3-thiazol-4-yl}-2-({[1-tert-butoxy-3-hydroxy-2-(hydroxymethyl)-1-oxopropan-2-yl]oxy}imino)acetyl]amino}-3-oxo-1,2-oxazolidin-2-yl]-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate (154)

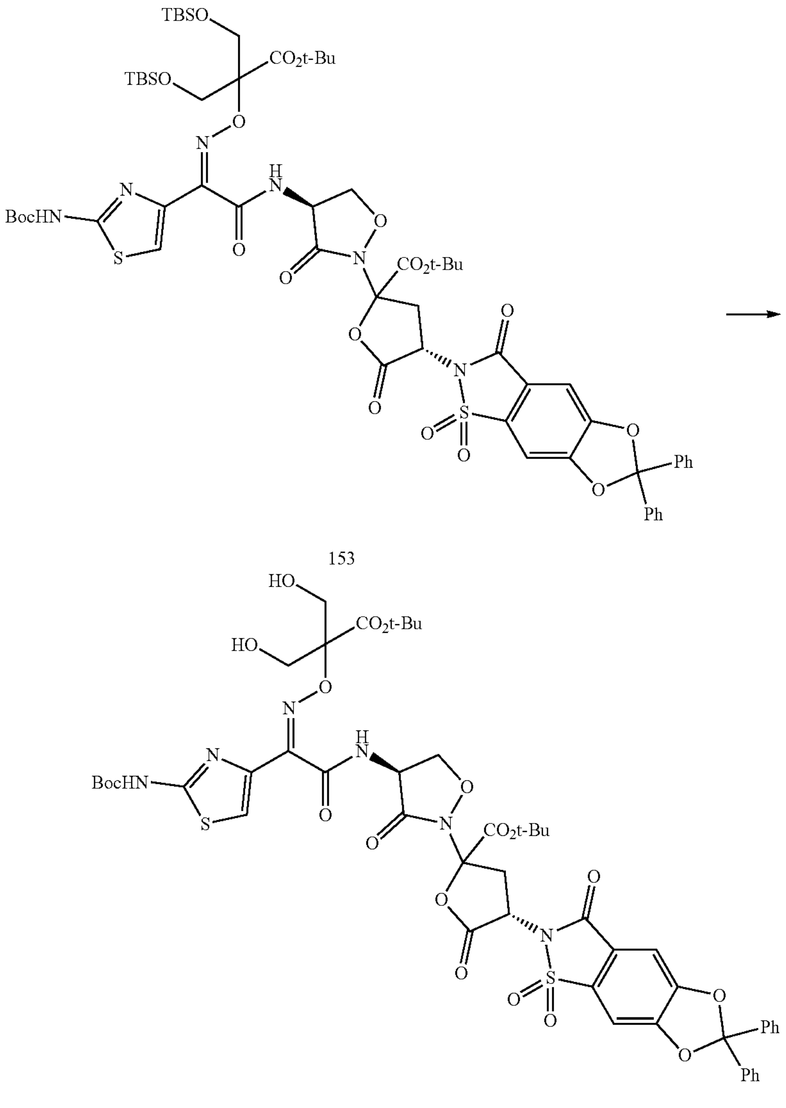

153

154

To a solution of tert-butyl (4S)-2-{(4S)-4-[(2Z)-5-(tert-butoxycarbonyl)-2-{2-[(tert-butoxycarbonyl)amino]-1,3-thiazol-4-yl}-5-({[tert-butyl(dimethyl)silyl]oxy}methyl)-8,8,9,9-tetramethyl-4,7-dioxa-3-aza-8-siladec-2-enamido]-3-oxo-1,2-oxazolidin-2-yl}-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate 153 (1.18 g, 0.88 mmol) in anhydrous MeOH (8 ml) was added acetyl chloride (0.04 ml, 0.56 mmol) at 0° C. The reaction mixture was stirred at 0° C. for 5 min and then at room temperature for 3 h. The reaction mixture was diluted with DCM and the organic phase was washed with water, dried over sodium sulfate, filtered, and concentrated under reduced pressure. The residue was purified by silica gel column chromatography using a gradient of 30% to 70% ethyl acetate in hexanes to afford tert-butyl (4S)-2-[(4S)-4-{[(2Z)-2-{2-[(tert-butoxycarbonyl)amino]-1,3-thiazol-4-yl}-2-({[1-tert-butoxy-3-hydroxy-2-(hydroxymethyl)-1-oxopropan-2-yl]oxy}imino)acetyl]amino}-3-oxo-1,2-oxazolidin-2-yl]-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate 154 (705 mg, 72%) as a white foam.

$^1$H NMR (400 MHz, $CDCl_3$) δ 8.58-8.44 (m, 1H), 7.56-7.51 (m, 4H), 7.47-7.42 (m, 7H), 7.40-7.39 (m, 1H), 7.34-7.33 (m, 1H), 5.25-4.74 (m, 3H), 4.48-4.36 (m, 1H), 4.13-3.98 (m, 4H), 3.72-3.43 (m, 1H), 3.00-2.88 (m, 1H), 1.57-1.55 (m, 18H), 1.52-1.51 (m, 9H).

Step 10. (4S)-2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid (Compound 43)

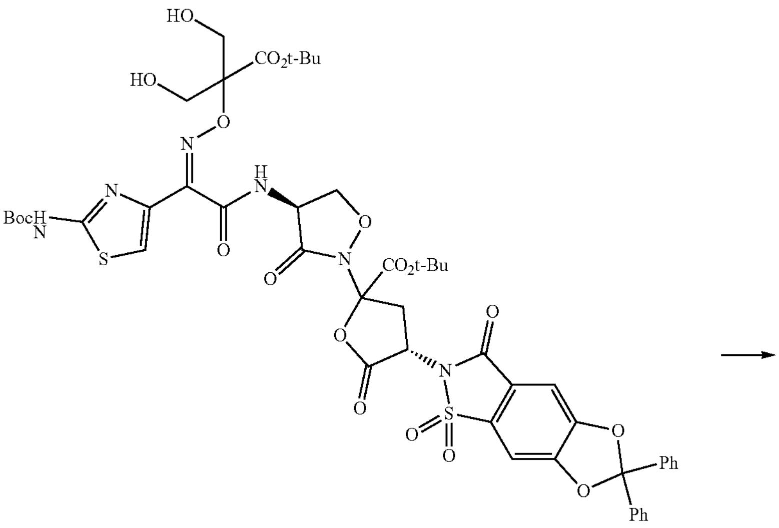

154

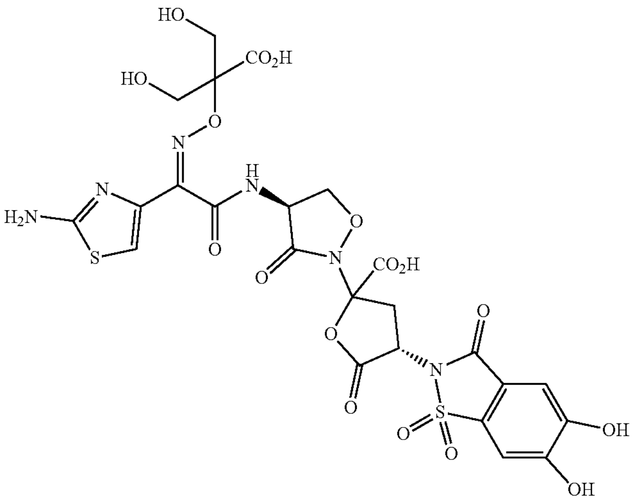

Compound 43

To a solution of tert-butyl (4S)-2-[(4S)-4-{[(2Z)-2-{2-[(tert-butoxycarbonyl)amino]-1,3-thiazol-4-yl}-2-({[1-tert-butoxy-3-hydroxy-2-(hydroxymethyl)-1-oxopropan-2-yl]oxy}imino)acetyl]amino}-3-oxo-1,2-oxazolidin-2-yl]-5-oxo-4-(1,1,3-trioxo-6,6-diphenyl-1,3-dihydro-2H,6H-1λ$^6$-[1,3]dioxolo[4,5-f][1,2]benzothiazol-2-yl)oxolane-2-carboxylate 154 (815 mg, 0.74 mmol) in anhydrous DCM (41 ml) was added dropwise boron trichloride (1.0 M in DCM, 6.63 ml, 6.63 mmol) at −50° C. The reaction mixture was stirred at −50° C. to −25° C. for 3 h and then $NaHCO_3$ (1.39 g) and $Na_2HPO_4$ (435 mg) dissolved in water (75 mL) were added at −50° C. The cooling bath was replaced with an ice-water bath, the mixture was stirred for 10 min at 0° C., and then at room temperature until the frozen phase thawed. The organic phase was carefully removed, and the aqueous layer was immediately subjected to C18 reverse phase chromatography using a Biotage system and mixtures of 0.1% formic acid in acetonitrile and 0.1% formic acid in water as eluents. The product-containing fractions were combined and lyophilized to afford (4S)-2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1,3-trioxo-1,3-dihydro-2H-1λ$^6$,2-benzothiazol-2-yl)-5-oxooxolane-2-carboxylic acid Compound 43 (339 mg, 63%) as a white solid.

$^1$H NMR (400 MHz, $D_2O$ and $CD_3CN$) δ 7.43 (s, 1H), 7.35 (s, 1H), 7.14-7.12 (m, 1H), 5.30-5.06 (m, 2H), 4.75-4.68 (m, 1H), 4.32-4.23 (m, 1H), 3.96-3.89 (m, 4H), 3.67-3.37 (m, 1H), 2.98-2.78 (m, 1H).

MS (ESI) m/z: $[M+H]^+$ 731.0

Biological Activity

Method for In Vitro Antibacterial Evaluation

Bacterial Isolates

Gram-negative and Gram-positive bacterial strains used during the in vitro minimum inhibitory concentration (MIC) determination were obtained either from the American Type Culture Collection (ATCC) or from clinical specimens. All strains were characterized genotypically and the respective antibiotic resistance markers for each strain were identified. Table 2 below represents the strains used and their respective resistance marker.

TABLE 2

Bacteria strains used for in vitro MIC testing

| Organism | Pos Molecular Tests |
|---|---|
| *Acinetobacter baumannii* | Wildtype |
| *Citrobacter freundli* species complex | OXA-181 |
| *Enterobacter cloacae* species complex | NDM-1 |
| *Escherichia coli* | Wildtype |
| *Escherichia coli* | pSMART_*Cfreundii*_AmpC |
| *Escherichia coli* | pSMART_*Ecloacae*_AmpC |
| *Escherichia coli* | Isogenic TEM-26 |
| *Escherichia coli* | Isogenic TEM-10 |
| *Escherichia coli* | CTX-M-15 |
| *Escherichia coli* | SHV-12 |
| *Escherichia coli* | CMY-2 |
| *Escherichia coli* | Empty pSMART plasmid |
| *Klebsiella gerogenes* | VIM-1, SHV-12 |
| *Klebsiella oxytoca* | KPC-2, TEM-1 |
| *Klebsiella pneumoniae* | OXA-163, OXA-1_OXA-30, SHV-1, TEM-1 |
| *Klebsiella pneumoniae* | KPC-3 |
| *Klebsiella pneumoniae* | OXA-48, SHV-1 |
| *Klebsiella pneumoniae* | SHV-12 |
| *Klebsiella pneumoniae* | KPC-2 |

TABLE 2-continued

Bacteria strains used for in vitro MIC testing

| Organism | Pos Molecular Tests |
|---|---|
| *Pseudomonas aeruginosa* | Wildtype |
| *Pseudomonas aeruginosa* | AmpC overexpressed |
| *Pseudomonas aeruginosa* | OprD negative |
| *Serratia marcescens* | SME-2 |
| *Serratia marcescens* | AmpC overexpressed |

MIC Determination

Isolates were sub-cultured onto appropriate media and stocked in skim milk at −80° C. Following two subcultures from frozen stock, in vitro antimicrobial susceptibility testing was performed using the Clinical and Laboratory Standards Institute (CLSI) broth microdilution method. Briefly, fresh cultures were suspended in culture media to give a final stock inoculum size of 5×10$^7$ colony forming units per milliliter of broth (CFU/mL). Test compounds were prepared at a stock solution concentration equal to 128 μg/mL, then diluted to give a final an initial working concentration of 32 μg/ml. 100 μL of the stock solutions were added to the first wells in a 96-well plate and were then diluted using a 2-fold dilution method to give a range of 32-0.025 μg/mL. 100 μL of the bacterial suspensions were then added to the 96-well plates to give a final working inoculum size of 5×10$^5$ CFU/mL The final compound concentration range was 16-0.0125 μg/mL. All compounds were tested in iron-depleted cation-adjusted Mueller-Hinton broth, and the minimum inhibitory concentration (MIC) was read as the first well in which growth was significantly reduced (a button <1 mm or faint turbidity) in comparison to the growth control. MICs for comparator agents were determined using custom-designed, in-house prepared 96-well broth microdilution panels.

Synergistic Activity Determination

The same method used to test the activity of the claimed compounds was used to determine their synergistic activity when combined with a β-lactamase inhibitor except that either a fixed concentration or fixed ratio of a β-lactamase inhibitor was added to the 96-well plates prior to adding the bacteria cultures. Synergistic activity was defined as the reduction of MIC of a given compound when tested using the β-lactamase inhibitor versus testing the compound in the absence of a β-lactamase inhibitor.

Testing Results

As shown in Tables 3-7, the indicated compounds exhibited activity against Gram-negative bacteria including resistant strains. MIC for the indicated compounds against wild-types strains of *Acinetobacter baumannii, Citrobacter, Escherichia coli*, and *Pseudomonas aeruginosa* ranged between 0.03 and >16 μg/mL. The compounds were also active against resistant strains of *Citrobacter freundii, Enterobacter cloacae, Escherichia coli, Klebsiella pneumoniae, Klebsiella aerogenes, Klebsiella oxytoca* and *Pseudomonas aeruginosa*. The MIC for these strains ranged between <0.015 to >16.0 μg/mL (Tables 3-7). The MIC of selected compounds was enhanced by the use of Avibactam. There was 3-4-fold reduction in MIC due to inhibition of beta-lactamase by Avibactam (Tables 8 and 9).

TABLE 3

| Antibacterial activity of the representative compounds | | | | | | | |
|---|---|---|---|---|---|---|---|
| Organism | Resistance Mechanism | Ceftazidime | Cmpd 4 | Cmpd 1 | Cmpd 40 | Cmpd 7 | Cmpd 5 |
| *Acinetobacter baumannii* | ATCC 19606 | 8 | 0.12 | 0.03 | 0.12 | >16 | 0.12 |
| *Citrobacter freundii* species complex | OXA-181 | 8 | 0.06 | 0.03 | 0.25 | 1 | 0.06 |
| *Enterobacter cloacae* species complex | NDM-1 | >32 | 0.25 | 0.12 | 2 | >16 | 0.25 |
| *Escherichia coil* | ATCC 25922 | 0.25 | 0.25 | 0.06 | 0.06 | 1 | 0.25 |
| *Escherichia coil* | pSMART_*Cfreundii*_AmpC | 32 | 0.12 | 0.06 | 0.12 | 1 | 0.25 |
| *Escherichia coil* | pSMART_*Ecloacae*_AmpC | 32 | 0.06 | 0.03 | 0.06 | 0.5 | 0.06 |
| *Escherichia coil* | Isogenic TEM-26 | >32 | 0.06 | 0.0149 | <=0.015 | 0.25 | 0.03 |
| *Escherichia coil* | Isogenic TEM-10 | >32 | 0.03 | 0.0149 | 0.03 | 0.12 | 0.03 |
| *Escherichia coil* | CTX-M-15 | 4 | 1 | 1 | 2 | 8 | 2 |
| *Escherichia coil* | SHV-12 | 32 | 1 | 0.5 | 1 | 1 | 1 |
| *Escherichia coil* | CMY-2 | >32 | 2 | 1 | 2 | 4 | 4 |
| *Escherichia coil* | Empty pSMART plasmid | 0.25 | <=0.015 | 0.06 | <=0.015 | 0.12 | <=0.015 |
| *Klebsiella aerogenes* | VIM-1, SHV-12 | >32 | 1 | 0.5 | 0.25 | 8 | 2 |
| *Klebsieila oxytoca* | KPC-2, TEM-1 | 1 | <=0.015 | 0.0149 | <=0.015 | 0.12 | <=0.015 |
| *Klebsiella pneumoniae* | OXA-163, OXA-1_OXA-30, SHV-1 TEM-1 | >32 | 0.06 | 0.06 | 0.06 | 0.5 | 0.06 |
| *Klebsiella pneumoniae* | KPC-3 | >32 | 0.03 | 0.0149 | 0.03 | 0.5 | 0.03 |
| *Kiebsiella pneumoniae* | OXA-48, SHV-1 | 0.5 | <=0.015 | 0.0149 | 0.03 | 0.12 | <=0.015 |
| *Kiebsiella pneumoniae* | SHV-12 | >32 | 0.03 | 0.0149 | <=0.015 | 0.5 | 0.03 |
| *Kiebsiella pneumoniae* | KPC-2 | >32 | 0.06 | 0.12 | <=0.015 | 0.5 | 0.06 |
| *Pseudomonas aeruginosa* | ATCC 27853 | 1 | 0.25 | 0.12 | 0.12 | >16 | 0.25 |
| *Pseudomonas aeruginosa* | AmpC overexpressed | 8 | 1 | 0.5 | 8 | >16 | 1 |
| *Pseudomonas aeruginosa* | OprD negative | 2 | 1 | 0.12 | 0.12 | >16 | 2 |
| *Serratia marcescens* | SME-2 | 0.25 | 0.06 | 0.06 | 0.06 | 0.5 | 0.12 |
| *Serratia marcescens* | AmpC overexpressed | 0.5 | 0.12 | 0.12 | 0.12 | >16 | 0.25 |

TABLE 4

| Antibacterial activity of the representative compounds | | | | | | |
|---|---|---|---|---|---|---|
| Organism | Resistance Mechanism | Ceftazidime | Cmpd 6 | Cmpd 8 | Cmpd 9 | Cmpd 10 |
| *Acinetobacter baumannii* | ATCC 19606 | 8 | 0.12 | 0.12 | 2 | 0.12 |
| *Citrobacter freundii* species complex | OXA-181 | 8 | <=0.015 | 0.0149 | 0.25 | <=0.015 |
| *Enterobacter cloacae* species complex | NDM-1 | >32 | 0.25 | 0.25 | 8 | 2 |
| *Escherichia coli* | ATCC 25922 | 0.25 | 0.12 | 0.06 | 0.5 | 0.12 |
| *Escherichia coli* | pSMART_*Cfreundii*_AmpC | 32 | 0.06 | 0.06 | 0.25 | 0.06 |
| *Escherichia coli* | pSMART_*Ecloacae*_AmpC | 32 | 0.06 | 0.03 | 0.25 | 0.03 |
| *Escherichia coli* | Isogenic TEM-26 | >32 | <=0.015 | 0.0149 | 0.12 | 0.03 |
| *Escherichia coli* | Isogenic TEM-10 | >32 | <=0.015 | 0.0149 | 0.12 | 0.12 |
| *Escherichia coli* | CTX-M-15 | 4 | 2 | 2 | 4 | 1 |
| *Escherichia coli* | SHV-12 | 32 | 1 | 1 | 2 | 2 |
| *Escherichia coli* | CMY-2 | >32 | 1 | 1 | 2 | 1 |
| *Escherichia coli* | Empty pSMART plasmid | 0.25 | <=0.015 | 0.06 | 0.12 | <=0.015 |
| *Klebsiella aerogenes* | VIM-1, SHV-12 | >32 | 0.5 | 2 | 0.5 | 0.12 |
| *Klebsiella oxytoca* | KPC-2, TEM-1 | 1 | <=0.015 | 0.0149 | 0.03 | <=0.015 |
| *Klebsiella pneumoniae* | OXA-163, OXA-1_OXA-30, SHV-1, TEM-1 | >32 | 0.03 | 0.06 | 0.25 | 0.06 |
| *Klebsiella pneumoniae* | KPC-3 | >32 | 0.03 | 0.0149 | 0.25 | 0.06 |
| *Klebsiella pneumoniae* | OXA-48, SHV-1 | 0.5 | <=0.015 | 0.0149 | 0.12 | <=0.015 |
| *Klebsiella pneumoniae* | SHV-12 | >32 | <=0.015 | 0.0149 | 0.12 | <=0.015 |
| *Klebsiella pneumoniae* | KPC-2 | >32 | 0.03 | 0.12 | 0.25 | 0.03 |
| *Pseudomonas aeruginosa* | ATCC 27853 | 1 | 0.25 | 0.12 | 4 | 0.12 |
| *Pseudomonas aeruginosa* | AmpC overexpressed | 8 | 1 | 0.5 | >16 | 2 |
| *Pseudomonas aeruginosa* | OprD negative | 2 | 2 | 0.12 | >16 | 0.25 |

TABLE 4-continued

| Antibacterial activity of the representative compounds | | | | | | |
|---|---|---|---|---|---|---|
| Organism | Resistance Mechanism | Ceftazidime | Cmpd 6 | Cmpd 8 | Cmpd 9 | Cmpd 10 |
| *Serratia marcescens* | SME-2 | 0.25 | 0.06 | 0.06 | 0.5 | 0.06 |
| *Serratia marcescens* | AmpC overexpressed | 0.5 | 0.12 | 0.06 | 4 | 0.12 |

TABLE 5

| Antibacterial activity of the representative compounds | | | | | | | |
|---|---|---|---|---|---|---|---|
| Organism | Resistance Mechanism | Cmpd 11 | Cmpd 12 | Cmpd 18 | Cmpd 36 | Cmpd 35 | Cmpd 13 |
| *Acinetobacter baumannii* | ATCC 19606 | 0.25 | 0.25 | 0.25 | 0.12 | 0.25 | 0.12 |
| *Citrobacter freundii* species complex | OXA-181 | 0.03 | 0.03 | 0.06 | 0.0149 | 0.25 | 0.0149 |
| *Enterobacter cloacae* species complex | NDM-1 | 2 | 2 | 0.5 | 0.25 | 1 | 1 |
| *Escherichia coli* | ATCC 25922 | 0.12 | 0.25 | 0.12 | 0.06 | 0.5 | 0.12 |
| *Escherichia coli* | pSMART_*Cfreundii*_AmpC | 0.06 | 0.06 | 0.25 | 0.06 | 0.5 | 0.06 |
| *Escherichia coli* | pSMART_*Ecloacae*_AmpC | 0.06 | 0.06 | 0.06 | 0.03 | 0.25 | 0.06 |
| *Escherichia coli* | Isogenic TEM-26 | 0.03 | 0.06 | 0.03 | 0.0149 | 0.12 | 0.03 |
| *Escherichia coli* | Isogenic TEM-10 | 0.06 | 0.06 | 0.03 | 0.0149 | 0.06 | 0.03 |
| *Escherichia coli* | CTX-M-15 | 2 | 4 | 1 | 2 | 1 | 4 |
| *Escherichia coli* | SHV-12 | 2 | 2 | 1 | 1 | 1 | 2 |
| *Escherichia coli* | CMY-2 | 1 | 1 | 2 | 1 | 8 | 0.5 |
| *Escherichia coli* | Empty pSMART plasmid | <=0.015 | 0.03 | 0.0149 | 0.06 | 0.06 | 0.12 |
| *Klebsiella aerogenes* | VIM-1, SHV-12 | 0.12 | 0.5 | 0.5 | 2 | 1 | 0.25 |
| *Klebsiella oxytoca* | KPC-2, TEM-1 | <=0.015 | <=0.015 | 0.0149 | 0.0149 | 0.0149 | 0.0149 |
| *Klebsiella pneumoniae* | OXA-163, OXA-1_OXA-30, SHV-1, TEM-1 | 0.12 | 0.12 | 0.12 | 0.06 | 0.5 | 0.12 |
| *Klebsiella pneumoniae* | KPC-3 | 0.06 | 0.06 | 0.06 | 0.0149 | 0.25 | 0.06 |
| *Klebsiella pneumoniae* | OXA-48, SHV-1 | <=0.015 | <=0.015 | 0.0149 | 0.0149 | 0.03 | 0.0149 |
| *Klebsiella pneumoniae* | SHV-12 | 0.03 | 0.03 | 0.03 | 0.0149 | 0.06 | 0.03 |
| *Klebsiella pneumoniae* | KPC-2 | 0.03 | 0.06 | 0.06 | 0.12 | 0.12 | 0.25 |
| *Pseudomonas aeruginosa* | ATCC 27853 | 0.25 | 0.25 | 0.12 | 0.12 | 0.5 | 0.25 |
| *Pseudomonas aeruginosa* | AmpC overexpressed | 2 | 2 | 1 | 0.5 | 2 | 1 |
| *Pseudomonas aeruginosa* | OprD negative | 0.25 | 0.25 | 0.12 | 0.12 | 0.5 | 0.25 |
| *Serratia marcescens* | SME-2 | 0.06 | 0.12 | 0.06 | 0.06 | 0.25 | 0.25 |
| *Serratia marcescens* | AmpC overexpressed | 0.06 | 0.25 | 0.5 | 0.06 | 0.5 | 0.12 |

TABLE 6

| Antibacterial activity of the representative compounds | | | | | | |
|---|---|---|---|---|---|---|
| Organism | Resistance Mechanism | Cmpd 26 | Cmpd 29 | Cmpd 30 | Cmpd 28 | Cmpd 27 |
| *Acinetobacter baumannii* | ATCC 19606 | 1 | 0.12 | 0.5 | 0.12 | 1 |
| *Citrobacter freundii* species complex | OXA-181 | 0.25 | 0.12 | 0.12 | 0.12 | 0.12 |
| *Enterobacter cloacae* species complex | NDM-1 | 2 | 4 | 4 | 2 | 2 |
| *Escherichia coli* | ATCC 25922 | 0.5 | 0.5 | 1 | 0.25 | 0.5 |
| *Escherichia coli* | pSMART_*Cfreundii*_AmpC | 0.5 | 0.25 | 0.25 | 0.5 | 0.25 |
| *Escherichia coli* | pSMART_*Ecloacae*_AmpC | 0.25 | 0.12 | 0.25 | 0.12 | 0.25 |
| *Escherichia coli* | Isogenic TEM-26 | 0.06 | 0.03 | 0.5 | 0.03 | 0.12 |
| *Escherichia coli* | Isogenic TEM-10 | 0.03 | 0.03 | 0.12 | 0.03 | 0.25 |
| *Escherichia coli* | CTX-M-15 | 4 | 2 | 8 | 1 | 8 |
| *Escherichia coli* | SHV-12 | 4 | 2 | 8 | 0.5 | 8 |
| *Escherichia coli* | CMY-2 | 4 | 2 | 4 | 8 | 4 |
| *Escherichia coli* | Empty pSMART plasmid | 0.25 | 0.5 | 1 | 0.12 | 0.25 |
| *Klebsiella aerogenes* | VIM-1, SHV-12 | 0.25 | 0.25 | 0.12 | 0.12 | 0.12 |
| *Klebsiella oxytoca* | KPC-2, TEM-1 | 0.0149 | 0.0149 | 0.03 | 0.0149 | 0.0149 |
| *Klebsiella pneumoniae* | OXA-163, OXA-1_OXA-30, SHV-1, TEM-1 | 0.12 | 0.25 | 1 | 0.25 | 0.25 |

TABLE 6-continued

Antibacterial activity of the representative compounds

| Organism | Resistance Mechanism | Cmpd 26 | Cmpd 29 | Cmpd 30 | Cmpd 28 | Cmpd 27 |
|---|---|---|---|---|---|---|
| *Klebsiella pneumoniae* | KPC-3 | 0.12 | 0.06 | 0.12 | 0.25 | 0.12 |
| *Klebsiella pneumoniae* | OXA-48, SHV-1 | 0.0149 | 0.03 | 0.06 | 0.0149 | 0.03 |
| *Klebsiella pneumoniae* | SHV-12 | 0.06 | 0.06 | 0.25 | 0.06 | 0.12 |
| *Klebsiella pneumoniae* | KPC-2 | 0.0149 | 0.0149 | 0.03 | 0.0149 | 0.06 |
| *Pseudomonas aeruginosa* | ATCC 27853 | 2 | 0.5 | 4 | 1 | 4 |
| *Pseudomonas aeruginosa* | AmpC overexpressed | 4 | 2 | 4 | 2 | 4 |
| *Pseudomonas aeruginosa* | OprD negative | 2 | 0.5 | 1 | 0.5 | 2 |
| *Serratia marcescens* | SME-2 | 0.5 | 0.25 | 0.5 | 0.12 | 1 |
| *Serratia marcescens* | AmpC overexpressed | 0.5 | 0.25 | 0.5 | 0.25 | 0.5 |

TABLE 7

Antibacterial activity of the representative compounds

| Organism | Resistance Mechanism | Cmpd 41 | Cmpd 42 | Cmpd 43 |
|---|---|---|---|---|
| *Acinetobacter baumannii* | Wildtype | 0.25 | 0.25 | >16 |
| *Citrobacter freundii* species complex | OXA-181 | 0.06 | 0.06 | 0.06 |
| *Enterobacter cloacae* species complex | NDM-1 | 2 | 1 | 0.5 |
| *Escherichia coli* | Wildtype | 0.12 | 0.25 | 0.12 |
| *Escherichia coli* | pSMART_*Cfreundii*_AmpC | 0.12 | 0.12 | 0.12 |
| *Escherichia coli* | pSMART_*Ecloacae*_AmpC | 0.06 | 0.12 | 0.06 |
| *Escherichia coli* | Isogenic TEM-26 | 0.03 | 0.06 | 0.03 |
| *Escherichia coli* | Isogenic TEM-10 | 0.03 | 0.03 | 0.03 |
| *Escherichia coli* | CTX-M-15 | 4 | 2 | 1 |
| *Escherichia coli* | CMY-141, PBP3 mutation (R333insYRIK) | 4 | 8 | 4 |
| *Escherichia coli* | SHV-12 | 2 | 1 | 1 |
| *Escherichia coli* | CMY-2 | 2 | 1 | 0.5 |
| *Escherichia coli* | Empty pSMART plasmid | 0.03 | 0.03 | 0.03 |
| *Klebsiella aerogenes* | VIM-1, SHV-12 | 0.5 | 0.5 | 0.25 |
| *Klebsiella oxytoca* | KPC-2, TEM-1 | <=0.015 | <=0.015 | 0.03 |
| *Klebsiella pneumoniae* | OXA-163, OXA-1_OXA-30, SHV-1, TEM-1 | 0.12 | 0.25 | 0.06 |
| *Klebsiella pneumoniae* | KPC-3 | 0.25 | 0.06 | 0.06 |
| *Klebsiella pneumoniae* | OXA-48, SHV-1 | 0.03 | <=0.015 | 0.03 |
| *Klebsiella pneumoniae* | SHV-12 | 0.06 | 0.06 | 0.03 |
| *Proteus mirabilis* | DHA-1 | 0.12 | 0.25 | 2 |
| *Pseudomonas aeruginosa* | Wildtype | 0.25 | 0.25 | 0.25 |
| *Pseudomonas aeruginosa* | AmpC overexpressed | 2 | 1 | 1 |
| *Pseudomonas aeruginosa* | OprD negative | 0.5 | 1 | 1 |

TABLE 8

MIC Against Elevated AmpC and CMY-DHA Producing-strains in the presence of Avibactam @ 4 µg/ml

| Organism | Cephalosporinase type | CAZ[1] Alone | CAZ + AVI[2] | Cmpd 1 Alone | Cmpd 1 + AVI | Cmpd 8 Alone | Cmpd 8 + AVI | Cmpd 10 Alone | Cmpd 10 + AVI |
|---|---|---|---|---|---|---|---|---|---|
| *Enterobacter cloacae* species complex | Elevated AmpC | >32 | 0.5 | 2 | 0.12 | 2 | 0.12 | 4 | 0.12 |
| *Escherichia coli* | Elevated AmpC | | 0.12 | 0.015 | <=0.008 | 0.015 | <=0.008 | 0.015 | <=0.008 |
| *Escherichia coli* | Elevated AmpC | 8 | 0.06 | 0,25 | <=0.008 | 0.12 | 0.03 | 0.12 | 0.03 |
| *Escherichia coli* | Elevated AmpC | | 0.12 | 0.5 | 0.015 | 0.25 | 0.03 | 0.12 | 0.03 |
| *Escherichia coli* | Elevated AmpC | | 0.12 | 0.06 | <=0.008 | 0.03 | <=0.008 | 0.03 | <=0.008 |
| *Escherichia coli* | Elevated AmpC | 16 | 0.12 | 0.06 | <=0.008 | 0.06 | <=0.008 | 0.03 | <=0.008 |
| *Escherichia coli* | Elevated AmpC | 16 | 0.5 | 0.12 | 0.06 | 0.12 | 0.06 | 0.25 | 0.06 |
| *Citrobacter freundii* species complex | Elevated AmpC | >32 | 0.25 | 0.5 | 0.03 | 0.25 | 0.03 | 0.25 | 0.03 |

TABLE 8-continued

MIC Against Elevated AmpC and CMY-DHA Producing-strains in the presence of Avibactam @ 4 μg/ml

| Organism | Cephalosporinase type | CAZ[1] Alone | CAZ + AVI[2] | Cmpd 1 Alone | Cmpd 1 + AVI | Cmpd 8 Alone | Cmpd 8 + AVI | Cmpd 10 Alone | Cmpd 10 + AVI |
|---|---|---|---|---|---|---|---|---|---|
| *Enterobacter cloacae* species complex | Elevated AmpC | 16 | 0.03 | 0.25 | <=0.008 | 0.12 | <=0.008 | 0.12 | <=0.008 |
| *Enterobacter cloacae* species complex | Elevated AmpC | 16 | 0.25 | 0.5 | 0.06 | 0.5 | 0.06 | 0.5 | 0.06 |
| *Escherichia coli* | CMY-DHA | 32 | 0.5 | 1 | 0.03 | 1 | 0.03 | 0.5 | 0.06 |
| *Escherichia coli* | CMY-DHA | 32 | 0.5 | 0.05 | <=0.008 | 0.06 | <=0.008 | 0.03 | <=0.008 |
| *Escherichia coli* | CMVY-DHA | | 0.06 | 0.25 | <=0.008 | 0.25 | <=0.008 | 0.25 | 0.03 |
| *Escherichia coli* | CMY-DHA | 32 | 0.12 | 0.5 | 0.06 | 0.5 | 0.06 | 0.5 | 0.06 |
| *Escherichia coli* | CMY-DHA | 4 | <=0.015 | 0.5 | <=0.008 | 0.25 | <=0.008 | 0.25 | <=0.008 |
| *Escherichia coli* | CMY-DHA | 32 | 0.12 | 2 | 0.06 | 1 | 0.06 | 1 | 0.06 |
| *Klebsiella pneumoniae* | CMY-DHA | 16 | 0.12 | 1 | 0.5 | | 0.25 | 0.5 | 0.25 |
| *Escherichia coli* | CMY-DHA | >32 | 0.5 | 0.25 | <=0.008 | 0.12 | 0.015 | 0.06 | 0.015 |
| *Escherichia coli* | CMY-DHA | >32 | 0.25 | 0.25 | <=0.008 | 0.25 | <=0.008 | 0.12 | 0.015 |
| *Proteus mirabilis* | CMY-DHA | 16 | 0.12 | 2 | 0.03 | 4 | 0.5 | 0.12 | 0.5 |

[1]CAZ ceftazidime;
[2]AVI Avibactam

TABLE 9

MIC Against Elevated AmpC and CMY-DHA Producing-strains in the presence of Avibactam @ 4 μg/ml

| Organism | Cephalosporinase type | Cmpd 18 Alone | Cmpd 18 + AVI | Cmpd 25 Alone | Cmpd 26 + AVI | Cmpd 28 Alone | Cmpd 28 + AVI |
|---|---|---|---|---|---|---|---|
| *Enterobacter cloacae* species complex | Elevated AmpC | 4 | 0.12 | 4 | 0.5 | 8 | 0.5 |
| *Escherichia coli* | Elevated AmpC | 0.03 | <=0.008 | 0.06 | 0.015 | 0.06 | 0.015 |
| *Escherichia coli* | Elevated AmpC | 0.25 | <=0.008 | 0.5 | 0.12 | 0.5 | 0.06 |
| *Escherichia coli* | Elevated AmpC | 0.5 | 0.06 | 2 | 0.25 | 1 | 0.03 |
| *Escherichia coli* | Elevated AmpC | 0.06 | <=0.008 | 0,06 | <=0.008 | 0.25 | <=0.008 |
| *Escherichia coli* | Elevated AmpC | 0.06 | <=0.008 | 0.12 | 0.015 | 0.12 | 0.06 |
| *Escherichia coli* | Elevated AmpC | 0.25 | 0.06 | 0.5 | 0.12 | 1 | 0.25 |
| *Citrobacter freundii* species complex | Elevated AmpC | 1 | 0.03 | 1 | 0.25 | 1 | 0.12 |
| *Enterobacter cloacae* species complex | Elevated AmpC | 0.25 | <=0.008 | 1 | <=0.008 | 1 | 0.015 |
| *Enterobacter cloacae* species complex | Elevated AmpC | 1 | 0.06 | 2 | 0.25 | 2 | 0.25 |
| *Escherichia coli* | CMY-DHA | 0.5 | 0.03 | 2 | 0.25 | 4 | 0.12 |
| *Escherichia coli* | CMVY-DHA | 0.12 | <=0.008 | 0.25 | 0.03 | 0.25 | <=0.008 |
| *Escherichia coli* | CMY-DHA | 0.25 | 0.03 | 1 | 0.06 | 0.5 | 0.06 |
| *Escherichia coli* | CMY-DHA | 1 | 0.06 | 2 | 0.5 | | 0.12 |
| *Escherichia coli* | CMY-DHA | .5 | <=0.008 | 1 | <=0.008 | 1 | <=0.008 |
| *Escherichia coli* | CMY-DHA | 2 | 0.06 | 8 | 0.5 | 8 | 0.12 |
| *Klebsiello pneumoniae* | CMY-DHA | 1 | 0.25 | 4 | 0.5 | 2 | 0.12 |
| *Escherichia coli* | CMY-DHA | 0.5 | 0.015 | 1 | 0.06 | 1 | 0.015 |
| *Escherichia coli* | CMY-DHA | 0.5 | 0.015 | 1 | 0.06 | 2 | 0.03 |
| *Proteus mirabilis* | CMY-DHA | 1 | 0.06 | 4 | 0.06 | 2 | 0.03 |

[1]CAZ ceftazidime;
[2]AVI Avibactam

What is claimed is:
1. A compound of formula (I)
(I)
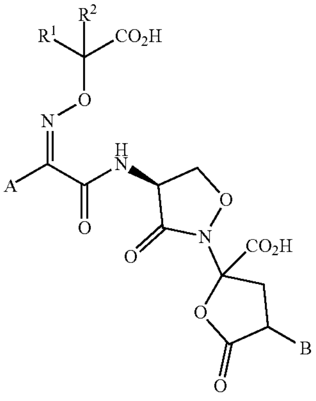
where A is defined by formula (Ia)
(Ia)
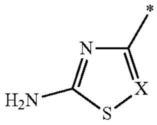
and wherein X is N or $CR^3$, and $R^3$ represents hydrogen or halogen;
where
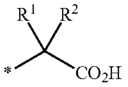
is selected from the group consisting of:
(i)
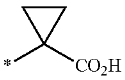
(ii)
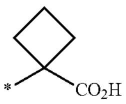
(iii)
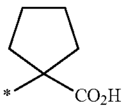
(iv)
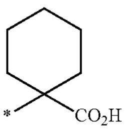
-continued
(v)
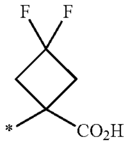
(vi)
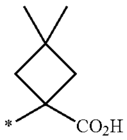
(vii)
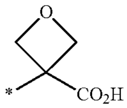
(viii)
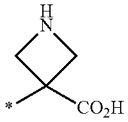
(ix)
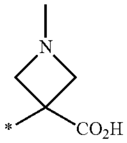
(x)
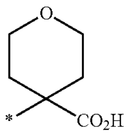
(xi)
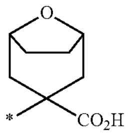
(xii)
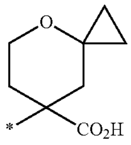
(xiii)
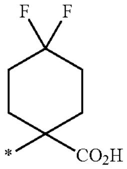
(xiv)
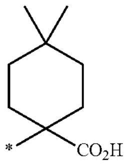

-continued
(xv)
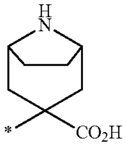
(xvi)
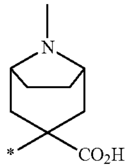
(xvii)
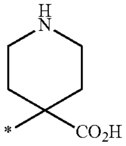
(xviii)
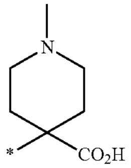
(xix)
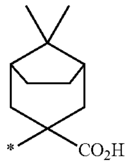
(xx)
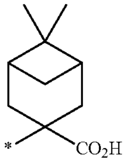
(xxi)
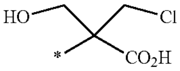
(xxii)
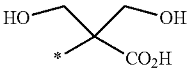
(xxiii)
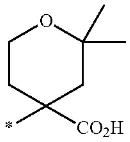
(xxiv)
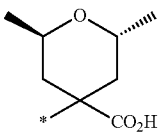 and
(xxv)
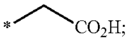
where B is selected from the group consisting of:
(d)
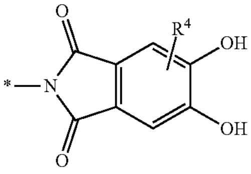
(e)
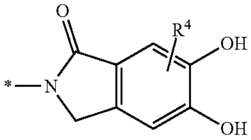
(f)
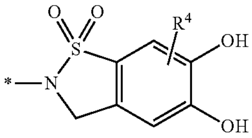
(g)
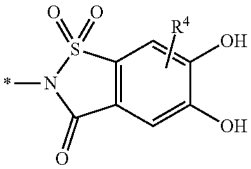
(h)
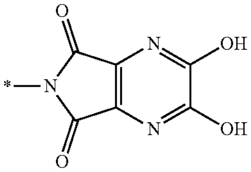
(i)
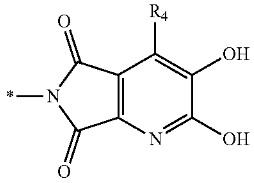
(j)
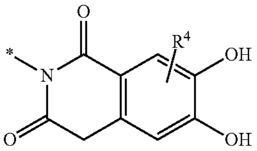
(k)
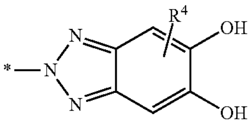
(l)
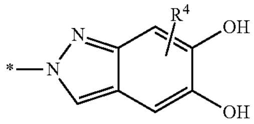

-continued (m)

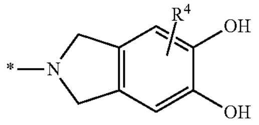

(n)

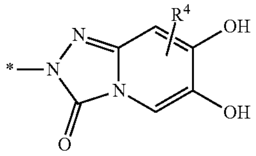

(o)

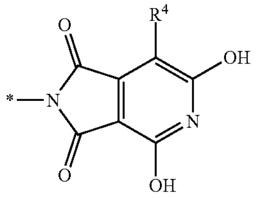

(p)

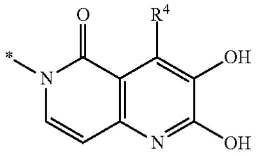

(q)

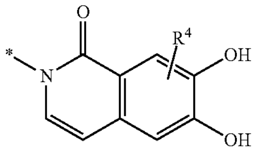

(r)

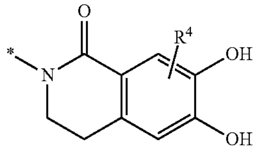

(s)

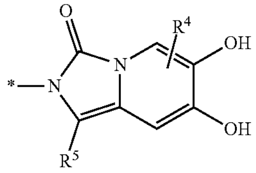

(t)

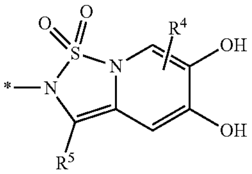

and (u)

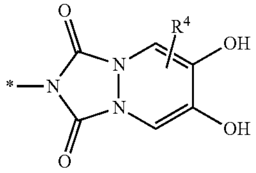

wherein $R^4$ is selected from the group consisting of hydrogen, $(C_1-C_3)$ alkyl, trifluoromethyl, cyano and halogen, and $R^5$ is hydrogen or $CH_3$, wherein * indicates point of attachment.

2. The compound according to claim 1, wherein the halogen of $R^3$ is fluorine or chlorine.

3. The compound according to claim 1, wherein the halogen of $R^4$ is fluorine or chlorine.

4. The compound according to claim 1, wherein the compound of formula (I) is:

41

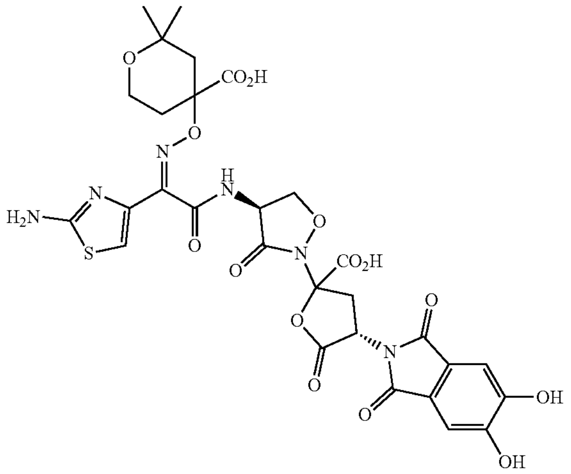

42

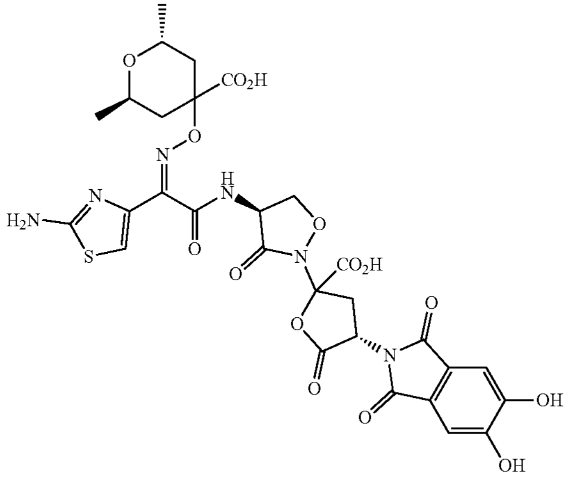

-continued
43
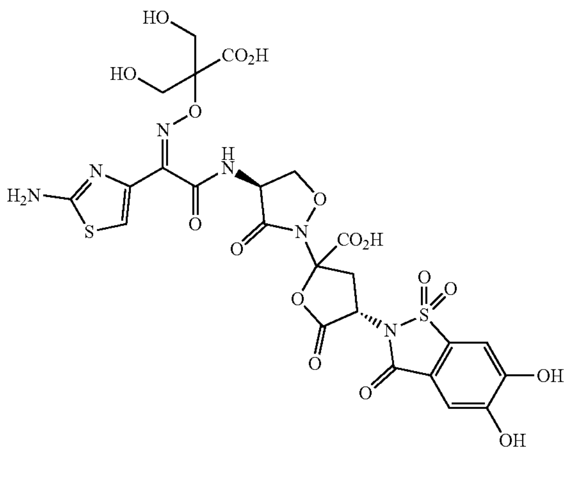
44
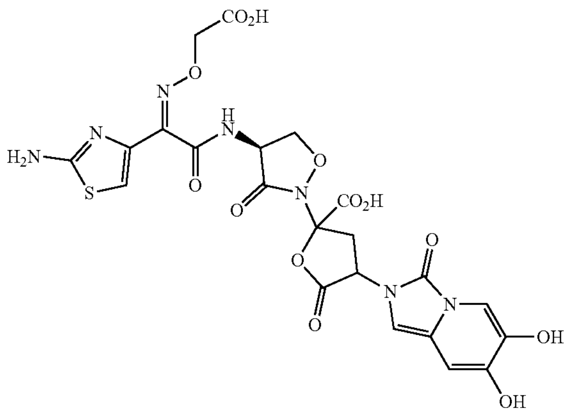
45
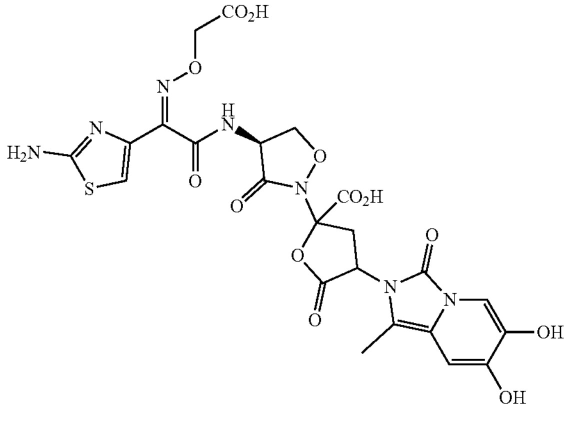
-continued
47
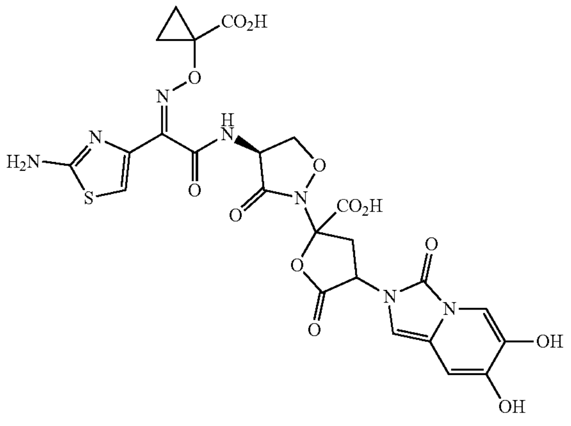
48
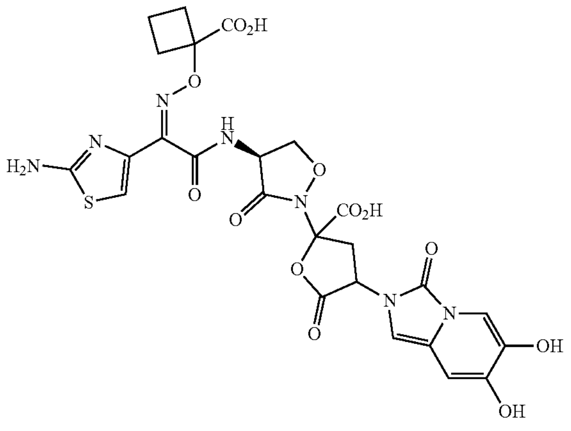
49
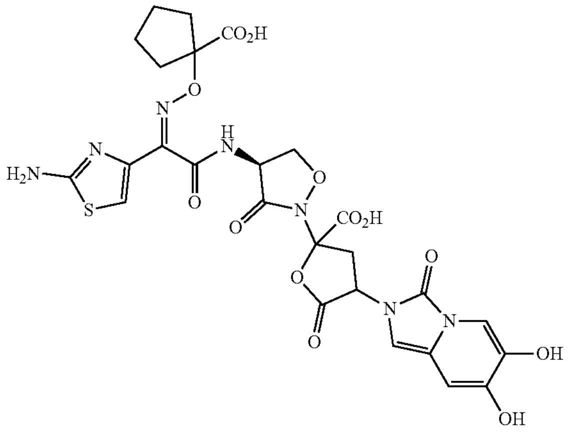

-continued
50
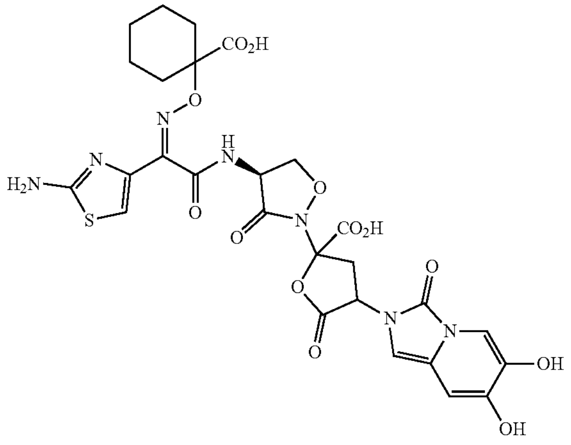
51
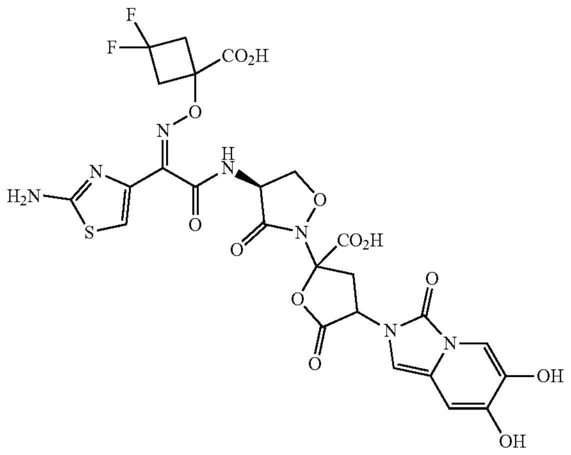
52
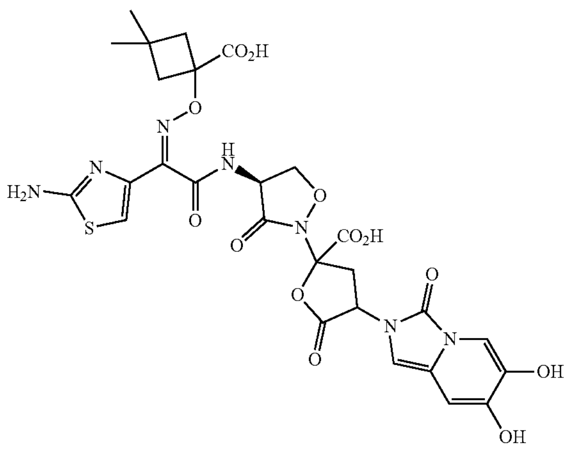
-continued
53
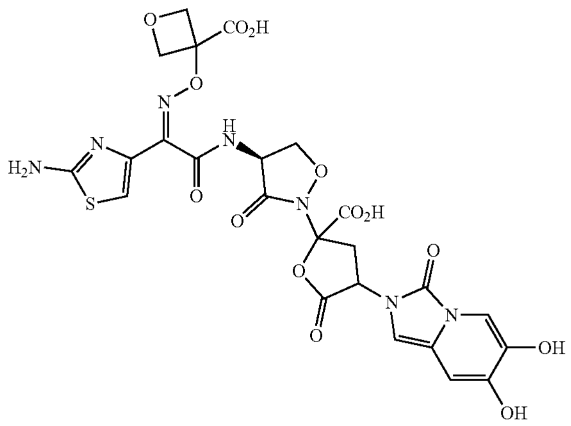
54
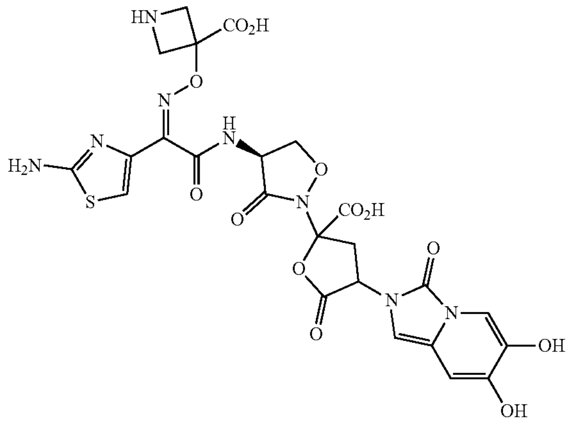
55
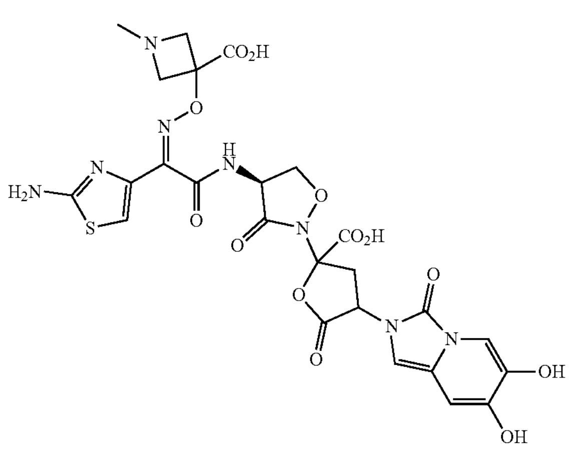

-continued
56
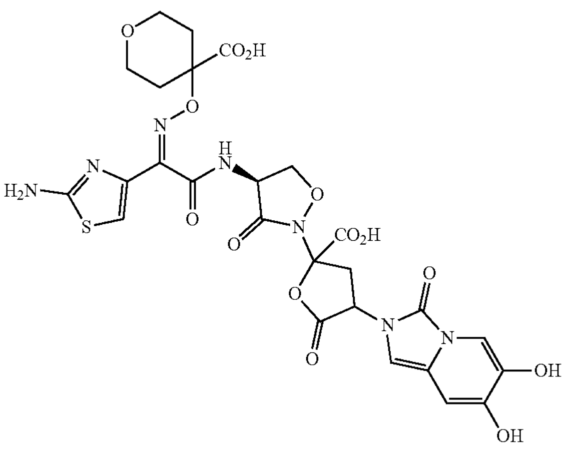
57
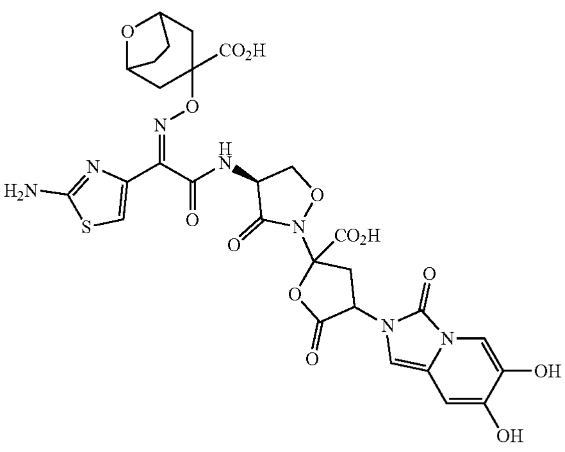
58
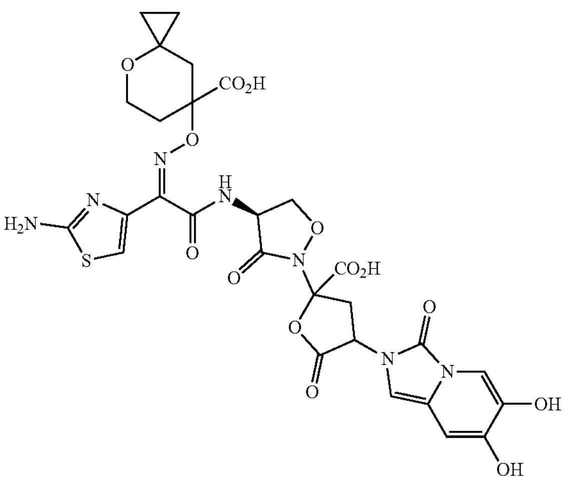
-continued
59
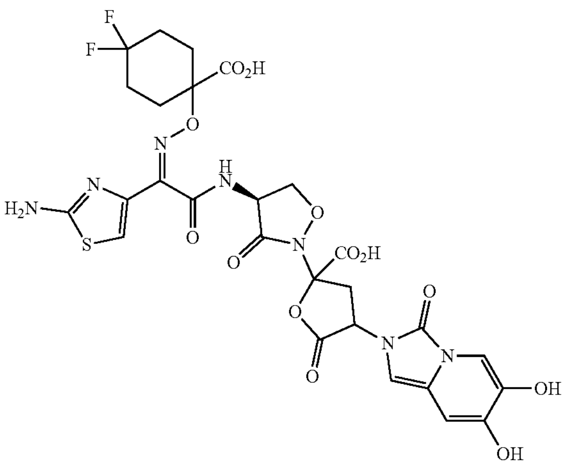
60
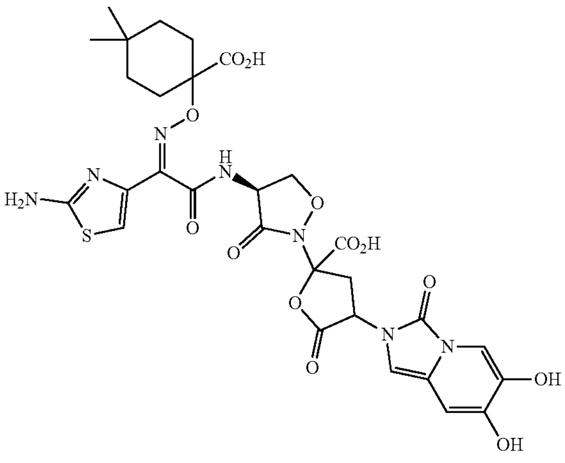
61
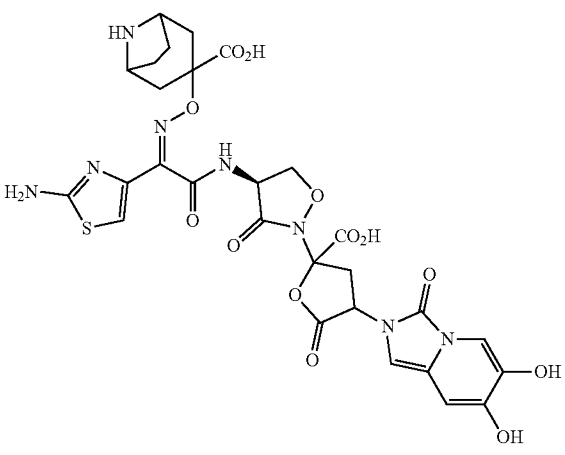

-continued
62
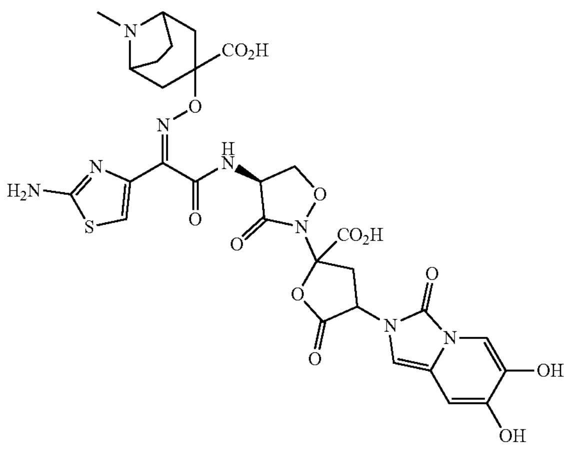
63
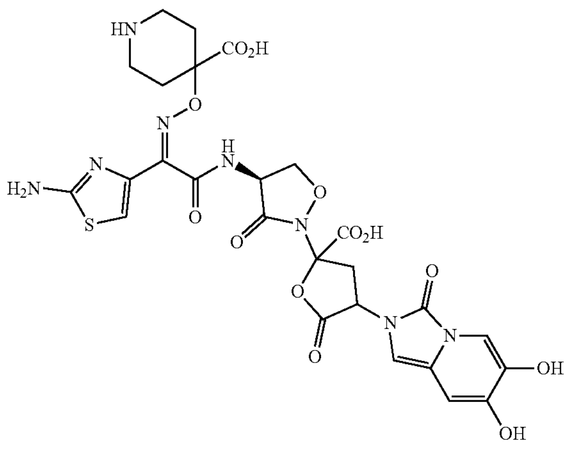
64
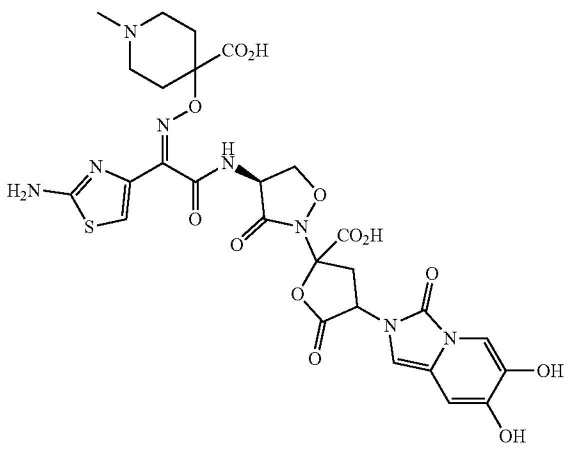
-continued
65
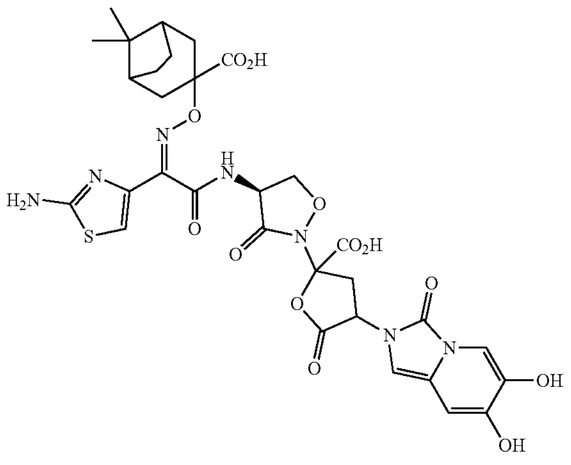
66
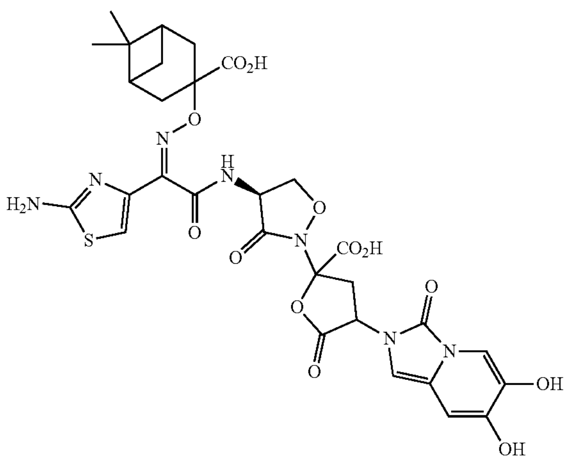
67
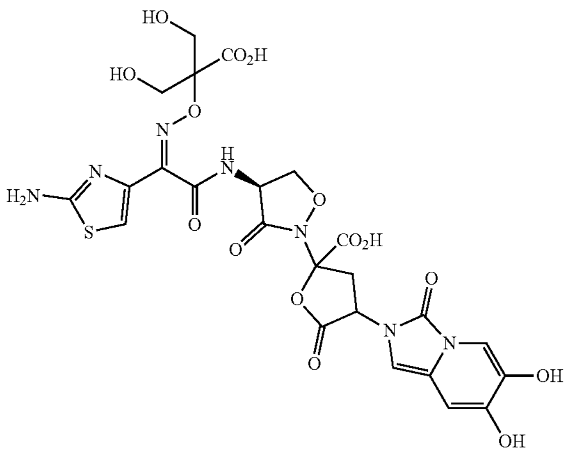

-continued
68
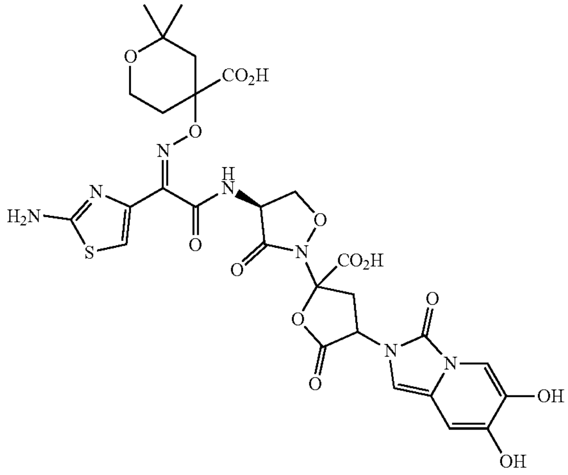
69
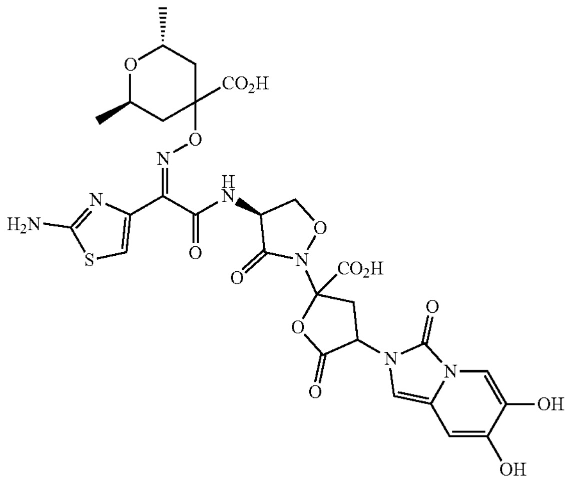
70
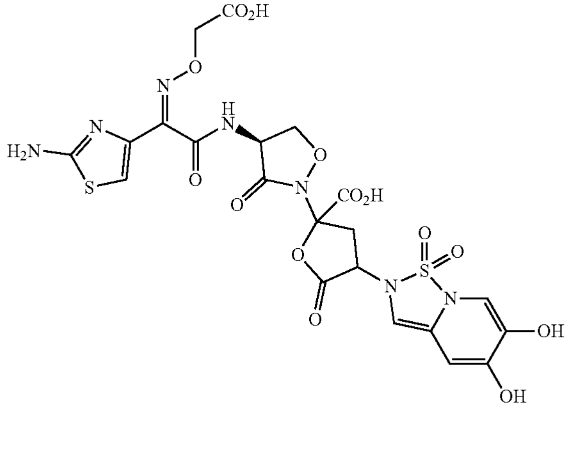
-continued
72
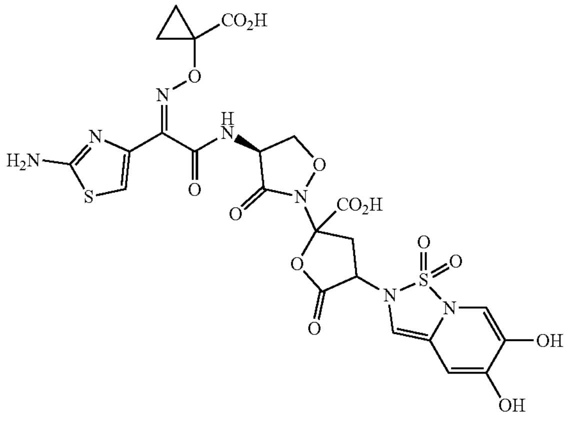
73
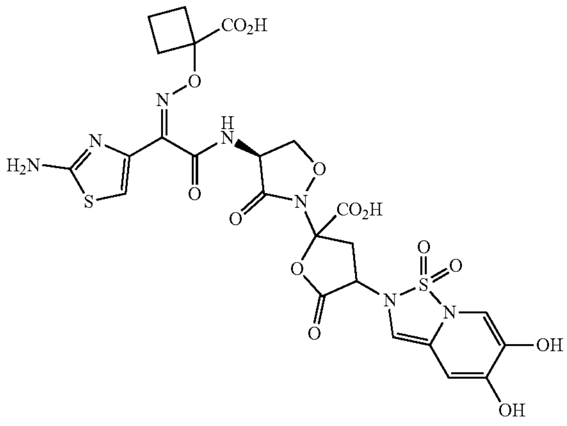
74
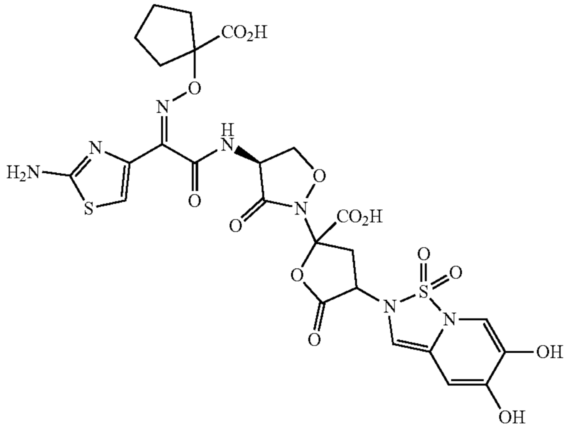

-continued
75
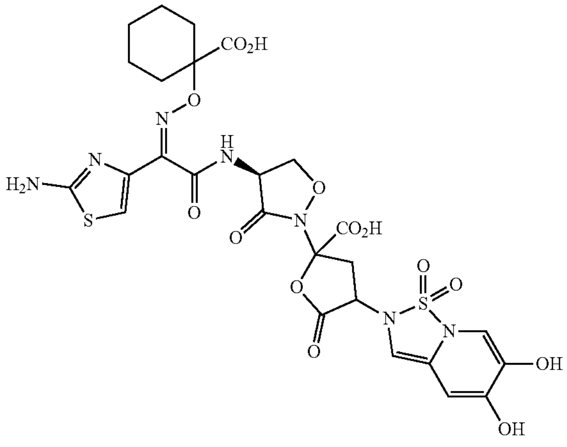
76
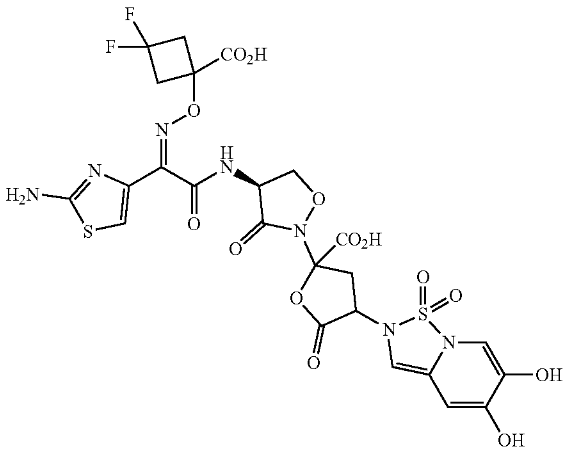
77
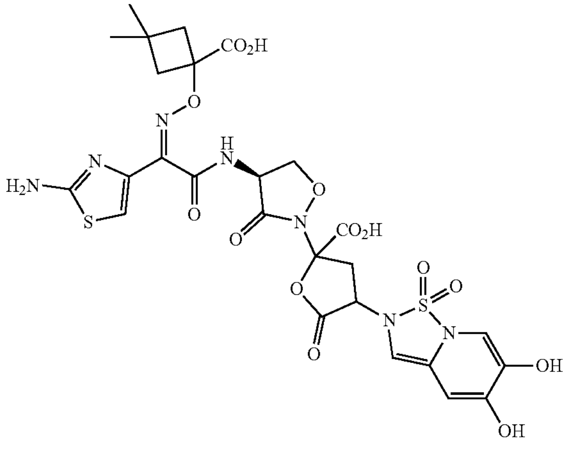
-continued
78
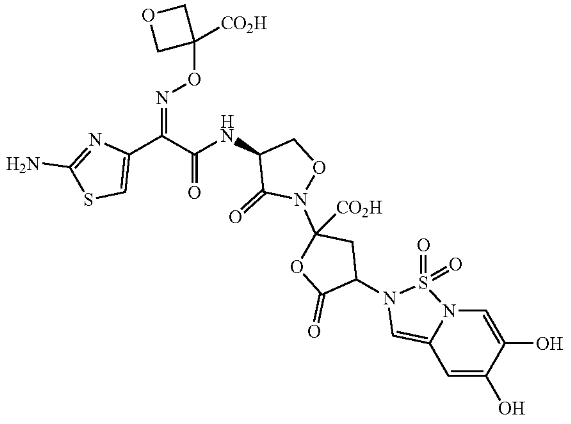
79
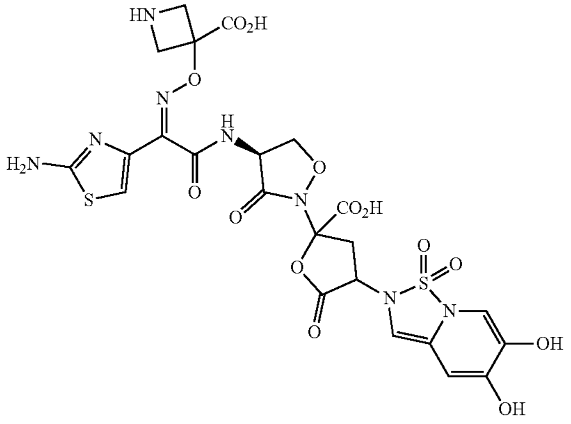
80
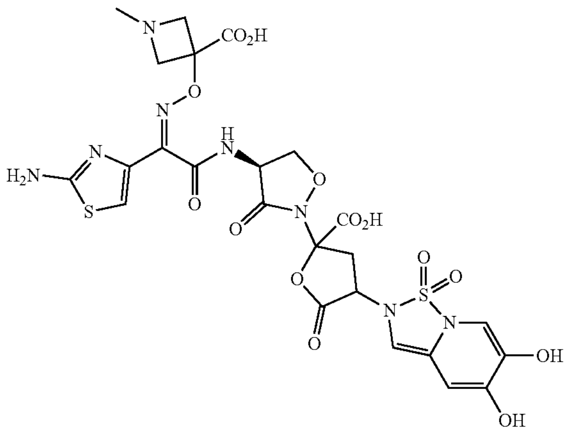

-continued
81
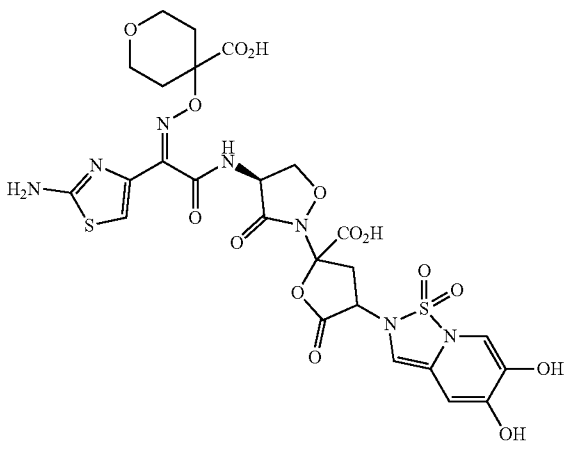
82
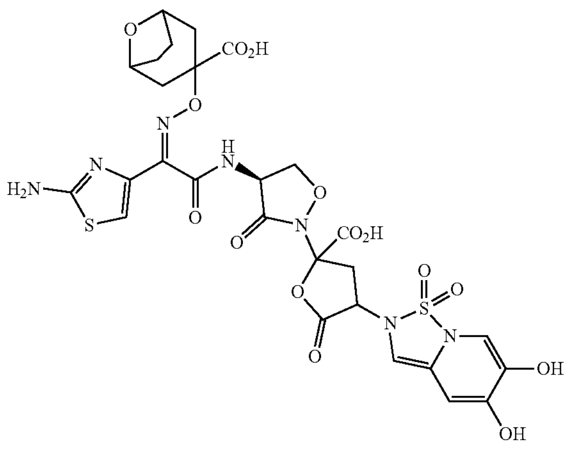
83
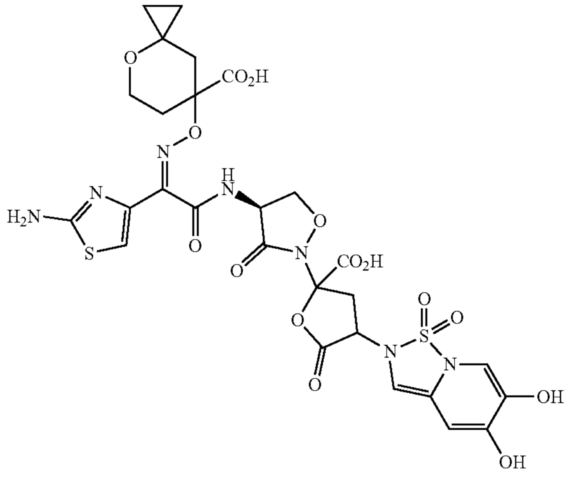
-continued
84
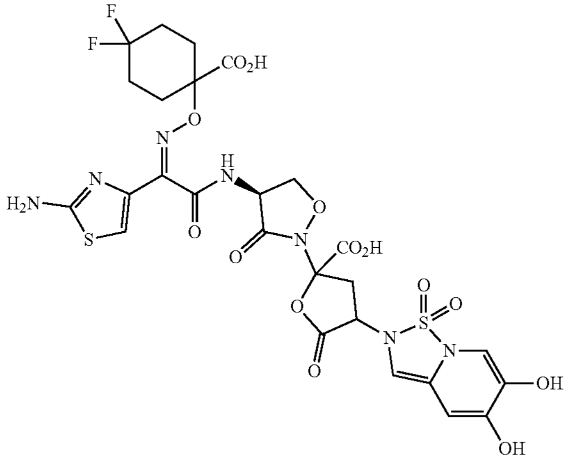
85
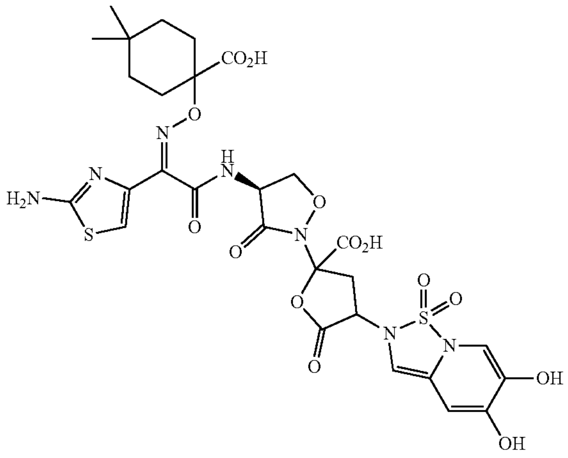
86
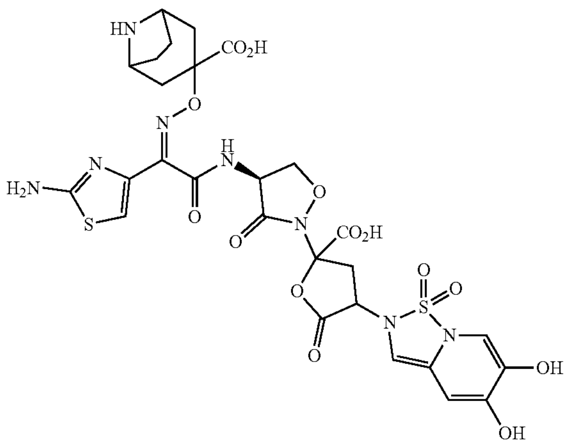

-continued
87
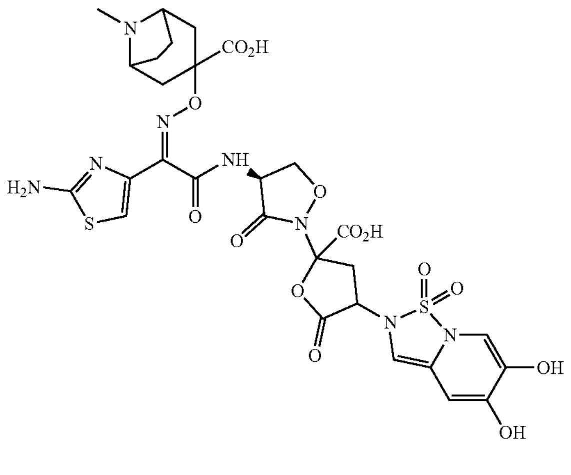
88
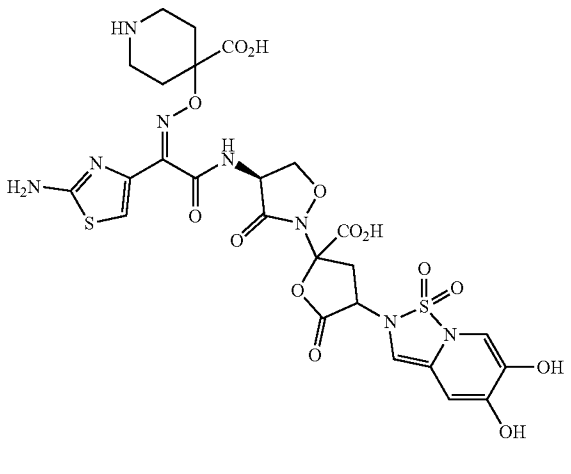
89
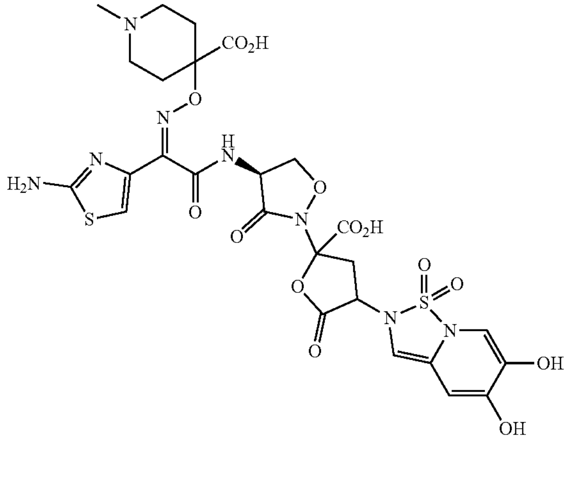
-continued
90
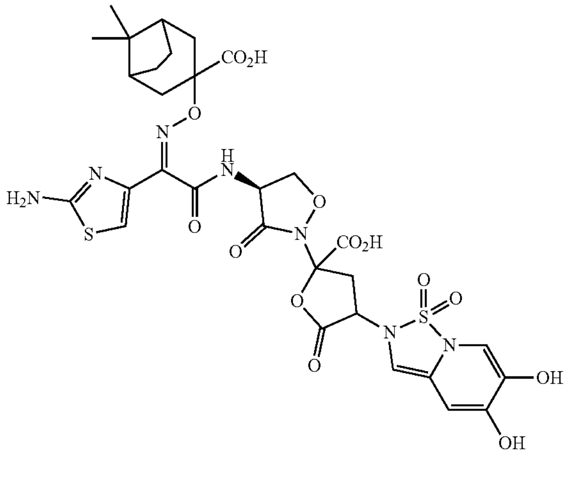
91
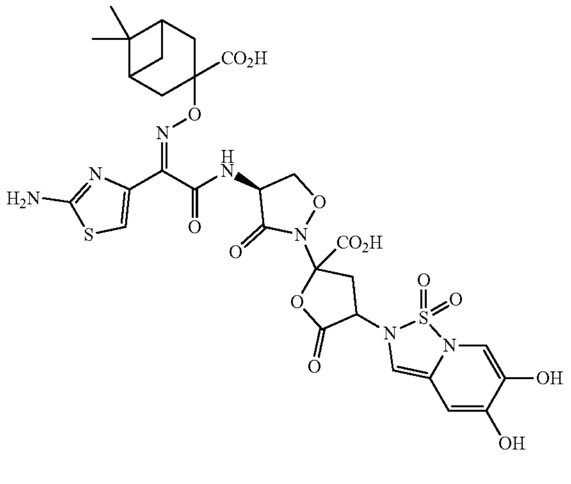
92
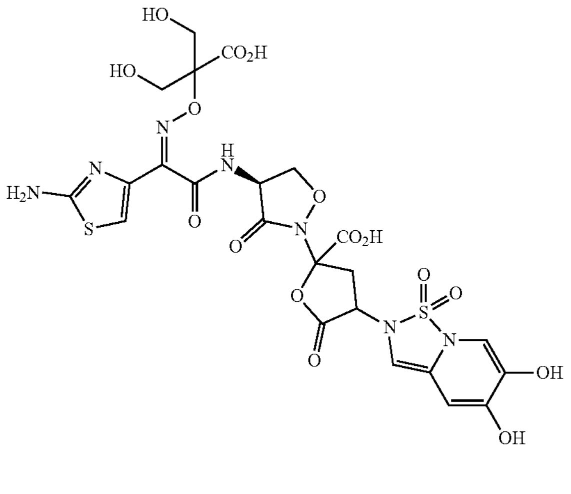

-continued
93
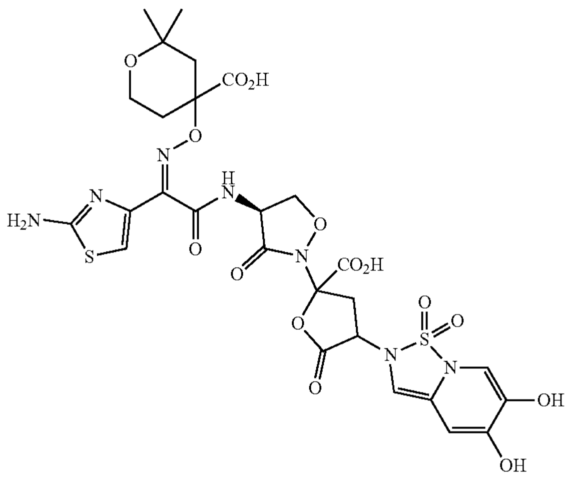
94
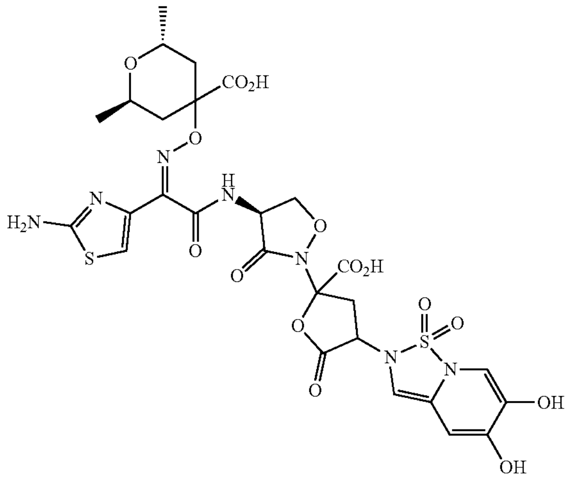
95
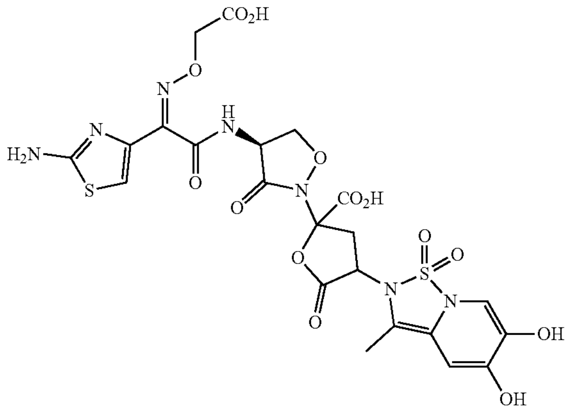
-continued
97
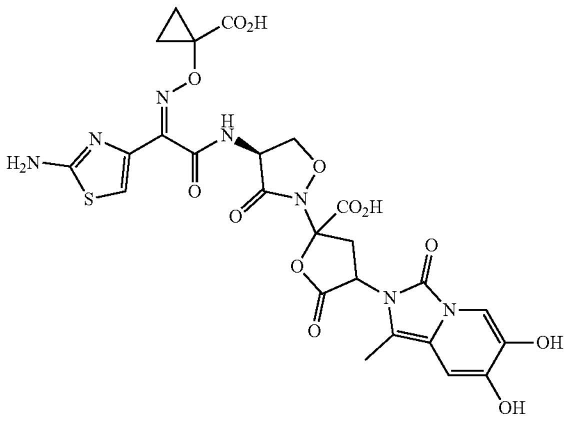
98
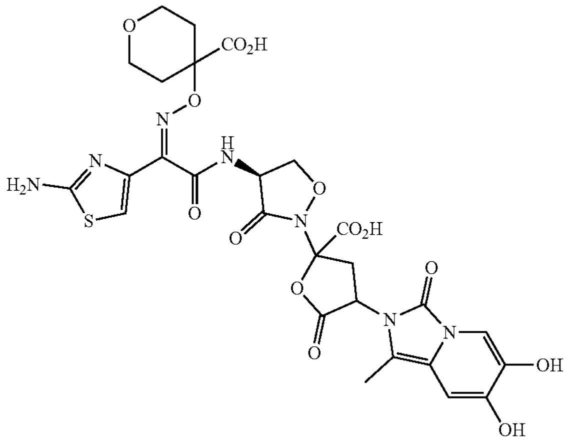
100
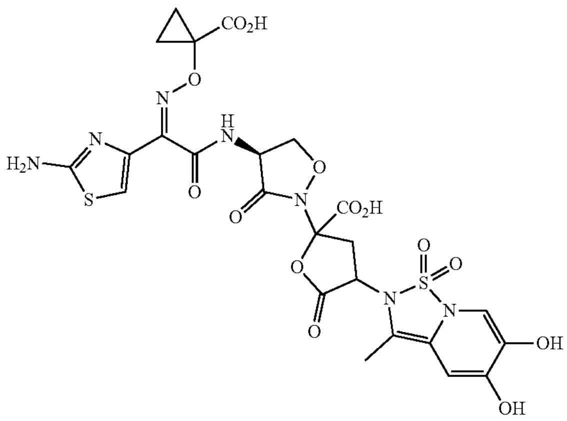

-continued

101

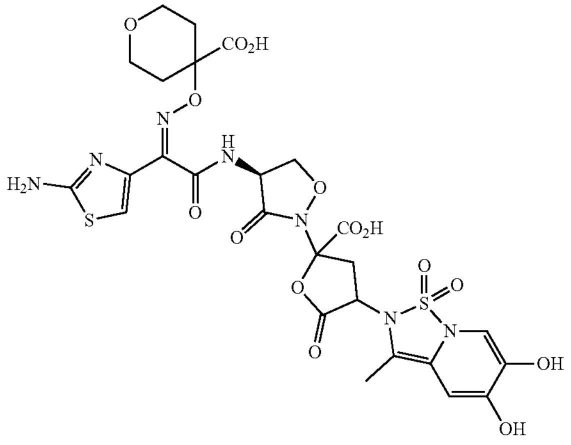

or

103

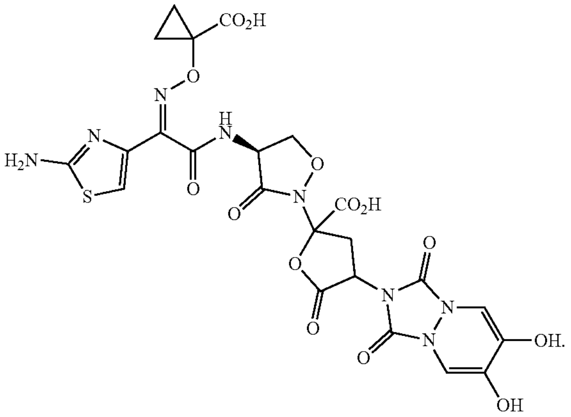

5. The compound according to claim 1, wherein the compound of formula (I) is:

4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,2-dimethyloxane-4-carboxylic acid, (2R,6R)-4-({(Z)-[1-(2-amino-1,3-thiazol-4-yl)-2-({(4S)-2-[(4S)-2-carboxy-4-(5,6-dihydroxy-1,3-dioxo-1,3-dihydro-2H-isoindol-2-yl)-5-oxooxolan-2-yl]-3-oxo-1,2-oxazolidin-4-yl}amino)-2-oxoethylidene]amino}oxy)-2,6-dimethyloxane-4-carboxylic acid, (4S)-2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1,3-trioxo-1,3-dihydro-2H-1$\lambda^6$,2-benzothiazol-2-yl)-5-oxooxolane-2-carboxylic acid, 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(6,7-dihydroxy-1-methyl-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxycyclobutyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxycyclopentyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxycyclohexyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxy-3,3-difluorocyclobutyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(3-carboxyoxetan-3-yl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 3-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)azetidine-3-carboxylic acid, 3-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-1-methylazetidine-3-carboxylic acid, 4-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)oxane-4-carboxylic acid, 3-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid, 7-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-4-oxaspiro[2.5]octane-7-carboxylic acid, 2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(1-carboxy-4,4-dimethylcyclohexyl)oxy]imino}acetyl]

amino}-3-oxo-1,2-oxazolidin-2-yl]-4-(6,7-dihydroxy-3-oxoimidazo[1,5-a]pyridin-2 (3H)-yl)-S-oxooxolane-2-carboxylic acid, 3-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-8-azabicyclo[3.2.1]octane-3-carboxylic acid, 3-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-8-methyl-8-azabicyclo[3.2.1]octane-3-carboxylic acid, 4-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)piperidine-4-carboxylic acid, 4-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-1-methylpiperidine-4-carboxylic acid, 2-[(4S)-4-{[(2Z)-2-(2-amino-1,3-thiazol-4-yl)-2-{[(3-carboxy-8,8-dimethylbicyclo[3.2.1]octan-3-yl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(3-carboxy-6,6-dimethylbicyclo[3.1.1]heptan-3-yl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(6,7-dihydroxy-3-oxoimidazo[1,5-a]pyridin-2 (3H)-yl)-5-oxooxolane-2-carboxylic acid, 4-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-2,2-dimethyloxane-4-carboxylic acid, (2R,6R)-4-({(Z)-[1-(2-amino-1,3-thiazol-4-yl)-2-({(4S)-2-[2-carboxy-4-(6,7-dihydroxy-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)-2,6-dimethyloxane-4-carboxylic acid, 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxycyclobutyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxycyclopentyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxycyclohexyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxy-3,3-difluorocyclobutyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxy-3,3-dimethylcyclobutyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(3-carboxyoxetan-3-yl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)azetidine-3-carboxylic acid, 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-1-methylazetidine-3-carboxylic acid, 4-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)oxane-4-carboxylic acid, 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-8-oxabicyclo[3.2.1]octane-3-carboxylic acid, 7-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-4-oxaspiro[2.5]octane-7-carboxylic acid, 2-[(4S)-4-{[(2Z)-2-(2-amino-1,3-thiazol-4-yl)-2-{[(1-carboxy-4,4-difluorocyclohexyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-S-oxooxolane-2-carboxylic acid, 2-[(4S)-4-{[(2Z)-2-(2-amino-1,3-thiazol-4-yl)-2-{[(1-carboxy-4,4-dimethylcyclohexyl)oxy]imino}acetyl]amino}-3-oxo-1,2-oxazolidin-2-yl]-4-(5,6-dihydroxy-1,1-dioxo-1λ$^6$-[1,2,5]thiadiazolo[2,3-a]pyridin-2 (1H)-yl)-5-oxooxolane-2-carboxylic acid, 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-8-azabicyclo[3.2.1]octane-3-carboxylic acid, 3-({(Z)-[1-(2-amino-1,3-thiazol-4-yl)-2-({(4S)-2-[2-carboxy-4-(5,6-dihydroxy-1,1-dioxo-1λ$^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-8-methyl-8-azabicyclo[3.2.1]octane-3-carboxylic acid, 4-({(Z)-[1-(2-amino-1,3-thiazol-4-yl)-2-({(4S)-2-[2-carboxy-4-(5,6-dihydroxy-1,1-dioxo-1$\lambda^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)piperidine-4-carboxylic acid, 4-({(Z)-[1-(2-amino-1,3-thiazol-4-yl)-2-({(4S)-2-[2-carboxy-4-(5,6-dihydroxy-1,1-dioxo-1$\lambda^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-1-methylpiperidine-4-carboxylic acid, 2-[(4S)-4-{[(2Z)-2-(2-amino-1,3-thiazol-4-yl)-2-{[(3-carboxy-8,8-dimethylbicyclo[3.2.1]octan-3-yl)oxy]imino}acetyl]amino}-3-oxo-1,2-oxazolidin-2-yl]-4-(5,6-dihydroxy-1,1-dioxo-1$\lambda^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(3-carboxy-6,6-dimethylbicyclo[3.1.1]heptan-3-yl)oxy]imino}acetyl]amino}-3-oxo-1,2-oxazolidin-2-yl]-4-(5,6-dihydroxy-1,1-dioxo-1$\lambda^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(2-carboxy-1,3-dihydroxypropan-2-yl)oxy]imino}acetyl]amino}-3-oxo-1,2-oxazolidin-2-yl]-4-(5,6-dihydroxy-1,1-dioxo-1$\lambda^6$-[1,2,5]thiadiazolo[2,3-a]pyridin-2 (1H)-yl)-5-oxooxolane-2-carboxylic acid, 4-({(Z)-[1-(2-amino-1,3-thiazol-4-yl)-2-({(4S)-2-[2-carboxy-4-(5,6-dihydroxy-1,1-dioxo-1$\lambda^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-2,2-dimethyloxane-4-carboxylic acid, (2R,6R)-4-({(Z)-[1-(2-amino-1,3-thiazol-4-yl)-2-({(4S)-2-[2-carboxy-4-(5,6-dihydroxy-1,1-dioxo-1$\lambda^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)-2,6-dimethyloxane-4-carboxylic acid, 2-[(4S)-4-({(2Z)-2-(2-amino-1,3-thiazol-4-yl)-2-[(carboxymethoxy)imino]acetyl}amino)-3-oxo-1,2-oxazolidin-2-yl]-4-(5,6-dihydroxy-3-methyl-1,1-dioxo-1$\lambda^6$-[1,2,5]thiadiazolo[2,3-a]pyridin-2 (1H)-yl)-5-oxooxolane-2-carboxylic acid, 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(6,7-dihydroxy-1-methyl-3-oxoimidazo[1,5-a]pyridin-2 (3H)-yl)-5-oxooxolane-2-carboxylic acid, 4-({(Z)-[1-(2-amino-1,3-thiazol-4-yl)-2-({(4S)-2-[2-carboxy-4-(6,7-dihydroxy-1-methyl-3-oxoimidazo[1,5-a]pyridin-2 (3H)-yl)-5-oxooxolan-2-yl]-3-oxo-1,2-oxazolidin-4-yl}amino)-2-oxoethylidene]amino}oxy)oxane-4-carboxylic acid, 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(5,6-dihydroxy-3-methyl-1,1-dioxo-1$\lambda^6$-[1,2,5]thiadiazolo[2,3-a]pyridin-2 (1H)-yl)-5-oxooxolane-2-carboxylic acid, 4-({(Z)-[1-(2-amino-1,3-thiazol-4-yl)-2-({(4S)-2-[2-carboxy-4-(5,6-dihydroxy-3-methyl-1,1-dioxo-1$\lambda^6$-[1,2,5]thiadiazolo[2,3-a]pyridin-2 (1H)-yl)-5-oxooxolan-2-yl]-3-oxo-1,2-oxazolidin-4-yl}amino)-2-oxoethylidene]amino}oxy)oxane-4-carboxylic acid, 2-[(4S)-4-{[(2Z)-2-(2-amino-1,3-thiazol-4-yl)-2-{[(1-carboxycyclopropyl)oxy]imino}acetyl]amino}-3-oxo-1,2-oxazolidin-2-yl]-4-(6,7-dihydroxy-1,3-dioxo-1H-

[1,2,4]triazolo[1,2-a]pyridazin-2 (3H)-yl)-5-oxooxolane-2-carboxylic acid.

6. A pharmaceutical composition comprising one or more of the compound of formula (I) of claim 1, or pharmaceutically acceptable salt thereof, and a pharmaceutically acceptable carrier or diluent.

7. A pharmaceutical composition comprising (i) one or more of the compound of formula (I) of claim 1, or pharmaceutically acceptable salt thereof, (ii) one or more β-lactamase inhibitors, and (iii) a pharmaceutically acceptable carrier or diluent.

8. A pharmaceutical composition comprising (i) one or more of the compound of formula (I) of claim 1, or pharmaceutically acceptable salt thereof, (ii) one or more antibiotics, and (iii) a pharmaceutically acceptable carrier or diluent.

9. A pharmaceutical composition comprising (i) one or more of the compound of formula (I) of claim 1, or pharmaceutically acceptable salt thereof, (ii) one or more β-lactamase inhibitors, (iii) one or more antibiotics, and (iv) a pharmaceutically acceptable carrier or diluent.

10. The pharmaceutical composition of claim 7 or 9, wherein the one or more β-lactamase inhibitors are selected from the group consisting of formula ($1^a$) to ($1^{z'}$):

$1^a$

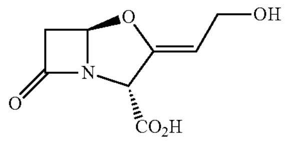

(clavulanic acid)

$1^b$

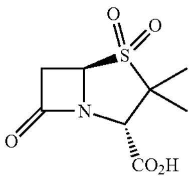

(sulbactam)

$1^c$

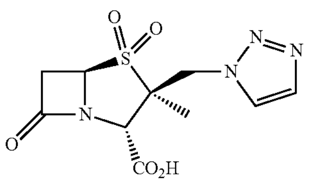

(tazobactam)

$1^d$

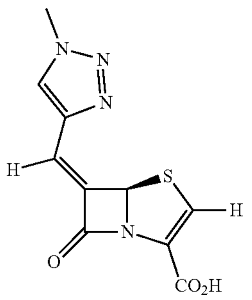

(BRL-42715)

-continued
$1^{e}$
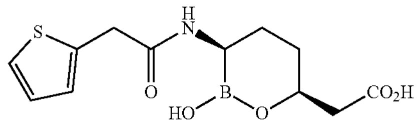
(vaborbactam)
$1^{f}$
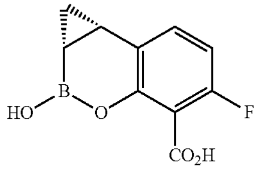
(QPX-7728)
$1^{g}$
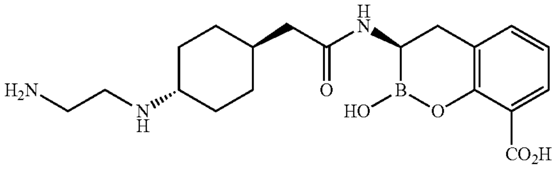
(taniborbactam, VNRX-5133)
$1^{h}$
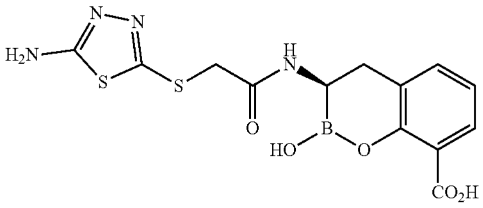
(RPX-7262)
$1^{i}$
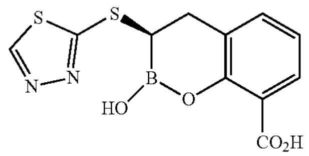
(RPX-7282)
$1^{j}$
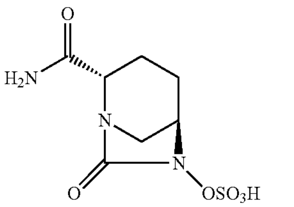
(NXL-104)
$1^{k}$
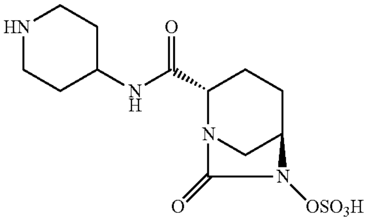
(relebactam)
-continued
$1^{l}$
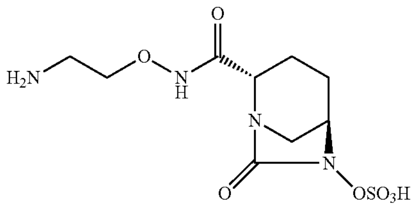
(nacubactam)
$1^{m}$
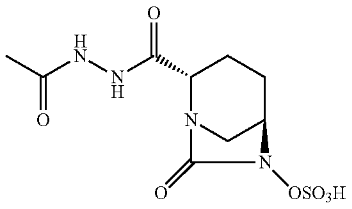
(FPI-1523)
$1^{n}$
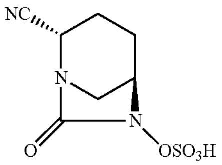
(WCK 4234)
$1^{o}$
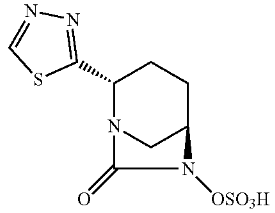
$1^{p}$
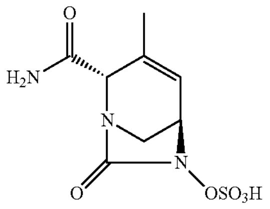
(durlobactam)
$1^{q}$
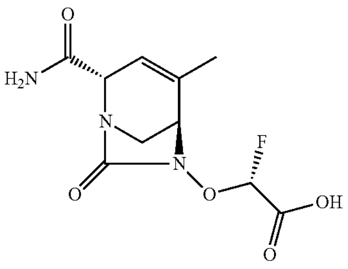
(ETX-1317)

-continued $1^r$

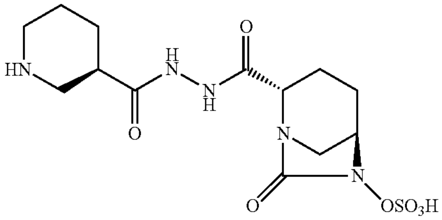

(zidebactam)

$1^s$

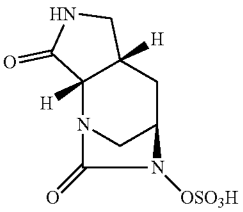

$1^t$

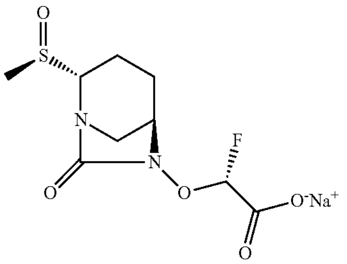

$1^u$

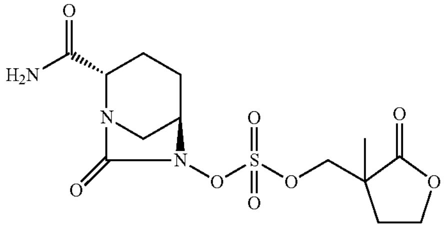

$1^v$

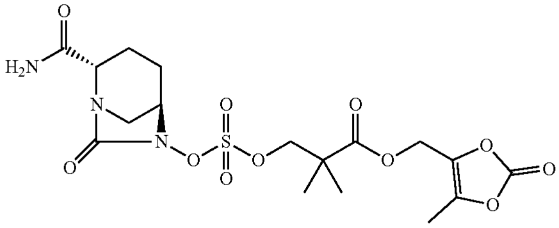

$1^w$

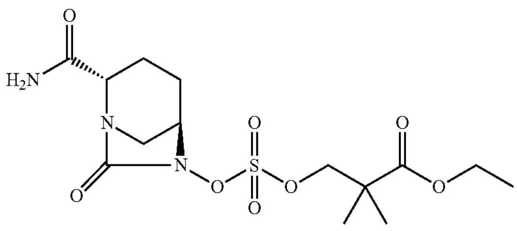

(ARX-1796)

-continued $1^x$

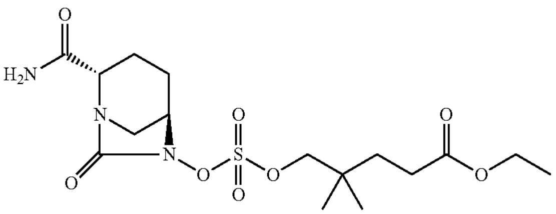

$1^y$

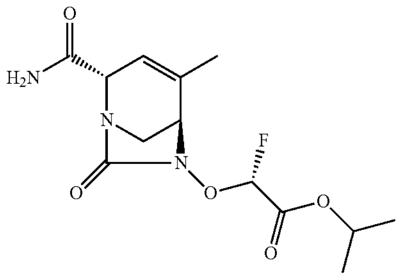

(ETX-0282)

$1^z$

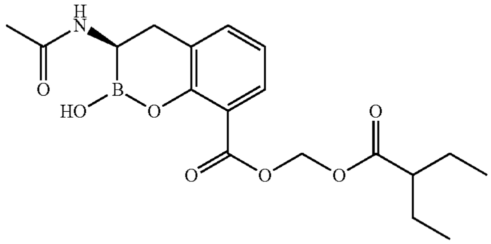

and (VNRX-7145)

$1^{z'}$

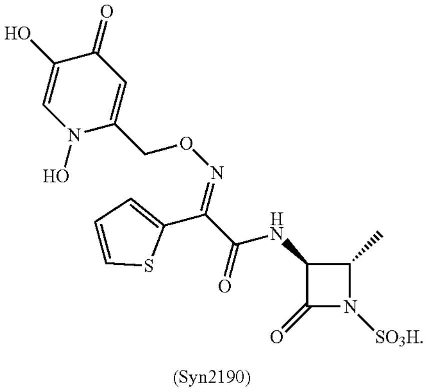

(Syn2190)

11. The pharmaceutical composition of claim 8 or 9, wherein the one or more antibiotics are selected from the group consisting of β-lactam antibiotics and non-β-lactam antibiotics.

12. The pharmaceutical composition of claim 8 or 9, wherein the one or more antibiotics are selected from the following classes of antibiotics: aminoglycosides, macrolides, ketolides, streptogramins, oxazolidinones, tetracyclines, fluoroquinolones, glycopeptides, and lipoglycopeptides.

13. The pharmaceutical composition of claim 8 or 9, wherein the one or more antibiotics are selected from the following groups of antibiotics: penicillin group, cephalosporin group, monobactam group, and carbapenem group.

14. The pharmaceutical composition of claim 8 or 9, wherein the one or more antibiotics are selected from the group consisting of fosfomycin, tobramycin, linezolid, daptomycin, and vancomycin.

15. A method of treating or preventing a bacterial infection in a subject, comprising administering a therapeutically effective amount of a pharmaceutical composition of any one of claims 7-9 to a subject having a bacterial infection, or a subject at risk of developing a bacterial infection, wherein the bacterial infection is caused by one or more bacteria selected from the group consisting of *Enterobacterales, Escherichia coli, Enterobacter spp., Klebsiella spp., Serratia spp., Pseudomonas spp., Stenotrophomonas spp., Citrobacter spp., Acinetobacter spp., Campylobacter spp., Helicobacter spp., Vibrio spp., Bordetella spp., Salmonella spp., Shigella spp., Francisella spp., Burkholderia spp., Clostridia spp., Alcaligenes spp., Moraxella spp., Proteus spp., Neisseria spp., Haemophilus spp., Achromobacter spp. and Erwinia spp.*

* * * * *